US006685946B2

(12) United States Patent
Dowling et al.

(10) Patent No.: US 6,685,946 B2
(45) Date of Patent: Feb. 3, 2004

(54) COLD-ADAPTED EQUINE INFLUENZA VIRUSES

(75) Inventors: Patricia W. Dowling, Pittsburgh, PA (US); Julius S. Youngner, Pittsburgh, PA (US)

(73) Assignee: The University of Pittsburgh-of the CommonWealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 10/065,133

(22) Filed: Sep. 19, 2002

(65) Prior Publication Data

US 2003/0199074 A1 Oct. 23, 2003

Related U.S. Application Data

(60) Division of application No. 09/506,286, filed on Feb. 16, 2000, now Pat. No. 6,482,414, which is a continuation-in-part of application No. PCT/US99/18583, filed on Aug. 12, 1999, and a continuation-in-part of application No. 09/133,921, filed on Aug. 13, 1998, now Pat. No. 6,177,082.

(51) Int. Cl.[7] ............................................. A61K 39/145

(52) U.S. Cl. ............................... 424/209.1; 424/204.1; 424/206.1; 435/91.1; 435/91.33; 435/91.41; 530/300; 536/23.72

(58) Field of Search .......................... 424/209.1, 204.1, 424/205.1; 435/91.1, 91.33, 91.41; 530/300; 536/23.72

(56) References Cited

U.S. PATENT DOCUMENTS

| | | | | |
|---|---|---|---|---|
| 3,518,347 | A | 6/1970 | Pavilanis et al. | 424/89 |
| 4,631,191 | A | 12/1986 | Dale et al. | 424/88 |
| 4,683,137 | A | 7/1987 | Coggins et al. | 424/89 |
| 4,693,893 | A | 9/1987 | Campbell et al. | 424/89 |
| 4,920,213 | A | 4/1990 | Dale et al. | 536/27 |
| 5,149,531 | A | 9/1992 | Youngner et al. | 424/89 |
| 5,690,937 | A | 11/1997 | Parkin et al. | 424/199.1 |

FOREIGN PATENT DOCUMENTS

| | | |
|---|---|---|
| WO | WO83/03546 | 10/1983 |
| WO | WO 92/00097 | 1/1992 |
| WO | WO 93/21310 | 10/1993 |
| WO | WO 00/09702 | 2/2000 |

OTHER PUBLICATIONS

Brundage–Anguish, et al., 1982, *Am J Vet Res*, 43(5), pp. 869–874.
Enami, et al., 1990, *PNAS*, vol. 87, pp. 3802–3805.
Estola, et al., 1976, *Nord Vet med* vol. 28(7–8), pp. 353–356.
Hannant, et al., Feb. 6, 1988, *Vet Rec*, pp. 125–128.
Holmes, et al., 1992, *Equine Infectious Diseases VI: Proceedings of the Sixth International Conference*, Jul. 7–11, 1991, pp. 253–258.
Ilobi, et al., 1998, *Arch Virol*, vol. 143, pp. 891–901.
Kucera, et al., 1977, *Can J Comp Med*, 41(3), pp. 326–331.
Mumford, et al., 1983, *J Hyg* (*Lond*), vol. 90(3), pp. 385–395.
Noble, et al., 1994, *J Gen Virol* vol. 75, pp. 3485–3491.
Reed, et al., 1938, *The American Journal of Hygiene*, vol. 27, pp. 493–497.
Timoney, P.J., 1996, *Comp Immunol Microbiol Infect Dis*, vol. 19(3), pp. 205–211.
USDA, 9 CFR 113.2XX, Oct. 28, 1994, Supplemental Assay Method for Conducting the Hemagglutination Inhibition Assay for Equine Influenza Antibody.
Van Maanen, et al., 1992, *Vet Q*, vol. 14(1), pp. 13–17.
Van Oirschot, et al., 1991, *Zentralbl Veterinarmed* [*B*], vol. 38(5), pp. 391–396.
Wood, et al., 1983, *J Hyg* (*Lond*) vol. 90(3), pp. 371–384.
Wilson, et al., 1993, *Vet Clin North Am Equine Practi*, vol. 9(2), pp. 257–282.
Youngner, et al., 1994, *J. of Clinical of Microbiology*, vol. 32(3), pp. 750–754.
Lunn et al., 1999, *Vaccine*, vol. 17, pp. 2245–2258.
Romanova et al., 1997, *Vaccine*, vol. 15, No. 6/7, pp. 653–658.
Talon et al., 2000, *PNAS*, vol. 97, No. 8, pp. 4309–4314.
Daly, et al., 1996, *Journal of General Virology*, vol. 77, pp. 661–671.
Lindstrom, et al., 1998, *Archives of Virology*, vol. 143, No. 8, pp. 1585–1598.

*Primary Examiner*—Ali R. Salimi
(74) *Attorney, Agent, or Firm*—Heska Corporation

(57) ABSTRACT

The present invention provides experimentally-generated cold-adapted equine influenza viruses, and reassortant influenza A viruses comprising at least one genome segment of such an equine influenza virus, wherein the equine influenza virus genome segment confers at least one identifying phenotype of the cold-adapted equine influenza virus, such as cold-adaptation, temperature sensitivity, dominant interference, or attenuation. Such viruses are formulated into therapeutic compositions to protect animals from diseases caused by influenza A viruses, and in particular, to protect horses from disease caused by equine influenza virus. The present invention also includes methods to protect animals from diseases caused by influenza A virus utilizing the claimed therapeutic compositions. Such methods include using a therapeutic composition as a vaccine to generate a protective immune response in an animal prior to exposure to a virulent virus, and using a therapeutic composition as a treatment for an animal that has been recently infected with a virulent virus, or is likely to be subsequently exposed to virulent virus in a few days whereby the therapeutic composition interferes with the growth of the virulent virus, even in the absence of immunity. The present invention also provides methods to produce cold-adapted equine influenza viruses, and reassortant influenza A viruses having at least one genome segment of an equine influenza virus generated by cold-adaptation.

4 Claims, No Drawings

```
                         SEQUENCE LISTING

<160> NUMBER OF SEQ ID NOS: 108

<210> SEQ ID NO 1
<211> LENGTH: 1023
<212> TYPE: DNA
<213> ORGANISM: Equine influenza virus H3N8
<220> FEATURE:
<221> NAME/KEY: CDS
<222> LOCATION: (25)..(780)
<223> OTHER INFORMATION:
<220> FEATURE:
<221> NAME/KEY: misc_feature
<222> LOCATION: (673)..(673)
<223> OTHER INFORMATION: At nucleotide 673, r = a or g
      At amino acid residue 213, Xaa = Val

<400> SEQUENCE: 1

gcaaaagcag gtagatattt aaag atg agt ctt ctg acc gag gtc gaa acg        51
                           Met Ser Leu Leu Thr Glu Val Glu Thr
                           1               5

tac gtt ctc tct atc gta cca tca ggc ccc ctc aaa gcc gag atc gcg        99
Tyr Val Leu Ser Ile Val Pro Ser Gly Pro Leu Lys Ala Glu Ile Ala
10                  15                  20                  25

cag aga ctt gaa gat gtc ttt gca ggg aag aac acc gat ctt gag gca       147
Gln Arg Leu Glu Asp Val Phe Ala Gly Lys Asn Thr Asp Leu Glu Ala
                30                  35                  40

ctc atg gaa tgg cta aag aca aga cca atc ctg tca cct ctg act aaa       195
Leu Met Glu Trp Leu Lys Thr Arg Pro Ile Leu Ser Pro Leu Thr Lys
            45                  50                  55

ggg att tta gga ttc gta ttc acg ctc acc gtg ccc agt gag cga gga       243
Gly Ile Leu Gly Phe Val Phe Thr Leu Thr Val Pro Ser Glu Arg Gly
        60                  65                  70

ctg cag cgt aga cgc ttt gtc caa aat gcc ctt agt gga aac gga gat       291
Leu Gln Arg Arg Arg Phe Val Gln Asn Ala Leu Ser Gly Asn Gly Asp
    75                  80                  85
```

-continued

```
cca aac aac atg gac aga gca gta aaa ctg tac agg aag ctt aaa aga      339
Pro Asn Asn Met Asp Arg Ala Val Lys Leu Tyr Arg Lys Leu Lys Arg
90                  95                  100                 105

gaa ata aca ttc cat ggg gca aaa gag gtg gca ctc agc tat tcc act      387
Glu Ile Thr Phe His Gly Ala Lys Glu Val Ala Leu Ser Tyr Ser Thr
                110                 115                 120

ggt gca cta gcc agc tgc atg gga ctc ata tac aac aga atg gga act      435
Gly Ala Leu Ala Ser Cys Met Gly Leu Ile Tyr Asn Arg Met Gly Thr
            125                 130                 135

gtg aca acc gaa gtg gca ttt ggc ctg gta tgc gcc aca tgt gaa cag      483
Val Thr Thr Glu Val Ala Phe Gly Leu Val Cys Ala Thr Cys Glu Gln
        140                 145                 150

atc gct gat tcc cag cat cga tct cac agg cag atg gtg aca aca acc      531
Ile Ala Asp Ser Gln His Arg Ser His Arg Gln Met Val Thr Thr Thr
    155                 160                 165

aac cca tta atc aga cat gaa aac aga atg gta tta gcc agt acc acg      579
Asn Pro Leu Ile Arg His Glu Asn Arg Met Val Leu Ala Ser Thr Thr
170                 175                 180                 185

gct aaa gcc atg gag cag atg gca ggg tcg agt gag cag gca gca gag      627
Ala Lys Ala Met Glu Gln Met Ala Gly Ser Ser Glu Gln Ala Ala Glu
                190                 195                 200

gcc atg gag gtt gct agt aag gct agg cag atg gtr cag gca atg aga      675
Ala Met Glu Val Ala Ser Lys Ala Arg Gln Met Xaa Gln Ala Met Arg
            205                 210                 215

acc att ggg acc cac cct agc tcc agt gcc ggt ttg aaa gat gat ctc      723
Thr Ile Gly Thr His Pro Ser Ser Ser Ala Gly Leu Lys Asp Asp Leu
        220                 225                 230

ctt gaa aat ttg cag gcc tac cag aaa cgg atg gga gtg caa atg cag      771
Leu Glu Asn Leu Gln Ala Tyr Gln Lys Arg Met Gly Val Gln Met Gln
    235                 240                 245

cga ttc aag tgatcctctc gttattgcag caagtatcat tgggatcttg              820
Arg Phe Lys
250

cacttgatat tgtggattct tgatcgcctt ttcttcaaat tcatttatcg tcgccttaaa    880

tacgggttga aaagagggcc ttctacggaa ggagtacctg agtctatgag ggaagaatat    940

cggcaggaac agcagaatgc tgtggatgtt gacgatggtc attttgtcaa catagagctg   1000

gagtaaaaaa ctaccttgtt tct                                           1023
```

```
<210> SEQ ID NO 2
<211> LENGTH: 252
<212> TYPE: PRT
<213> ORGANISM: Equine influenza virus H3N8
<220> FEATURE:
<221> NAME/KEY: misc_feature
<222> LOCATION: (213)..(213)
<223> OTHER INFORMATION: The 'Xaa' at location 213 stands for Val.

<400> SEQUENCE: 2

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80
```

-continued

Gln Asn Ala Leu Ser Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Lys
        195                 200                 205

Ala Arg Gln Met Xaa Gln Ala Met Arg Thr Ile Gly Thr His Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 3
<211> LENGTH: 756
<212> TYPE: DNA
<213> ORGANISM: Equine influenza virus H3N8

<400> SEQUENCE: 3
atgagtcttc tgaccgaggt cgaaacgtac gttctctcta tcgtaccatc aggccccctc 60
aaagccgaga tcgcgcagag acttgaagat gtctttgcag ggaagaacac cgatcttgag 120
gcactcatgg aatggctaaa gacaagacca atcctgtcac ctctgactaa agggatttta 180
ggattcgtat tcacgctcac cgtgcccagt gagcgaggac tgcagcgtag acgctttgtc 240
caaaatgccc ttagtggaaa cggagatcca aacaacatgg acagagcagt aaaactgtac 300
aggaagctta aaagagaaat aacattccat ggggcaaaag aggtggcact cagctattcc 360
actggtgcac tagccagctg catgggactc atatacaaca gaatgggaac tgtgacaacc 420
gaagtggcat ttggcctggt atgcgccaca tgtgaacaga tcgctgattc ccagcatcga 480
tctcacaggc agatggtgac aacaaccaac ccattaatca gacatgaaaa cagaatggta 540
ttagccagta ccacggctaa agccatggag cagatggcag ggtcgagtga gcaggcagca 600
gaggccatgg aggttgctag taaggctagg cagatggtrc aggcaatgag aaccattggg 660
acccacccta gctccagtgc cggtttgaaa gatgatctcc ttgaaaattt gcaggcctac 720
cagaaacgga tgggagtgca aatgcagcga ttcaag 756

<210> SEQ ID NO 4
<211> LENGTH: 1023
<212> TYPE: DNA
<213> ORGANISM: Equine influenza virus H3N8
<220> FEATURE:
<221> NAME/KEY: CDS
<222> LOCATION: (25)..(780)
<223> OTHER INFORMATION:

<400> SEQUENCE: 4

-continued

```
gcaaaagcag gtagatattt aaag atg agt ctt ctg acc gag gtc gaa acg        51
                           Met Ser Leu Leu Thr Glu Val Glu Thr
                           1               5

tac gtt ctc tct atc tta cca tca ggc ccc ctc aaa gcc gag atc gcg        99
Tyr Val Leu Ser Ile Leu Pro Ser Gly Pro Leu Lys Ala Glu Ile Ala
10                  15                  20                  25

cag aga ctt gaa gat gtc ttt gca ggg aag aac acc gat ctt gag gca       147
Gln Arg Leu Glu Asp Val Phe Ala Gly Lys Asn Thr Asp Leu Glu Ala
                30                  35                  40

ctc atg gaa tgg cta aag aca aga cca atc ctg tca cct ctg act aaa       195
Leu Met Glu Trp Leu Lys Thr Arg Pro Ile Leu Ser Pro Leu Thr Lys
            45                  50                  55

ggg att tta gga ttc gta ttc acg ctc acc gtg ccc agt gag cga gga       243
Gly Ile Leu Gly Phe Val Phe Thr Leu Thr Val Pro Ser Glu Arg Gly
        60                  65                  70

ctg cag cgt aga cgc ttt gtc caa aat gcc ctt agt gga aac gga gat       291
Leu Gln Arg Arg Arg Phe Val Gln Asn Ala Leu Ser Gly Asn Gly Asp
    75                  80                  85

cca aac aac atg gac aga gca gta aaa ctg tac agg aag ctt aaa aga       339
Pro Asn Asn Met Asp Arg Ala Val Lys Leu Tyr Arg Lys Leu Lys Arg
90                  95                  100                 105

gaa ata aca ttc cat ggg gca aaa gag gtg gca ctc agc tat tcc act       387
Glu Ile Thr Phe His Gly Ala Lys Glu Val Ala Leu Ser Tyr Ser Thr
                110                 115                 120

ggt gca cta gcc agc tgc atg gga ctc ata tac aac aga atg gga act       435
Gly Ala Leu Ala Ser Cys Met Gly Leu Ile Tyr Asn Arg Met Gly Thr
            125                 130                 135

gtg aca acc gaa gtg gca ttt ggc ctg gta tgc gcc aca tgt gaa cag       483
Val Thr Thr Glu Val Ala Phe Gly Leu Val Cys Ala Thr Cys Glu Gln
        140                 145                 150

atc gct gat tcc cag cat cga tct cac agg cag atg gtg aca ata acc       531
Ile Ala Asp Ser Gln His Arg Ser His Arg Gln Met Val Thr Ile Thr
    155                 160                 165

aac cca tta atc aga cat gaa aac aga atg gta tta gcc agt acc acg       579
Asn Pro Leu Ile Arg His Glu Asn Arg Met Val Leu Ala Ser Thr Thr
170                 175                 180                 185

gct aaa gcc atg gag cag atg gca ggg tcg agt gag cag gca gca gag       627
Ala Lys Ala Met Glu Gln Met Ala Gly Ser Ser Glu Gln Ala Ala Glu
                190                 195                 200

gcc atg gag gtt gct agt aag gct agg cag atg gta cag gca atg aga       675
Ala Met Glu Val Ala Ser Lys Ala Arg Gln Met Val Gln Ala Met Arg
            205                 210                 215

acc att ggg acc cac cct agc tcc agt gcc ggt ttg aaa gat gat ctc       723
Thr Ile Gly Thr His Pro Ser Ser Ser Ala Gly Leu Lys Asp Asp Leu
        220                 225                 230

ctt gaa aat ttg cag gcc tac cag aaa cgg atg gga gtg caa atg cag       771
Leu Glu Asn Leu Gln Ala Tyr Gln Lys Arg Met Gly Val Gln Met Gln
    235                 240                 245

cga ttc aag tgatcctctc gttattgcag caagtatcat tgggatcttg               820
Arg Phe Lys
250

cacttgatat tgtggattct tgatcgcctt ttcttcaaat tcatttatcg tcgccttaaa    880

tacggcttga aaagagggcc ttctacggaa ggagtacctg agtctatgag ggaagaatat    940

cggcaggaac agcagaatgc tgtggatgtt gacgatggtc attttgtcaa catagagctg   1000

gagtaaaaaa ctaccttgtt tct                                            1023
```

<210> SEQ ID NO 5

-continued

<211> LENGTH: 252
<212> TYPE: PRT
<213> ORGANISM: Equine influenza virus H3N8

<400> SEQUENCE: 5

Met Ser Leu Leu Thr Glu Val Glu Thr Tyr Val Leu Ser Ile Leu Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Ser Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Ile Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Lys
        195                 200                 205

Ala Arg Gln Met Val Gln Ala Met Arg Thr Ile Gly Thr His Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 6
<211> LENGTH: 756
<212> TYPE: DNA
<213> ORGANISM: Equine influenza virus H3N8

<400> SEQUENCE: 6
atgagtcttc tgaccgaggt cgaaacgtac gttctctcta tcttaccatc aggccccctc 60
aaagccgaga tcgcgcagag acttgaagat gtctttgcag ggaagaacac cgatcttgag 120
gcactcatgg aatggctaaa gacaagacca atcctgtcac ctctgactaa agggatttta 180
ggattcgtat tcacgctcac cgtgcccagt gagcgaggac tgcagcgtag acgctttgtc 240
caaaatgccc ttagtggaaa cggagatcca aacaacatgg acagagcagt aaaactgtac 300
aggaagctta aaagagaaat aacattccat ggggcaaaag aggtggcact cagctattcc 360
actggtgcac tagccagctg catgggactc atatacaaca gaatgggaac tgtgacaacc 420
gaagtggcat ttggcctggt atgcgccaca tgtgaacaga tcgctgattc ccagcatcga 480
tctcacaggc agatggtgac aataaccaac ccattaatca gacatgaaaa cagaatggta 540

-continued

```
ttagccagta ccacggctaa agccatggag cagatggcag ggtcgagtga gcaggcagca    600

gaggccatgg aggttgctag taaggctagg cagatggtac aggcaatgag aaccattggg    660

acccacccta gctccagtgc cggtttgaaa gatgatctcc ttgaaaattt gcaggcctac    720

cagaaacgga tgggagtgca aatgcagcga ttcaag                              756


<210> SEQ ID NO 7
<211> LENGTH: 1762
<212> TYPE: DNA
<213> ORGANISM: Equine influenza virus H3N8
<220> FEATURE:
<221> NAME/KEY: CDS
<222> LOCATION: (30)..(1724)
<223> OTHER INFORMATION:

<400> SEQUENCE: 7

agcaaaagca ggggatattt ctgtcaatc atg aag aca acc att att ttg ata       53
                                Met Lys Thr Thr Ile Ile Leu Ile
                                1               5

cca ctg acc cat tgg gtc tac agt caa aac cca acc agt ggc aac aac      101
Pro Leu Thr His Trp Val Tyr Ser Gln Asn Pro Thr Ser Gly Asn Asn
    10                  15                  20

aca gcc aca tta tgt ctg gga cac cat gca gta gca aat gga aca ttg      149
Thr Ala Thr Leu Cys Leu Gly His His Ala Val Ala Asn Gly Thr Leu
25                  30                  35                  40

gta aaa aca ata act gat gac caa att gag gtg aca aat gct act gaa      197
Val Lys Thr Ile Thr Asp Asp Gln Ile Glu Val Thr Asn Ala Thr Glu
                45                  50                  55

tta gtt cag agc att tca ata ggg aaa ata tgc aac aac tca tat aga      245
Leu Val Gln Ser Ile Ser Ile Gly Lys Ile Cys Asn Asn Ser Tyr Arg
            60                  65                  70

gtt cta gat gga aga aat tgc aca tta ata gat gca atg cta gga gac      293
Val Leu Asp Gly Arg Asn Cys Thr Leu Ile Asp Ala Met Leu Gly Asp
        75                  80                  85

ccc cac tgt gat gtc ttt cag tat gag aat tgg gac ctc ttc ata gaa      341
Pro His Cys Asp Val Phe Gln Tyr Glu Asn Trp Asp Leu Phe Ile Glu
    90                  95                  100

aga agc agc gct ttc agc agt tgc tac cca tat gac atc cct gac tat      389
Arg Ser Ser Ala Phe Ser Ser Cys Tyr Pro Tyr Asp Ile Pro Asp Tyr
105                 110                 115                 120

gca tcg ctc cgg tcc att gta gca tcc tca gga aca ttg gaa ttc aca      437
Ala Ser Leu Arg Ser Ile Val Ala Ser Ser Gly Thr Leu Glu Phe Thr
                125                 130                 135

gca gag gga ttc aca tgg aca ggt gtc act caa aac gga aga agt gga      485
Ala Glu Gly Phe Thr Trp Thr Gly Val Thr Gln Asn Gly Arg Ser Gly
            140                 145                 150

tcc tgc aaa agg gga tca gcc gat agt ttc ttt agc cga ctg aat tgg      533
Ser Cys Lys Arg Gly Ser Ala Asp Ser Phe Phe Ser Arg Leu Asn Trp
        155                 160                 165

cta aca gaa tct gga aac tct tac ccc aca ttg aat gtg aca atg cct      581
Leu Thr Glu Ser Gly Asn Ser Tyr Pro Thr Leu Asn Val Thr Met Pro
    170                 175                 180

aac aat aaa aat ttc gac aaa cta tac atc tgg ggg att cat cac ccg      629
Asn Asn Lys Asn Phe Asp Lys Leu Tyr Ile Trp Gly Ile His His Pro
185                 190                 195                 200

agc tca aac aaa gag cag aca aaa ttg tac atc caa gaa tcg gga cga      677
Ser Ser Asn Lys Glu Gln Thr Lys Leu Tyr Ile Gln Glu Ser Gly Arg
                205                 210                 215

gta aca gtc tca aca aaa aga agt caa caa aca ata atc cct aac atc      725
Val Thr Val Ser Thr Lys Arg Ser Gln Gln Thr Ile Ile Pro Asn Ile
```

-continued

```
            220                 225                 230

gga tct aga ccg cgg gtc agg ggt caa tca ggc agg ata agc ata tac      773
Gly Ser Arg Pro Arg Val Arg Gly Gln Ser Gly Arg Ile Ser Ile Tyr
        235                 240                 245

tgg acc att gta aaa cct gga gat atc cta atg ata aac agt aat ggc      821
Trp Thr Ile Val Lys Pro Gly Asp Ile Leu Met Ile Asn Ser Asn Gly
    250                 255                 260

aac tta gtt gca ccg cgg gga tat ttt aaa ttg aaa aca ggg aaa agc      869
Asn Leu Val Ala Pro Arg Gly Tyr Phe Lys Leu Lys Thr Gly Lys Ser
265                 270                 275                 280

tct gta atg aga tca gat gca ccc ata gac att tgt gtg tct gaa tgt      917
Ser Val Met Arg Ser Asp Ala Pro Ile Asp Ile Cys Val Ser Glu Cys
                285                 290                 295

att aca cca aat gga agc atc ccc aac gac aaa cca ttt caa aat gtg      965
Ile Thr Pro Asn Gly Ser Ile Pro Asn Asp Lys Pro Phe Gln Asn Val
            300                 305                 310

aac aaa gtt aca tat gga aaa tgc ccc aag tat atc agg caa aac act     1013
Asn Lys Val Thr Tyr Gly Lys Cys Pro Lys Tyr Ile Arg Gln Asn Thr
        315                 320                 325

tta aag ctg gcc act ggg atg agg aat gta cca gaa aag caa atc aga     1061
Leu Lys Leu Ala Thr Gly Met Arg Asn Val Pro Glu Lys Gln Ile Arg
    330                 335                 340

gga atc ttt gga gca ata gcg gga ttc ata gaa aac ggc tgg gaa gga     1109
Gly Ile Phe Gly Ala Ile Ala Gly Phe Ile Glu Asn Gly Trp Glu Gly
345                 350                 355                 360

atg gtt gat ggg tgg tat gga ttc cga tat caa aac tcg gaa gga aca     1157
Met Val Asp Gly Trp Tyr Gly Phe Arg Tyr Gln Asn Ser Glu Gly Thr
                365                 370                 375

gga caa gct gca gat cta aag agc act caa gca gcc atc gac cag atc     1205
Gly Gln Ala Ala Asp Leu Lys Ser Thr Gln Ala Ala Ile Asp Gln Ile
            380                 385                 390

aat gga aaa tta aac aga gtg att gaa agg acc aat gag aaa ttc cat     1253
Asn Gly Lys Leu Asn Arg Val Ile Glu Arg Thr Asn Glu Lys Phe His
        395                 400                 405

caa ata gag aag gaa ttc tca gaa gta gaa ggg agg atc cag gac ttg     1301
Gln Ile Glu Lys Glu Phe Ser Glu Val Glu Gly Arg Ile Gln Asp Leu
    410                 415                 420

gag aag tat gta gaa gac acc aaa ata gac cta tgg tcc tac aat gca     1349
Glu Lys Tyr Val Glu Asp Thr Lys Ile Asp Leu Trp Ser Tyr Asn Ala
425                 430                 435                 440

gaa ttg ctg gtg gct cta aaa aat caa cat aca att gac tta aca gat     1397
Glu Leu Leu Val Ala Leu Lys Asn Gln His Thr Ile Asp Leu Thr Asp
                445                 450                 455

gca gaa atg aat aaa tta ttc gag aag act aga cgc cag tta aga gaa     1445
Ala Glu Met Asn Lys Leu Phe Glu Lys Thr Arg Arg Gln Leu Arg Glu
            460                 465                 470

aac gcg gaa gac atg gga ggt gga tgt ttc aag ata tac cac aaa tgt     1493
Asn Ala Glu Asp Met Gly Gly Gly Cys Phe Lys Ile Tyr His Lys Cys
        475                 480                 485

gat aat gca tgc att gga tca ata aga aat ggg aca tat gac cat tac     1541
Asp Asn Ala Cys Ile Gly Ser Ile Arg Asn Gly Thr Tyr Asp His Tyr
    490                 495                 500

ata tac aga gat gaa gca tta aac aac cgg ttt caa atc aaa ggt gtt     1589
Ile Tyr Arg Asp Glu Ala Leu Asn Asn Arg Phe Gln Ile Lys Gly Val
   505                 510                 515                 520

gag ttg aaa tca ggc tac aaa gat tgg ata ctg tgg att tca ttc gcc     1637
Glu Leu Lys Ser Gly Tyr Lys Asp Trp Ile Leu Trp Ile Ser Phe Ala
                525                 530                 535

ata tca tgc ttc tta att tgc gtt gtt cta ttg ggt ttc att atg tgg     1685
```

-continued

```
Ile Ser Cys Phe Leu Ile Cys Val Val Leu Leu Gly Phe Ile Met Trp
            540                 545                 550

gct tgc caa aaa ggc aac atc aga tgc aac att tgc att tgagtaaact      1734
Ala Cys Gln Lys Gly Asn Ile Arg Cys Asn Ile Cys Ile
        555                 560                 565

gatagttaaa aacacccttg tttctact                                      1762


<210> SEQ ID NO 8
<211> LENGTH: 565
<212> TYPE: PRT
<213> ORGANISM: Equine influenza virus H3N8

<400> SEQUENCE: 8

Met Lys Thr Thr Ile Ile Leu Ile Pro Leu Thr His Trp Val Tyr Ser
1               5                   10                  15

Gln Asn Pro Thr Ser Gly Asn Asn Thr Ala Thr Leu Cys Leu Gly His
            20                  25                  30

His Ala Val Ala Asn Gly Thr Leu Val Lys Thr Ile Thr Asp Asp Gln
        35                  40                  45

Ile Glu Val Thr Asn Ala Thr Glu Leu Val Gln Ser Ile Ser Ile Gly
    50                  55                  60

Lys Ile Cys Asn Asn Ser Tyr Arg Val Leu Asp Gly Arg Asn Cys Thr
65                  70                  75                  80

Leu Ile Asp Ala Met Leu Gly Asp Pro His Cys Asp Val Phe Gln Tyr
                85                  90                  95

Glu Asn Trp Asp Leu Phe Ile Glu Arg Ser Ser Ala Phe Ser Ser Cys
            100                 105                 110

Tyr Pro Tyr Asp Ile Pro Asp Tyr Ala Ser Leu Arg Ser Ile Val Ala
        115                 120                 125

Ser Ser Gly Thr Leu Glu Phe Thr Ala Glu Gly Phe Thr Trp Thr Gly
    130                 135                 140

Val Thr Gln Asn Gly Arg Ser Gly Ser Cys Lys Arg Gly Ser Ala Asp
145                 150                 155                 160

Ser Phe Phe Ser Arg Leu Asn Trp Leu Thr Glu Ser Gly Asn Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Lys Glu Gln Thr Lys
        195                 200                 205

Leu Tyr Ile Gln Glu Ser Gly Arg Val Thr Val Ser Thr Lys Arg Ser
    210                 215                 220

Gln Gln Thr Ile Ile Pro Asn Ile Gly Ser Arg Pro Arg Val Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Lys Thr Gly Lys Ser Ser Val Met Arg Ser Asp Ala Pro
        275                 280                 285

Ile Asp Ile Cys Val Ser Glu Cys Ile Thr Pro Asn Gly Ser Ile Pro
    290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335
```

-continued

```
Asn Val Pro Glu Lys Gln Ile Arg Gly Ile Phe Gly Ala Ile Ala Gly
            340                 345                 350

Phe Ile Glu Asn Gly Trp Glu Gly Met Val Asp Gly Trp Tyr Gly Phe
        355                 360                 365

Arg Tyr Gln Asn Ser Glu Gly Thr Gly Gln Ala Ala Asp Leu Lys Ser
    370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Lys Asn
        435                 440                 445

Gln His Thr Ile Asp Leu Thr Asp Ala Glu Met Asn Lys Leu Phe Glu
    450                 455                 460

Lys Thr Arg Arg Gln Leu Arg Glu Asn Ala Glu Asp Met Gly Gly Gly
465                 470                 475                 480

Cys Phe Lys Ile Tyr His Lys Cys Asp Asn Ala Cys Ile Gly Ser Ile
                485                 490                 495

Arg Asn Gly Thr Tyr Asp His Tyr Ile Tyr Arg Asp Glu Ala Leu Asn
            500                 505                 510

Asn Arg Phe Gln Ile Lys Gly Val Glu Leu Lys Ser Gly Tyr Lys Asp
        515                 520                 525

Trp Ile Leu Trp Ile Ser Phe Ala Ile Ser Cys Phe Leu Ile Cys Val
    530                 535                 540

Val Leu Leu Gly Phe Ile Met Trp Ala Cys Gln Lys Gly Asn Ile Arg
545                 550                 555                 560

Cys Asn Ile Cys Ile
                565


<210> SEQ ID NO 9
<211> LENGTH: 1695
<212> TYPE: DNA
<213> ORGANISM: Equine influenza virus H3N8

<400> SEQUENCE: 9

atgaagacaa ccattatttt gataccactg acccattggg tctacagtca aaacccaacc      60

agtggcaaca acacagccac attatgtctg ggacaccatg cagtagcaaa tggaacattg     120

gtaaaaacaa taactgatga ccaaattgag gtgacaaatg ctactgaatt agttcagagc     180

atttcaatag ggaaaatatg caacaactca tatagagttc tagatggaag aaattgcaca     240

ttaatagatg caatgctagg agacccccac tgtgatgtct ttcagtatga gaattgggac     300

ctcttcatag aaagaagcag cgctttcagc agttgctacc catatgacat ccctgactat     360

gcatcgctcc ggtccattgt agcatcctca ggaacattgg aattcacagc agagggattc     420

acatggacag gtgtcactca aaacggaaga agtggatcct gcaaaagggg atcagccgat     480

agtttcttta gccgactgaa ttggctaaca gaatctggaa actcttaccc cacattgaat     540

gtgacaatgc ctaacaataa aaatttcgac aaactataca tctgggggat tcatcacccg     600

agctcaaaca aagagcagac aaaattgtac atccaagaat cgggacgagt aacagtctca     660

acaaaaagaa gtcaacaaac aataatccct aacatcggat ctagaccgcg ggtcaggggt     720

caatcaggca ggataagcat atactggacc attgtaaaac ctggagatat cctaatgata     780
```

-continued

```
aacagtaatg gcaacttagt tgcaccgcgg ggatatttta aattgaaaac agggaaaagc    840

tctgtaatga gatcagatgc acccatagac atttgtgtgt ctgaatgtat tacaccaaat    900

ggaagcatcc ccaacgacaa accatttcaa aatgtgaaca aagttacata tggaaaatgc    960

cccaagtata tcaggcaaaa cactttaaag ctggccactg ggatgaggaa tgtaccagaa   1020

aagcaaatca gaggaatctt tggagcaata gcgggattca tagaaaacgg ctgggaagga   1080

atggttgatg ggtggtatgg attccgatat caaaactcgg aaggaacagg acaagctgca   1140

gatctaaaga gcactcaagc agccatcgac cagatcaatg gaaaattaaa cagagtgatt   1200

gaaaggacca atgagaaatt ccatcaaata gagaaggaat tctcagaagt agaagggagg   1260

atccaggact tggagaagta tgtagaagac accaaaatag acctatggtc ctacaatgca   1320

gaattgctgg tggctctaaa aaatcaacat acaattgact taacagatgc agaaatgaat   1380

aaattattcg agaagactag acgccagtta agagaaaacg cggaagacat gggaggtgga   1440

tgtttcaaga tataccacaa atgtgataat gcatgcattg gatcaataag aaatgggaca   1500

tatgaccatt acatatacag agatgaagca ttaaacaacc ggtttcaaat caaaggtgtt   1560

gagttgaaat caggctacaa agattggata ctgtggattt cattcgccat atcatgcttc   1620

ttaatttgcg ttgttctatt gggtttcatt atgtgggctt gccaaaaagg caacatcaga   1680

tgcaacattt gcatt                                                    1695


<210> SEQ ID NO 10
<211> LENGTH: 1762
<212> TYPE: DNA
<213> ORGANISM: Equine influenza virus H3N8
<220> FEATURE:
<221> NAME/KEY: CDS
<222> LOCATION: (30)..(1724)
<223> OTHER INFORMATION:

<400> SEQUENCE: 10

agcaaaagca ggggatattt ctgtcaatc atg aag aca acc att att ttg ata       53
                                Met Lys Thr Thr Ile Ile Leu Ile
                                1               5

cta ctg acc cat tgg gtc tac agt caa aac cca acc agt ggc aac aac      101
Leu Leu Thr His Trp Val Tyr Ser Gln Asn Pro Thr Ser Gly Asn Asn
    10                  15                  20

aca gcc aca tta tgt ctg gga cac cat gca gta gca aat gga aca ttg      149
Thr Ala Thr Leu Cys Leu Gly His His Ala Val Ala Asn Gly Thr Leu
25                  30                  35                  40

gta aaa aca ata act gat gac caa att gag gtg aca aat gct act gaa      197
Val Lys Thr Ile Thr Asp Asp Gln Ile Glu Val Thr Asn Ala Thr Glu
                45                  50                  55

tta gtt cag agc att tca ata ggg aaa ata tgc aac aac tca tat aga      245
Leu Val Gln Ser Ile Ser Ile Gly Lys Ile Cys Asn Asn Ser Tyr Arg
            60                  65                  70

gtt cta gat gga aga aat tgc aca tta ata gat gca atg cta gga gac      293
Val Leu Asp Gly Arg Asn Cys Thr Leu Ile Asp Ala Met Leu Gly Asp
        75                  80                  85

ccc cac tgt gat gtc ttt cag tat gag aat tgg gac ctc ttc ata gaa      341
Pro His Cys Asp Val Phe Gln Tyr Glu Asn Trp Asp Leu Phe Ile Glu
    90                  95                  100

aga agc agc gct ttc agc agt tgc tac cca tat gac atc cct gac tat      389
Arg Ser Ser Ala Phe Ser Ser Cys Tyr Pro Tyr Asp Ile Pro Asp Tyr
105                 110                 115                 120

gca tcg ctc cgg tcc att gta gca tcc tca gga aca ttg gaa ttc aca      437
Ala Ser Leu Arg Ser Ile Val Ala Ser Ser Gly Thr Leu Glu Phe Thr
```

-continued

```
               125                130                135

gca gag gga ttc aca tgg aca ggt gtc act caa aac gga aga agt gga      485
Ala Glu Gly Phe Thr Trp Thr Gly Val Thr Gln Asn Gly Arg Ser Gly
           140                145                150

tcc tgc aaa agg gaa tca gcc gat agt ttc ttt agc cga ctg aat tgg      533
Ser Cys Lys Arg Glu Ser Ala Asp Ser Phe Phe Ser Arg Leu Asn Trp
             155                160                165

cta aca gaa tct gga aac tct tac ccc aca ttg aat gtg aca atg cct      581
Leu Thr Glu Ser Gly Asn Ser Tyr Pro Thr Leu Asn Val Thr Met Pro
    170                175                180

aac aat aaa aat ttc gac aaa cta tac atc tgg ggg att cat cac ccg      629
Asn Asn Lys Asn Phe Asp Lys Leu Tyr Ile Trp Gly Ile His His Pro
185                190                195                200

agc tca aac aaa gag cag aca aaa ttg tac atc caa gaa tca gga cga      677
Ser Ser Asn Lys Glu Gln Thr Lys Leu Tyr Ile Gln Glu Ser Gly Arg
               205                210                215

gta aca gtc tca aca aaa aga agt caa caa aca ata atc cct aac atc      725
Val Thr Val Ser Thr Lys Arg Ser Gln Gln Thr Ile Ile Pro Asn Ile
           220                225                230

gga tct aga ccg tgg gtc agg ggt caa tca ggc agg ata agc ata tac      773
Gly Ser Arg Pro Trp Val Arg Gly Gln Ser Gly Arg Ile Ser Ile Tyr
        235                240                245

tgg acc att gta aaa cct gga gat atc cta acg ata aac agt aat ggc      821
Trp Thr Ile Val Lys Pro Gly Asp Ile Leu Thr Ile Asn Ser Asn Gly
    250                255                260

aac tta gtt gca ccg cgg gga tat ttt aaa ttg aaa aca ggg aaa agc      869
Asn Leu Val Ala Pro Arg Gly Tyr Phe Lys Leu Lys Thr Gly Lys Ser
265                270                275                280

tct gta atg aga tca gat gca ccc ata gac att tgt gtg tct gaa tgt      917
Ser Val Met Arg Ser Asp Ala Pro Ile Asp Ile Cys Val Ser Glu Cys
               285                290                295

att aca cca aat gga agc atc ccc aac gac aaa cca ttt caa aat gtg      965
Ile Thr Pro Asn Gly Ser Ile Pro Asn Asp Lys Pro Phe Gln Asn Val
           300                305                310

aac aaa gtt aca tat gga aaa tgc ccc aag tat atc agg caa aac act     1013
Asn Lys Val Thr Tyr Gly Lys Cys Pro Lys Tyr Ile Arg Gln Asn Thr
        315                320                325

tta aag ctg gcc act ggg atg agg aat gta cca gaa aag caa atc aga     1061
Leu Lys Leu Ala Thr Gly Met Arg Asn Val Pro Glu Lys Gln Ile Arg
          330                335                340

gga atc ttt gga gca ata gcg gga ttc ata gaa aac ggc tgg gaa gga     1109
Gly Ile Phe Gly Ala Ile Ala Gly Phe Ile Glu Asn Gly Trp Glu Gly
345                350                355                360

atg gtt gat ggg tgg tat gga ttc cga tat caa aac tcg gaa gga aca     1157
Met Val Asp Gly Trp Tyr Gly Phe Arg Tyr Gln Asn Ser Glu Gly Thr
               365                370                375

gga caa gct gca gat cta aag agc act caa gca gcc atc gac cag atc     1205
Gly Gln Ala Ala Asp Leu Lys Ser Thr Gln Ala Ala Ile Asp Gln Ile
           380                385                390

aat gga aaa tta aac aga gtg att gaa agg acc aat gag aaa ttc cat     1253
Asn Gly Lys Leu Asn Arg Val Ile Glu Arg Thr Asn Glu Lys Phe His
        395                400                405

caa ata gag aag gaa ttc tca gaa gta gaa ggg aga atc cag gac ttg     1301
Gln Ile Glu Lys Glu Phe Ser Glu Val Glu Gly Arg Ile Gln Asp Leu
    410                415                420

gag aag tat gta gaa gac acc aaa ata gac cta tgg tcc tac aat gca     1349
Glu Lys Tyr Val Glu Asp Thr Lys Ile Asp Leu Trp Ser Tyr Asn Ala
425                430                435                440

gaa ttg ctg gtg gct cta gaa aat caa cat aca att gac tta aca gat     1397
```

-continued

```
Glu Leu Leu Val Ala Leu Glu Asn Gln His Thr Ile Asp Leu Thr Asp
            445                 450                 455

gca gaa atg aat aaa tta ttc gag aag act aga cgc cag tta aga gaa     1445
Ala Glu Met Asn Lys Leu Phe Glu Lys Thr Arg Arg Gln Leu Arg Glu
            460                 465                 470

aac gcg gaa gac atg gga ggt gga tgt ttc aag ata tac cac aaa tgt     1493
Asn Ala Glu Asp Met Gly Gly Gly Cys Phe Lys Ile Tyr His Lys Cys
        475                 480                 485

gat aat gca tgc att gga tca ata aga aat ggg aca tat gac cat tac     1541
Asp Asn Ala Cys Ile Gly Ser Ile Arg Asn Gly Thr Tyr Asp His Tyr
    490                 495                 500

ata tac aga gat gaa gca tta aac aac cgg ttt caa atc aaa ggt gtt     1589
Ile Tyr Arg Asp Glu Ala Leu Asn Asn Arg Phe Gln Ile Lys Gly Val
505                 510                 515                 520

gag ttg aaa tca ggc tac aaa gat tgg ata ctg tgg att tca ttc gcc     1637
Glu Leu Lys Ser Gly Tyr Lys Asp Trp Ile Leu Trp Ile Ser Phe Ala
            525                 530                 535

ata tca tgc ttc tta att tgc gtt gtt cta ttg ggt ttc att atg tgg     1685
Ile Ser Cys Phe Leu Ile Cys Val Val Leu Leu Gly Phe Ile Met Trp
            540                 545                 550

gct tgc caa aaa ggc aac atc aga tgc aac att tgc att tgagtaaact      1734
Ala Cys Gln Lys Gly Asn Ile Arg Cys Asn Ile Cys Ile
        555                 560                 565

gatagttaaa aacacccttg tttctact                                      1762


<210> SEQ ID NO 11
<211> LENGTH: 565
<212> TYPE: PRT
<213> ORGANISM: Equine influenza virus H3N8

<400> SEQUENCE: 11

Met Lys Thr Thr Ile Ile Leu Ile Leu Leu Thr His Trp Val Tyr Ser
1               5                   10                  15

Gln Asn Pro Thr Ser Gly Asn Asn Thr Ala Thr Leu Cys Leu Gly His
            20                  25                  30

His Ala Val Ala Asn Gly Thr Leu Val Lys Thr Ile Thr Asp Asp Gln
        35                  40                  45

Ile Glu Val Thr Asn Ala Thr Glu Leu Val Gln Ser Ile Ser Ile Gly
    50                  55                  60

Lys Ile Cys Asn Asn Ser Tyr Arg Val Leu Asp Gly Arg Asn Cys Thr
65                  70                  75                  80

Leu Ile Asp Ala Met Leu Gly Asp Pro His Cys Asp Val Phe Gln Tyr
                85                  90                  95

Glu Asn Trp Asp Leu Phe Ile Glu Arg Ser Ser Ala Phe Ser Ser Cys
            100                 105                 110

Tyr Pro Tyr Asp Ile Pro Asp Tyr Ala Ser Leu Arg Ser Ile Val Ala
        115                 120                 125

Ser Ser Gly Thr Leu Glu Phe Thr Ala Glu Gly Phe Thr Trp Thr Gly
    130                 135                 140

Val Thr Gln Asn Gly Arg Ser Gly Ser Cys Lys Arg Glu Ser Ala Asp
145                 150                 155                 160

Ser Phe Phe Ser Arg Leu Asn Trp Leu Thr Glu Ser Gly Asn Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Lys Glu Gln Thr Lys
        195                 200                 205
```

-continued

```
Leu Tyr Ile Gln Glu Ser Gly Arg Val Thr Val Ser Thr Lys Arg Ser
    210                 215                 220

Gln Gln Thr Ile Ile Pro Asn Ile Gly Ser Arg Pro Trp Val Arg Gly
225                 230                 235                 240

Gln Ser Gly Arg Ile Ser Ile Tyr Trp Thr Ile Val Lys Pro Gly Asp
                245                 250                 255

Ile Leu Thr Ile Asn Ser Asn Gly Asn Leu Val Ala Pro Arg Gly Tyr
            260                 265                 270

Phe Lys Leu Lys Thr Gly Lys Ser Ser Val Met Arg Ser Asp Ala Pro
        275                 280                 285

Ile Asp Ile Cys Val Ser Glu Cys Ile Thr Pro Asn Gly Ser Ile Pro
    290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Ile Arg Gly Ile Phe Gly Ala Ile Ala Gly
            340                 345                 350

Phe Ile Glu Asn Gly Trp Glu Gly Met Val Asp Gly Trp Tyr Gly Phe
        355                 360                 365

Arg Tyr Gln Asn Ser Glu Gly Thr Gly Gln Ala Ala Asp Leu Lys Ser
    370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Glu Asn
        435                 440                 445

Gln His Thr Ile Asp Leu Thr Asp Ala Glu Met Asn Lys Leu Phe Glu
    450                 455                 460

Lys Thr Arg Arg Gln Leu Arg Glu Asn Ala Glu Asp Met Gly Gly Gly
465                 470                 475                 480

Cys Phe Lys Ile Tyr His Lys Cys Asp Asn Ala Cys Ile Gly Ser Ile
                485                 490                 495

Arg Asn Gly Thr Tyr Asp His Tyr Ile Tyr Arg Asp Glu Ala Leu Asn
            500                 505                 510

Asn Arg Phe Gln Ile Lys Gly Val Glu Leu Lys Ser Gly Tyr Lys Asp
        515                 520                 525

Trp Ile Leu Trp Ile Ser Phe Ala Ile Ser Cys Phe Leu Ile Cys Val
    530                 535                 540

Val Leu Leu Gly Phe Ile Met Trp Ala Cys Gln Lys Gly Asn Ile Arg
545                 550                 555                 560

Cys Asn Ile Cys Ile
                565

<210> SEQ ID NO 12
<211> LENGTH: 1695
<212> TYPE: DNA
<213> ORGANISM: Equine influenza virus H3N8

<400> SEQUENCE: 12

atgaagacaa ccattatttt gatactactg acccattggg tctacagtca aaacccaacc     60
```

-continued

```
agtggcaaca acacagccac attatgtctg ggacaccatg cagtagcaaa tggaacattg    120

gtaaaaacaa taactgatga ccaaattgag gtgacaaatg ctactgaatt agttcagagc    180

atttcaatag ggaaaatatg caacaactca tatagagttc tagatggaag aaattgcaca    240

ttaatagatg caatgctagg agacccccac tgtgatgtct ttcagtatga gaattgggac    300

ctcttcatag aaagaagcag cgctttcagc agttgctacc catatgacat ccctgactat    360

gcatcgctcc ggtccattgt agcatcctca ggaacattgg aattcacagc agagggattc    420

acatggacag gtgtcactca aaacggaaga agtggatcct gcaaaaggga atcagccgat    480

agtttcttta gccgactgaa ttggctaaca gaatctggaa actcttaccc cacattgaat    540

gtgacaatgc ctaacaataa aaatttcgac aaactataca tctgggggat tcatcacccg    600

agctcaaaca aagagcagac aaaattgtac atccaagaat caggacgagt aacagtctca    660

acaaaaagaa gtcaacaaac aataatccct aacatcggat ctagaccgtg ggtcaggggt    720

caatcaggca ggataagcat atactggacc attgtaaaac ctggagatat cctaacgata    780

aacagtaatg gcaacttagt tgcaccgcgg ggatatttta aattgaaaac agggaaaagc    840

tctgtaatga gatcagatgc acccatagac atttgtgtgt ctgaatgtat tacaccaaat    900

ggaagcatcc ccaacgacaa accatttcaa aatgtgaaca aagttacata tggaaaatgc    960

cccaagtata tcaggcaaaa cactttaaag ctggccactg ggatgaggaa tgtaccagaa   1020

aagcaaatca gaggaatctt tggagcaata gcgggattca tagaaaacgg ctgggaagga   1080

atggttgatg ggtggtatgg attccgatat caaaactcgg aaggaacagg acaagctgca   1140

gatctaaaga gcactcaagc agccatcgac cagatcaatg gaaaattaaa cagagtgatt   1200

gaaaggacca atgagaaatt ccatcaaata gagaaggaat tctcagaagt agaagggaga   1260

atccaggact tggagaagta tgtagaagac accaaaatag acctatggtc ctacaatgca   1320

gaattgctgg tggctctaga aaatcaacat acaattgact taacagatgc agaaatgaat   1380

aaattattcg agaagactag acgccagtta agagaaaacg cggaagacat gggaggtgga   1440

tgtttcaaga tataccacaa atgtgataat gcatgcattg gatcaataag aaatgggaca   1500

tatgaccatt acatatacag agatgaagca ttaaacaacc ggtttcaaat caaaggtgtt   1560

gagttgaaat caggctacaa agattggata ctgtggattt cattcgccat atcatgcttc   1620

ttaatttgcg ttgttctatt gggtttcatt atgtgggctt gccaaaaagg caacatcaga   1680

tgcaacattt gcatt                                                    1695


<210> SEQ ID NO 13
<211> LENGTH: 1241
<212> TYPE: DNA
<213> ORGANISM: Equine influenza virus H3N8
<220> FEATURE:
<221> NAME/KEY: CDS
<222> LOCATION: (28)..(1239)
<223> OTHER INFORMATION:

<400> SEQUENCE: 13

agcaaaagca ggtcaaatat attcaat atg gag aga ata aaa gaa ctg aga gat      54
                              Met Glu Arg Ile Lys Glu Leu Arg Asp
                              1               5

cta atg tca caa tcc cgc acc cgc gag ata cta aca aaa act act gtg      102
Leu Met Ser Gln Ser Arg Thr Arg Glu Ile Leu Thr Lys Thr Thr Val
10                  15                  20                  25

gac cac atg gcc ata atc aag aaa tac aca tca gga aga caa gag aag      150
Asp His Met Ala Ile Ile Lys Lys Tyr Thr Ser Gly Arg Gln Glu Lys
```

-continued

```
                30                  35                  40

aac ccc gca ctt agg atg aag tgg atg atg gca atg aaa tac cca att      198
Asn Pro Ala Leu Arg Met Lys Trp Met Met Ala Met Lys Tyr Pro Ile
            45                  50                  55

aca gca gat aag agg ata atg gaa atg att cct gag aga aat gaa cag      246
Thr Ala Asp Lys Arg Ile Met Glu Met Ile Pro Glu Arg Asn Glu Gln
        60                  65                  70

ggg caa acc ctt tgg agc aaa acg aac gat gct ggc tca gac cgc gta      294
Gly Gln Thr Leu Trp Ser Lys Thr Asn Asp Ala Gly Ser Asp Arg Val
    75                  80                  85

atg gta tca cct ctg gca gtg aca tgg tgg aat agg aat gga cca aca      342
Met Val Ser Pro Leu Ala Val Thr Trp Trp Asn Arg Asn Gly Pro Thr
90                  95                  100                 105

acg agc aca att cat tat cca aaa gtc tac aaa act tat ttt gaa aaa      390
Thr Ser Thr Ile His Tyr Pro Lys Val Tyr Lys Thr Tyr Phe Glu Lys
                110                 115                 120

gtt gaa aga tta aaa cac gga acc ttt ggc ccc gtt cat ttt agg aat      438
Val Glu Arg Leu Lys His Gly Thr Phe Gly Pro Val His Phe Arg Asn
            125                 130                 135

caa gtc aag ata aga cgg aga gtt gat gta aac cct ggt cac gcg gac      486
Gln Val Lys Ile Arg Arg Arg Val Asp Val Asn Pro Gly His Ala Asp
        140                 145                 150

ctc agt gcc aaa gaa gca caa gat gtg atc atg gaa gtt gtt ttc cca      534
Leu Ser Ala Lys Glu Ala Gln Asp Val Ile Met Glu Val Val Phe Pro
          155                 160                 165

aat gaa gtg gga gcc aga att cta aca tcg gaa tca caa cta aca ata      582
Asn Glu Val Gly Ala Arg Ile Leu Thr Ser Glu Ser Gln Leu Thr Ile
170                 175                 180                 185

acc aaa gag aaa aaa gaa gaa ctt cag gac tgc aaa att gcc ccc ttg      630
Thr Lys Glu Lys Lys Glu Glu Leu Gln Asp Cys Lys Ile Ala Pro Leu
                190                 195                 200

atg gta gca tac atg cta gaa aga gag ttg gtc cga aaa aca aga ttc      678
Met Val Ala Tyr Met Leu Glu Arg Glu Leu Val Arg Lys Thr Arg Phe
            205                 210                 215

ctc cca gtg gct ggc gga aca agc agt gta tac att gaa gtg ttg cat      726
Leu Pro Val Ala Gly Gly Thr Ser Ser Val Tyr Ile Glu Val Leu His
        220                 225                 230

ctg act cag gga aca tgc tgg gaa caa atg tac acc cca gga gga gaa      774
Leu Thr Gln Gly Thr Cys Trp Glu Gln Met Tyr Thr Pro Gly Gly Glu
    235                 240                 245

gtt aga aac gat gac att gat caa agt tta att att gct gcc cgg aac      822
Val Arg Asn Asp Asp Ile Asp Gln Ser Leu Ile Ile Ala Ala Arg Asn
250                 255                 260                 265

ata gtg aga aga gcg aca gta tca gca gat cca cta gca tcc ctg ctg      870
Ile Val Arg Arg Ala Thr Val Ser Ala Asp Pro Leu Ala Ser Leu Leu
                270                 275                 280

gaa atg tgc cac agt aca cag att ggt gga ata agg atg gta gac atc      918
Glu Met Cys His Ser Thr Gln Ile Gly Gly Ile Arg Met Val Asp Ile
            285                 290                 295

ctt aag cag aat cca aca gag gaa caa gct gtg gat ata tgc aaa gca      966
Leu Lys Gln Asn Pro Thr Glu Glu Gln Ala Val Asp Ile Cys Lys Ala
        300                 305                 310

gca atg ggg tta aga att agc tca tca ttc agc ttt ggt gga ttc acc     1014
Ala Met Gly Leu Arg Ile Ser Ser Ser Phe Ser Phe Gly Gly Phe Thr
    315                 320                 325

ttt aag aga aca agt gga tca tca gtc aag aga gaa gaa gaa atg ctt     1062
Phe Lys Arg Thr Ser Gly Ser Ser Val Lys Arg Glu Glu Glu Met Leu
      330                 335                 340                 345

acg ggc aac ctt caa aca ttg aaa ata aga gtg cat gaa ggc tat gaa     1110
```

-continued

```
Thr Gly Asn Leu Gln Thr Leu Lys Ile Arg Val His Glu Gly Tyr Glu
                350                 355                 360

gaa ttc aca atg gtc gga aga aga gca aca gcc att ctc aga aag gca     1158
Glu Phe Thr Met Val Gly Arg Arg Ala Thr Ala Ile Leu Arg Lys Ala
            365                 370                 375

acc aga aga ttg att caa ttg ata gta agt ggg aga gat gaa caa tca     1206
Thr Arg Arg Leu Ile Gln Leu Ile Val Ser Gly Arg Asp Glu Gln Ser
        380                 385                 390

att gct gaa gca ata att gta gcc atg gtg ttt tc                      1241
Ile Ala Glu Ala Ile Ile Val Ala Met Val Phe
    395                 400


<210> SEQ ID NO 14
<211> LENGTH: 404
<212> TYPE: PRT
<213> ORGANISM: Equine influenza virus H3N8

<400> SEQUENCE: 14

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Ile His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300
```

-continued

```
Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe


<210> SEQ ID NO 15
<211> LENGTH: 1214
<212> TYPE: DNA
<213> ORGANISM: Equine influenza virus H3N8

<400> SEQUENCE: 15

atggagagaa taaaagaact gagagatcta atgtcacaat cccgcacccg cgagatacta      60

acaaaaacta ctgtggacca catggccata atcaagaaat acacatcagg aagacaagag     120

aagaaccccg cacttaggat gaagtggatg atggcaatga aataccaat  tacagcagat     180

aagaggataa tggaaatgat tcctgagaga aatgaacagg ggcaaaccct ttggagcaaa     240

acgaacgatg ctggctcaga ccgcgtaatg gtatcacctc tggcagtgac atggtggaat     300

aggaatggac caacaacgag cacaattcat tatccaaaag tctacaaaac ttattttgaa     360

aaagttgaaa gattaaaaca cggaaccttt ggccccgttc attttaggaa tcaagtcaag     420

ataagacgga gagttgatgt aaaccctggt cacgcggacc tcagtgccaa agaagcacaa     480

gatgtgatca tggaagttgt tttcccaaat gaagtgggag ccagaattct aacatcggaa     540

tcacaactaa caataaccaa agagaaaaaa gaagaacttc aggactgcaa aattgccccc     600

ttgatggtag catacatgct agaaagagag ttggtccgaa aaacaagatt cctcccagtg     660

gctggcggaa caagcagtgt atacattgaa gtgttgcatc tgactcaggg aacatgctgg     720

gaacaaatgt acaccccagg aggagaagtt agaaacgatg acattgatca aagtttaatt     780

attgctgccc ggaacatagt gagaagagcg acagtatcag cagatccact agcatccctg     840

ctggaaatgt gccacagtac acagattggt ggaataagga tggtagacat ccttaagcag     900

aatccaacag aggaacaagc tgtggatata tgcaaagcag caatggggtt aagaattagc     960

tcatcattca gctttggtgg attcaccttt aagagaacaa gtggatcatc agtcaagaga    1020

gaagaagaaa tgcttacggg caaccttcaa acattgaaaa taagagtgca tgaaggctat    1080

gaagaattca caatggtcgg aagaagagca acagccattc tcagaaaggc aaccagaaga    1140

ttgattcaat tgatagtaag tgggagagat gaacaatcaa ttgctgaagc aataattgta    1200

gccatggtgt tttc                                                      1214


<210> SEQ ID NO 16
<211> LENGTH: 1241
<212> TYPE: DNA
<213> ORGANISM: Equine influenza virus H3N8
<220> FEATURE:
<221> NAME/KEY: CDS
<222> LOCATION: (28)..(1239)
```

-continued

```
<223> OTHER INFORMATION:

<400> SEQUENCE: 16

agcaaaagca ggtcaaatat attcaat atg gag aga ata aaa gaa ctg aga gat      54
                              Met Glu Arg Ile Lys Glu Leu Arg Asp
                              1               5

cta atg tca caa tcc cgc acc cgc gag ata cta aca aaa act act gtg      102
Leu Met Ser Gln Ser Arg Thr Arg Glu Ile Leu Thr Lys Thr Thr Val
10                  15                  20                  25

gac cac atg gcc ata atc aag aaa tac aca tca gga aga caa gag aag      150
Asp His Met Ala Ile Ile Lys Lys Tyr Thr Ser Gly Arg Gln Glu Lys
                30                  35                  40

aac ccc gca ctt agg atg aag tgg atg atg gca atg aaa tac cca att      198
Asn Pro Ala Leu Arg Met Lys Trp Met Met Ala Met Lys Tyr Pro Ile
            45                  50                  55

aca gca gat aag agg ata atg gaa atg att cct gag aga aat gaa cag      246
Thr Ala Asp Lys Arg Ile Met Glu Met Ile Pro Glu Arg Asn Glu Gln
        60                  65                  70

ggg caa acc ctt tgg agc aaa acg aac gat gct ggc tca gac cgc gta      294
Gly Gln Thr Leu Trp Ser Lys Thr Asn Asp Ala Gly Ser Asp Arg Val
    75                  80                  85

atg gta tca cct ctg gca gtg aca tgg tgg aat agg aat gga cca aca      342
Met Val Ser Pro Leu Ala Val Thr Trp Trp Asn Arg Asn Gly Pro Thr
90                  95                  100                 105

acg agc aca att cat tat cca aaa gtc cac aaa act tat ttt gaa aaa      390
Thr Ser Thr Ile His Tyr Pro Lys Val His Lys Thr Tyr Phe Glu Lys
                110                 115                 120

gtt gaa aga tta aaa cac gga acc ttt ggc ccc gtt cat ttt agg aat      438
Val Glu Arg Leu Lys His Gly Thr Phe Gly Pro Val His Phe Arg Asn
            125                 130                 135

caa gtc aag ata aga cgg aga gtt gat gta aac cct ggt cac gcg gac      486
Gln Val Lys Ile Arg Arg Arg Val Asp Val Asn Pro Gly His Ala Asp
        140                 145                 150

ctc agt gcc aaa gaa gca caa gat gtg atc atg gaa gtt gtt ttc cca      534
Leu Ser Ala Lys Glu Ala Gln Asp Val Ile Met Glu Val Val Phe Pro
    155                 160                 165

aat gaa gtg gga gcc aga att cta aca tcg gaa tca caa cta aca ata      582
Asn Glu Val Gly Ala Arg Ile Leu Thr Ser Glu Ser Gln Leu Thr Ile
170                 175                 180                 185

acc aaa gag aaa aaa gaa gaa ctt cag gac tgc aaa att gcc ccc ttg      630
Thr Lys Glu Lys Lys Glu Glu Leu Gln Asp Cys Lys Ile Ala Pro Leu
                190                 195                 200

atg gta gca tac atg cta gaa aga gag ttg gtc cga aaa aca aga ttc      678
Met Val Ala Tyr Met Leu Glu Arg Glu Leu Val Arg Lys Thr Arg Phe
            205                 210                 215

ctc cca gtg gct ggc gga aca agc agt gta tac att gaa gtg ttg cat      726
Leu Pro Val Ala Gly Gly Thr Ser Ser Val Tyr Ile Glu Val Leu His
        220                 225                 230

ctg act cag gga aca tgc tgg gaa caa atg tac acc cca gga gga gaa      774
Leu Thr Gln Gly Thr Cys Trp Glu Gln Met Tyr Thr Pro Gly Gly Glu
    235                 240                 245

gtt aga aac gat gac att gat caa agt tta att att gct gcc cgg aac      822
Val Arg Asn Asp Asp Ile Asp Gln Ser Leu Ile Ile Ala Ala Arg Asn
250                 255                 260                 265

ata gtg aga aga gcg aca gta tca gca gat cca cta gca tcc ctg ctg      870
Ile Val Arg Arg Ala Thr Val Ser Ala Asp Pro Leu Ala Ser Leu Leu
                270                 275                 280

gaa atg tgc cac agt aca cag att ggt gga ata agg atg gta gac atc      918
Glu Met Cys His Ser Thr Gln Ile Gly Gly Ile Arg Met Val Asp Ile
            285                 290                 295
```

-continued

```
ctt aag cag aat cca aca gag gaa caa gct gtg gat ata tgc aaa gca      966
Leu Lys Gln Asn Pro Thr Glu Glu Gln Ala Val Asp Ile Cys Lys Ala
        300                 305                 310

gca atg ggg tta aga att agc tca tca ttc agc ttt ggt gga ttc acc     1014
Ala Met Gly Leu Arg Ile Ser Ser Ser Phe Ser Phe Gly Gly Phe Thr
    315                 320                 325

ttt aag aga aca agt gga tca tca gtc aag aga gaa gaa gaa atg ctt     1062
Phe Lys Arg Thr Ser Gly Ser Ser Val Lys Arg Glu Glu Glu Met Leu
330                 335                 340                 345

acg ggc aac ctt caa aca ttg aaa ata aga gtg cat gaa ggc tat gaa     1110
Thr Gly Asn Leu Gln Thr Leu Lys Ile Arg Val His Glu Gly Tyr Glu
                350                 355                 360

gaa ttc aca atg gtc gga aga aga gca aca gcc att ctc aga aag gca     1158
Glu Phe Thr Met Val Gly Arg Arg Ala Thr Ala Ile Leu Arg Lys Ala
            365                 370                 375

acc aga aga ttg att caa ttg ata gta agt ggg aga gat gaa caa tca     1206
Thr Arg Arg Leu Ile Gln Leu Ile Val Ser Gly Arg Asp Glu Gln Ser
        380                 385                 390

att gct gaa gca ata att gta gcc atg gtg ttt tc                      1241
Ile Ala Glu Ala Ile Ile Val Ala Met Val Phe
    395                 400


<210> SEQ ID NO 17
<211> LENGTH: 404
<212> TYPE: PRT
<213> ORGANISM: Equine influenza virus H3N8

<400> SEQUENCE: 17

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Ile His Tyr Pro
            100                 105                 110

Lys Val His Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220
```

-continued

```
Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe


<210> SEQ ID NO 18
<211> LENGTH: 1214
<212> TYPE: DNA
<213> ORGANISM: Equine influenza virus H3N8

<400> SEQUENCE: 18

atggagagaa taaaagaact gagagatcta atgtcacaat cccgcacccg cgagatacta      60

acaaaaacta ctgtggacca catggccata atcaagaaat acacatcagg aagacaagag     120

aagaaccccg cacttaggat gaagtggatg atggcaatga aatacccaat tacagcagat     180

aagaggataa tggaaatgat tcctgagaga aatgaacagg ggcaaaccct ttggagcaaa     240

acgaacgatg ctggctcaga ccgcgtaatg gtatcacctc tggcagtgac atggtggaat     300

aggaatggac caacaacgag cacaattcat tatccaaaag tccacaaaac ttattttgaa     360

aaagttgaaa gattaaaaca cggaaccttt ggccccgttc attttaggaa tcaagtcaag     420

ataagacgga gagttgatgt aaaccctggt cacgcggacc tcagtgccaa agaagcacaa     480

gatgtgatca tggaagttgt tttcccaaat gaagtgggag ccagaattct aacatcggaa     540

tcacaactaa caataaccaa agagaaaaaa gaagaacttc aggactgcaa aattgccccc     600

ttgatggtag catacatgct agaaagagag ttggtccgaa aaacaagatt cctcccagtg     660

gctggcggaa caagcagtgt atacattgaa gtgttgcatc tgactcaggg aacatgctgg     720

gaacaaatgt acaccccagg aggagaagtt agaaacgatg acattgatca aagtttaatt     780

attgctgccc ggaacatagt gagaagagcg acagtatcag cagatccact agcatccctg     840

ctggaaatgt gccacagtac acagattggt ggaataagga tggtagacat ccttaagcag     900

aatccaacag aggaacaagc tgtggatata tgcaaagcag caatggggtt aagaattagc     960

tcatcattca gctttggtgg attcaccttt aagagaacaa gtggatcatc agtcaagaga    1020

gaagaagaaa tgcttacggg caaccttcaa acattgaaaa taagagtgca tgaaggctat    1080
```

-continued gaagaattca caatggtcgg aagaagagca acagccattc tcagaaaggc aaccagaaga 1140
ttgattcaat tgatagtaag tgggagagat gaacaatcaa ttgctgaagc aataattgta 1200
gccatggtgt tttc 1214

<210> SEQ ID NO 19
<211> LENGTH: 1233
<212> TYPE: DNA
<213> ORGANISM: Equine influenza virus H3N8
<220> FEATURE:
<221> NAME/KEY: CDS
<222> LOCATION: (3)..(1196)
<223> OTHER INFORMATION:

<400> SEQUENCE: 19

```
ta gaa ttc aca atg gtc gga aga aga gca aca gcc att ctc aga aag        47
   Glu Phe Thr Met Val Gly Arg Arg Ala Thr Ala Ile Leu Arg Lys
   1               5                   10                  15

gca acc aga aga ttg att caa ttg ata gta agt ggg aga gat gaa caa       95
Ala Thr Arg Arg Leu Ile Gln Leu Ile Val Ser Gly Arg Asp Glu Gln
                20                  25                  30

tca att gct gaa gca ata att gta gcc atg gtg ttt tcg caa gaa gat      143
Ser Ile Ala Glu Ala Ile Ile Val Ala Met Val Phe Ser Gln Glu Asp
            35                  40                  45

tgc atg ata aaa gca gtt cga ggc gat ttg aac ttc gtt aat aga gca      191
Cys Met Ile Lys Ala Val Arg Gly Asp Leu Asn Phe Val Asn Arg Ala
        50                  55                  60

aat cag cgc ttg aac ccc atg cat caa ctc ttg agg cat ttc caa aaa      239
Asn Gln Arg Leu Asn Pro Met His Gln Leu Leu Arg His Phe Gln Lys
    65                  70                  75

gat gca aaa gtg ctt ttc cag aat tgg ggg att gaa ccc atc gac aat      287
Asp Ala Lys Val Leu Phe Gln Asn Trp Gly Ile Glu Pro Ile Asp Asn
80                  85                  90                  95

gtg atg gga atg att gga ata ttg cct gac atg acc cca agc acc gag      335
Val Met Gly Met Ile Gly Ile Leu Pro Asp Met Thr Pro Ser Thr Glu
                100                 105                 110

atg tca ttg aga gga gtg aga gtc agc aaa atg gga gtg gat gag tac      383
Met Ser Leu Arg Gly Val Arg Val Ser Lys Met Gly Val Asp Glu Tyr
            115                 120                 125

tcc agc act gag aga gtg gtg gtg agc att gac cgt ttt tta aga gtt      431
Ser Ser Thr Glu Arg Val Val Val Ser Ile Asp Arg Phe Leu Arg Val
        130                 135                 140

cgg gat caa agg gga aac ata cta ctg tcc cct gaa gag gtc agt gaa      479
Arg Asp Gln Arg Gly Asn Ile Leu Leu Ser Pro Glu Glu Val Ser Glu
    145                 150                 155

aca caa gga acg gaa aag ctg aca ata att tat tca tca tca atg atg      527
Thr Gln Gly Thr Glu Lys Leu Thr Ile Ile Tyr Ser Ser Ser Met Met
160                 165                 170                 175

tgg gag att aat ggt ccc gaa tca gtg ttg gtc aat act tat caa tgg      575
Trp Glu Ile Asn Gly Pro Glu Ser Val Leu Val Asn Thr Tyr Gln Trp
                180                 185                 190

atc atc agg aac tgg gaa att gtg aaa att caa tgg tca cag gat ccc      623
Ile Ile Arg Asn Trp Glu Ile Val Lys Ile Gln Trp Ser Gln Asp Pro
            195                 200                 205

aca atg tta tac aat aag ata gaa ttt gag cca ttc cag tcc ctg gtc      671
Thr Met Leu Tyr Asn Lys Ile Glu Phe Glu Pro Phe Gln Ser Leu Val
        210                 215                 220

cct agg gcc acc aga agc caa tac agc ggt ttc gta aga acc ctg ttt      719
Pro Arg Ala Thr Arg Ser Gln Tyr Ser Gly Phe Val Arg Thr Leu Phe
    225                 230                 235

cag caa atg cga gat gta ctt gga aca ttt gat act gct caa ata ata      767
```

-continued

```
Gln Gln Met Arg Asp Val Leu Gly Thr Phe Asp Thr Ala Gln Ile Ile
240                 245                 250                 255

aaa ctc ctc cct ttt gcc gct gct cct ccg gaa cag agt agg atg cag      815
Lys Leu Leu Pro Phe Ala Ala Ala Pro Pro Glu Gln Ser Arg Met Gln
                260                 265                 270

ttc tct tct ttg act gtt aat gta aga gga tcg gga atg agg ata ctt      863
Phe Ser Ser Leu Thr Val Asn Val Arg Gly Ser Gly Met Arg Ile Leu
            275                 280                 285

gta aga ggc aat tcc cca gtg ttc aac tac aat aaa gcc act aag agg      911
Val Arg Gly Asn Ser Pro Val Phe Asn Tyr Asn Lys Ala Thr Lys Arg
        290                 295                 300

ctc aca gtc ctc gga aag gat gca ggt gcg ctt act gaa gac cca gat      959
Leu Thr Val Leu Gly Lys Asp Ala Gly Ala Leu Thr Glu Asp Pro Asp
    305                 310                 315

gaa ggt acg gct gga gta gaa tct gct gtt cta aga ggg ttt ctc att     1007
Glu Gly Thr Ala Gly Val Glu Ser Ala Val Leu Arg Gly Phe Leu Ile
320                 325                 330                 335

tta ggt aaa gaa aac aag aga tat ggc cca gca cta agc atc aat gaa     1055
Leu Gly Lys Glu Asn Lys Arg Tyr Gly Pro Ala Leu Ser Ile Asn Glu
                340                 345                 350

ctg agc aaa ctt gca aaa ggg gag aaa gct aat gtg cta att ggg caa     1103
Leu Ser Lys Leu Ala Lys Gly Glu Lys Ala Asn Val Leu Ile Gly Gln
            355                 360                 365

ggg gac gtg gtg ttg gta atg aaa cgg aaa cgt gac tct agc ata ctt     1151
Gly Asp Val Val Leu Val Met Lys Arg Lys Arg Asp Ser Ser Ile Leu
        370                 375                 380

act gac agc cag aca gcg acc aaa agg att cgg atg gcc atc aat         1196
Thr Asp Ser Gln Thr Ala Thr Lys Arg Ile Arg Met Ala Ile Asn
    385                 390                 395

tagtgttgaa ttgtttaaaa acgaccttgt ttctact                            1233


<210> SEQ ID NO 20
<211> LENGTH: 398
<212> TYPE: PRT
<213> ORGANISM: Equine influenza virus H3N8

<400> SEQUENCE: 20

Glu Phe Thr Met Val Gly Arg Arg Ala Thr Ala Ile Leu Arg Lys Ala
1               5                   10                  15

Thr Arg Arg Leu Ile Gln Leu Ile Val Ser Gly Arg Asp Glu Gln Ser
            20                  25                  30

Ile Ala Glu Ala Ile Ile Val Ala Met Val Phe Ser Gln Glu Asp Cys
        35                  40                  45

Met Ile Lys Ala Val Arg Gly Asp Leu Asn Phe Val Asn Arg Ala Asn
    50                  55                  60

Gln Arg Leu Asn Pro Met His Gln Leu Leu Arg His Phe Gln Lys Asp
65                  70                  75                  80

Ala Lys Val Leu Phe Gln Asn Trp Gly Ile Glu Pro Ile Asp Asn Val
                85                  90                  95

Met Gly Met Ile Gly Ile Leu Pro Asp Met Thr Pro Ser Thr Glu Met
            100                 105                 110

Ser Leu Arg Gly Val Arg Val Ser Lys Met Gly Val Asp Glu Tyr Ser
        115                 120                 125

Ser Thr Glu Arg Val Val Val Ser Ile Asp Arg Phe Leu Arg Val Arg
    130                 135                 140

Asp Gln Arg Gly Asn Ile Leu Leu Ser Pro Glu Glu Val Ser Glu Thr
145                 150                 155                 160
```

-continued

```
Gln Gly Thr Glu Lys Leu Thr Ile Ile Tyr Ser Ser Ser Met Met Trp
                165                 170                 175

Glu Ile Asn Gly Pro Glu Ser Val Leu Val Asn Thr Tyr Gln Trp Ile
            180                 185                 190

Ile Arg Asn Trp Glu Ile Val Lys Ile Gln Trp Ser Gln Asp Pro Thr
        195                 200                 205

Met Leu Tyr Asn Lys Ile Glu Phe Glu Pro Phe Gln Ser Leu Val Pro
    210                 215                 220

Arg Ala Thr Arg Ser Gln Tyr Ser Gly Phe Val Arg Thr Leu Phe Gln
225                 230                 235                 240

Gln Met Arg Asp Val Leu Gly Thr Phe Asp Thr Ala Gln Ile Ile Lys
                245                 250                 255

Leu Leu Pro Phe Ala Ala Ala Pro Pro Glu Gln Ser Arg Met Gln Phe
            260                 265                 270

Ser Ser Leu Thr Val Asn Val Arg Gly Ser Gly Met Arg Ile Leu Val
        275                 280                 285

Arg Gly Asn Ser Pro Val Phe Asn Tyr Asn Lys Ala Thr Lys Arg Leu
    290                 295                 300

Thr Val Leu Gly Lys Asp Ala Gly Ala Leu Thr Glu Asp Pro Asp Glu
305                 310                 315                 320

Gly Thr Ala Gly Val Glu Ser Ala Val Leu Arg Gly Phe Leu Ile Leu
                325                 330                 335

Gly Lys Glu Asn Lys Arg Tyr Gly Pro Ala Leu Ser Ile Asn Glu Leu
            340                 345                 350

Ser Lys Leu Ala Lys Gly Glu Lys Ala Asn Val Leu Ile Gly Gln Gly
        355                 360                 365

Asp Val Val Leu Val Met Lys Arg Lys Arg Asp Ser Ser Ile Leu Thr
    370                 375                 380

Asp Ser Gln Thr Ala Thr Lys Arg Ile Arg Met Ala Ile Asn
385                 390                 395


<210> SEQ ID NO 21
<211> LENGTH: 1194
<212> TYPE: DNA
<213> ORGANISM: Equine influenza virus H3N8

<400> SEQUENCE: 21

gaattcacaa tggtcggaag aagagcaaca gccattctca gaaaggcaac cagaagattg      60

attcaattga tagtaagtgg gagagatgaa caatcaattg ctgaagcaat aattgtagcc     120

atggtgtttt cgcaagaaga ttgcatgata aaagcagttc gaggcgattt gaacttcgtt     180

aatagagcaa atcagcgctt gaaccccatg catcaactct tgaggcattt ccaaaaagat     240

gcaaaagtgc ttttccagaa ttgggggatt gaacccatcg acaatgtgat gggaatgatt     300

ggaatattgc ctgacatgac cccaagcacc gagatgtcat tgagaggagt gagagtcagc     360

aaaatgggag tggatgagta ctccagcact gagagagtgg tggtgagcat tgaccgtttt     420

ttaagagttc gggatcaaag gggaaacata ctactgtccc ctgaagaggt cagtgaaaca     480

caaggaacgg aaaagctgac aataatttat tcatcatcaa tgatgtggga gattaatggt     540

cccgaatcag tgttggtcaa tacttatcaa tggatcatca ggaactggga aattgtgaaa     600

attcaatggt cacaggatcc cacaatgtta tacaataaga tagaatttga gccattccag     660

tccctggtcc ctagggccac cagaagccaa tacagcggtt tcgtaagaac cctgtttcag     720

caaatgcgag atgtacttgg aacatttgat actgctcaaa taataaaact cctccctttt     780
```

-continued

```
gccgctgctc ctccggaaca gagtaggatg cagttctctt ctttgactgt taatgtaaga    840

ggatcgggaa tgaggatact tgtaagaggc aattccccag tgttcaacta caataaagcc    900

actaagaggc tcacagtcct cggaaaggat gcaggtgcgc ttactgaaga cccagatgaa    960

ggtacggctg gagtagaatc tgctgttcta agagggtttc tcattttagg taaagaaaac   1020

aagagatatg gcccagcact aagcatcaat gaactgagca aacttgcaaa aggggagaaa   1080

gctaatgtgc taattgggca aggggacgtg gtgttggtaa tgaaacggaa acgtgactct   1140

agcatactta ctgacagcca gacagcgacc aaaaggattc ggatggccat caat         1194


<210> SEQ ID NO 22
<211> LENGTH: 1232
<212> TYPE: DNA
<213> ORGANISM: Equine influenza virus H3N8

<400> SEQUENCE: 22

agaattcaca atggtcggaa gaagagcaac agccattctc agaaaggcaa ccagaagatt     60

gattcaattg atagtaagtg ggagagatga acaatcaatt gctgaagcaa taattgtagc    120

catggtgttt tcgcaagaag attgcatgat aaaagcagtt cgaggcgatt tgaacttcgt    180

taatagagca aatcagcgct tgaaccccat gcatcaactc ttgaggcatt tccaaaaaga    240

tgcaaaagtg cttttccaga attgggggat tgaacccatc gacaatgtga tgggaatgat    300

tggaatattg cctgacatga ccccaagcac cgagatgtca ttgagaggag tgagagtcag    360

caaaatggga gtggatgagt actccagcac tgagagagtg gtggtgagca ttgaccgttt    420

tttaagagtt cgggatcaaa ggggaaacat actactgtcc cctgaagagg tcagtgaaac    480

acaaggaacg gaaaagctga caataattta ttcatcatca atgatgtggg agattaatgg    540

tcccgaatca gtgttggtca atacttatca atggatcatc aggaactggg aaattgtgaa    600

aattcaatgg tcacaggatc ccacaatgtt atacaataag atagaatttg agccattcca    660

gtccctggtc cctagggcca ccagaagcca atacagcggt ttcgtaagaa ccctgtttca    720

gcaaatgcga gatgtacttg gaacatttga tactgctcaa ataataaaac tcctcccttt    780

tgccgctgct cctccggaac agagtaggat gcagttctct tctttgactg ttaatgtaag    840

aggatcggga atgaggatac ttgtaagagg caattcccca gtgttcaact acaataaagc    900

cactaagagg ctcacagtcc tcggaaagga tgcaggtgcg cttactgaag acccagatga    960

aggtacggct ggagtagaat ctgctgttct aagagggttt ctcattttag gtaaagaaaa   1020

caagagatat ggcccagcac taagcatcaa tgaactgagc aaacttgcaa aaggggagaa   1080

agctaatgtg ctaattgggc aaggggacgt ggtgttggta atgaaacgga aacgtgactc   1140

tagcatactt actgacagcc agacagcgac caaaaggatt cggatggcca tcaattagtg   1200

ttgaattgtt taaaaacgac cttgtttcta ct                                 1232


<210> SEQ ID NO 23
<211> LENGTH: 1232
<212> TYPE: DNA
<213> ORGANISM: Equine influenza virus H3N8
<220> FEATURE:
<221> NAME/KEY: CDS
<222> LOCATION: (2)..(1195)
<223> OTHER INFORMATION:

<400> SEQUENCE: 23

a gaa ttc aca atg gtc gga aga aga gca aca gcc att ctc aga aag gca     49
  Glu Phe Thr Met Val Gly Arg Arg Ala Thr Ala Ile Leu Arg Lys Ala
  1               5                   10                  15
```

-continued

```
acc aga aga ttg att caa ttg ata gta agt ggg aga gat gaa caa tca       97
Thr Arg Arg Leu Ile Gln Leu Ile Val Ser Gly Arg Asp Glu Gln Ser
            20                  25                  30

att gct gaa gca ata att gta gcc atg gtg ttt tcg caa gaa gat tgc      145
Ile Ala Glu Ala Ile Ile Val Ala Met Val Phe Ser Gln Glu Asp Cys
        35                  40                  45

atg ata caa gca gtt cga ggc gat ttg aac ttc gtt aat aga gca aat      193
Met Ile Gln Ala Val Arg Gly Asp Leu Asn Phe Val Asn Arg Ala Asn
    50                  55                  60

cag cgc ttg aac ccc atg cat caa ctc ttg agg cat ttc caa aaa gat      241
Gln Arg Leu Asn Pro Met His Gln Leu Leu Arg His Phe Gln Lys Asp
65                  70                  75                  80

gca aaa gtg ctt ttc cag aat tgg ggg att gaa ccc atc gac aat gtg      289
Ala Lys Val Leu Phe Gln Asn Trp Gly Ile Glu Pro Ile Asp Asn Val
                85                  90                  95

atg gga atg att gga ata ttg cct gac atg acc cca agc acc gag atg      337
Met Gly Met Ile Gly Ile Leu Pro Asp Met Thr Pro Ser Thr Glu Met
            100                 105                 110

tca ttg aga gga gtg aga gtc agc aaa atg gga gtg gat gag tac tcc      385
Ser Leu Arg Gly Val Arg Val Ser Lys Met Gly Val Asp Glu Tyr Ser
        115                 120                 125

agc act gag aga gtg gtg gtg agc att gac cgt ttt tta aga gtt cgg      433
Ser Thr Glu Arg Val Val Val Ser Ile Asp Arg Phe Leu Arg Val Arg
    130                 135                 140

gat caa agg gga aac ata cta ctg tcc cct gaa gag gtc agt gaa aca      481
Asp Gln Arg Gly Asn Ile Leu Leu Ser Pro Glu Glu Val Ser Glu Thr
145                 150                 155                 160

caa gga acg gaa aag ctg aca ata att tat tca tca tca atg atg tgg      529
Gln Gly Thr Glu Lys Leu Thr Ile Ile Tyr Ser Ser Ser Met Met Trp
                165                 170                 175

gag att aat ggt ccc gaa tca gtg ttg gtc aat act tat caa tgg atc      577
Glu Ile Asn Gly Pro Glu Ser Val Leu Val Asn Thr Tyr Gln Trp Ile
            180                 185                 190

atc agg aac tgg gaa att gtg aaa att caa tgg tca cag gat ccc aca      625
Ile Arg Asn Trp Glu Ile Val Lys Ile Gln Trp Ser Gln Asp Pro Thr
        195                 200                 205

atg tta tac aat aag ata gaa ttt gag cca ttc cag tcc ctg gtc cct      673
Met Leu Tyr Asn Lys Ile Glu Phe Glu Pro Phe Gln Ser Leu Val Pro
    210                 215                 220

agg gcc acc aga agc caa tac agc ggt ttc gta aga acc ctg ttt cag      721
Arg Ala Thr Arg Ser Gln Tyr Ser Gly Phe Val Arg Thr Leu Phe Gln
225                 230                 235                 240

caa atg cga gat gta ctt gga aca ttt gat act gct caa ata ata aaa      769
Gln Met Arg Asp Val Leu Gly Thr Phe Asp Thr Ala Gln Ile Ile Lys
                245                 250                 255

ctc ctc cct ttt gcc gct gct cct ccg gaa cag agt agg atg cag ttc      817
Leu Leu Pro Phe Ala Ala Ala Pro Pro Glu Gln Ser Arg Met Gln Phe
            260                 265                 270

tct tct ttg act gtt aat gta aga gga tcg gga atg agg ata ctt gta      865
Ser Ser Leu Thr Val Asn Val Arg Gly Ser Gly Met Arg Ile Leu Val
        275                 280                 285

aga ggc aat tcc cca gtg ttc aac tac aat aaa gcc act aag agg ctc      913
Arg Gly Asn Ser Pro Val Phe Asn Tyr Asn Lys Ala Thr Lys Arg Leu
    290                 295                 300

aca gtc ctc gga aaa gat gca ggt gcg ctt act gaa gac cca gat gaa      961
Thr Val Leu Gly Lys Asp Ala Gly Ala Leu Thr Glu Asp Pro Asp Glu
305                 310                 315                 320

ggt acg gct gga gta gaa tct gct gtt cta aga ggg ttt ctc att tta     1009
Gly Thr Ala Gly Val Glu Ser Ala Val Leu Arg Gly Phe Leu Ile Leu
```

-continued

```
                325                 330                 335

ggt aaa gaa aac aag aga tat ggc cca gca cta agc atc aat gaa ctg      1057
Gly Lys Glu Asn Lys Arg Tyr Gly Pro Ala Leu Ser Ile Asn Glu Leu
            340                 345                 350

agc aaa ctt gca aaa ggg gag aaa gct aat gtg cta att ggg caa ggg      1105
Ser Lys Leu Ala Lys Gly Glu Lys Ala Asn Val Leu Ile Gly Gln Gly
        355                 360                 365

gac gtg gtg ttg gta atg aaa cgg aaa cgt gac tct agc ata ctt act      1153
Asp Val Val Leu Val Met Lys Arg Lys Arg Asp Ser Ser Ile Leu Thr
    370                 375                 380

gac agc cag aca gcg acc aaa agg att cgg atg gcc atc aat              1195
Asp Ser Gln Thr Ala Thr Lys Arg Ile Arg Met Ala Ile Asn
385                 390                 395

tagtgttgaa ttgtttaaaa acgaccttgt ttctact                             1232


<210> SEQ ID NO 24
<211> LENGTH: 398
<212> TYPE: PRT
<213> ORGANISM: Equine influenza virus H3N8

<400> SEQUENCE: 24

Glu Phe Thr Met Val Gly Arg Arg Ala Thr Ala Ile Leu Arg Lys Ala
1               5                   10                  15

Thr Arg Arg Leu Ile Gln Leu Ile Val Ser Gly Arg Asp Glu Gln Ser
            20                  25                  30

Ile Ala Glu Ala Ile Ile Val Ala Met Val Phe Ser Gln Glu Asp Cys
        35                  40                  45

Met Ile Gln Ala Val Arg Gly Asp Leu Asn Phe Val Asn Arg Ala Asn
    50                  55                  60

Gln Arg Leu Asn Pro Met His Gln Leu Leu Arg His Phe Gln Lys Asp
65                  70                  75                  80

Ala Lys Val Leu Phe Gln Asn Trp Gly Ile Glu Pro Ile Asp Asn Val
                85                  90                  95

Met Gly Met Ile Gly Ile Leu Pro Asp Met Thr Pro Ser Thr Glu Met
            100                 105                 110

Ser Leu Arg Gly Val Arg Val Ser Lys Met Gly Val Asp Glu Tyr Ser
        115                 120                 125

Ser Thr Glu Arg Val Val Val Ser Ile Asp Arg Phe Leu Arg Val Arg
    130                 135                 140

Asp Gln Arg Gly Asn Ile Leu Leu Ser Pro Glu Glu Val Ser Glu Thr
145                 150                 155                 160

Gln Gly Thr Glu Lys Leu Thr Ile Ile Tyr Ser Ser Ser Met Met Trp
                165                 170                 175

Glu Ile Asn Gly Pro Glu Ser Val Leu Val Asn Thr Tyr Gln Trp Ile
            180                 185                 190

Ile Arg Asn Trp Glu Ile Val Lys Ile Gln Trp Ser Gln Asp Pro Thr
        195                 200                 205

Met Leu Tyr Asn Lys Ile Glu Phe Glu Pro Phe Gln Ser Leu Val Pro
    210                 215                 220

Arg Ala Thr Arg Ser Gln Tyr Ser Gly Phe Val Arg Thr Leu Phe Gln
225                 230                 235                 240

Gln Met Arg Asp Val Leu Gly Thr Phe Asp Thr Ala Gln Ile Ile Lys
                245                 250                 255

Leu Leu Pro Phe Ala Ala Ala Pro Pro Glu Gln Ser Arg Met Gln Phe
            260                 265                 270
```

-continued

```
Ser Ser Leu Thr Val Asn Val Arg Gly Ser Gly Met Arg Ile Leu Val
        275                 280                 285

Arg Gly Asn Ser Pro Val Phe Asn Tyr Asn Lys Ala Thr Lys Arg Leu
    290                 295                 300

Thr Val Leu Gly Lys Asp Ala Gly Ala Leu Thr Glu Asp Pro Asp Glu
305                 310                 315                 320

Gly Thr Ala Gly Val Glu Ser Ala Val Leu Arg Gly Phe Leu Ile Leu
                325                 330                 335

Gly Lys Glu Asn Lys Arg Tyr Gly Pro Ala Leu Ser Ile Asn Glu Leu
            340                 345                 350

Ser Lys Leu Ala Lys Gly Glu Lys Ala Asn Val Leu Ile Gly Gln Gly
        355                 360                 365

Asp Val Val Leu Val Met Lys Arg Lys Arg Asp Ser Ser Ile Leu Thr
    370                 375                 380

Asp Ser Gln Thr Ala Thr Lys Arg Ile Arg Met Ala Ile Asn
385                 390                 395


<210> SEQ ID NO 25
<211> LENGTH: 1194
<212> TYPE: DNA
<213> ORGANISM: Equine influenza virus H3N8

<400> SEQUENCE: 25

gaattcacaa tggtcggaag aagagcaaca gccattctca gaaaggcaac cagaagattg      60

attcaattga tagtaagtgg gagagatgaa caatcaattg ctgaagcaat aattgtagcc     120

atggtgtttt cgcaagaaga ttgcatgata caagcagttc gaggcgattt gaacttcgtt     180

aatagagcaa atcagcgctt gaaccccatg catcaactct tgaggcattt ccaaaaagat     240

gcaaaagtgc ttttccagaa ttgggggatt gaacccatcg acaatgtgat gggaatgatt     300

ggaatattgc ctgacatgac cccaagcacc gagatgtcat tgagaggagt gagagtcagc     360

aaaatgggag tggatgagta ctccagcact gagagagtgg tggtgagcat tgaccgtttt     420

ttaagagttc gggatcaaag gggaaacata ctactgtccc ctgaagaggt cagtgaaaca     480

caaggaacgg aaaagctgac aataatttat tcatcatcaa tgatgtggga gattaatggt     540

cccgaatcag tgttggtcaa tacttatcaa tggatcatca ggaactggga aattgtgaaa     600

attcaatggt cacaggatcc cacaatgtta tacaataaga tagaatttga gccattccag     660

tccctggtcc ctagggccac cagaagccaa tacagcggtt tcgtaagaac cctgtttcag     720

caaatgcgag atgtacttgg aacatttgat actgctcaaa taataaaact cctccctttt     780

gccgctgctc ctccggaaca gagtaggatg cagttctctt ctttgactgt taatgtaaga     840

ggatcgggaa tgaggatact tgtaagaggc aattccccag tgttcaacta caataaagcc     900

actaagaggc tcacagtcct cggaaaagat gcaggtgcgc ttactgaaga cccagatgaa     960

ggtacggctg gagtagaatc tgctgttcta agagggtttc tcattttagg taaagaaaac    1020

aagagatatg gcccagcact aagcatcaat gaactgagca aacttgcaaa aggggagaaa    1080

gctaatgtgc taattgggca aggggacgtg gtgttggtaa tgaaacggaa acgtgactct    1140

agcatactta ctgacagcca gacagcgacc aaaaggattc ggatggccat caat          1194


<210> SEQ ID NO 26
<211> LENGTH: 23
<212> TYPE: DNA
<213> ORGANISM: Artificial sequence
<220> FEATURE:
<223> OTHER INFORMATION: Synthetic Primer
```

-continued

<400> SEQUENCE: 26
agcaaaagca ggtagatatt gaa 23

<210> SEQ ID NO 27
<211> LENGTH: 24
<212> TYPE: DNA
<213> ORGANISM: Artificial sequence
<220> FEATURE:
<223> OTHER INFORMATION: Synthetic Primer

<400> SEQUENCE: 27
agtagaaaca aggtagtttt ttac 24

<210> SEQ ID NO 28
<211> LENGTH: 18
<212> TYPE: DNA
<213> ORGANISM: Artificial sequence
<220> FEATURE:
<223> OTHER INFORMATION: Synthetic Primer

<400> SEQUENCE: 28
caggaaacag ctatgacc 18

<210> SEQ ID NO 29
<211> LENGTH: 20
<212> TYPE: DNA
<213> ORGANISM: Artificial sequence
<220> FEATURE:
<223> OTHER INFORMATION: Synthetic Primer

<400> SEQUENCE: 29
taatacgact cactataggg 20

<210> SEQ ID NO 30
<211> LENGTH: 18
<212> TYPE: DNA
<213> ORGANISM: Artificial sequence
<220> FEATURE:
<223> OTHER INFORMATION: Synthetic Primer

<400> SEQUENCE: 30
tggtgcacta gccagctg 18

<210> SEQ ID NO 31
<211> LENGTH: 18
<212> TYPE: DNA
<213> ORGANISM: Artificial sequence
<220> FEATURE:
<223> OTHER INFORMATION: Synthetic Primer

<400> SEQUENCE: 31
ttgcctgtac catctgcc 18

<210> SEQ ID NO 32
<211> LENGTH: 23
<212> TYPE: DNA
<213> ORGANISM: Artificial sequence
<220> FEATURE:
<223> OTHER INFORMATION: Synthetic Primer

<400> SEQUENCE: 32
agcaaaagca ggggatattt ctg 23

<210> SEQ ID NO 33

-continued

<211> LENGTH: 23
<212> TYPE: DNA
<213> ORGANISM: Artificial sequence
<220> FEATURE:
<223> OTHER INFORMATION: Synthetic Primer

<400> SEQUENCE: 33
agtagaaaca agggtgtttt taa 23

<210> SEQ ID NO 34
<211> LENGTH: 16
<212> TYPE: DNA
<213> ORGANISM: Artificial sequence
<220> FEATURE:
<223> OTHER INFORMATION: Synthetic Primer

<400> SEQUENCE: 34
gacatccctg actatg 16

<210> SEQ ID NO 35
<211> LENGTH: 16
<212> TYPE: DNA
<213> ORGANISM: Artificial sequence
<220> FEATURE:
<223> OTHER INFORMATION: Synthetic Primer

<400> SEQUENCE: 35
gcatctgtta agtcaa 16

<210> SEQ ID NO 36
<211> LENGTH: 25
<212> TYPE: DNA
<213> ORGANISM: Artificial sequence
<220> FEATURE:
<223> OTHER INFORMATION: Synthetic Primer

<400> SEQUENCE: 36
agcaaaagca ggtcaaatat attca 25

<210> SEQ ID NO 37
<211> LENGTH: 26
<212> TYPE: DNA
<213> ORGANISM: Artificial sequence
<220> FEATURE:
<223> OTHER INFORMATION: Synthetic Primer

<400> SEQUENCE: 37
gaaaacacca tggctacaat tattgc 26

<210> SEQ ID NO 38
<211> LENGTH: 27
<212> TYPE: DNA
<213> ORGANISM: Artificial sequence
<220> FEATURE:
<223> OTHER INFORMATION: Synthetic Primer

<400> SEQUENCE: 38
agaattcaca atggtcggaa gaagagc 27

<210> SEQ ID NO 39
<211> LENGTH: 27
<212> TYPE: DNA
<213> ORGANISM: Artificial sequence
<220> FEATURE:
<223> OTHER INFORMATION: Synthetic Primer

<400> SEQUENCE: 39

-continued

```
agtagaaaca aggtcgtttt taaacaa                                           27


<210> SEQ ID NO 40
<211> LENGTH: 19
<212> TYPE: DNA
<213> ORGANISM: Artificial sequence
<220> FEATURE:
<223> OTHER INFORMATION: Synthetic Primer

<400> SEQUENCE: 40

agccgtacct tcatctggg                                                    19


<210> SEQ ID NO 41
<211> LENGTH: 19
<212> TYPE: DNA
<213> ORGANISM: Artificial sequence
<220> FEATURE:
<223> OTHER INFORMATION: Synthetic Primer

<400> SEQUENCE: 41

agcactgaga gagtggtgg                                                    19


<210> SEQ ID NO 42
<211> LENGTH: 19
<212> TYPE: DNA
<213> ORGANISM: Artificial sequence
<220> FEATURE:
<223> OTHER INFORMATION: Synthetic Primer

<400> SEQUENCE: 42

gtaagaggca attccccag                                                    19


<210> SEQ ID NO 43
<211> LENGTH: 18
<212> TYPE: DNA
<213> ORGANISM: Artificial sequence
<220> FEATURE:
<223> OTHER INFORMATION: Synthetic Primer

<400> SEQUENCE: 43

cagcttttcc gttccttg                                                     18


<210> SEQ ID NO 44
<211> LENGTH: 2341
<212> TYPE: DNA
<213> ORGANISM: Equine influenza virus H3N8
<220> FEATURE:
<221> NAME/KEY: CDS
<222> LOCATION: (28)..(2304)
<223> OTHER INFORMATION:

<400> SEQUENCE: 44

agcaaaagca ggtcaaatat attcaat atg gag aga ata aaa gaa ctg aga gat      54
                              Met Glu Arg Ile Lys Glu Leu Arg Asp
                              1               5

cta atg tca caa tcc cgc acc cgc gag ata cta aca aaa act act gtg       102
Leu Met Ser Gln Ser Arg Thr Arg Glu Ile Leu Thr Lys Thr Thr Val
10                  15                  20                  25

gac cac atg gcc ata atc aag aaa tac aca tca gga aga caa gag aag       150
Asp His Met Ala Ile Ile Lys Lys Tyr Thr Ser Gly Arg Gln Glu Lys
                30                  35                  40

aac ccc gca ctt agg atg aag tgg atg atg gca atg aaa tac cca att       198
Asn Pro Ala Leu Arg Met Lys Trp Met Met Ala Met Lys Tyr Pro Ile
            45                  50                  55
```

-continued

```
aca gca gat aag agg ata atg gaa atg att cct gag aga aat gaa cag      246
Thr Ala Asp Lys Arg Ile Met Glu Met Ile Pro Glu Arg Asn Glu Gln
        60                  65                  70

ggg caa acc ctt tgg agc aaa acg aac gat gct ggc tca gac cgc gta      294
Gly Gln Thr Leu Trp Ser Lys Thr Asn Asp Ala Gly Ser Asp Arg Val
    75                  80                  85

atg gta tca cct ctg gca gtg aca tgg tgg aat agg aat gga cca aca      342
Met Val Ser Pro Leu Ala Val Thr Trp Trp Asn Arg Asn Gly Pro Thr
90                  95                  100                 105

acg agc aca att cat tat cca aaa gtc tac aaa act tat ttt gaa aaa      390
Thr Ser Thr Ile His Tyr Pro Lys Val Tyr Lys Thr Tyr Phe Glu Lys
                110                 115                 120

gtt gaa aga tta aaa cac gga acc ttt ggc ccc gtt cat ttt agg aat      438
Val Glu Arg Leu Lys His Gly Thr Phe Gly Pro Val His Phe Arg Asn
            125                 130                 135

caa gtc aag ata aga cgg aga gtt gat gta aac cct ggt cac gcg gac      486
Gln Val Lys Ile Arg Arg Arg Val Asp Val Asn Pro Gly His Ala Asp
        140                 145                 150

ctc agt gcc aaa gaa gca caa gat gtg atc atg gaa gtt gtt ttc cca      534
Leu Ser Ala Lys Glu Ala Gln Asp Val Ile Met Glu Val Val Phe Pro
    155                 160                 165

aat gaa gtg gga gcc aga att cta aca tcg gaa tca caa cta aca ata      582
Asn Glu Val Gly Ala Arg Ile Leu Thr Ser Glu Ser Gln Leu Thr Ile
170                 175                 180                 185

acc aaa gag aaa aaa gaa gaa ctt cag gac tgc aaa att gcc ccc ttg      630
Thr Lys Glu Lys Lys Glu Glu Leu Gln Asp Cys Lys Ile Ala Pro Leu
                190                 195                 200

atg gta gca tac atg cta gaa aga gag ttg gtc cga aaa aca aga ttc      678
Met Val Ala Tyr Met Leu Glu Arg Glu Leu Val Arg Lys Thr Arg Phe
            205                 210                 215

ctc cca gtg gct ggc gga aca agc agt gta tac att gaa gtg ttg cat      726
Leu Pro Val Ala Gly Gly Thr Ser Ser Val Tyr Ile Glu Val Leu His
        220                 225                 230

ctg act cag gga aca tgc tgg gaa caa atg tac acc cca gga gga gaa      774
Leu Thr Gln Gly Thr Cys Trp Glu Gln Met Tyr Thr Pro Gly Gly Glu
    235                 240                 245

gtt aga aac gat gac att gat caa agt tta att att gct gcc cgg aac      822
Val Arg Asn Asp Asp Ile Asp Gln Ser Leu Ile Ile Ala Ala Arg Asn
250                 255                 260                 265

ata gtg aga aga gcg aca gta tca gca gat cca cta gca tcc ctg ctg      870
Ile Val Arg Arg Ala Thr Val Ser Ala Asp Pro Leu Ala Ser Leu Leu
                270                 275                 280

gaa atg tgc cac agt aca cag att ggt gga ata agg atg gta gac atc      918
Glu Met Cys His Ser Thr Gln Ile Gly Gly Ile Arg Met Val Asp Ile
            285                 290                 295

ctt aag cag aat cca aca gag gaa caa gct gtg gat ata tgc aaa gca      966
Leu Lys Gln Asn Pro Thr Glu Glu Gln Ala Val Asp Ile Cys Lys Ala
        300                 305                 310

gca atg ggg tta aga att agc tca tca ttc agc ttt ggt gga ttc acc     1014
Ala Met Gly Leu Arg Ile Ser Ser Ser Phe Ser Phe Gly Gly Phe Thr
    315                 320                 325

ttt aag aga aca agt gga tca tca gtc aag aga gaa gaa gaa atg ctt     1062
Phe Lys Arg Thr Ser Gly Ser Ser Val Lys Arg Glu Glu Glu Met Leu
330                 335                 340                 345

acg ggc aac ctt caa aca ttg aaa ata aga gtg cat gaa ggc tat gaa     1110
Thr Gly Asn Leu Gln Thr Leu Lys Ile Arg Val His Glu Gly Tyr Glu
                350                 355                 360

gaa ttc aca atg gtc gga aga aga gca aca gcc att ctc aga aag gca     1158
Glu Phe Thr Met Val Gly Arg Arg Ala Thr Ala Ile Leu Arg Lys Ala
            365                 370                 375
```

-continued

```
acc aga aga ttg att caa ttg ata gta agt ggg aga gat gaa caa tca     1206
Thr Arg Arg Leu Ile Gln Leu Ile Val Ser Gly Arg Asp Glu Gln Ser
        380                 385                 390

att gct gaa gca ata att gta gcc atg gtg ttt tcg caa gaa gat tgc     1254
Ile Ala Glu Ala Ile Ile Val Ala Met Val Phe Ser Gln Glu Asp Cys
    395                 400                 405

atg ata aaa gca gtt cga ggc gat ttg aac ttc gtt aat aga gca aat     1302
Met Ile Lys Ala Val Arg Gly Asp Leu Asn Phe Val Asn Arg Ala Asn
410                 415                 420                 425

cag cgc ttg aac ccc atg cat caa ctc ttg agg cat ttc caa aaa gat     1350
Gln Arg Leu Asn Pro Met His Gln Leu Leu Arg His Phe Gln Lys Asp
                430                 435                 440

gca aaa gtg ctt ttc cag aat tgg ggg att gaa ccc atc gac aat gtg     1398
Ala Lys Val Leu Phe Gln Asn Trp Gly Ile Glu Pro Ile Asp Asn Val
            445                 450                 455

atg gga atg att gga ata ttg cct gac atg acc cca agc acc gag atg     1446
Met Gly Met Ile Gly Ile Leu Pro Asp Met Thr Pro Ser Thr Glu Met
        460                 465                 470

tca ttg aga gga gtg aga gtc agc aaa atg gga gtg gat gag tac tcc     1494
Ser Leu Arg Gly Val Arg Val Ser Lys Met Gly Val Asp Glu Tyr Ser
    475                 480                 485

agc act gag aga gtg gtg gtg agc att gac cgt ttt tta aga gtt cgg     1542
Ser Thr Glu Arg Val Val Val Ser Ile Asp Arg Phe Leu Arg Val Arg
490                 495                 500                 505

gat caa agg gga aac ata cta ctg tcc cct gaa gag gtc agt gaa aca     1590
Asp Gln Arg Gly Asn Ile Leu Leu Ser Pro Glu Glu Val Ser Glu Thr
                510                 515                 520

caa gga acg gaa aag ctg aca ata att tat tca tca tca atg atg tgg     1638
Gln Gly Thr Glu Lys Leu Thr Ile Ile Tyr Ser Ser Ser Met Met Trp
            525                 530                 535

gag att aat ggt ccc gaa tca gtg ttg gtc aat act tat caa tgg atc     1686
Glu Ile Asn Gly Pro Glu Ser Val Leu Val Asn Thr Tyr Gln Trp Ile
        540                 545                 550

atc agg aac tgg gaa att gtg aaa att caa tgg tca cag gat ccc aca     1734
Ile Arg Asn Trp Glu Ile Val Lys Ile Gln Trp Ser Gln Asp Pro Thr
    555                 560                 565

atg tta tac aat aag ata gaa ttt gag cca ttc cag tcc ctg gtc cct     1782
Met Leu Tyr Asn Lys Ile Glu Phe Glu Pro Phe Gln Ser Leu Val Pro
570                 575                 580                 585

agg gcc acc aga agc caa tac agc ggt ttc gta aga acc ctg ttt cag     1830
Arg Ala Thr Arg Ser Gln Tyr Ser Gly Phe Val Arg Thr Leu Phe Gln
                590                 595                 600

caa atg cga gat gta ctt gga aca ttt gat act gct caa ata ata aaa     1878
Gln Met Arg Asp Val Leu Gly Thr Phe Asp Thr Ala Gln Ile Ile Lys
            605                 610                 615

ctc ctc cct ttt gcc gct gct cct ccg gaa cag agt agg atg cag ttc     1926
Leu Leu Pro Phe Ala Ala Ala Pro Pro Glu Gln Ser Arg Met Gln Phe
        620                 625                 630

tct tct ttg act gtt aat gta aga gga tcg gga atg agg ata ctt gta     1974
Ser Ser Leu Thr Val Asn Val Arg Gly Ser Gly Met Arg Ile Leu Val
    635                 640                 645

aga ggc aat tcc cca gtg ttc aac tac aat aaa gcc act aag agg ctc     2022
Arg Gly Asn Ser Pro Val Phe Asn Tyr Asn Lys Ala Thr Lys Arg Leu
650                 655                 660                 665

aca gtc ctc gga aag gat gca ggt gcg ctt act gaa gac cca gat gaa     2070
Thr Val Leu Gly Lys Asp Ala Gly Ala Leu Thr Glu Asp Pro Asp Glu
                670                 675                 680

ggt acg gct gga gta gaa tct gct gtt cta aga ggg ttt ctc att tta     2118
Gly Thr Ala Gly Val Glu Ser Ala Val Leu Arg Gly Phe Leu Ile Leu
```

-continued

```
            685                 690                 695

ggt aaa gaa aac aag aga tat ggc cca gca cta agc atc aat gaa ctg     2166
Gly Lys Glu Asn Lys Arg Tyr Gly Pro Ala Leu Ser Ile Asn Glu Leu
        700                 705                 710

agc aaa ctt gca aaa ggg gag aaa gct aat gtg cta att ggg caa ggg     2214
Ser Lys Leu Ala Lys Gly Glu Lys Ala Asn Val Leu Ile Gly Gln Gly
    715                 720                 725

gac gtg gtg ttg gta atg aaa cgg aaa cgt gac tct agc ata ctt act     2262
Asp Val Val Leu Val Met Lys Arg Lys Arg Asp Ser Ser Ile Leu Thr
730                 735                 740                 745

gac agc cag aca gcg acc aaa agg att cgg atg gcc atc aat             2304
Asp Ser Gln Thr Ala Thr Lys Arg Ile Arg Met Ala Ile Asn
                750                 755

tagtgttgaa ttgtttaaaa acgaccttgt ttctact                            2341


<210> SEQ ID NO 45
<211> LENGTH: 759
<212> TYPE: PRT
<213> ORGANISM: Equine influenza virus H3N8

<400> SEQUENCE: 45

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Ile His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Thr Val
            260                 265                 270
```

-continued

```
Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu Pro Ile Asp Asn Val Met Gly Met Ile Gly Ile Leu
    450                 455                 460

Pro Asp Met Thr Pro Ser Thr Glu Met Ser Leu Arg Gly Val Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Ile Leu
            500                 505                 510

Leu Ser Pro Glu Glu Val Ser Glu Thr Gln Gly Thr Glu Lys Leu Thr
        515                 520                 525

Ile Ile Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Ile Val
545                 550                 555                 560

Lys Ile Gln Trp Ser Gln Asp Pro Thr Met Leu Tyr Asn Lys Ile Glu
                565                 570                 575

Phe Glu Pro Phe Gln Ser Leu Val Pro Arg Ala Thr Arg Ser Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asn Lys Arg Tyr
```

-continued

```
    690                 695                 700

Gly Pro Ala Leu Ser Ile Asn Glu Leu Ser Lys Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755


<210> SEQ ID NO 46
<211> LENGTH: 2277
<212> TYPE: DNA
<213> ORGANISM: Equine influenza virus H3N8

<400> SEQUENCE: 46

atggagagaa taaaagaact gagagatcta atgtcacaat cccgcacccg cgagatacta      60

acaaaaacta ctgtggacca catggccata atcaagaaat acacatcagg aagacaagag     120

aagaaccccg cacttaggat gaagtggatg atggcaatga aataccaat tacagcagat      180

aagaggataa tggaaatgat tcctgagaga aatgaacagg ggcaaaccct ttggagcaaa     240

acgaacgatg ctggctcaga ccgcgtaatg gtatcacctc tggcagtgac atggtggaat     300

aggaatggac caacaacgag cacaattcat tatccaaaag tctacaaaac ttattttgaa     360

aaagttgaaa gattaaaaca cggaaccttt ggccccgttc attttaggaa tcaagtcaag     420

ataagacgga gagttgatgt aaaccctggt cacgcggacc tcagtgccaa agaagcacaa     480

gatgtgatca tggaagttgt tttcccaaat gaagtgggag ccagaattct aacatcggaa     540

tcacaactaa caataaccaa agagaaaaaa gaagaacttc aggactgcaa aattgccccc     600

ttgatggtag catacatgct agaaagagag ttggtccgaa aaacaagatt cctcccagtg     660

gctggcggaa caagcagtgt atacattgaa gtgttgcatc tgactcaggg aacatgctgg     720

gaacaaatgt acaccccagg aggagaagtt agaaacgatg acattgatca aagtttaatt     780

attgctgccc ggaacatagt gagaagagcg acagtatcag cagatccact agcatccctg     840

ctggaaatgt gccacagtac acagattggt ggaataagga tggtagacat ccttaagcag     900

aatccaacag aggaacaagc tgtggatata tgcaaagcag caatggggtt aagaattagc     960

tcatcattca gctttggtgg attcaccttt aagagaacaa gtggatcatc agtcaagaga    1020

gaagaagaaa tgcttacggg caaccttcaa acattgaaaa taagagtgca tgaaggctat    1080

gaagaattca caatggtcgg aagaagagca acagccattc tcagaaaggc aaccagaaga    1140

ttgattcaat tgatagtaag tgggagagat gaacaatcaa ttgctgaagc aataattgta    1200

gccatggtgt tttcgcaaga agattgcatg ataaaagcag ttcgaggcga tttgaacttc    1260

gttaatagag caaatcagcg cttgaacccc atgcatcaac tcttgaggca tttccaaaaa    1320

gatgcaaaag tgcttttcca gaattggggg attgaaccca tcgacaatgt gatgggaatg    1380

attggaatat tgcctgacat gaccccaagc accgagatgt cattgagagg agtgagagtc    1440

agcaaaatgg gagtggatga gtactccagc actgagagag tggtggtgag cattgaccgt    1500

tttttaagag ttcgggatca aaggggaaac atactactgt cccctgaaga ggtcagtgaa    1560

acacaaggaa cggaaaagct gacaataatt tattcatcat caatgatgtg ggagattaat    1620

ggtcccgaat cagtgttggt caatacttat caatggatca tcaggaactg ggaaattgtg    1680

aaaattcaat ggtcacagga tcccacaatg ttatacaata agatagaatt tgagccattc    1740
```

-continued

```
cagtccctgg tccctagggc caccagaagc caatacagcg gtttcgtaag aaccctgttt   1800

cagcaaatgc gagatgtact tggaacattt gatactgctc aaataataaa actcctccct   1860

tttgccgctg ctcctccgga acagagtagg atgcagttct cttctttgac tgttaatgta   1920

agaggatcgg gaatgaggat acttgtaaga ggcaattccc cagtgttcaa ctacaataaa   1980

gccactaaga ggctcacagt cctcggaaag gatgcaggtg cgcttactga agacccagat   2040

gaaggtacgg ctggagtaga atctgctgtt ctaagagggt ttctcatttt aggtaaagaa   2100

aacaagagat atggcccagc actaagcatc aatgaactga gcaaacttgc aaaaggggag   2160

aaagctaatg tgctaattgg gcaaggggac gtggtgttgg taatgaaacg gaaacgtgac   2220

tctagcatac ttactgacag ccagacagcg accaaaagga ttcggatggc catcaat      2277
```

<210> SEQ ID NO 47
<211> LENGTH: 2341
<212> TYPE: DNA
<213> ORGANISM: Equine influenza virus H3N8
<220> FEATURE:
<221> NAME/KEY: CDS
<222> LOCATION: (28)..(2304)
<223> OTHER INFORMATION:

<400> SEQUENCE: 47

```
agcaaaagca ggtcaaatat attcaat atg gag aga ata aaa gaa ctg aga gat      54
                              Met Glu Arg Ile Lys Glu Leu Arg Asp
                              1               5

cta atg tca caa tcc cgc acc cgc gag ata cta aca aaa act act gtg       102
Leu Met Ser Gln Ser Arg Thr Arg Glu Ile Leu Thr Lys Thr Thr Val
10                  15                  20                  25

gac cac atg gcc ata atc aag aaa tac aca tca gga aga caa gag aag       150
Asp His Met Ala Ile Ile Lys Lys Tyr Thr Ser Gly Arg Gln Glu Lys
                30                  35                  40

aac ccc gca ctt agg atg aag tgg atg atg gca atg aaa tac cca att       198
Asn Pro Ala Leu Arg Met Lys Trp Met Met Ala Met Lys Tyr Pro Ile
            45                  50                  55

aca gca gat aag agg ata atg gaa atg att cct gag aga aat gaa cag       246
Thr Ala Asp Lys Arg Ile Met Glu Met Ile Pro Glu Arg Asn Glu Gln
        60                  65                  70

ggg caa acc ctt tgg agc aaa acg aac gat gct ggc tca gac cgc gta       294
Gly Gln Thr Leu Trp Ser Lys Thr Asn Asp Ala Gly Ser Asp Arg Val
    75                  80                  85

atg gta tca cct ctg gca gtg aca tgg tgg aat agg aat gga cca aca       342
Met Val Ser Pro Leu Ala Val Thr Trp Trp Asn Arg Asn Gly Pro Thr
90                  95                  100                 105

acg agc aca att cat tat cca aaa gtc cac aaa act tat ttt gaa aaa       390
Thr Ser Thr Ile His Tyr Pro Lys Val His Lys Thr Tyr Phe Glu Lys
                110                 115                 120

gtt gaa aga tta aaa cac gga acc ttt ggc ccc gtt cat ttt agg aat       438
Val Glu Arg Leu Lys His Gly Thr Phe Gly Pro Val His Phe Arg Asn
            125                 130                 135

caa gtc aag ata aga cgg aga gtt gat gta aac cct ggt cac gcg gac       486
Gln Val Lys Ile Arg Arg Arg Val Asp Val Asn Pro Gly His Ala Asp
        140                 145                 150

ctc agt gcc aaa gaa gca caa gat gtg atc atg gaa gtt gtt ttc cca       534
Leu Ser Ala Lys Glu Ala Gln Asp Val Ile Met Glu Val Val Phe Pro
    155                 160                 165

aat gaa gtg gga gcc aga att cta aca tcg gaa tca caa cta aca ata       582
Asn Glu Val Gly Ala Arg Ile Leu Thr Ser Glu Ser Gln Leu Thr Ile
170                 175                 180                 185
```

-continued

```
acc aaa gag aaa aaa gaa gaa ctt cag gac tgc aaa att gcc ccc ttg       630
Thr Lys Glu Lys Lys Glu Glu Leu Gln Asp Cys Lys Ile Ala Pro Leu
                190                 195                 200

atg gta gca tac atg cta gaa aga gag ttg gtc cga aaa aca aga ttc       678
Met Val Ala Tyr Met Leu Glu Arg Glu Leu Val Arg Lys Thr Arg Phe
            205                 210                 215

ctc cca gtg gct ggc gga aca agc agt gta tac att gaa gtg ttg cat       726
Leu Pro Val Ala Gly Gly Thr Ser Ser Val Tyr Ile Glu Val Leu His
        220                 225                 230

ctg act cag gga aca tgc tgg gaa caa atg tac acc cca gga gga gaa       774
Leu Thr Gln Gly Thr Cys Trp Glu Gln Met Tyr Thr Pro Gly Gly Glu
    235                 240                 245

gtt aga aac gat gac att gat caa agt tta att att gct gcc cgg aac       822
Val Arg Asn Asp Asp Ile Asp Gln Ser Leu Ile Ile Ala Ala Arg Asn
250                 255                 260                 265

ata gtg aga aga gcg aca gta tca gca gat cca cta gca tcc ctg ctg       870
Ile Val Arg Arg Ala Thr Val Ser Ala Asp Pro Leu Ala Ser Leu Leu
                270                 275                 280

gaa atg tgc cac agt aca cag att ggt gga ata agg atg gta gac atc       918
Glu Met Cys His Ser Thr Gln Ile Gly Gly Ile Arg Met Val Asp Ile
            285                 290                 295

ctt aag cag aat cca aca gag gaa caa gct gtg gat ata tgc aaa gca       966
Leu Lys Gln Asn Pro Thr Glu Glu Gln Ala Val Asp Ile Cys Lys Ala
        300                 305                 310

gca atg ggg tta aga att agc tca tca ttc agc ttt ggt gga ttc acc      1014
Ala Met Gly Leu Arg Ile Ser Ser Ser Phe Ser Phe Gly Gly Phe Thr
    315                 320                 325

ttt aag aga aca agt gga tca tca gtc aag aga gaa gaa gaa atg ctt      1062
Phe Lys Arg Thr Ser Gly Ser Ser Val Lys Arg Glu Glu Glu Met Leu
330                 335                 340                 345

acg ggc aac ctt caa aca ttg aaa ata aga gtg cat gaa ggc tat gaa      1110
Thr Gly Asn Leu Gln Thr Leu Lys Ile Arg Val His Glu Gly Tyr Glu
                350                 355                 360

gaa ttc aca atg gtc gga aga aga gca aca gcc att ctc aga aag gca      1158
Glu Phe Thr Met Val Gly Arg Arg Ala Thr Ala Ile Leu Arg Lys Ala
            365                 370                 375

acc aga aga ttg att caa ttg ata gta agt ggg aga gat gaa caa tca      1206
Thr Arg Arg Leu Ile Gln Leu Ile Val Ser Gly Arg Asp Glu Gln Ser
        380                 385                 390

att gct gaa gca ata att gta gcc atg gtg ttt tcg caa gaa gat tgc      1254
Ile Ala Glu Ala Ile Ile Val Ala Met Val Phe Ser Gln Glu Asp Cys
    395                 400                 405

atg ata caa gca gtt cga ggc gat ttg aac ttc gtt aat aga gca aat      1302
Met Ile Gln Ala Val Arg Gly Asp Leu Asn Phe Val Asn Arg Ala Asn
410                 415                 420                 425

cag cgc ttg aac ccc atg cat caa ctc ttg agg cat ttc caa aaa gat      1350
Gln Arg Leu Asn Pro Met His Gln Leu Leu Arg His Phe Gln Lys Asp
                430                 435                 440

gca aaa gtg ctt ttc cag aat tgg ggg att gaa ccc atc gac aat gtg      1398
Ala Lys Val Leu Phe Gln Asn Trp Gly Ile Glu Pro Ile Asp Asn Val
            445                 450                 455

atg gga atg att gga ata ttg cct gac atg acc cca agc acc gag atg      1446
Met Gly Met Ile Gly Ile Leu Pro Asp Met Thr Pro Ser Thr Glu Met
        460                 465                 470

tca ttg aga gga gtg aga gtc agc aaa atg gga gtg gat gag tac tcc      1494
Ser Leu Arg Gly Val Arg Val Ser Lys Met Gly Val Asp Glu Tyr Ser
    475                 480                 485

agc act gag aga gtg gtg gtg agc att gac cgt ttt tta aga gtt cgg      1542
Ser Thr Glu Arg Val Val Val Ser Ile Asp Arg Phe Leu Arg Val Arg
490                 495                 500                 505
```

-continued

```
gat caa agg gga aac ata cta ctg tcc cct gaa gag gtc agt gaa aca      1590
Asp Gln Arg Gly Asn Ile Leu Leu Ser Pro Glu Glu Val Ser Glu Thr
            510                 515                 520

caa gga acg gaa aag ctg aca ata att tat tca tca tca atg atg tgg      1638
Gln Gly Thr Glu Lys Leu Thr Ile Ile Tyr Ser Ser Ser Met Met Trp
            525                 530                 535

gag att aat ggt ccc gaa tca gtg ttg gtc aat act tat caa tgg atc      1686
Glu Ile Asn Gly Pro Glu Ser Val Leu Val Asn Thr Tyr Gln Trp Ile
        540                 545                 550

atc agg aac tgg gaa att gtg aaa att caa tgg tca cag gat ccc aca      1734
Ile Arg Asn Trp Glu Ile Val Lys Ile Gln Trp Ser Gln Asp Pro Thr
    555                 560                 565

atg tta tac aat aag ata gaa ttt gag cca ttc cag tcc ctg gtc cct      1782
Met Leu Tyr Asn Lys Ile Glu Phe Glu Pro Phe Gln Ser Leu Val Pro
570                 575                 580                 585

agg gcc acc aga agc caa tac agc ggt ttc gta aga acc ctg ttt cag      1830
Arg Ala Thr Arg Ser Gln Tyr Ser Gly Phe Val Arg Thr Leu Phe Gln
            590                 595                 600

caa atg cga gat gta ctt gga aca ttt gat act gct caa ata ata aaa      1878
Gln Met Arg Asp Val Leu Gly Thr Phe Asp Thr Ala Gln Ile Ile Lys
            605                 610                 615

ctc ctc cct ttt gcc gct gct cct ccg gaa cag agt agg atg cag ttc      1926
Leu Leu Pro Phe Ala Ala Ala Pro Pro Glu Gln Ser Arg Met Gln Phe
        620                 625                 630

tct tct ttg act gtt aat gta aga gga tcg gga atg agg ata ctt gta      1974
Ser Ser Leu Thr Val Asn Val Arg Gly Ser Gly Met Arg Ile Leu Val
    635                 640                 645

aga ggc aat tcc cca gtg ttc aac tac aat aaa gcc act aag agg ctc      2022
Arg Gly Asn Ser Pro Val Phe Asn Tyr Asn Lys Ala Thr Lys Arg Leu
650                 655                 660                 665

aca gtc ctc gga aaa gat gca ggt gcg ctt act gaa gac cca gat gaa      2070
Thr Val Leu Gly Lys Asp Ala Gly Ala Leu Thr Glu Asp Pro Asp Glu
            670                 675                 680

ggt acg gct gga gta gaa tct gct gtt cta aga ggg ttt ctc att tta      2118
Gly Thr Ala Gly Val Glu Ser Ala Val Leu Arg Gly Phe Leu Ile Leu
            685                 690                 695

ggt aaa gaa aac aag aga tat ggc cca gca cta agc atc aat gaa ctg      2166
Gly Lys Glu Asn Lys Arg Tyr Gly Pro Ala Leu Ser Ile Asn Glu Leu
        700                 705                 710

agc aaa ctt gca aaa ggg gag aaa gct aat gtg cta att ggg caa ggg      2214
Ser Lys Leu Ala Lys Gly Glu Lys Ala Asn Val Leu Ile Gly Gln Gly
    715                 720                 725

gac gtg gtg ttg gta atg aaa cgg aaa cgt gac tct agc ata ctt act      2262
Asp Val Val Leu Val Met Lys Arg Lys Arg Asp Ser Ser Ile Leu Thr
730                 735                 740                 745

gac agc cag aca gcg acc aaa agg att cgg atg gcc atc aat              2304
Asp Ser Gln Thr Ala Thr Lys Arg Ile Arg Met Ala Ile Asn
            750                 755

tagtgttgaa ttgtttaaaa acgaccttgt ttctact                             2341


<210> SEQ ID NO 48
<211> LENGTH: 759
<212> TYPE: PRT
<213> ORGANISM: Equine influenza virus H3N8

<400> SEQUENCE: 48

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
```

-continued

```
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Ile His Tyr Pro
            100                 105                 110

Lys Val His Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Gln Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445
```

-continued

```
Trp Gly Ile Glu Pro Ile Asp Asn Val Met Gly Met Ile Gly Ile Leu
    450                 455                 460

Pro Asp Met Thr Pro Ser Thr Glu Met Ser Leu Arg Gly Val Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Ile Leu
            500                 505                 510

Leu Ser Pro Glu Glu Val Ser Glu Thr Gln Gly Thr Glu Lys Leu Thr
        515                 520                 525

Ile Ile Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Ile Val
545                 550                 555                 560

Lys Ile Gln Trp Ser Gln Asp Pro Thr Met Leu Tyr Asn Lys Ile Glu
                565                 570                 575

Phe Glu Pro Phe Gln Ser Leu Val Pro Arg Ala Thr Arg Ser Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asn Lys Arg Tyr
    690                 695                 700

Gly Pro Ala Leu Ser Ile Asn Glu Leu Ser Lys Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755
```

<210> SEQ ID NO 49
<211> LENGTH: 2277
<212> TYPE: DNA
<213> ORGANISM: Equine influenza virus H3N8

<400> SEQUENCE: 49

```
atggagagaa taaaagaact gagagatcta atgtcacaat cccgcacccg cgagatacta      60

acaaaaacta ctgtggacca catggccata atcaagaaat acacatcagg aagacaagag     120

aagaaccccg cacttaggat gaagtggatg atggcaatga aataccaat tacagcagat      180

aagaggataa tggaaatgat tcctgagaga aatgaacagg ggcaaaccct ttggagcaaa     240

acgaacgatg ctggctcaga ccgcgtaatg gtatcacctc tggcagtgac atggtggaat     300
```

-continued

```
aggaatggac caacaacgag cacaattcat tatccaaaag tccacaaaac ttattttgaa     360

aaagttgaaa gattaaaaca cggaaccttt ggccccgttc attttaggaa tcaagtcaag     420

ataagacgga gagttgatgt aaaccctggt cacgcggacc tcagtgccaa agaagcacaa     480

gatgtgatca tggaagttgt tttcccaaat gaagtgggag ccagaattct aacatcggaa     540

tcacaactaa caataaccaa agagaaaaaa gaagaacttc aggactgcaa aattgccccc     600

ttgatggtag catacatgct agaaagagag ttggtccgaa aaacaagatt cctcccagtg     660

gctggcggaa caagcagtgt atacattgaa gtgttgcatc tgactcaggg aacatgctgg     720

gaacaaatgt acaccccagg aggagaagtt agaaacgatg acattgatca aagtttaatt     780

attgctgccc ggaacatagt gagaagagcg acagtatcag cagatccact agcatccctg     840

ctggaaatgt gccacagtac acagattggt ggaataagga tggtagacat ccttaagcag     900

aatccaacag aggaacaagc tgtggatata tgcaaagcag caatggggtt aagaattagc     960

tcatcattca gctttggtgg attcaccttt aagagaacaa gtggatcatc agtcaagaga    1020

gaagaagaaa tgcttacggg caaccttcaa acattgaaaa taagagtgca tgaaggctat    1080

gaagaattca caatggtcgg aagaagagca acagccattc tcagaaaggc aaccagaaga    1140

ttgattcaat tgatagtaag tgggagagat gaacaatcaa ttgctgaagc aataattgta    1200

gccatggtgt tttcgcaaga agattgcatg atacaagcag ttcgaggcga tttgaacttc    1260

gttaatagag caaatcagcg cttgaacccc atgcatcaac tcttgaggca tttccaaaaa    1320

gatgcaaaag tgcttttcca gaattggggg attgaaccca tcgacaatgt gatgggaatg    1380

attggaatat tgcctgacat gaccccaagc accgagatgt cattgagagg agtgagagtc    1440

agcaaaatgg gagtggatga gtactccagc actgagagag tggtggtgag cattgaccgt    1500

tttttaagag ttcgggatca aaggggaaac atactactgt cccctgaaga ggtcagtgaa    1560

acacaaggaa cggaaaagct gacaataatt tattcatcat caatgatgtg ggagattaat    1620

ggtcccgaat cagtgttggt caatacttat caatggatca tcaggaactg ggaaattgtg    1680

aaaattcaat ggtcacagga tcccacaatg ttatacaata agatagaatt tgagccattc    1740

cagtccctgg tccctagggc caccagaagc caatacagcg gtttcgtaag aaccctgttt    1800

cagcaaatgc gagatgtact tggaacattt gatactgctc aaataataaa actcctccct    1860

tttgccgctg ctcctccgga acagagtagg atgcagttct cttctttgac tgttaatgta    1920

agaggatcgg gaatgaggat acttgtaaga ggcaattccc cagtgttcaa ctacaataaa    1980

gccactaaga ggctcacagt cctcggaaaa gatgcaggtg cgcttactga agacccagat    2040

gaaggtacgg ctggagtaga atctgctgtt ctaagagggt ttctcatttt aggtaaagaa    2100

aacaagagat atggcccagc actaagcatc aatgaactga gcaaacttgc aaaaggggag    2160

aaagctaatg tgctaattgg gcaaggggac gtggtgttgg taatgaaacg gaaacgtgac    2220

tctagcatac ttactgacag ccagacagcg accaaaagga ttcggatggc catcaat       2277
```

```
<210> SEQ ID NO 50
<211> LENGTH: 891
<212> TYPE: DNA
<213> ORGANISM: Equine influenza virus H3N8
<220> FEATURE:
<221> NAME/KEY: CDS
<222> LOCATION: (27)..(716)
<223> OTHER INFORMATION:

<400> SEQUENCE: 50

agcaaaagca gggtgacaaa aacata atg gat tcc aac act gtg tca agc ttt      53
```

-continued

```
                              Met Asp Ser Asn Thr Val Ser Ser Phe
                              1               5

cag gta gac tgt ttt ctt tgg cat gtc cgc aaa cga ttt gca gac caa      101
Gln Val Asp Cys Phe Leu Trp His Val Arg Lys Arg Phe Ala Asp Gln
10                  15                  20                  25

gaa ctg ggt gat gcc cca ttc ctt gac cgg ctt cgc cga gac cag aag      149
Glu Leu Gly Asp Ala Pro Phe Leu Asp Arg Leu Arg Arg Asp Gln Lys
                30                  35                  40

tcc cta aaa gga aga ggt agc act ctt ggt ctg gac atc gaa aca gcc      197
Ser Leu Lys Gly Arg Gly Ser Thr Leu Gly Leu Asp Ile Glu Thr Ala
            45                  50                  55

act cgt gca gga aag cag ata gtg gag cag att ctg gaa gag gaa tca      245
Thr Arg Ala Gly Lys Gln Ile Val Glu Gln Ile Leu Glu Glu Glu Ser
        60                  65                  70

gat gag gca ctt aaa atg acc att gcc tct gtt cct gct tca cgc tac      293
Asp Glu Ala Leu Lys Met Thr Ile Ala Ser Val Pro Ala Ser Arg Tyr
    75                  80                  85

tta act gac atg act ctt gat gag atg tca aga gac tgg ttc atg ctc      341
Leu Thr Asp Met Thr Leu Asp Glu Met Ser Arg Asp Trp Phe Met Leu
90                  95                  100                 105

atg ccc aag cag aaa gta aca ggc tcc cta tgt ata aga atg gac cag      389
Met Pro Lys Gln Lys Val Thr Gly Ser Leu Cys Ile Arg Met Asp Gln
                110                 115                 120

gca atc atg gat aag aac atc ata ctt aaa gca aac ttt agt gtg att      437
Ala Ile Met Asp Lys Asn Ile Ile Leu Lys Ala Asn Phe Ser Val Ile
            125                 130                 135

ttc gaa agg ctg gag aca cta ata cta ctt aga gcc ttc acc gaa gaa      485
Phe Glu Arg Leu Glu Thr Leu Ile Leu Leu Arg Ala Phe Thr Glu Glu
        140                 145                 150

gga gca gtc gtt ggc gaa att tca cca ttg cct tct ctt cca gga cat      533
Gly Ala Val Val Gly Glu Ile Ser Pro Leu Pro Ser Leu Pro Gly His
    155                 160                 165

act aat gag gat gtc aaa aat gca att ggg gtc ctc atc gga gga ctt      581
Thr Asn Glu Asp Val Lys Asn Ala Ile Gly Val Leu Ile Gly Gly Leu
170                 175                 180                 185

aaa tgg aat gat aat acg gtt aga atc tct gaa act cta cag aga ttc      629
Lys Trp Asn Asp Asn Thr Val Arg Ile Ser Glu Thr Leu Gln Arg Phe
                190                 195                 200

gct tgg aga agc agt cat gag aat ggg aga cct tca ttc cct cca aag      677
Ala Trp Arg Ser Ser His Glu Asn Gly Arg Pro Ser Phe Pro Pro Lys
            205                 210                 215

cag aaa cga aaa atg gag aga aca att gag cca gaa gtt tgaagaaata       726
Gln Lys Arg Lys Met Glu Arg Thr Ile Glu Pro Glu Val
        220                 225                 230

agatggttga ttgaagaagt gcgacataga ttgaaaaata cagaaaatag ttttgaacaa    786

ataacattta tgcaagcctt acaactattg cttgaagtag gacaagagat aagaactttc    846

tcgtttcagc ttatttaatg ataaaaaaca cccttgtttc tacta                    891


<210> SEQ ID NO 51
<211> LENGTH: 230
<212> TYPE: PRT
<213> ORGANISM: Equine influenza virus H3N8

<400> SEQUENCE: 51

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30
```

-continued

```
Leu Asp Arg Leu Arg Arg Asp Gln Lys Ser Leu Lys Gly Arg Gly Ser
        35                  40                  45

Thr Leu Gly Leu Asp Ile Glu Thr Ala Thr Arg Ala Gly Lys Gln Ile
    50                  55                  60

Val Glu Gln Ile Leu Glu Glu Glu Ser Asp Glu Ala Leu Lys Met Thr
65                  70                  75                  80

Ile Ala Ser Val Pro Ala Ser Arg Tyr Leu Thr Asp Met Thr Leu Asp
                85                  90                  95

Glu Met Ser Arg Asp Trp Phe Met Leu Met Pro Lys Gln Lys Val Thr
            100                 105                 110

Gly Ser Leu Cys Ile Arg Met Asp Gln Ala Ile Met Asp Lys Asn Ile
        115                 120                 125

Ile Leu Lys Ala Asn Phe Ser Val Ile Phe Glu Arg Leu Glu Thr Leu
    130                 135                 140

Ile Leu Leu Arg Ala Phe Thr Glu Glu Gly Ala Val Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Lys Trp Asn Asp Asn Thr Val
            180                 185                 190

Arg Ile Ser Glu Thr Leu Gln Arg Phe Ala Trp Arg Ser Ser His Glu
        195                 200                 205

Asn Gly Arg Pro Ser Phe Pro Pro Lys Gln Lys Arg Lys Met Glu Arg
    210                 215                 220

Thr Ile Glu Pro Glu Val
225                 230
```

<210> SEQ ID NO 52
<211> LENGTH: 690
<212> TYPE: DNA
<213> ORGANISM: Equine influenza virus H3N8

<400> SEQUENCE: 52

```
atggattcca acactgtgtc aagctttcag gtagactgtt ttctttggca tgtccgcaaa      60

cgatttgcag accaagaact gggtgatgcc ccattccttg accggcttcg ccgagaccag     120

aagtccctaa aaggaagagg tagcactctt ggtctggaca tcgaaacagc cactcgtgca     180

ggaaagcaga tagtggagca gattctggaa gaggaatcag atgaggcact taaaatgacc     240

attgcctctg ttcctgcttc acgctactta actgacatga ctcttgatga gatgtcaaga     300

gactggttca tgctcatgcc caagcagaaa gtaacaggct ccctatgtat aagaatggac     360

caggcaatca tggataagaa catcatactt aaagcaaact ttagtgtgat tttcgaaagg     420

ctggagacac taatactact tagagccttc accgaagaag gagcagtcgt tggcgaaatt     480

tcaccattgc cttctcttcc aggacatact aatgaggatg tcaaaaatgc aattggggtc     540

ctcatcggag gacttaaatg gaatgataat acggttagaa tctctgaaac tctacagaga     600

ttcgcttgga gaagcagtca tgagaatggg agaccttcat tccctccaaa gcagaaacga     660

aaaatggaga gaacaattga gccagaagtt                                      690
```

<210> SEQ ID NO 53
<211> LENGTH: 888
<212> TYPE: DNA
<213> ORGANISM: Equine influenza virus H3N8

<400> SEQUENCE: 53

-continued

```
caaaagcagg gtgacaaaaa catgatggat tccaacactg tgtcaagctt tcaggtagac     60

tgttttcttt ggcatgtccg caaacgattt gcagaccaag aactgggtga tgccccattc    120

cttgaccggc ttcgccgaga ccagaagtcc ctaaaaggaa gaggtagcac tcttggtctg    180

gacatcgaaa cagccactcg tgcaggaaag cagatagtgg agcagattct ggaagaggaa    240

tcagatgagg cacttaaaat gaccattgcc tctgttcctg cttcacgcta cttaactgac    300

atgactcttg atgagatgtc aagagactgg ttcatgctca tgcccaagca gaaagtaaca    360

ggctccctat gtataagaat ggaccaggca atcatggata agaacatcat acttaaagca    420

aactttagtg tgattttcga aaggctggag acactaatac tacttagagc cttcaccgaa    480

gaaggagcag tcgttggcga aatttcacca ttgccttctc ttccaggaca tactaatgag    540

gatgtcaaaa atgcaattgg ggtcctcatc ggaggactta aatggaatga taatacggtt    600

agaatctctg aaactctaca gagattcgct tggagaagca gtcatgagaa tgggagacct    660

tcattccctc caaagcagaa acgaaaaatg gagagaacaa ttgagccaga agtttgaaga    720

aataagatgg ttgattgaag aagtgcgaca tagattgaaa aatacagaaa atagttttga    780

acaaataaca tttatgcaag ccttacaact attgcttgaa gtagaacaag agataagaac    840

tttctcgttt cagcttattt aatgataaaa aacacccttg tttctact                 888
```

```
<210> SEQ ID NO 54
<211> LENGTH: 468
<212> TYPE: DNA
<213> ORGANISM: Equine influenza virus H3N8
<220> FEATURE:
<221> NAME/KEY: CDS
<222> LOCATION: (3)..(293)
<223> OTHER INFORMATION:

<400> SEQUENCE: 54

ac ttt agt gtg att ttc gaa agg ctg gag aca cta ata cta ctt aga        47
   Phe Ser Val Ile Phe Glu Arg Leu Glu Thr Leu Ile Leu Leu Arg
   1               5                   10                  15

gcc ttc acc gaa gaa gga gca gtc gtt ggc gaa att tca cca ttg cct       95
Ala Phe Thr Glu Glu Gly Ala Val Val Gly Glu Ile Ser Pro Leu Pro
                20                  25                  30

tct ctt cca gga cat act aat gag gat gtc aaa aat gca att ggg gtc      143
Ser Leu Pro Gly His Thr Asn Glu Asp Val Lys Asn Ala Ile Gly Val
            35                  40                  45

ctc atc gga gga ctt aaa tgg aat gat aat acg gtt aga atc tct gaa      191
Leu Ile Gly Gly Leu Lys Trp Asn Asp Asn Thr Val Arg Ile Ser Glu
        50                  55                  60

act cta cag aga ttc gct cgg aga agc agt cat gag aat ggg aga cct      239
Thr Leu Gln Arg Phe Ala Arg Arg Ser Ser His Glu Asn Gly Arg Pro
    65                  70                  75

tca ttc cct cca aag cag aaa cga aaa atg gag aga aca att gag cca      287
Ser Phe Pro Pro Lys Gln Lys Arg Lys Met Glu Arg Thr Ile Glu Pro
80                  85                  90                  95

gaa gtt tgaagaaata agatggttga ttgaagaagt gcgacataga ttgaaaaata      343
Glu Val

cagaaaatag ttttgaacaa ataacattta tgcaagcctt acaactattg cttgaagtag    403

aacaagagat aagaactttc tcgtttcagc ttatttaatg ataaaaaaca cccttgtttc    463

tacta                                                                468

<210> SEQ ID NO 55
<211> LENGTH: 97
<212> TYPE: PRT
```

-continued

<213> ORGANISM: Equine influenza virus H3N8

<400> SEQUENCE: 55

```
Phe Ser Val Ile Phe Glu Arg Leu Glu Thr Leu Ile Leu Leu Arg Ala
1               5                   10                  15

Phe Thr Glu Glu Gly Ala Val Val Gly Glu Ile Ser Pro Leu Pro Ser
            20                  25                  30

Leu Pro Gly His Thr Asn Glu Asp Val Lys Asn Ala Ile Gly Val Leu
        35                  40                  45

Ile Gly Gly Leu Lys Trp Asn Asp Asn Thr Val Arg Ile Ser Glu Thr
    50                  55                  60

Leu Gln Arg Phe Ala Arg Arg Ser Ser His Glu Asn Gly Arg Pro Ser
65                  70                  75                  80

Phe Pro Pro Lys Gln Lys Arg Lys Met Glu Arg Thr Ile Glu Pro Glu
                85                  90                  95

Val
```

<210> SEQ ID NO 56
<211> LENGTH: 293
<212> TYPE: DNA
<213> ORGANISM: Equine influenza virus H3N8

<400> SEQUENCE: 56

```
actttagtgt gattttcgaa aggctggaga cactaatact acttagagcc ttcaccgaag     60

aaggagcagt cgttggcgaa atttcaccat tgccttctct tccaggacat actaatgagg    120

atgtcaaaaa tgcaattggg gtcctcatcg gaggacttaa atggaatgat aatacggtta    180

gaatctctga aactctacag agattcgctc ggagaagcag tcatgagaat gggagacctt    240

cattccctcc aaagcagaaa cgaaaaatgg agagaacaat tgagccagaa gtt           293
```

<210> SEQ ID NO 57
<211> LENGTH: 888
<212> TYPE: DNA
<213> ORGANISM: Equine influenza virus H3N8
<220> FEATURE:
<221> NAME/KEY: CDS
<222> LOCATION: (27)..(716)
<223> OTHER INFORMATION:

<400> SEQUENCE: 57

```
agcaaaagca gggtgacaaa aacata atg gat tcc aac act gtg tca agc ttt      53
                             Met Asp Ser Asn Thr Val Ser Ser Phe
                             1               5

cag gta gac tgt ttt ctt tgg cat gtc cgc aaa cga ttt gca gac caa      101
Gln Val Asp Cys Phe Leu Trp His Val Arg Lys Arg Phe Ala Asp Gln
10                  15                  20                  25

gaa ctg ggt gat gcc cca ttc ctt gac cgg ctt cgc cga gac cag aag      149
Glu Leu Gly Asp Ala Pro Phe Leu Asp Arg Leu Arg Arg Asp Gln Lys
                30                  35                  40

tcc cta aaa gga aga ggt agc act ctt ggt ctg gac atc gaa aca gcc      197
Ser Leu Lys Gly Arg Gly Ser Thr Leu Gly Leu Asp Ile Glu Thr Ala
            45                  50                  55

act cgt gca gga aag cag ata gtg gag cag att ctg gaa gag gaa tca      245
Thr Arg Ala Gly Lys Gln Ile Val Glu Gln Ile Leu Glu Glu Glu Ser
        60                  65                  70

gat gag gca ctt aaa atg acc att gcc tct gtt cct gct tca cgc tac      293
Asp Glu Ala Leu Lys Met Thr Ile Ala Ser Val Pro Ala Ser Arg Tyr
    75                  80                  85

tta act gac atg act ctt gat gag atg tca aga gac tgg ttc atg ctc      341
```

-continued

```
Leu Thr Asp Met Thr Leu Asp Glu Met Ser Arg Asp Trp Phe Met Leu
90                  95                  100                 105

atg ccc aag cag aaa gta aca ggc tcc cta tgt ata aga atg gac cag      389
Met Pro Lys Gln Lys Val Thr Gly Ser Leu Cys Ile Arg Met Asp Gln
                110                 115                 120

gca atc atg gat aag aac atc ata ctt aaa gca aac ttt agt gtg att      437
Ala Ile Met Asp Lys Asn Ile Ile Leu Lys Ala Asn Phe Ser Val Ile
            125                 130                 135

ttc gaa agg ctg gag aca cta ata cta ctt aga gcc ttc acc gaa gaa      485
Phe Glu Arg Leu Glu Thr Leu Ile Leu Leu Arg Ala Phe Thr Glu Glu
        140                 145                 150

gga gca gtc gtt ggc gaa att tca cca ttg cct tct ctt cca gga cat      533
Gly Ala Val Val Gly Glu Ile Ser Pro Leu Pro Ser Leu Pro Gly His
    155                 160                 165

act aat gag gat gtc aaa aat gca att ggg gtc ctc atc gga gga ctt      581
Thr Asn Glu Asp Val Lys Asn Ala Ile Gly Val Leu Ile Gly Gly Leu
170                 175                 180                 185

aaa tgg aat gat aat acg gtt aga atc tct gaa act cta cag aga ttc      629
Lys Trp Asn Asp Asn Thr Val Arg Ile Ser Glu Thr Leu Gln Arg Phe
                190                 195                 200

gct tgg aga agc agt cat gag aat ggg aga cct tca ttc cct cca aag      677
Ala Trp Arg Ser Ser His Glu Asn Gly Arg Pro Ser Phe Pro Pro Lys
            205                 210                 215

cag aaa cga aaa atg gag aga aca att gag cca gaa gtt tgaagaaata      726
Gln Lys Arg Lys Met Glu Arg Thr Ile Glu Pro Glu Val
        220                 225                 230

agatggttga ttgaagaagt gcgacataga ttgaaaaata cagaaaatag ttttgaacaa    786

ataacattta tgcaagcctt acaactattg cttgaagtag aacaagagat aagaactttc    846

tcgtttcagc ttatttaatg ataaaaaaca cccttgtttc ta                       888


<210> SEQ ID NO 58
<211> LENGTH: 230
<212> TYPE: PRT
<213> ORGANISM: Equine influenza virus H3N8

<400> SEQUENCE: 58

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Lys Gly Arg Gly Ser
        35                  40                  45

Thr Leu Gly Leu Asp Ile Glu Thr Ala Thr Arg Ala Gly Lys Gln Ile
    50                  55                  60

Val Glu Gln Ile Leu Glu Glu Glu Ser Asp Glu Ala Leu Lys Met Thr
65                  70                  75                  80

Ile Ala Ser Val Pro Ala Ser Arg Tyr Leu Thr Asp Met Thr Leu Asp
                85                  90                  95

Glu Met Ser Arg Asp Trp Phe Met Leu Met Pro Lys Gln Lys Val Thr
            100                 105                 110

Gly Ser Leu Cys Ile Arg Met Asp Gln Ala Ile Met Asp Lys Asn Ile
        115                 120                 125

Ile Leu Lys Ala Asn Phe Ser Val Ile Phe Glu Arg Leu Glu Thr Leu
    130                 135                 140

Ile Leu Leu Arg Ala Phe Thr Glu Glu Gly Ala Val Val Gly Glu Ile
145                 150                 155                 160
```

-continued

```
Ser Pro Leu Pro Ser Leu Pro Gly His Thr Asn Glu Asp Val Lys Asn
            165                 170                 175

Ala Ile Gly Val Leu Ile Gly Gly Leu Lys Trp Asn Asp Asn Thr Val
        180                 185                 190

Arg Ile Ser Glu Thr Leu Gln Arg Phe Ala Trp Arg Ser Ser His Glu
    195                 200                 205

Asn Gly Arg Pro Ser Phe Pro Pro Lys Gln Lys Arg Lys Met Glu Arg
210                 215                 220

Thr Ile Glu Pro Glu Val
225                 230


<210> SEQ ID NO 59
<211> LENGTH: 690
<212> TYPE: DNA
<213> ORGANISM: Equine influenza virus H3N8

<400> SEQUENCE: 59

atggattcca acactgtgtc aagctttcag gtagactgtt ttctttggca tgtccgcaaa      60

cgatttgcag accaagaact gggtgatgcc ccattccttg accggcttcg ccgagaccag     120

aagtccctaa aaggaagagg tagcactctt ggtctggaca tcgaaacagc cactcgtgca     180

ggaaagcaga tagtggagca gattctggaa gaggaatcag atgaggcact taaaatgacc     240

attgcctctg ttcctgcttc acgctactta actgacatga ctcttgatga gatgtcaaga     300

gactggttca tgctcatgcc caagcagaaa gtaacaggct ccctatgtat aagaatggac     360

caggcaatca tggataagaa catcatactt aaagcaaact ttagtgtgat tttcgaaagg     420

ctggagacac taatactact tagagccttc accgaagaag gagcagtcgt tggcgaaatt     480

tcaccattgc cttctcttcc aggacatact aatgaggatg tcaaaaatgc aattggggtc     540

ctcatcggag gacttaaatg gaatgataat acggttagaa tctctgaaac tctacagaga     600

ttcgcttgga gaagcagtca tgagaatggg agaccttcat tccctccaaa gcagaaacga     660

aaaatggaga gaacaattga gccagaagtt                                      690


<210> SEQ ID NO 60
<211> LENGTH: 21
<212> TYPE: DNA
<213> ORGANISM: Artificial sequence
<220> FEATURE:
<223> OTHER INFORMATION: Synthetic Primer

<400> SEQUENCE: 60

agcaaagcag gtgacaaaaa c                                                21


<210> SEQ ID NO 61
<211> LENGTH: 19
<212> TYPE: DNA
<213> ORGANISM: Artificial sequence
<220> FEATURE:
<223> OTHER INFORMATION: Synthetic Primer

<400> SEQUENCE: 61

agtagaaaca agggtgttt                                                   19


<210> SEQ ID NO 62
<211> LENGTH: 1229
<212> TYPE: DNA
<213> ORGANISM: Equine influenza virus H3N8
<220> FEATURE:
<221> NAME/KEY: CDS
<222> LOCATION: (36)..(1229)
```

-continued

```
<223> OTHER INFORMATION:

<400> SEQUENCE: 62

gaattcggct tagcaaaagc aggcaaacta tttga atg gat gtc aat ccg act       53
                                       Met Asp Val Asn Pro Thr
                                       1               5

cta ctc ttc tta aag gtg cca gcg caa aat gct ata agc aca aca ttc     101
Leu Leu Phe Leu Lys Val Pro Ala Gln Asn Ala Ile Ser Thr Thr Phe
            10                  15                  20

cct tat act gga gat cct ccc tac agt cat gga aca ggg aca gga tac     149
Pro Tyr Thr Gly Asp Pro Pro Tyr Ser His Gly Thr Gly Thr Gly Tyr
        25                  30                  35

acc atg gat act gtc aac aga aca cat caa tac tca gaa aag ggg aaa     197
Thr Met Asp Thr Val Asn Arg Thr His Gln Tyr Ser Glu Lys Gly Lys
    40                  45                  50

tgg aca aca aac act gag att gga gca cca caa ctt aat cca atc gat     245
Trp Thr Thr Asn Thr Glu Ile Gly Ala Pro Gln Leu Asn Pro Ile Asp
55                  60                  65                  70

gga ccg ctt cct gaa gac aat gaa cca agt ggg tac gcc caa aca gat     293
Gly Pro Leu Pro Glu Asp Asn Glu Pro Ser Gly Tyr Ala Gln Thr Asp
                75                  80                  85

tgt gta ttg gaa gca atg gct ttc ctt gaa gaa tcc cat ccc gga atc     341
Cys Val Leu Glu Ala Met Ala Phe Leu Glu Glu Ser His Pro Gly Ile
            90                  95                  100

ttt gaa aat tcg tgt ctt gaa aca atg gag gtg gtt cag cag aca aga     389
Phe Glu Asn Ser Cys Leu Glu Thr Met Glu Val Val Gln Gln Thr Arg
        105                 110                 115

gtg gac aaa cta aca caa ggc cga caa act tac gat tgg acc ttg aat     437
Val Asp Lys Leu Thr Gln Gly Arg Gln Thr Tyr Asp Trp Thr Leu Asn
    120                 125                 130

agg aat caa cct gcc gca aca gca ctt gct aat aca att gaa gtg ttc     485
Arg Asn Gln Pro Ala Ala Thr Ala Leu Ala Asn Thr Ile Glu Val Phe
135                 140                 145                 150

aga tca aat gat ctg act tcc agt gag tca ggg aga tta atg gac ttc     533
Arg Ser Asn Asp Leu Thr Ser Ser Glu Ser Gly Arg Leu Met Asp Phe
                155                 160                 165

ctc aaa gat gtc atg gag tcc atg aac aag gaa gaa atg gaa ata aca     581
Leu Lys Asp Val Met Glu Ser Met Asn Lys Glu Glu Met Glu Ile Thr
            170                 175                 180

aca cac ttc caa cgg aag aga aga gta aga gac aac atg aca aag aga     629
Thr His Phe Gln Arg Lys Arg Arg Val Arg Asp Asn Met Thr Lys Arg
        185                 190                 195

atg gtg aca cag aga acc ata ggg aag aaa aaa caa cga tta aac aga     677
Met Val Thr Gln Arg Thr Ile Gly Lys Lys Lys Gln Arg Leu Asn Arg
    200                 205                 210

aag agc tat ctg atc agg gca tta acc tta aac aca atg acc aag gac     725
Lys Ser Tyr Leu Ile Arg Ala Leu Thr Leu Asn Thr Met Thr Lys Asp
215                 220                 225                 230

gct gag aga ggg aaa ttg aaa cga cga gca att gca acc cca gga atg     773
Ala Glu Arg Gly Lys Leu Lys Arg Arg Ala Ile Ala Thr Pro Gly Met
                235                 240                 245

cag ata aga ggg ttt gta tat ttt gtt gaa aca tta gcc cga aga ata     821
Gln Ile Arg Gly Phe Val Tyr Phe Val Glu Thr Leu Ala Arg Arg Ile
            250                 255                 260

tgt gaa aag ctt gaa caa tca gga ttg cca gtt ggc ggt aat gag aaa     869
Cys Glu Lys Leu Glu Gln Ser Gly Leu Pro Val Gly Gly Asn Glu Lys
        265                 270                 275

aag gcc aaa ctg gct aat gtc gtc aga aaa atg atg act aat tcc caa     917
Lys Ala Lys Leu Ala Asn Val Val Arg Lys Met Met Thr Asn Ser Gln
    280                 285                 290
```

-continued

```
gac act gaa ctc tcc ttc acc atc act ggg gac aat acc aaa tgg aat      965
Asp Thr Glu Leu Ser Phe Thr Ile Thr Gly Asp Asn Thr Lys Trp Asn
295                 300                 305                 310

gaa aat cag aac cca cgc atg ttc ctg gca atg atc aca tac ata act     1013
Glu Asn Gln Asn Pro Arg Met Phe Leu Ala Met Ile Thr Tyr Ile Thr
                315                 320                 325

aga aac cag cca gaa tgg ttc aga aat gtt cta agc att gca ccg att     1061
Arg Asn Gln Pro Glu Trp Phe Arg Asn Val Leu Ser Ile Ala Pro Ile
            330                 335                 340

atg ttc tca aat aaa atg gca aga ctg ggg aaa gga tat atg ttt gaa     1109
Met Phe Ser Asn Lys Met Ala Arg Leu Gly Lys Gly Tyr Met Phe Glu
        345                 350                 355

agc aaa agt atg aaa ttg aga act caa ata cca gca gaa atg ctc gca     1157
Ser Lys Ser Met Lys Leu Arg Thr Gln Ile Pro Ala Glu Met Leu Ala
    360                 365                 370

agc att gat ctg aaa tat ttc aat gat tca aca aaa aag aaa att gag     1205
Ser Ile Asp Leu Lys Tyr Phe Asn Asp Ser Thr Lys Lys Lys Ile Glu
375                 380                 385                 390

aag ata cga cca caa gcc gaa ttc                                     1229
Lys Ile Arg Pro Gln Ala Glu Phe
                395


<210> SEQ ID NO 63
<211> LENGTH: 398
<212> TYPE: PRT
<213> ORGANISM: Equine influenza virus H3N8

<400> SEQUENCE: 63

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Asp Leu Thr Ser Ser Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu Asn Arg Lys Ser Tyr Leu Ile Arg Ala Leu Thr Leu
    210                 215                 220
```

-continued

```
Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Lys Ile Arg Pro Gln Ala Glu Phe
385                 390                 395


<210> SEQ ID NO 64
<211> LENGTH: 1194
<212> TYPE: DNA
<213> ORGANISM: Equine influenza virus H3N8

<400> SEQUENCE: 64

atggatgtca atccgactct actcttctta aaggtgccag cgcaaaatgc tataagcaca     60

acattccctt atactggaga tcctccctac agtcatggaa cagggacagg atacaccatg    120

gatactgtca acagaacaca tcaatactca gaaaagggga aatggacaac aaacactgag    180

attggagcac cacaacttaa tccaatcgat ggaccgcttc ctgaagacaa tgaaccaagt    240

gggtacgccc aaacagattg tgtattggaa gcaatggctt tccttgaaga atcccatccc    300

ggaatctttg aaaattcgtg tcttgaaaca atggaggtgg ttcagcagac aagagtggac    360

aaactaacac aaggccgaca aacttacgat tggaccttga ataggaatca acctgccgca    420

acagcacttg ctaatacaat tgaagtgttc agatcaaatg atctgacttc cagtgagtca    480

gggagattaa tggacttcct caaagatgtc atggagtcca tgaacaagga agaaatggaa    540

ataacaacac acttccaacg gaagagaaga gtaagagaca acatgacaaa gagaatggtg    600

acacagagaa ccatagggaa gaaaaaacaa cgattaaaca gaaagagcta tctgatcagg    660

gcattaacct taaacacaat gaccaaggac gctgagagag ggaaattgaa acgacgagca    720

attgcaaccc caggaatgca gataagaggg tttgtatatt ttgttgaaac attagcccga    780

agaatatgtg aaaagcttga acaatcagga ttgccagttg gcggtaatga gaaaaaggcc    840

aaactggcta atgtcgtcag aaaaatgatg actaattccc aagacactga actctccttc    900

accatcactg gggacaatac caaatggaat gaaaatcaga acccacgcat gttcctggca    960

atgatcacat acataactag aaaccagcca gaatggttca gaaatgttct aagcattgca   1020

ccgattatgt tctcaaataa aatggcaaga ctggggaaag gatatatgtt tgaaagcaaa   1080

agtatgaaat tgagaactca aataccagca gaaatgctcg caagcattga tctgaaatat   1140
```

-continued

```
ttcaatgatt caacaaaaaa gaaaattgag aagatacgac cacaagccga attc        1194


<210> SEQ ID NO 65
<211> LENGTH: 673
<212> TYPE: DNA
<213> ORGANISM: Equine influenza virus H3N8
<220> FEATURE:
<221> NAME/KEY: CDS
<222> LOCATION: (36)..(671)
<223> OTHER INFORMATION:

<400> SEQUENCE: 65

gaattcggct tagcaaaagc aggcaaacta tttga atg gat gtc aat ccg act       53
                                       Met Asp Val Asn Pro Thr
                                       1               5

cta ctc ttc tta aag gtg cca gcg caa aat gct ata agc aca aca ttc     101
Leu Leu Phe Leu Lys Val Pro Ala Gln Asn Ala Ile Ser Thr Thr Phe
            10                  15                  20

cct tat act gga gat cct ccc tac agt cat gga aca ggg aca gga tac     149
Pro Tyr Thr Gly Asp Pro Pro Tyr Ser His Gly Thr Gly Thr Gly Tyr
        25                  30                  35

acc atg gat act gtc aac aga aca cat caa tac tca gaa aag ggg aaa     197
Thr Met Asp Thr Val Asn Arg Thr His Gln Tyr Ser Glu Lys Gly Lys
    40                  45                  50

tgg aca aca aac act gag att gga gca cca caa ctt aat cca atc gat     245
Trp Thr Thr Asn Thr Glu Ile Gly Ala Pro Gln Leu Asn Pro Ile Asp
55                  60                  65                  70

gga ccg ctt cct gaa gac aat gaa cca agt ggg tac gcc caa aca gat     293
Gly Pro Leu Pro Glu Asp Asn Glu Pro Ser Gly Tyr Ala Gln Thr Asp
                75                  80                  85

tgt gta ttg gaa gca atg gct ttc ctt gaa gaa tcc cat ccc gga atc     341
Cys Val Leu Glu Ala Met Ala Phe Leu Glu Glu Ser His Pro Gly Ile
            90                  95                  100

ttt gaa aat tcg tgt ctt gaa aca atg gag gtg gtt cag cag aca aga     389
Phe Glu Asn Ser Cys Leu Glu Thr Met Glu Val Val Gln Gln Thr Arg
        105                 110                 115

gtg gac aaa cta aca caa ggc cga caa act tac gat tgg acc ttg aat     437
Val Asp Lys Leu Thr Gln Gly Arg Gln Thr Tyr Asp Trp Thr Leu Asn
    120                 125                 130

agg aat caa cct gcc gca aca gca ctt gct aat aca att gaa gtg ttc     485
Arg Asn Gln Pro Ala Ala Thr Ala Leu Ala Asn Thr Ile Glu Val Phe
135                 140                 145                 150

aga tca aat gat ctg act tcc agt gag tca ggg aga tta atg gac ttc     533
Arg Ser Asn Asp Leu Thr Ser Ser Glu Ser Gly Arg Leu Met Asp Phe
                155                 160                 165

ctc aaa gat gtc atg gag tcc atg aac aag gaa gaa atg gaa ata aca     581
Leu Lys Asp Val Met Glu Ser Met Asn Lys Glu Glu Met Glu Ile Thr
            170                 175                 180

aca cac ttc caa cgg aag aga aga gta aga gac aac atg aca aag aga     629
Thr His Phe Gln Arg Lys Arg Arg Val Arg Asp Asn Met Thr Lys Arg
        185                 190                 195

atg gtg aca cag aga acc ata ggg aag aaa aaa caa cga tta aa          673
Met Val Thr Gln Arg Thr Ile Gly Lys Lys Lys Gln Arg Leu
    200                 205                 210


<210> SEQ ID NO 66
<211> LENGTH: 212
<212> TYPE: PRT
<213> ORGANISM: Equine influenza virus H3N8

<400> SEQUENCE: 66

Met Asp Val Asn Pro Thr Leu Leu Phe Leu Lys Val Pro Ala Gln Asn
```

-continued

```
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
              115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Asp Leu Thr Ser Ser Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu
    210
```

```
<210> SEQ ID NO 67
<211> LENGTH: 636
<212> TYPE: DNA
<213> ORGANISM: Equine influenza virus H3N8

<400> SEQUENCE: 67

atggatgtca atccgactct actcttctta aaggtgccag cgcaaaatgc tataagcaca     60

acattccctt atactggaga tcctccctac agtcatggaa cagggacagg atacaccatg    120

gatactgtca acagaacaca tcaatactca gaaaagggga aatggacaac aaacactgag    180

attggagcac cacaacttaa tccaatcgat ggaccgcttc ctgaagacaa tgaaccaagt    240

gggtacgccc aaacagattg tgtattggaa gcaatggctt tccttgaaga atcccatccc    300

ggaatctttg aaaattcgtg tcttgaaaca atggaggtgg ttcagcagac aagagtggac    360

aaactaacac aaggccgaca aacttacgat tggaccttga ataggaatca acctgccgca    420

acagcacttg ctaatacaat tgaagtgttc agatcaaatg atctgacttc cagtgagtca    480

gggagattaa tggacttcct caaagatgtc atggagtcca tgaacaagga agaaatggaa    540

ataacaacac acttccaacg gaagagaaga gtaagagaca acatgacaaa gagaatggtg    600

acacagagaa ccatagggaa gaaaaaacaa cgatta                              636

<210> SEQ ID NO 68
<211> LENGTH: 1225
<212> TYPE: DNA
<213> ORGANISM: Equine influenza virus H3N8
<220> FEATURE:
<221> NAME/KEY: CDS
<222> LOCATION: (34)..(1218)
```

-continued

<223> OTHER INFORMATION:

<400> SEQUENCE: 68

```
gaattcagga gcaaaagcag gcaaactatt tga atg gat gtc aat ccg act cta      54
                                     Met Asp Val Asn Pro Thr Leu
                                     1               5

ctc ttc tta aag gtg cca gcg caa aat gct ata agc aca aca ttc cct      102
Leu Phe Leu Lys Val Pro Ala Gln Asn Ala Ile Ser Thr Thr Phe Pro
        10                  15                  20

tat act gga gat cct ccc tac agt cat gga aca ggg aca gga tac acc      150
Tyr Thr Gly Asp Pro Pro Tyr Ser His Gly Thr Gly Thr Gly Tyr Thr
    25                  30                  35

atg gat act gtc aac aga aca cat caa tac tca gaa aag ggg aaa tgg      198
Met Asp Thr Val Asn Arg Thr His Gln Tyr Ser Glu Lys Gly Lys Trp
40                  45                  50                  55

aca aca aac act gag att gga gca cca caa ctt aat cca atc gat gga      246
Thr Thr Asn Thr Glu Ile Gly Ala Pro Gln Leu Asn Pro Ile Asp Gly
                60                  65                  70

ccg ctt cct gaa gac aat gaa cca agt ggg tac gcc caa aca gat tgt      294
Pro Leu Pro Glu Asp Asn Glu Pro Ser Gly Tyr Ala Gln Thr Asp Cys
            75                  80                  85

gta ttg gaa gca atg gct ttc ctt gaa gaa tcc cat ccc gga atc ttt      342
Val Leu Glu Ala Met Ala Phe Leu Glu Glu Ser His Pro Gly Ile Phe
        90                  95                  100

gaa aat tcg tgt ctt gaa aca atg gag gtg gtt cag cag aca aga gtg      390
Glu Asn Ser Cys Leu Glu Thr Met Glu Val Val Gln Gln Thr Arg Val
    105                 110                 115

gac aaa cta aca caa ggc cga caa act tac gat tgg acc ttg aat agg      438
Asp Lys Leu Thr Gln Gly Arg Gln Thr Tyr Asp Trp Thr Leu Asn Arg
120                 125                 130                 135

aat caa cct gcc gca aca gca ctt gct aat aca att gaa gtg ttc aga      486
Asn Gln Pro Ala Ala Thr Ala Leu Ala Asn Thr Ile Glu Val Phe Arg
                140                 145                 150

tca aat gat ctg act tcc agt gag tca ggg aga tta atg gac ttc ctc      534
Ser Asn Asp Leu Thr Ser Ser Glu Ser Gly Arg Leu Met Asp Phe Leu
            155                 160                 165

aaa gat gtc atg gag tcc atg aac aag gaa gaa atg gaa ata aca aca      582
Lys Asp Val Met Glu Ser Met Asn Lys Glu Glu Met Glu Ile Thr Thr
        170                 175                 180

cac ttc caa cgg aag aga aga gta aga gac aac atg aca aag aga atg      630
His Phe Gln Arg Lys Arg Arg Val Arg Asp Asn Met Thr Lys Arg Met
    185                 190                 195

gtg aca cag aga acc ata ggg aag aaa aaa caa cga tta aac aga aag      678
Val Thr Gln Arg Thr Ile Gly Lys Lys Lys Gln Arg Leu Asn Arg Lys
200                 205                 210                 215

agc tat ctg atc agg gca tta acc tta aac aca atg acc aag gac gct      726
Ser Tyr Leu Ile Arg Ala Leu Thr Leu Asn Thr Met Thr Lys Asp Ala
                220                 225                 230

gag aga ggg aaa ttg aaa cga cga gca att gca acc cca gga atg cag      774
Glu Arg Gly Lys Leu Lys Arg Arg Ala Ile Ala Thr Pro Gly Met Gln
            235                 240                 245

ata aga ggg ttt gta tat ttt gtt gaa aca tta gcc cga aga ata tgt      822
Ile Arg Gly Phe Val Tyr Phe Val Glu Thr Leu Ala Arg Arg Ile Cys
        250                 255                 260

gaa aag ctt gaa caa tca gga ttg cca gtt ggc ggt aat gag aaa aag      870
Glu Lys Leu Glu Gln Ser Gly Leu Pro Val Gly Gly Asn Glu Lys Lys
    265                 270                 275

gcc aaa ctg gct aat gtc gtc aga aaa atg atg act aat tcc caa gac      918
Ala Lys Leu Ala Asn Val Val Arg Lys Met Met Thr Asn Ser Gln Asp
280                 285                 290                 295
```

-continued

```
act gaa ctc tcc ttc acc atc act ggg gac aat acc aaa tgg aat gaa      966
Thr Glu Leu Ser Phe Thr Ile Thr Gly Asp Asn Thr Lys Trp Asn Glu
                300                 305                 310

aat cag aac cca cgc atg ttc ctg gca atg atc aca tac ata act aga     1014
Asn Gln Asn Pro Arg Met Phe Leu Ala Met Ile Thr Tyr Ile Thr Arg
            315                 320                 325

aac cag cca gaa tgg ttc aga aat gtt cta agc att gca ccg att atg     1062
Asn Gln Pro Glu Trp Phe Arg Asn Val Leu Ser Ile Ala Pro Ile Met
        330                 335                 340

ttc tca aat aaa atg gca aga ctg ggg aaa gga tat atg ttt gaa agc     1110
Phe Ser Asn Lys Met Ala Arg Leu Gly Lys Gly Tyr Met Phe Glu Ser
    345                 350                 355

aaa agt atg aaa ttg aga act caa ata cca gca gaa atg ctc gca agc     1158
Lys Ser Met Lys Leu Arg Thr Gln Ile Pro Ala Glu Met Leu Ala Ser
360                 365                 370                 375

att gat ctg aaa tat ttc aat gat tca aca aaa aag aaa att gag aag     1206
Ile Asp Leu Lys Tyr Phe Asn Asp Ser Thr Lys Lys Lys Ile Glu Lys
                380                 385                 390

ata cga cca ccc tgaattc                                             1225
Ile Arg Pro Pro
            395


<210> SEQ ID NO 69
<211> LENGTH: 395
<212> TYPE: PRT
<213> ORGANISM: Equine influenza virus H3N8

<400> SEQUENCE: 69

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Asp Leu Thr Ser Ser Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu Asn Arg Lys Ser Tyr Leu Ile Arg Ala Leu Thr Leu
    210                 215                 220
```

-continued

```
Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Lys Ile Arg Pro Pro
385                 390                 395


<210> SEQ ID NO 70
<211> LENGTH: 1185
<212> TYPE: DNA
<213> ORGANISM: Equine influenza virus H3N8

<400> SEQUENCE: 70

atggatgtca atccgactct actcttctta aaggtgccag cgcaaaatgc tataagcaca      60

acattccctt atactggaga tcctccctac agtcatggaa cagggacagg atacaccatg     120

gatactgtca acagaacaca tcaatactca gaaaagggga aatggacaac aaacactgag     180

attggagcac cacaacttaa tccaatcgat ggaccgcttc ctgaagacaa tgaaccaagt     240

gggtacgccc aaacagattg tgtattggaa gcaatggctt tccttgaaga atcccatccc     300

ggaatctttg aaaattcgtg tcttgaaaca atggaggtgg ttcagcagac aagagtggac     360

aaactaacac aaggccgaca aacttacgat tggaccttga ataggaatca acctgccgca     420

acagcacttg ctaatacaat tgaagtgttc agatcaaatg atctgacttc cagtgagtca     480

gggagattaa tggacttcct caaagatgtc atggagtcca tgaacaagga agaaatggaa     540

ataacaacac acttccaacg gaagagaaga gtaagagaca acatgacaaa gagaatggtg     600

acacagagaa ccatagggaa gaaaaaacaa cgattaaaca gaaagagcta tctgatcagg     660

gcattaacct taaacacaat gaccaaggac gctgagagag ggaaattgaa acgacgagca     720

attgcaaccc caggaatgca gataagaggg tttgtatatt ttgttgaaac attagcccga     780

agaatatgtg aaaagcttga acaatcagga ttgccagttg gcggtaatga gaaaaaggcc     840

aaactggcta atgtcgtcag aaaaatgatg actaattccc aagacactga actctccttc     900

accatcactg gggacaatac caaatggaat gaaaatcaga acccacgcat gttcctggca     960

atgatcacat acataactag aaaccagcca gaatggttca gaaatgttct aagcattgca    1020

ccgattatgt tctcaaataa aatggcaaga ctggggaaag gatatatgtt tgaaagcaaa    1080

agtatgaaat tgagaactca aataccagca gaaatgctcg caagcattga tctgaaatat    1140
```

-continued

```
ttcaatgatt caacaaaaaa gaaaattgag aagatacgac caccc                 1185


<210> SEQ ID NO 71
<211> LENGTH: 1221
<212> TYPE: DNA
<213> ORGANISM: Equine influenza virus H3N8

<400> SEQUENCE: 71

gaattcagga aagcaggcaa actatttgaa tggatgtcaa tccgactcta ctcttcttaa   60

aggtgccagc gcaaaatgct ataagcacaa cattccctta tactggagat cctccctaca  120

gtcatggaac agggacagga tacaccatgg atactgtcaa cagaacacat caatactcag  180

aaaaggggaa atggacaaca aacactgaga ttggagcacc acaacttaat ccaatcgatg  240

gaccgcttcc tgaagacaat gaaccaagtg ggtacgccca aacagattgt gtattggaag  300

caatggcttt ccttgaagaa tcccatcccg gaatctttga aaattcgtgt cttgaaacaa  360

tggaggtggt tcagcagaca agagtggaca aactaacaca aggccgacaa acttacgatt  420

ggaccttgaa taggaatcaa cctgccgcaa cagcacttgc taatacaatt gaagtgttca  480

gatcaaatga tctgacttcc agtgagtcag ggagattaat ggacttcctc aaagatgtca  540

tggagtccat gaacaaggaa gaaatggaaa taacaacaca cttccaacgg aagagaagag  600

taagagacaa catgacaaag agaatggtga cacagagaac catagggaag aaaaaacaac  660

gattaaacag aaagagctat ctgatcaggg cattaacctt aaacacaatg accaaggacg  720

ctgagagagg gaaattgaaa cgacgagcaa ttgcaacccc aggaatgcag ataagagggt  780

ttgtatattt tgttgaaaca ttagcccgaa gaatatgtga aaagcttgaa caatcaggat  840

tgccagttgg cggtaatgag aaaaaggcca aactggctaa tgtcgtcaga aaaatgatga  900

ctaattccca agacactgaa ctctccttca ccatcactgg ggacaatacc aaatggaatg  960

aaaatcagaa cccacgcatg ttcctggcaa tgatcacata cataactaga aaccagccag 1020

aatggttcag aaatgttcta agcattgcac cgattatgtt ctcaaataaa atggcaagac 1080

tggggaaagg atatatgttt gaaagcaaaa gtatgaaatt gagaactcaa ataccagcag 1140

aaatgctcgc aagcattgat ctgaaatatt tcaatgattc aacaaaaaag aaaattgaga 1200

agatacgacc accctgaatt c                                           1221


<210> SEQ ID NO 72
<211> LENGTH: 18
<212> TYPE: DNA
<213> ORGANISM: Artificial sequence
<220> FEATURE:
<223> OTHER INFORMATION: Synthetic Primer

<400> SEQUENCE: 72

gcaaatgcag gaccaaag                                                 18


<210> SEQ ID NO 73
<211> LENGTH: 18
<212> TYPE: DNA
<213> ORGANISM: Artificial sequence
<220> FEATURE:
<223> OTHER INFORMATION: Synthetic Primer

<400> SEQUENCE: 73

gactgaggac tcagcttc                                                 18


<210> SEQ ID NO 74
<211> LENGTH: 19
```

-continued

<212> TYPE: DNA
<213> ORGANISM: Artificial sequence
<220> FEATURE:
<223> OTHER INFORMATION: Synthetic Primer

<400> SEQUENCE: 74
caatatcctc cccaatttc 19

<210> SEQ ID NO 75
<211> LENGTH: 19
<212> TYPE: DNA
<213> ORGANISM: Artificial sequence
<220> FEATURE:
<223> OTHER INFORMATION: Synthetic Primer

<400> SEQUENCE: 75
ggaaggtttg caggacctt 19

<210> SEQ ID NO 76
<211> LENGTH: 1228
<212> TYPE: DNA
<213> ORGANISM: Equine influenza virus H3N8
<220> FEATURE:
<221> NAME/KEY: CDS
<222> LOCATION: (3)..(1166)
<223> OTHER INFORMATION:

<400> SEQUENCE: 76 gg ggc ggg tac cca aac tat ctc caa gct tgg aag caa gta tta gca 47
Gly Gly Tyr Pro Asn Tyr Leu Gln Ala Trp Lys Gln Val Leu Ala
1 5 10 15 gaa cta caa gac ctt gag aac gaa gaa aag acc cct aag acc aag aat 95
Glu Leu Gln Asp Leu Glu Asn Glu Glu Lys Thr Pro Lys Thr Lys Asn
20 25 30 atg aaa aaa aca agc caa ttg aaa tgg gca ctc ggt gaa aat atg gca 143
Met Lys Lys Thr Ser Gln Leu Lys Trp Ala Leu Gly Glu Asn Met Ala
35 40 45 cca gag aaa gtg gat ttt gag gat tgt aaa gac atc aat gat ttg aaa 191
Pro Glu Lys Val Asp Phe Glu Asp Cys Lys Asp Ile Asn Asp Leu Lys
50 55 60 cag tat gac agt gat gag cca gaa aca agg tct ctt gca agt tgg att 239
Gln Tyr Asp Ser Asp Glu Pro Glu Thr Arg Ser Leu Ala Ser Trp Ile
65 70 75 caa agt gag ttc aac aaa gct tgt gag ctg aca gat tca agc tgg ata 287
Gln Ser Glu Phe Asn Lys Ala Cys Glu Leu Thr Asp Ser Ser Trp Ile
80 85 90 95 gag ctc gat gaa att ggg gag gat att gcc cca ata gaa tac att gcg 335
Glu Leu Asp Glu Ile Gly Glu Asp Ile Ala Pro Ile Glu Tyr Ile Ala
100 105 110 agc atg agg aga aat tat ttt act gct gag gtt tcc cat tgt aga gca 383
Ser Met Arg Arg Asn Tyr Phe Thr Ala Glu Val Ser His Cys Arg Ala
115 120 125 aca gaa tat ata atg aag gga gtg tac atc aac act gct cta ctc aat 431
Thr Glu Tyr Ile Met Lys Gly Val Tyr Ile Asn Thr Ala Leu Leu Asn
130 135 140 gca tcc tgt gct gcg atg gat gaa ttc caa tta att ccg atg ata agc 479
Ala Ser Cys Ala Ala Met Asp Glu Phe Gln Leu Ile Pro Met Ile Ser
145 150 155 aaa tgc agg acc aaa gaa ggg aga agg aag aca aat tta tat gga ttc 527
Lys Cys Arg Thr Lys Glu Gly Arg Arg Lys Thr Asn Leu Tyr Gly Phe
160 165 170 175 ata ata aag gga agg tcc cat tta agg aat gat acc gac gtg gta aac 575
Ile Ile Lys Gly Arg Ser His Leu Arg Asn Asp Thr Asp Val Val Asn -continued

```
                180                 185                 190

ttt gta agt atg gaa ttt tct ctc act gat cca aga ttt gag cca cat      623
Phe Val Ser Met Glu Phe Ser Leu Thr Asp Pro Arg Phe Glu Pro His
            195                 200                 205

aaa tgg gaa aaa tac tgc gtt cta gaa att gga gac atg ctc cta agg      671
Lys Trp Glu Lys Tyr Cys Val Leu Glu Ile Gly Asp Met Leu Leu Arg
        210                 215                 220

act gct gta ggt caa gtg tca aga ccc atg ttt ttg tat gta agg aca      719
Thr Ala Val Gly Gln Val Ser Arg Pro Met Phe Leu Tyr Val Arg Thr
    225                 230                 235

aat gga acc tct aaa att aaa atg aaa cgg gga atg gaa atg aga cgc      767
Asn Gly Thr Ser Lys Ile Lys Met Lys Arg Gly Met Glu Met Arg Arg
240                 245                 250                 255

tgc ctc ctt cag tct ctg caa cag att gaa agc atg atc gaa gct gag      815
Cys Leu Leu Gln Ser Leu Gln Gln Ile Glu Ser Met Ile Glu Ala Glu
                260                 265                 270

tcc tca gtc aaa gaa aag gac atg acc aaa gaa ttc ttt gag aac aaa      863
Ser Ser Val Lys Glu Lys Asp Met Thr Lys Glu Phe Phe Glu Asn Lys
            275                 280                 285

tca gag aca tgg cct ata gga gag tcc ccc aaa gga gtg gaa gag ggc      911
Ser Glu Thr Trp Pro Ile Gly Glu Ser Pro Lys Gly Val Glu Glu Gly
        290                 295                 300

tca atc ggg aag gtt tgc agg acc tta tta gca aaa tct gtg ttt aac      959
Ser Ile Gly Lys Val Cys Arg Thr Leu Leu Ala Lys Ser Val Phe Asn
    305                 310                 315

agt ttg tat gca tct cca caa ctg gaa ggg ttt tca gct gaa tct agg     1007
Ser Leu Tyr Ala Ser Pro Gln Leu Glu Gly Phe Ser Ala Glu Ser Arg
320                 325                 330                 335

aaa tta ctt ctc att gtt cag gcc ctt agg gat aac ctg gaa cct gga     1055
Lys Leu Leu Leu Ile Val Gln Ala Leu Arg Asp Asn Leu Glu Pro Gly
                340                 345                 350

acc ttt gat att ggg ggg tta tat gaa tca att gag gag tgc ctg att     1103
Thr Phe Asp Ile Gly Gly Leu Tyr Glu Ser Ile Glu Glu Cys Leu Ile
            355                 360                 365

aat gat ccc tgg gtt ttg ctc aat gca tct tgg ttc aac tcc ttc ctt     1151
Asn Asp Pro Trp Val Leu Leu Asn Ala Ser Trp Phe Asn Ser Phe Leu
        370                 375                 380

aca cat gca ctg aag tagttgtagc aatgctacta tttgctatcc atactgtcca     1206
Thr His Ala Leu Lys
    385

aaaaagtact cgagccccca ag                                            1228


<210> SEQ ID NO 77
<211> LENGTH: 388
<212> TYPE: PRT
<213> ORGANISM: Equine influenza virus H3N8

<400> SEQUENCE: 77

Gly Gly Tyr Pro Asn Tyr Leu Gln Ala Trp Lys Gln Val Leu Ala Glu
1               5                   10                  15

Leu Gln Asp Leu Glu Asn Glu Glu Lys Thr Pro Lys Thr Lys Asn Met
            20                  25                  30

Lys Lys Thr Ser Gln Leu Lys Trp Ala Leu Gly Glu Asn Met Ala Pro
        35                  40                  45

Glu Lys Val Asp Phe Glu Asp Cys Lys Asp Ile Asn Asp Leu Lys Gln
    50                  55                  60

Tyr Asp Ser Asp Glu Pro Glu Thr Arg Ser Leu Ala Ser Trp Ile Gln
65                  70                  75                  80
```

-continued

```
Ser Glu Phe Asn Lys Ala Cys Glu Leu Thr Asp Ser Ser Trp Ile Glu
                85                  90                  95

Leu Asp Glu Ile Gly Glu Asp Ile Ala Pro Ile Glu Tyr Ile Ala Ser
            100                 105                 110

Met Arg Arg Asn Tyr Phe Thr Ala Glu Val Ser His Cys Arg Ala Thr
        115                 120                 125

Glu Tyr Ile Met Lys Gly Val Tyr Ile Asn Thr Ala Leu Leu Asn Ala
    130                 135                 140

Ser Cys Ala Ala Met Asp Glu Phe Gln Leu Ile Pro Met Ile Ser Lys
145                 150                 155                 160

Cys Arg Thr Lys Glu Gly Arg Arg Lys Thr Asn Leu Tyr Gly Phe Ile
                165                 170                 175

Ile Lys Gly Arg Ser His Leu Arg Asn Asp Thr Asp Val Val Asn Phe
            180                 185                 190

Val Ser Met Glu Phe Ser Leu Thr Asp Pro Arg Phe Glu Pro His Lys
        195                 200                 205

Trp Glu Lys Tyr Cys Val Leu Glu Ile Gly Asp Met Leu Leu Arg Thr
    210                 215                 220

Ala Val Gly Gln Val Ser Arg Pro Met Phe Leu Tyr Val Arg Thr Asn
225                 230                 235                 240

Gly Thr Ser Lys Ile Lys Met Lys Arg Gly Met Glu Met Arg Arg Cys
                    245                 250                 255

Leu Leu Gln Ser Leu Gln Gln Ile Glu Ser Met Ile Glu Ala Glu Ser
            260                 265                 270

Ser Val Lys Glu Lys Asp Met Thr Lys Glu Phe Phe Glu Asn Lys Ser
        275                 280                 285

Glu Thr Trp Pro Ile Gly Glu Ser Pro Lys Gly Val Glu Glu Gly Ser
    290                 295                 300

Ile Gly Lys Val Cys Arg Thr Leu Leu Ala Lys Ser Val Phe Asn Ser
305                 310                 315                 320

Leu Tyr Ala Ser Pro Gln Leu Glu Gly Phe Ser Ala Glu Ser Arg Lys
                325                 330                 335

Leu Leu Leu Ile Val Gln Ala Leu Arg Asp Asn Leu Glu Pro Gly Thr
            340                 345                 350

Phe Asp Ile Gly Gly Leu Tyr Glu Ser Ile Glu Glu Cys Leu Ile Asn
        355                 360                 365

Asp Pro Trp Val Leu Leu Asn Ala Ser Trp Phe Asn Ser Phe Leu Thr
    370                 375                 380

His Ala Leu Lys
385


<210> SEQ ID NO 78
<211> LENGTH: 1164
<212> TYPE: DNA
<213> ORGANISM: Equine influenza virus H3N8

<400> SEQUENCE: 78

ggcgggtacc caaactatct ccaagcttgg aagcaagtat tagcagaact acaagacctt      60

gagaacgaag aaaagacccc taagaccaag aatatgaaaa aaacaagcca attgaaatgg     120

gcactcggtg aaaatatggc accagagaaa gtggattttg aggattgtaa agacatcaat     180

gatttgaaac agtatgacag tgatgagcca gaaacaaggt ctcttgcaag ttggattcaa     240

agtgagttca acaaagcttg tgagctgaca gattcaagct ggatagagct cgatgaaatt     300

ggggaggata ttgccccaat agaatacatt gcgagcatga ggagaaatta ttttactgct     360
```

-continued

```
gaggtttccc attgtagagc aacagaatat ataatgaagg gagtgtacat caacactgct    420

ctactcaatg catcctgtgc tgcgatggat gaattccaat taattccgat gataagcaaa    480

tgcaggacca aagaagggag aaggaagaca aatttatatg gattcataat aaagggaagg    540

tcccatttaa ggaatgatac cgacgtggta aactttgtaa gtatggaatt ttctctcact    600

gatccaagat ttgagccaca taaatgggaa aaatactgcg ttctagaaat tggagacatg    660

ctcctaagga ctgctgtagg tcaagtgtca agacccatgt ttttgtatgt aaggacaaat    720

ggaacctcta aaattaaaat gaaacgggga atggaaatga gacgctgcct ccttcagtct    780

ctgcaacaga ttgaaagcat gatcgaagct gagtcctcag tcaaagaaaa ggacatgacc    840

aaagaattct ttgagaacaa atcagagaca tggcctatag gagagtcccc caaaggagtg    900

gaagagggct caatcgggaa ggtttgcagg accttattag caaaatctgt gtttaacagt    960

ttgtatgcat ctccacaact ggaagggttt tcagctgaat ctaggaaatt acttctcatt   1020

gttcaggccc ttagggataa cctggaacct ggaacctttg atattggggg gttatatgaa   1080

tcaattgagg agtgcctgat taatgatccc tgggttttgc tcaatgcatc ttggttcaac   1140

tccttcctta cacatgcact gaag                                          1164


<210> SEQ ID NO 79
<211> LENGTH: 1223
<212> TYPE: DNA
<213> ORGANISM: Equine influenza virus H3N8

<400> SEQUENCE: 79

ggggcgggta cccaaactat ctccaagctt ggaagcaagt attagcagaa ctacaagacc      60

ttgagaacga agaaaagacc cctaagacca agaatatgaa aaaaacaagc caattgaaat    120

gggcactcgg tgaaaatatg gcaccagaga aagtggattt tgaggattgt aaagacatca    180

atgatttgaa acagtatgac agtgatgagc cagaaacaag gtctcttgca agttggattc    240

aaagtgagtt caacaaagct tgtgagctga cagattcaag ctggatagag ctcgatgaaa    300

ttggggagga tattgcccca atagaataca ttgcgagcat gaggagaaat tattttactg    360

ctgaggtttc ccattgtaga gcaacagaat atataatgaa gggagtgtac atcaacactg    420

ctctactcaa tgcatcctgt gctgcgatgg atgaattcca attaattccg atgataagca    480

aatgcaggac caaagaaggg agaaggaaga caaatttata tggattcata ataaagggaa    540

ggtcccattt aaggaatgat accgacgtgg taaactttgt aagtatggaa ttttctctca    600

ctgatccaag atttgagcca cataaatggg aaaaatactg cgttctagaa attggagaca    660

tgctcctaag gactgctgta ggtcaagtgt caagacccat gtttttgtat gtaaggacaa    720

atggaacctc taaaattaaa atgaaatggg gaatggaaat gagacgctgc ctccttcagt    780

ctctgcaaca gattgaaagc atgatcgaag ctgagtcctc agtcaaagaa aaggacatga    840

ccaaagaatt ctttgagaac aaatcagaga catggcctat aggagagtcc cccaaaggag    900

tggaagaggg ctcaatcggg aaggtttgca ggaccttatt agcaaaatct gtgtttaaca    960

gtttgtatgc atctccacaa ctggaagggt tttcagctga atctaggaaa ttacttctca   1020

ttgttcaggc ccttagggat aacctggaac ctggaacctt tgatattggg gggttatatg   1080

aatcaattga ggagtgcctg attaatgatc cctgggtttt gctcaatgca tcttggttca   1140

actccttcct tacacatgca ctgaagtagt tgtagcaatg ctactatttg ctatccatac   1200

tgtccaaaaa agtactcgag ccc                                           1223
```

-continued

<210> SEQ ID NO 80
<211> LENGTH: 1233
<212> TYPE: DNA
<213> ORGANISM: Equine influenza virus H3N8
<220> FEATURE:
<221> NAME/KEY: CDS
<222> LOCATION: (3)..(1172)
<223> OTHER INFORMATION:

<400> SEQUENCE: 80 at gaa aag ggt ata aac cca aac tat ctc caa gct tgg aag caa gta 47
Glu Lys Gly Ile Asn Pro Asn Tyr Leu Gln Ala Trp Lys Gln Val
1 5 10 15 tta gca gaa cta caa gac ctt gag aac gaa gaa aag acc cct aag acc 95
Leu Ala Glu Leu Gln Asp Leu Glu Asn Glu Glu Lys Thr Pro Lys Thr
20 25 30 aag aat atg aaa aaa aca agc caa ttg aaa tgg gca ctc ggt gaa aat 143
Lys Asn Met Lys Lys Thr Ser Gln Leu Lys Trp Ala Leu Gly Glu Asn
35 40 45 atg gca cca gag aaa gtg gat ttt gag gat tgt aaa gac atc aat gat 191
Met Ala Pro Glu Lys Val Asp Phe Glu Asp Cys Lys Asp Ile Asn Asp
50 55 60 ttg aaa cag tat gac agt gat gag cca gaa aca agg tct ctt gca agt 239
Leu Lys Gln Tyr Asp Ser Asp Glu Pro Glu Thr Arg Ser Leu Ala Ser
65 70 75 tgg att caa agt gag ttc aac aaa gct tgt gag ctg aca gat tca agc 287
Trp Ile Gln Ser Glu Phe Asn Lys Ala Cys Glu Leu Thr Asp Ser Ser
80 85 90 95 tgg ata gag ctc gat gaa att ggg gag gat att gcc cca ata gaa tac 335
Trp Ile Glu Leu Asp Glu Ile Gly Glu Asp Ile Ala Pro Ile Glu Tyr
100 105 110 att gcg agc atg agg aga aat tat ttt act gct gag gtt tcc cat tgt 383
Ile Ala Ser Met Arg Arg Asn Tyr Phe Thr Ala Glu Val Ser His Cys
115 120 125 aga gca aca gaa tat ata atg aag gga gtg tac atc aac act gct cta 431
Arg Ala Thr Glu Tyr Ile Met Lys Gly Val Tyr Ile Asn Thr Ala Leu
130 135 140 ctc aat gca tcc tgt gct gcg atg gat gaa ttc caa tta att ccg atg 479
Leu Asn Ala Ser Cys Ala Ala Met Asp Glu Phe Gln Leu Ile Pro Met
145 150 155 ata agc aaa tgc agg acc aaa gaa ggg aga agg aag aca aat tta tat 527
Ile Ser Lys Cys Arg Thr Lys Glu Gly Arg Arg Lys Thr Asn Leu Tyr
160 165 170 175 gga ttc ata ata aag gga agg tcc cat tta agg aat gat acc gac gtg 575
Gly Phe Ile Ile Lys Gly Arg Ser His Leu Arg Asn Asp Thr Asp Val
180 185 190 gta aac ttt gta agt atg gaa ttt tct ctc act gat cca aga ttt gag 623
Val Asn Phe Val Ser Met Glu Phe Ser Leu Thr Asp Pro Arg Phe Glu
195 200 205 cca cat aaa tgg gaa aaa tac tgc gtt cta gaa att gga gac atg ctc 671
Pro His Lys Trp Glu Lys Tyr Cys Val Leu Glu Ile Gly Asp Met Leu
210 215 220 cta agg act gct gta ggt caa gtg tca aga ccc atg ttt ttg tat gta 719
Leu Arg Thr Ala Val Gly Gln Val Ser Arg Pro Met Phe Leu Tyr Val
225 230 235 agg aca aat gga acc tct aaa att aaa atg aaa tgg gga atg gaa atg 767
Arg Thr Asn Gly Thr Ser Lys Ile Lys Met Lys Trp Gly Met Glu Met
240 245 250 255 aga cgc tgc ctc ctt cag tct ctg caa cag att gaa agc atg atc gaa 815
Arg Arg Cys Leu Leu Gln Ser Leu Gln Gln Ile Glu Ser Met Ile Glu
260 265 270

-continued

```
gct gag tcc tca gtc aaa gaa aag gac atg acc aaa gaa ttc ttt gag      863
Ala Glu Ser Ser Val Lys Glu Lys Asp Met Thr Lys Glu Phe Phe Glu
            275                 280                 285

aac aaa tca gag aca tgg cct ata gga gag tcc ccc aaa gga gtg gaa      911
Asn Lys Ser Glu Thr Trp Pro Ile Gly Glu Ser Pro Lys Gly Val Glu
        290                 295                 300

gag ggc tca atc ggg aag gtt tgc agg acc tta tta gca aaa tct gtg      959
Glu Gly Ser Ile Gly Lys Val Cys Arg Thr Leu Leu Ala Lys Ser Val
    305                 310                 315

ttt aac agt ttg tat gca tct cca caa ctg gaa ggg ttt tca gct gaa     1007
Phe Asn Ser Leu Tyr Ala Ser Pro Gln Leu Glu Gly Phe Ser Ala Glu
320                 325                 330                 335

tct agg aaa tta ctt ctc att gtt cag gcc ctt agg gat aac ctg gaa     1055
Ser Arg Lys Leu Leu Leu Ile Val Gln Ala Leu Arg Asp Asn Leu Glu
                340                 345                 350

cct gga acc ttt gat att ggg ggg tta tat gaa tca att gag gag tgc     1103
Pro Gly Thr Phe Asp Ile Gly Gly Leu Tyr Glu Ser Ile Glu Glu Cys
            355                 360                 365

ctg att aat gat ccc tgg gtt ttg ctc aat gca tct tgg ttc aac tcc     1151
Leu Ile Asn Asp Pro Trp Val Leu Leu Asn Ala Ser Trp Phe Asn Ser
        370                 375                 380

ttc ctt aca cat gca ctg aag tagttgtagc aatgctacta tttgctatcc        1202
Phe Leu Thr His Ala Leu Lys
    385                 390

atactgtcca aaaaagtacc ttgtttctac t                                  1233


<210> SEQ ID NO 81
<211> LENGTH: 390
<212> TYPE: PRT
<213> ORGANISM: Equine influenza virus H3N8

<400> SEQUENCE: 81

Glu Lys Gly Ile Asn Pro Asn Tyr Leu Gln Ala Trp Lys Gln Val Leu
1               5                   10                  15

Ala Glu Leu Gln Asp Leu Glu Asn Glu Glu Lys Thr Pro Lys Thr Lys
            20                  25                  30

Asn Met Lys Lys Thr Ser Gln Leu Lys Trp Ala Leu Gly Glu Asn Met
        35                  40                  45

Ala Pro Glu Lys Val Asp Phe Glu Asp Cys Lys Asp Ile Asn Asp Leu
    50                  55                  60

Lys Gln Tyr Asp Ser Asp Glu Pro Glu Thr Arg Ser Leu Ala Ser Trp
65                  70                  75                  80

Ile Gln Ser Glu Phe Asn Lys Ala Cys Glu Leu Thr Asp Ser Ser Trp
                85                  90                  95

Ile Glu Leu Asp Glu Ile Gly Glu Asp Ile Ala Pro Ile Glu Tyr Ile
            100                 105                 110

Ala Ser Met Arg Arg Asn Tyr Phe Thr Ala Glu Val Ser His Cys Arg
              115                 120                 125

Ala Thr Glu Tyr Ile Met Lys Gly Val Tyr Ile Asn Thr Ala Leu Leu
    130                 135                 140

Asn Ala Ser Cys Ala Ala Met Asp Glu Phe Gln Leu Ile Pro Met Ile
145                 150                 155                 160

Ser Lys Cys Arg Thr Lys Glu Gly Arg Arg Lys Thr Asn Leu Tyr Gly
                165                 170                 175

Phe Ile Ile Lys Gly Arg Ser His Leu Arg Asn Asp Thr Asp Val Val
            180                 185                 190
```

-continued

```
Asn Phe Val Ser Met Glu Phe Ser Leu Thr Asp Pro Arg Phe Glu Pro
        195                 200                 205

His Lys Trp Glu Lys Tyr Cys Val Leu Glu Ile Gly Asp Met Leu Leu
    210                 215                 220

Arg Thr Ala Val Gly Gln Val Ser Arg Pro Met Phe Leu Tyr Val Arg
225                 230                 235                 240

Thr Asn Gly Thr Ser Lys Ile Lys Met Lys Trp Gly Met Glu Met Arg
                245                 250                 255

Arg Cys Leu Leu Gln Ser Leu Gln Gln Ile Glu Ser Met Ile Glu Ala
            260                 265                 270

Glu Ser Ser Val Lys Glu Lys Asp Met Thr Lys Glu Phe Phe Glu Asn
        275                 280                 285

Lys Ser Glu Thr Trp Pro Ile Gly Glu Ser Pro Lys Gly Val Glu Glu
    290                 295                 300

Gly Ser Ile Gly Lys Val Cys Arg Thr Leu Leu Ala Lys Ser Val Phe
305                 310                 315                 320

Asn Ser Leu Tyr Ala Ser Pro Gln Leu Glu Gly Phe Ser Ala Glu Ser
                325                 330                 335

Arg Lys Leu Leu Leu Ile Val Gln Ala Leu Arg Asp Asn Leu Glu Pro
            340                 345                 350

Gly Thr Phe Asp Ile Gly Gly Leu Tyr Glu Ser Ile Glu Glu Cys Leu
        355                 360                 365

Ile Asn Asp Pro Trp Val Leu Leu Asn Ala Ser Trp Phe Asn Ser Phe
    370                 375                 380

Leu Thr His Ala Leu Lys
385                 390


<210> SEQ ID NO 82
<211> LENGTH: 1170
<212> TYPE: DNA
<213> ORGANISM: Equine influenza virus H3N8

<400> SEQUENCE: 82

gaaaagggta taaacccaaa ctatctccaa gcttggaagc aagtattagc agaactacaa     60

gaccttgaga acgaagaaaa gacccctaag accaagaata tgaaaaaaac aagccaattg    120

aaatgggcac tcggtgaaaa tatggcacca gagaaagtgg attttgagga ttgtaaagac    180

atcaatgatt tgaaacagta tgacagtgat gagccagaaa caaggtctct tgcaagttgg    240

attcaaagtg agttcaacaa agcttgtgag ctgacagatt caagctggat agagctcgat    300

gaaattgggg aggatattgc cccaatagaa tacattgcga gcatgaggag aaattatttt    360

actgctgagg tttcccattg tagagcaaca gaatatataa tgaagggagt gtacatcaac    420

actgctctac tcaatgcatc ctgtgctgcg atggatgaat tccaattaat tccgatgata    480

agcaaatgca ggaccaaaga agggagaagg aagacaaatt tatatggatt cataataaag    540

ggaaggtccc atttaaggaa tgataccgac gtggtaaact ttgtaagtat ggaattttct    600

ctcactgatc caagatttga gccacataaa tgggaaaaat actgcgttct agaaattgga    660

gacatgctcc taaggactgc tgtaggtcaa gtgtcaagac ccatgttttt gtatgtaagg    720

acaaatggaa cctctaaaat taaaatgaaa tggggaatgg aaatgagacg ctgcctcctt    780

cagtctctgc aacagattga aagcatgatc gaagctgagt cctcagtcaa agaaaaggac    840

atgaccaaag aattctttga gaacaaatca gagacatggc ctataggaga gtcccccaaa    900

ggagtggaag agggctcaat cgggaaggtt tgcaggacct tattagcaaa atctgtgttt    960
```

-continued aacagtttgt atgcatctcc acaactggaa gggttttcag ctgaatctag gaaattactt 1020
ctcattgttc aggcccttag ggataacctg gaacctggaa cctttgatat tgggggggtta 1080 tatgaatcaa ttgaggagtg cctgattaat gatccctggg ttttgctcaa tgcatcttgg 1140
ttcaactcct tccttacaca tgcactgaag 1170

<210> SEQ ID NO 83
<211> LENGTH: 25
<212> TYPE: DNA
<213> ORGANISM: Artificial sequence
<220> FEATURE:
<223> OTHER INFORMATION: Synthetic Primer

<400> SEQUENCE: 83
ggggcgggta cccaaactat ctcca 25

<210> SEQ ID NO 84
<211> LENGTH: 27
<212> TYPE: DNA
<213> ORGANISM: Artificial sequence
<220> FEATURE:
<223> OTHER INFORMATION: Synthetic Primer

<400> SEQUENCE: 84
gggggctcga gtactttttt ggacagt 27

<210> SEQ ID NO 85
<211> LENGTH: 1234
<212> TYPE: DNA
<213> ORGANISM: Equine influenza virus H3N8
<220> FEATURE:
<221> NAME/KEY: CDS
<222> LOCATION: (1)..(1188)
<223> OTHER INFORMATION:

<400> SEQUENCE: 85 atg aaa ttg aga act caa ata cca gca gaa atg ctc gca agc att gat 48
Met Lys Leu Arg Thr Gln Ile Pro Ala Glu Met Leu Ala Ser Ile Asp
1 5 10 15 ctg aaa tat ttc aat gat tca aca aaa aag aaa att gag aag ata cga 96
Leu Lys Tyr Phe Asn Asp Ser Thr Lys Lys Lys Ile Glu Lys Ile Arg
20 25 30 cca ctt ctg gtc gat ggg act gct tca ctg agt cct ggc atg atg atg 144
Pro Leu Leu Val Asp Gly Thr Ala Ser Leu Ser Pro Gly Met Met Met
35 40 45 gga atg ttc aac atg ttg agc act gta cta ggt gta tcc ata tta aac 192
Gly Met Phe Asn Met Leu Ser Thr Val Leu Gly Val Ser Ile Leu Asn
50 55 60 ctg ggc cag agg aaa tac aca aag acc aca tac tgg tgg gat ggt ctg 240
Leu Gly Gln Arg Lys Tyr Thr Lys Thr Thr Tyr Trp Trp Asp Gly Leu
65 70 75 80 caa tca tcc gat gat ttt gct ttg ata gtg aat gcg cct aat cat gaa 288
Gln Ser Ser Asp Asp Phe Ala Leu Ile Val Asn Ala Pro Asn His Glu
85 90 95 gga ata cag gct gga gta gac aga ttc tat aga act tgc aaa ctg gtc 336
Gly Ile Gln Ala Gly Val Asp Arg Phe Tyr Arg Thr Cys Lys Leu Val
100 105 110 ggg atc aac atg agc aaa aag aag tcc tac ata aat aga acc ggc aca 384
Gly Ile Asn Met Ser Lys Lys Lys Ser Tyr Ile Asn Arg Thr Gly Thr
115 120 125 ttc gaa ttc aca agc ttt ttc tac cgg tat ggt ttt gtc gcc aat ttc 432
Phe Glu Phe Thr Ser Phe Phe Tyr Arg Tyr Gly Phe Val Ala Asn Phe
130 135 140

-continued

```
agc atg gag cta ccc agt ttt ggg gtt tcc ggg ata aat gaa tct gca      480
Ser Met Glu Leu Pro Ser Phe Gly Val Ser Gly Ile Asn Glu Ser Ala
145                 150                 155                 160

gac atg agc att gga atg aca gtt atc aaa aac aac atg ata aat aat      528
Asp Met Ser Ile Gly Met Thr Val Ile Lys Asn Asn Met Ile Asn Asn
                165                 170                 175

gat ctc ggt ccc gcc acg gca caa atg gca ctc caa ctc ttc att aag      576
Asp Leu Gly Pro Ala Thr Ala Gln Met Ala Leu Gln Leu Phe Ile Lys
            180                 185                 190

gat tat cgg tac aca tac cgg tgc cat aga ggc gat acc cag ata caa      624
Asp Tyr Arg Tyr Thr Tyr Arg Cys His Arg Gly Asp Thr Gln Ile Gln
        195                 200                 205

acc aga aga tcc ttt gag ttg aag aaa ctg tgg gaa cag act cga tca      672
Thr Arg Arg Ser Phe Glu Leu Lys Lys Leu Trp Glu Gln Thr Arg Ser
    210                 215                 220

aag act ggt cta ctg gta tca gat ggg ggt cca aac cta tac aac atc      720
Lys Thr Gly Leu Leu Val Ser Asp Gly Gly Pro Asn Leu Tyr Asn Ile
225                 230                 235                 240

aga aac cta cac atc ccg gaa gtc tgt ttg aaa tgg gag ctg atg gat      768
Arg Asn Leu His Ile Pro Glu Val Cys Leu Lys Trp Glu Leu Met Asp
                245                 250                 255

gaa gat tat aaa ggg agg cta tgt aat cca ttg aat cct ttc gtt agc      816
Glu Asp Tyr Lys Gly Arg Leu Cys Asn Pro Leu Asn Pro Phe Val Ser
            260                 265                 270

cac aaa gaa att gaa tca gtg aac agt gca gta gta atg cct gcg cat      864
His Lys Glu Ile Glu Ser Val Asn Ser Ala Val Val Met Pro Ala His
        275                 280                 285

ggc cct gcc aaa agc atg gag tat gat gct gtt gca aca aca cac tct      912
Gly Pro Ala Lys Ser Met Glu Tyr Asp Ala Val Ala Thr Thr His Ser
    290                 295                 300

tgg atc ccc aag agg aac cgg tcc ata ttg aac aca agt caa agg gga      960
Trp Ile Pro Lys Arg Asn Arg Ser Ile Leu Asn Thr Ser Gln Arg Gly
305                 310                 315                 320

ata ctc gaa gat gag cag atg tat cag aaa tgc tgc aac ctg ttt gaa     1008
Ile Leu Glu Asp Glu Gln Met Tyr Gln Lys Cys Cys Asn Leu Phe Glu
                325                 330                 335

aaa ttc ttc ccc agc agc tca tac aga aga cca gtc gga att tct agt     1056
Lys Phe Phe Pro Ser Ser Ser Tyr Arg Arg Pro Val Gly Ile Ser Ser
            340                 345                 350

atg gtt gag gcc atg gtg tcc agg gcc cgc att gat gca cga att gac     1104
Met Val Glu Ala Met Val Ser Arg Ala Arg Ile Asp Ala Arg Ile Asp
        355                 360                 365

ttc gaa tct gga cgg ata aag aag gat gag ttc gct gag atc atg aag     1152
Phe Glu Ser Gly Arg Ile Lys Lys Asp Glu Phe Ala Glu Ile Met Lys
    370                 375                 380

atc tgt tcc acc att gaa gag ctc aga cgg caa aaa tagtgaattt          1198
Ile Cys Ser Thr Ile Glu Glu Leu Arg Arg Gln Lys
385                 390                 395

agcttgatct tcgtgaaaaa atgccttgtt tctact                             1234


<210> SEQ ID NO 86
<211> LENGTH: 396
<212> TYPE: PRT
<213> ORGANISM: Equine influenza virus H3N8

<400> SEQUENCE: 86

Met Lys Leu Arg Thr Gln Ile Pro Ala Glu Met Leu Ala Ser Ile Asp
1               5                   10                  15

Leu Lys Tyr Phe Asn Asp Ser Thr Lys Lys Lys Ile Glu Lys Ile Arg
```

-continued

```
            20                  25                  30

Pro Leu Leu Val Asp Gly Thr Ala Ser Leu Ser Pro Gly Met Met Met
        35                  40                  45

Gly Met Phe Asn Met Leu Ser Thr Val Leu Gly Val Ser Ile Leu Asn
    50                  55                  60

Leu Gly Gln Arg Lys Tyr Thr Lys Thr Thr Tyr Trp Trp Asp Gly Leu
65                  70                  75                  80

Gln Ser Ser Asp Asp Phe Ala Leu Ile Val Asn Ala Pro Asn His Glu
                85                  90                  95

Gly Ile Gln Ala Gly Val Asp Arg Phe Tyr Arg Thr Cys Lys Leu Val
            100                 105                 110

Gly Ile Asn Met Ser Lys Lys Lys Ser Tyr Ile Asn Arg Thr Gly Thr
        115                 120                 125

Phe Glu Phe Thr Ser Phe Phe Tyr Arg Tyr Gly Phe Val Ala Asn Phe
    130                 135                 140

Ser Met Glu Leu Pro Ser Phe Gly Val Ser Gly Ile Asn Glu Ser Ala
145                 150                 155                 160

Asp Met Ser Ile Gly Met Thr Val Ile Lys Asn Asn Met Ile Asn Asn
                165                 170                 175

Asp Leu Gly Pro Ala Thr Ala Gln Met Ala Leu Gln Leu Phe Ile Lys
            180                 185                 190

Asp Tyr Arg Tyr Thr Tyr Arg Cys His Arg Gly Asp Thr Gln Ile Gln
        195                 200                 205

Thr Arg Arg Ser Phe Glu Leu Lys Lys Leu Trp Glu Gln Thr Arg Ser
    210                 215                 220

Lys Thr Gly Leu Leu Val Ser Asp Gly Gly Pro Asn Leu Tyr Asn Ile
225                 230                 235                 240

Arg Asn Leu His Ile Pro Glu Val Cys Leu Lys Trp Glu Leu Met Asp
                245                 250                 255

Glu Asp Tyr Lys Gly Arg Leu Cys Asn Pro Leu Asn Pro Phe Val Ser
            260                 265                 270

His Lys Glu Ile Glu Ser Val Asn Ser Ala Val Val Met Pro Ala His
        275                 280                 285

Gly Pro Ala Lys Ser Met Glu Tyr Asp Ala Val Ala Thr Thr His Ser
    290                 295                 300

Trp Ile Pro Lys Arg Asn Arg Ser Ile Leu Asn Thr Ser Gln Arg Gly
305                 310                 315                 320

Ile Leu Glu Asp Glu Gln Met Tyr Gln Lys Cys Cys Asn Leu Phe Glu
                325                 330                 335

Lys Phe Phe Pro Ser Ser Ser Tyr Arg Arg Pro Val Gly Ile Ser Ser
            340                 345                 350

Met Val Glu Ala Met Val Ser Arg Ala Arg Ile Asp Ala Arg Ile Asp
        355                 360                 365

Phe Glu Ser Gly Arg Ile Lys Lys Asp Glu Phe Ala Glu Ile Met Lys
    370                 375                 380

Ile Cys Ser Thr Ile Glu Glu Leu Arg Arg Gln Lys
385                 390                 395
```

<210> SEQ ID NO 87
<211> LENGTH: 1188
<212> TYPE: DNA
<213> ORGANISM: Equine influenza virus H3N8

<400> SEQUENCE: 87

-continued

```
atgaaattga gaactcaaat accagcagaa atgctcgcaa gcattgatct gaaatatttc     60

aatgattcaa caaaaaagaa aattgagaag atacgaccac ttctggtcga tgggactgct    120

tcactgagtc ctggcatgat gatgggaatg ttcaacatgt tgagcactgt actaggtgta    180

tccatattaa acctgggcca gaggaaatac acaaagacca catactggtg ggatggtctg    240

caatcatccg atgattttgc tttgatagtg aatgcgccta atcatgaagg aatacaggct    300

ggagtagaca gattctatag aacttgcaaa ctggtcggga tcaacatgag caaaaagaag    360

tcctacataa atagaaccgg cacattcgaa ttcacaagct tttctaccg gtatggtttt    420

gtcgccaatt tcagcatgga gctacccagt tttggggttt ccgggataaa tgaatctgca    480

gacatgagca ttggaatgac agttatcaaa aacaacatga taaataatga tctcggtccc    540

gccacggcac aaatggcact ccaactcttc attaaggatt atcggtacac ataccggtgc    600

catagaggcg atacccagat acaaaccaga agatcctttg agttgaagaa actgtgggaa    660

cagactcgat caaagactgg tctactggta tcagatgggg gtccaaacct atacaacatc    720

agaaacctac acatcccgga agtctgtttg aaatgggagc tgatggatga agattataaa    780

gggaggctat gtaatccatt gaatcctttc gttagccaca aagaaattga atcagtgaac    840

agtgcagtag taatgcctgc gcatggccct gccaaaagca tggagtatga tgctgttgca    900

acaacacact cttggatccc caagaggaac cggtccatat tgaacacaag tcaaagggga    960

atactcgaag atgagcagat gtatcagaaa tgctgcaacc tgtttgaaaa attcttcccc   1020

agcagctcat acagaagacc agtcggaatt tctagtatgg ttgaggccat ggtgtccagg   1080

gcccgcattg atgcacgaat tgacttcgaa tctggacgga taaagaagga tgagttcgct   1140

gagatcatga agatctgttc caccattgaa gagctcagac ggcaaaaa                1188


<210> SEQ ID NO 88
<211> LENGTH: 1240
<212> TYPE: DNA
<213> ORGANISM: Equine influenza virus H3N8
<220> FEATURE:
<221> NAME/KEY: CDS
<222> LOCATION: (8)..(1195)
<223> OTHER INFORMATION:

<400> SEQUENCE: 88

caaaagt atg aaa ttg aga act caa ata cca gca gaa atg ctc gca agc       49
        Met Lys Leu Arg Thr Gln Ile Pro Ala Glu Met Leu Ala Ser
        1               5                   10

att gat ctg aaa tat ttc aat gat tca aca aaa aag aaa att gag aag       97
Ile Asp Leu Lys Tyr Phe Asn Asp Ser Thr Lys Lys Lys Ile Glu Lys
15                  20                  25                  30

ata cga cca ctt ctg gtc gat ggg act gct tca ctg agt cct ggc atg      145
Ile Arg Pro Leu Leu Val Asp Gly Thr Ala Ser Leu Ser Pro Gly Met
                35                  40                  45

atg atg gga atg ttc aac atg ttg agc act gta cta ggt gta tcc ata      193
Met Met Gly Met Phe Asn Met Leu Ser Thr Val Leu Gly Val Ser Ile
            50                  55                  60

tta aac ctg ggc cag agg aaa tac aca aag acc aca tac tgg tgg gat      241
Leu Asn Leu Gly Gln Arg Lys Tyr Thr Lys Thr Thr Tyr Trp Trp Asp
        65                  70                  75

ggt ctg caa tca tcc gat gat ttt gct ttg ata gtg aat gcg cct aat      289
Gly Leu Gln Ser Ser Asp Asp Phe Ala Leu Ile Val Asn Ala Pro Asn
    80                  85                  90

cat gaa gga ata cag gct gga gta gac aga ttc tat aga act tgc aaa      337
His Glu Gly Ile Gln Ala Gly Val Asp Arg Phe Tyr Arg Thr Cys Lys
95                  100                 105                 110
```

-continued

```
ctg gtc ggg atc aac atg agc aaa aag aag tcc tac ata aat aga acc      385
Leu Val Gly Ile Asn Met Ser Lys Lys Lys Ser Tyr Ile Asn Arg Thr
                115                 120                 125

ggc tca ttc gaa ttc aca agc ttt ttc tac cgg tat ggt ttt gtc gcc      433
Gly Ser Phe Glu Phe Thr Ser Phe Phe Tyr Arg Tyr Gly Phe Val Ala
            130                 135                 140

aat ttc agc atg gag cta ccc agt ttt ggg gtt tcc ggg ata aat gaa      481
Asn Phe Ser Met Glu Leu Pro Ser Phe Gly Val Ser Gly Ile Asn Glu
        145                 150                 155

tct gca gac atg agc att gga atg aca gtt atc aaa aac aac atg ata      529
Ser Ala Asp Met Ser Ile Gly Met Thr Val Ile Lys Asn Asn Met Ile
    160                 165                 170

aat aat gat ctc ggt ccc gcc acg gca caa atg gca ctc caa ctc ttc      577
Asn Asn Asp Leu Gly Pro Ala Thr Ala Gln Met Ala Leu Gln Leu Phe
175                 180                 185                 190

att aag gat tat cgg tac aca tac cgg tgc cat aga ggc gat acc cag      625
Ile Lys Asp Tyr Arg Tyr Thr Tyr Arg Cys His Arg Gly Asp Thr Gln
                195                 200                 205

ata caa acc aga aga tcc ttt gag ttg aag aaa ctg tgg gaa cag act      673
Ile Gln Thr Arg Arg Ser Phe Glu Leu Lys Lys Leu Trp Glu Gln Thr
            210                 215                 220

cga tca aag act ggt cta ctg gta tca gat ggg ggt cca aac cta tac      721
Arg Ser Lys Thr Gly Leu Leu Val Ser Asp Gly Gly Pro Asn Leu Tyr
        225                 230                 235

aac atc aga aac cta cac atc ccg gaa gtc tgt ttg aaa tgg gag ctg      769
Asn Ile Arg Asn Leu His Ile Pro Glu Val Cys Leu Lys Trp Glu Leu
    240                 245                 250

atg gat gaa gat tat aaa ggg agg cta tgt aat cca ttg aat cct ttc      817
Met Asp Glu Asp Tyr Lys Gly Arg Leu Cys Asn Pro Leu Asn Pro Phe
255                 260                 265                 270

gtt agc cac aaa gaa att gaa tca gtg aac agt gca gta gta atg cct      865
Val Ser His Lys Glu Ile Glu Ser Val Asn Ser Ala Val Val Met Pro
                275                 280                 285

gcg cat ggc cct gcc aaa agc atg gag tat gat gct gtt gca aca aca      913
Ala His Gly Pro Ala Lys Ser Met Glu Tyr Asp Ala Val Ala Thr Thr
            290                 295                 300

cac tct tgg atc ccc aag agg aac cgg tcc ata ttg aac aca agt caa      961
His Ser Trp Ile Pro Lys Arg Asn Arg Ser Ile Leu Asn Thr Ser Gln
        305                 310                 315

agg gga ata ctc gaa gat gag cag atg tat cag aaa tgc tgc aac ctg     1009
Arg Gly Ile Leu Glu Asp Glu Gln Met Tyr Gln Lys Cys Cys Asn Leu
    320                 325                 330

ttt gaa aaa ttc ttc ccc agc agc tca tac aga aga cca gtc gga att     1057
Phe Glu Lys Phe Phe Pro Ser Ser Ser Tyr Arg Arg Pro Val Gly Ile
335                 340                 345                 350

tct agt atg gtt gag gcc atg gtg tcc agg gcc cgc att gat gca cga     1105
Ser Ser Met Val Glu Ala Met Val Ser Arg Ala Arg Ile Asp Ala Arg
                355                 360                 365

att gac ttc gaa tct gga cgg ata aag aag gat gag ttc gct gag atc     1153
Ile Asp Phe Glu Ser Gly Arg Ile Lys Lys Asp Glu Phe Ala Glu Ile
            370                 375                 380

atg aag atc tgt tcc acc att gaa gag ctc aga cgg caa aaa             1195
Met Lys Ile Cys Ser Thr Ile Glu Glu Leu Arg Arg Gln Lys
        385                 390                 395

tagtgaattt agcttgatct tcgtgaaaaa atgccttgtt ctact                  1240
```

<210> SEQ ID NO 89
<211> LENGTH: 396
<212> TYPE: PRT

-continued

<213> ORGANISM: Equine influenza virus H3N8

<400> SEQUENCE: 89

```
Met Lys Leu Arg Thr Gln Ile Pro Ala Glu Met Leu Ala Ser Ile Asp
1               5                   10                  15

Leu Lys Tyr Phe Asn Asp Ser Thr Lys Lys Lys Ile Glu Lys Ile Arg
            20                  25                  30

Pro Leu Leu Val Asp Gly Thr Ala Ser Leu Ser Pro Gly Met Met Met
        35                  40                  45

Gly Met Phe Asn Met Leu Ser Thr Val Leu Gly Val Ser Ile Leu Asn
    50                  55                  60

Leu Gly Gln Arg Lys Tyr Thr Lys Thr Thr Tyr Trp Trp Asp Gly Leu
65                  70                  75                  80

Gln Ser Ser Asp Asp Phe Ala Leu Ile Val Asn Ala Pro Asn His Glu
                85                  90                  95

Gly Ile Gln Ala Gly Val Asp Arg Phe Tyr Arg Thr Cys Lys Leu Val
            100                 105                 110

Gly Ile Asn Met Ser Lys Lys Lys Ser Tyr Ile Asn Arg Thr Gly Ser
        115                 120                 125

Phe Glu Phe Thr Ser Phe Phe Tyr Arg Tyr Gly Phe Val Ala Asn Phe
    130                 135                 140

Ser Met Glu Leu Pro Ser Phe Gly Val Ser Gly Ile Asn Glu Ser Ala
145                 150                 155                 160

Asp Met Ser Ile Gly Met Thr Val Ile Lys Asn Asn Met Ile Asn Asn
                165                 170                 175

Asp Leu Gly Pro Ala Thr Ala Gln Met Ala Leu Gln Leu Phe Ile Lys
            180                 185                 190

Asp Tyr Arg Tyr Thr Tyr Arg Cys His Arg Gly Asp Thr Gln Ile Gln
        195                 200                 205

Thr Arg Arg Ser Phe Glu Leu Lys Lys Leu Trp Glu Gln Thr Arg Ser
    210                 215                 220

Lys Thr Gly Leu Leu Val Ser Asp Gly Gly Pro Asn Leu Tyr Asn Ile
225                 230                 235                 240

Arg Asn Leu His Ile Pro Glu Val Cys Leu Lys Trp Glu Leu Met Asp
                245                 250                 255

Glu Asp Tyr Lys Gly Arg Leu Cys Asn Pro Leu Asn Pro Phe Val Ser
            260                 265                 270

His Lys Glu Ile Glu Ser Val Asn Ser Ala Val Val Met Pro Ala His
        275                 280                 285

Gly Pro Ala Lys Ser Met Glu Tyr Asp Ala Val Ala Thr Thr His Ser
    290                 295                 300

Trp Ile Pro Lys Arg Asn Arg Ser Ile Leu Asn Thr Ser Gln Arg Gly
305                 310                 315                 320

Ile Leu Glu Asp Glu Gln Met Tyr Gln Lys Cys Cys Asn Leu Phe Glu
                325                 330                 335

Lys Phe Phe Pro Ser Ser Ser Tyr Arg Arg Pro Val Gly Ile Ser Ser
            340                 345                 350

Met Val Glu Ala Met Val Ser Arg Ala Arg Ile Asp Ala Arg Ile Asp
        355                 360                 365

Phe Glu Ser Gly Arg Ile Lys Lys Asp Glu Phe Ala Glu Ile Met Lys
    370                 375                 380

Ile Cys Ser Thr Ile Glu Glu Leu Arg Arg Gln Lys
385                 390                 395
```

-continued

<210> SEQ ID NO 90
<211> LENGTH: 1188
<212> TYPE: DNA
<213> ORGANISM: Equine influenza virus H3N8

<400> SEQUENCE: 90

```
atgaaattga gaactcaaat accagcagaa atgctcgcaa gcattgatct gaaatatttc     60

aatgattcaa caaaaaagaa aattgagaag atacgaccac ttctggtcga tgggactgct    120

tcactgagtc ctggcatgat gatgggaatg ttcaacatgt tgagcactgt actaggtgta    180

tccatattaa acctgggcca gaggaaatac acaaagacca catactggtg ggatggtctg    240

caatcatccg atgattttgc tttgatagtg aatgcgccta atcatgaagg aatacaggct    300

ggagtagaca gattctatag aacttgcaaa ctggtcggga tcaacatgag caaaaagaag    360

tcctacataa atagaaccgg ctcattcgaa ttcacaagct tttctaccg gtatggtttt    420

gtcgccaatt tcagcatgga gctacccagt tttggggttt ccgggataaa tgaatctgca    480

gacatgagca ttggaatgac agttatcaaa aacaacatga taaataatga tctcggtccc    540

gccacggcac aaatggcact ccaactcttc attaaggatt atcggtacac ataccggtgc    600

catagaggcg atacccagat acaaaccaga agatcctttg agttgaagaa actgtgggaa    660

cagactcgat caaagactgg tctactggta tcagatgggg gtccaaacct atacaacatc    720

agaaacctac acatcccgga agtctgtttg aaatgggagc tgatggatga agattataaa    780

gggaggctat gtaatccatt gaatcctttc gttagccaca aagaaattga atcagtgaac    840

agtgcagtag taatgcctgc gcatggccct gccaaaagca tggagtatga tgctgttgca    900

acaacacact cttggatccc caagaggaac cggtccatat tgaacacaag tcaaagggga    960

atactcgaag atgagcagat gtatcagaaa tgctgcaacc tgtttgaaaa attcttcccc   1020

agcagctcat acagaagacc agtcggaatt tctagtatgg ttgaggccat ggtgtccagg   1080

gcccgcattg atgcacgaat tgacttcgaa tctggacgga taaagaagga tgagttcgct   1140

gagatcatga agatctgttc caccattgaa gagctcagac ggcaaaaa                 1188
```

<210> SEQ ID NO 91
<211> LENGTH: 1241
<212> TYPE: DNA
<213> ORGANISM: Equine influenza virus H3N8
<220> FEATURE:
<221> NAME/KEY: CDS
<222> LOCATION: (8)..(1195)
<223> OTHER INFORMATION:

<400> SEQUENCE: 91

```
caaaagt atg aaa ttg aga act caa ata cca gca gaa atg ctc gca agc       49
        Met Lys Leu Arg Thr Gln Ile Pro Ala Glu Met Leu Ala Ser
        1               5                   10

att gat ctg aaa tat ttc aat gat tca aca aaa aag aaa att gag aag       97
Ile Asp Leu Lys Tyr Phe Asn Asp Ser Thr Lys Lys Lys Ile Glu Lys
15                  20                  25                  30

ata cga cca ctt ctg gtc gat ggg act gct tca ctg agt cct ggc atg      145
Ile Arg Pro Leu Leu Val Asp Gly Thr Ala Ser Leu Ser Pro Gly Met
                35                  40                  45

atg atg gga atg ttc aac atg ttg agc act gta cta ggt gta tcc ata      193
Met Met Gly Met Phe Asn Met Leu Ser Thr Val Leu Gly Val Ser Ile
            50                  55                  60

tta aac ctg ggc cag agg aaa tac aca aag acc aca tac tgg tgg gat      241
Leu Asn Leu Gly Gln Arg Lys Tyr Thr Lys Thr Thr Tyr Trp Trp Asp
        65                  70                  75
```

-continued

```
ggt ctg caa tca tcc gat gat ttt gct ttg ata gtg aat gcg cct aat      289
Gly Leu Gln Ser Ser Asp Asp Phe Ala Leu Ile Val Asn Ala Pro Asn
    80                  85                  90

cat gaa gga ata cag gct gga gta gac aga ttc tat aga act tgc aaa      337
His Glu Gly Ile Gln Ala Gly Val Asp Arg Phe Tyr Arg Thr Cys Lys
95                  100                 105                 110

ctg gtc ggg atc aac atg agc aaa aag aag tcc tac ata aat aga acc      385
Leu Val Gly Ile Asn Met Ser Lys Lys Lys Ser Tyr Ile Asn Arg Thr
                115                 120                 125

ggc aca ttc gaa ttc aca agc ttt ttc tac cgg tat ggt ttt gtc gcc      433
Gly Thr Phe Glu Phe Thr Ser Phe Phe Tyr Arg Tyr Gly Phe Val Ala
            130                 135                 140

aat ttc agc atg gag cta ccc agt ttt ggg gtt tcc ggg ata aat gaa      481
Asn Phe Ser Met Glu Leu Pro Ser Phe Gly Val Ser Gly Ile Asn Glu
        145                 150                 155

tct gca gac atg agc att gga atg aca gtt atc aaa aac aac atg ata      529
Ser Ala Asp Met Ser Ile Gly Met Thr Val Ile Lys Asn Asn Met Ile
    160                 165                 170

aat aat gat ctc ggt ccc gcc acg gca caa atg gca ctc caa ctc ttc      577
Asn Asn Asp Leu Gly Pro Ala Thr Ala Gln Met Ala Leu Gln Leu Phe
175                 180                 185                 190

att aag gat tat cgg tac aca tac cgg tgt caa aga ggc gat acc cag      625
Ile Lys Asp Tyr Arg Tyr Thr Tyr Arg Cys Gln Arg Gly Asp Thr Gln
                195                 200                 205

ata caa acc aga aga tcc ttt gag ttg aag aaa ctg tgg gaa cag act      673
Ile Gln Thr Arg Arg Ser Phe Glu Leu Lys Lys Leu Trp Glu Gln Thr
            210                 215                 220

cga tca aag act ggt cta ctg gta tca gat ggg ggt cca aac cta tac      721
Arg Ser Lys Thr Gly Leu Leu Val Ser Asp Gly Gly Pro Asn Leu Tyr
        225                 230                 235

aac atc aga aac cta cac atc ccg gaa gtc tgt ttg aaa tgg gag ctg      769
Asn Ile Arg Asn Leu His Ile Pro Glu Val Cys Leu Lys Trp Glu Leu
    240                 245                 250

atg gat gaa gat tat aaa ggg agg cta tgt aat cca ttg aat cct ttc      817
Met Asp Glu Asp Tyr Lys Gly Arg Leu Cys Asn Pro Leu Asn Pro Phe
255                 260                 265                 270

gtt agc cac aaa gaa att gaa tca gtg aac agt gca gta gta atg cct      865
Val Ser His Lys Glu Ile Glu Ser Val Asn Ser Ala Val Val Met Pro
                275                 280                 285

gcg cat ggc cct gcc aaa agc atg gag tat gat gct gtt gca aca aca      913
Ala His Gly Pro Ala Lys Ser Met Glu Tyr Asp Ala Val Ala Thr Thr
            290                 295                 300

cac tct tgg atc ccc aag agg aac cgg tcc ata ttg aac aca agt caa      961
His Ser Trp Ile Pro Lys Arg Asn Arg Ser Ile Leu Asn Thr Ser Gln
        305                 310                 315

agg gga ata ctc gaa gat gag cag atg tat cag aaa tgc tgc aac ctg     1009
Arg Gly Ile Leu Glu Asp Glu Gln Met Tyr Gln Lys Cys Cys Asn Leu
    320                 325                 330

ttt gaa aaa ttc ttc ccc agc agc tca tac aga aaa cca gtc gga att     1057
Phe Glu Lys Phe Phe Pro Ser Ser Ser Tyr Arg Lys Pro Val Gly Ile
335                 340                 345                 350

tct agt atg gtt gag gcc atg gtg tcc agg gcc cgc att gat gca cga     1105
Ser Ser Met Val Glu Ala Met Val Ser Arg Ala Arg Ile Asp Ala Arg
                355                 360                 365

att gac ttc gaa tct gga cgg ata aag aag gat gag ttc gct gag atc     1153
Ile Asp Phe Glu Ser Gly Arg Ile Lys Lys Asp Glu Phe Ala Glu Ile
            370                 375                 380

atg aag atc tgt tcc acc att gaa gag ctc aga cgg caa aaa             1195
Met Lys Ile Cys Ser Thr Ile Glu Glu Leu Arg Arg Gln Lys
```

-continued

```
        385                 390                 395

tagtgaattt agcttgatct tcgtgaaaaa atgccttgtt tctact                1241


<210> SEQ ID NO 92
<211> LENGTH: 396
<212> TYPE: PRT
<213> ORGANISM: Equine influenza virus H3N8

<400> SEQUENCE: 92

Met Lys Leu Arg Thr Gln Ile Pro Ala Glu Met Leu Ala Ser Ile Asp
1               5                   10                  15

Leu Lys Tyr Phe Asn Asp Ser Thr Lys Lys Lys Ile Glu Lys Ile Arg
            20                  25                  30

Pro Leu Leu Val Asp Gly Thr Ala Ser Leu Ser Pro Gly Met Met Met
        35                  40                  45

Gly Met Phe Asn Met Leu Ser Thr Val Leu Gly Val Ser Ile Leu Asn
    50                  55                  60

Leu Gly Gln Arg Lys Tyr Thr Lys Thr Thr Tyr Trp Trp Asp Gly Leu
65                  70                  75                  80

Gln Ser Ser Asp Asp Phe Ala Leu Ile Val Asn Ala Pro Asn His Glu
                85                  90                  95

Gly Ile Gln Ala Gly Val Asp Arg Phe Tyr Arg Thr Cys Lys Leu Val
            100                 105                 110

Gly Ile Asn Met Ser Lys Lys Lys Ser Tyr Ile Asn Arg Thr Gly Thr
        115                 120                 125

Phe Glu Phe Thr Ser Phe Phe Tyr Arg Tyr Gly Phe Val Ala Asn Phe
    130                 135                 140

Ser Met Glu Leu Pro Ser Phe Gly Val Ser Gly Ile Asn Glu Ser Ala
145                 150                 155                 160

Asp Met Ser Ile Gly Met Thr Val Ile Lys Asn Asn Met Ile Asn Asn
                165                 170                 175

Asp Leu Gly Pro Ala Thr Ala Gln Met Ala Leu Gln Leu Phe Ile Lys
            180                 185                 190

Asp Tyr Arg Tyr Thr Tyr Arg Cys Gln Arg Gly Asp Thr Gln Ile Gln
        195                 200                 205

Thr Arg Arg Ser Phe Glu Leu Lys Lys Leu Trp Glu Gln Thr Arg Ser
    210                 215                 220

Lys Thr Gly Leu Leu Val Ser Asp Gly Gly Pro Asn Leu Tyr Asn Ile
225                 230                 235                 240

Arg Asn Leu His Ile Pro Glu Val Cys Leu Lys Trp Glu Leu Met Asp
                245                 250                 255

Glu Asp Tyr Lys Gly Arg Leu Cys Asn Pro Leu Asn Pro Phe Val Ser
            260                 265                 270

His Lys Glu Ile Glu Ser Val Asn Ser Ala Val Val Met Pro Ala His
        275                 280                 285

Gly Pro Ala Lys Ser Met Glu Tyr Asp Ala Val Ala Thr Thr His Ser
    290                 295                 300

Trp Ile Pro Lys Arg Asn Arg Ser Ile Leu Asn Thr Ser Gln Arg Gly
305                 310                 315                 320

Ile Leu Glu Asp Glu Gln Met Tyr Gln Lys Cys Cys Asn Leu Phe Glu
                325                 330                 335

Lys Phe Phe Pro Ser Ser Ser Tyr Arg Lys Pro Val Gly Ile Ser Ser
            340                 345                 350

Met Val Glu Ala Met Val Ser Arg Ala Arg Ile Asp Ala Arg Ile Asp
```

-continued

```
        355                 360                 365

Phe Glu Ser Gly Arg Ile Lys Lys Asp Glu Phe Ala Glu Ile Met Lys
    370                 375                 380

Ile Cys Ser Thr Ile Glu Glu Leu Arg Arg Gln Lys
385                 390                 395


<210> SEQ ID NO 93
<211> LENGTH: 1188
<212> TYPE: DNA
<213> ORGANISM: Equine influenza virus H3N8

<400> SEQUENCE: 93

atgaaattga gaactcaaat accagcagaa atgctcgcaa gcattgatct gaaatatttc      60

aatgattcaa caaaaaagaa aattgagaag atacgaccac ttctggtcga tgggactgct     120

tcactgagtc ctggcatgat gatgggaatg ttcaacatgt tgagcactgt actaggtgta     180

tccatattaa acctgggcca gaggaaatac acaaagacca catactggtg ggatggtctg     240

caatcatccg atgattttgc tttgatagtg aatgcgccta atcatgaagg aatacaggct     300

ggagtagaca gattctatag aacttgcaaa ctggtcggga tcaacatgag caaaaagaag     360

tcctacataa atagaaccgg cacattcgaa ttcacaagct tttctaccg gtatggtttt     420

gtcgccaatt tcagcatgga gctacccagt tttggggttt ccgggataaa tgaatctgca     480

gacatgagca ttggaatgac agttatcaaa aacaacatga taaataatga tctcggtccc     540

gccacggcac aaatggcact ccaactcttc attaaggatt atcggtacac ataccggtgt     600

caaagaggcg atacccagat acaaaccaga agatcctttg agttgaagaa actgtgggaa     660

cagactcgat caaagactgg tctactggta tcagatgggg gtccaaacct atacaacatc     720

agaaacctac acatcccgga agtctgtttg aaatgggagc tgatggatga agattataaa     780

gggaggctat gtaatccatt gaatcctttc gttagccaca aagaaattga atcagtgaac     840

agtgcagtag taatgcctgc gcatggccct gccaaaagca tggagtatga tgctgttgca     900

acaacacact cttggatccc caagaggaac cggtccatat tgaacacaag tcaaagggga     960

atactcgaag atgagcagat gtatcagaaa tgctgcaacc tgtttgaaaa attcttcccc    1020

agcagctcat acagaaaacc agtcggaatt tctagtatgg ttgaggccat ggtgtccagg    1080

gcccgcattg atgcacgaat tgacttcgaa tctggacgga taaagaagga tgagttcgct    1140

gagatcatga agatctgttc caccattgaa gagctcagac ggcaaaaa                 1188


<210> SEQ ID NO 94
<211> LENGTH: 1241
<212> TYPE: DNA
<213> ORGANISM: Equine influenza virus H3N8
<220> FEATURE:
<221> NAME/KEY: CDS
<222> LOCATION: (8)..(1195)
<223> OTHER INFORMATION:

<400> SEQUENCE: 94

caaaagt atg aaa ttg aga act caa ata cca gca gaa atg ctc gca agc       49
        Met Lys Leu Arg Thr Gln Ile Pro Ala Glu Met Leu Ala Ser
        1               5                   10

att gat ctg aaa tat ttc aat gat tca aca aaa aag aaa att gag aag       97
Ile Asp Leu Lys Tyr Phe Asn Asp Ser Thr Lys Lys Lys Ile Glu Lys
15                  20                  25                  30

ata cga cca ctt ctg gtc gat ggg act gct tca ctg agt cct ggc atg      145
Ile Arg Pro Leu Leu Val Asp Gly Thr Ala Ser Leu Ser Pro Gly Met
                35                  40                  45
```

-continued

```
atg atg gga atg ttc aac atg ttg agc act gta cta ggt gta tcc ata      193
Met Met Gly Met Phe Asn Met Leu Ser Thr Val Leu Gly Val Ser Ile
            50                  55                  60

tta aac ctg ggc cag agg aaa tac aca aag acc aca tac tgg tgg gat      241
Leu Asn Leu Gly Gln Arg Lys Tyr Thr Lys Thr Thr Tyr Trp Trp Asp
        65                  70                  75

ggt ctg caa tca tcc gat gat ttt gct ttg ata gtg aat gcg cct aat      289
Gly Leu Gln Ser Ser Asp Asp Phe Ala Leu Ile Val Asn Ala Pro Asn
    80                  85                  90

cat gaa gga ata cag gct gga gta gac aga ttc tat aga act tgc aaa      337
His Glu Gly Ile Gln Ala Gly Val Asp Arg Phe Tyr Arg Thr Cys Lys
95                  100                 105                 110

ctg gtc ggg atc aac atg agc aaa aag aag tcc tac ata aat aga acc      385
Leu Val Gly Ile Asn Met Ser Lys Lys Lys Ser Tyr Ile Asn Arg Thr
                115                 120                 125

ggc aca ttc gaa ttc aca agc ttt ttc tac cgg tat ggt ttt gtc gcc      433
Gly Thr Phe Glu Phe Thr Ser Phe Phe Tyr Arg Tyr Gly Phe Val Ala
            130                 135                 140

aat ttc agc atg gag cta ccc agt ttt ggg gtt tcc ggg ata aat gaa      481
Asn Phe Ser Met Glu Leu Pro Ser Phe Gly Val Ser Gly Ile Asn Glu
        145                 150                 155

tct gca gac atg agc att gga atg aca gtt atc aaa aac aac atg ata      529
Ser Ala Asp Met Ser Ile Gly Met Thr Val Ile Lys Asn Asn Met Ile
    160                 165                 170

aat aat gat ctc ggt ccc gcc acg gca caa atg gca ctc caa ctc ttc      577
Asn Asn Asp Leu Gly Pro Ala Thr Ala Gln Met Ala Leu Gln Leu Phe
175                 180                 185                 190

att aag gat tat cgg tac aca tac cgg tgt caa aga ggc gat acc cag      625
Ile Lys Asp Tyr Arg Tyr Thr Tyr Arg Cys Gln Arg Gly Asp Thr Gln
                195                 200                 205

ata caa acc aga aga tcc ttt gag ttg aag aaa ctg tgg gaa cag act      673
Ile Gln Thr Arg Arg Ser Phe Glu Leu Lys Lys Leu Trp Glu Gln Thr
            210                 215                 220

cga tca aag act ggt cta ctg gta tca gat ggg ggt cca aac cta tac      721
Arg Ser Lys Thr Gly Leu Leu Val Ser Asp Gly Gly Pro Asn Leu Tyr
        225                 230                 235

aac atc aga aac cta cac atc ccg gaa gtc tgt ttg aaa tgg gag ctg      769
Asn Ile Arg Asn Leu His Ile Pro Glu Val Cys Leu Lys Trp Glu Leu
    240                 245                 250

atg gat gaa gat tat aaa ggg agg cta tgt aat cca ttg aat cct ttc      817
Met Asp Glu Asp Tyr Lys Gly Arg Leu Cys Asn Pro Leu Asn Pro Phe
255                 260                 265                 270

gtt agc cac aaa gaa att gaa tca gtg aac agt gca gta gta atg cct      865
Val Ser His Lys Glu Ile Glu Ser Val Asn Ser Ala Val Val Met Pro
                275                 280                 285

gcg cat ggc cct gcc aaa agc atg gag tat gat gct gtt gca aca aca      913
Ala His Gly Pro Ala Lys Ser Met Glu Tyr Asp Ala Val Ala Thr Thr
            290                 295                 300

cac tct tgg atc ccc aag agg aac cgg tcc ata ttg aac aca agt caa      961
His Ser Trp Ile Pro Lys Arg Asn Arg Ser Ile Leu Asn Thr Ser Gln
        305                 310                 315

agg gga ata ctc gaa gat gag cag atg tat cag aaa tgc tgc aac ctg     1009
Arg Gly Ile Leu Glu Asp Glu Gln Met Tyr Gln Lys Cys Cys Asn Leu
    320                 325                 330

ttt gaa aaa ttc ttc ccc agc agc tca tac aga aga cca gtc gga att     1057
Phe Glu Lys Phe Phe Pro Ser Ser Ser Tyr Arg Arg Pro Val Gly Ile
335                 340                 345                 350

tct agt atg gtt gag gcc atg gtg tcc agg gcc cgc att gat gca cga     1105
Ser Ser Met Val Glu Ala Met Val Ser Arg Ala Arg Ile Asp Ala Arg
```

-continued 355 360 365 att gac ttc gaa tct gga cgg ata aag aag gat gag ttc gct gag atc 1153
Ile Asp Phe Glu Ser Gly Arg Ile Lys Lys Asp Glu Phe Ala Glu Ile
370 375 380 atg aag atc tgt tcc acc att gaa gag ctc aga cgg caa aaa 1195
Met Lys Ile Cys Ser Thr Ile Glu Glu Leu Arg Arg Gln Lys
385 390 395 tagtgaattt agcttgatct tcgtgaaaaa atgccttgtt tctact 1241

<210> SEQ ID NO 95
<211> LENGTH: 396
<212> TYPE: PRT
<213> ORGANISM: Equine influenza virus H3N8

<400> SEQUENCE: 95

Met Lys Leu Arg Thr Gln Ile Pro Ala Glu Met Leu Ala Ser Ile Asp
1 5 10 15

Leu Lys Tyr Phe Asn Asp Ser Thr Lys Lys Lys Ile Glu Lys Ile Arg
20 25 30

Pro Leu Leu Val Asp Gly Thr Ala Ser Leu Ser Pro Gly Met Met Met
35 40 45

Gly Met Phe Asn Met Leu Ser Thr Val Leu Gly Val Ser Ile Leu Asn
50 55 60

Leu Gly Gln Arg Lys Tyr Thr Lys Thr Thr Tyr Trp Trp Asp Gly Leu
65 70 75 80

Gln Ser Ser Asp Asp Phe Ala Leu Ile Val Asn Ala Pro Asn His Glu
85 90 95

Gly Ile Gln Ala Gly Val Asp Arg Phe Tyr Arg Thr Cys Lys Leu Val
100 105 110

Gly Ile Asn Met Ser Lys Lys Lys Ser Tyr Ile Asn Arg Thr Gly Thr
115 120 125

Phe Glu Phe Thr Ser Phe Phe Tyr Arg Tyr Gly Phe Val Ala Asn Phe
130 135 140

Ser Met Glu Leu Pro Ser Phe Gly Val Ser Gly Ile Asn Glu Ser Ala
145 150 155 160

Asp Met Ser Ile Gly Met Thr Val Ile Lys Asn Asn Met Ile Asn Asn
165 170 175

Asp Leu Gly Pro Ala Thr Ala Gln Met Ala Leu Gln Leu Phe Ile Lys
180 185 190

Asp Tyr Arg Tyr Thr Tyr Arg Cys Gln Arg Gly Asp Thr Gln Ile Gln
195 200 205

Thr Arg Arg Ser Phe Glu Leu Lys Lys Leu Trp Glu Gln Thr Arg Ser
210 215 220

Lys Thr Gly Leu Leu Val Ser Asp Gly Gly Pro Asn Leu Tyr Asn Ile
225 230 235 240

Arg Asn Leu His Ile Pro Glu Val Cys Leu Lys Trp Glu Leu Met Asp
245 250 255

Glu Asp Tyr Lys Gly Arg Leu Cys Asn Pro Leu Asn Pro Phe Val Ser
260 265 270

His Lys Glu Ile Glu Ser Val Asn Ser Ala Val Val Met Pro Ala His
275 280 285

Gly Pro Ala Lys Ser Met Glu Tyr Asp Ala Val Ala Thr Thr His Ser
290 295 300

Trp Ile Pro Lys Arg Asn Arg Ser Ile Leu Asn Thr Ser Gln Arg Gly
305 310 315 320

-continued

Ile Leu Glu Asp Glu Gln Met Tyr Gln Lys Cys Cys Asn Leu Phe Glu
325 330 335

Lys Phe Phe Pro Ser Ser Ser Tyr Arg Arg Pro Val Gly Ile Ser Ser
340 345 350

Met Val Glu Ala Met Val Ser Arg Ala Arg Ile Asp Ala Arg Ile Asp
355 360 365

Phe Glu Ser Gly Arg Ile Lys Lys Asp Glu Phe Ala Glu Ile Met Lys
370 375 380

Ile Cys Ser Thr Ile Glu Glu Leu Arg Arg Gln Lys
385 390 395

<210> SEQ ID NO 96
<211> LENGTH: 1188
<212> TYPE: DNA
<213> ORGANISM: Equine influenza virus H3N8

<400> SEQUENCE: 96
atgaaattga gaactcaaat accagcagaa atgctcgcaa gcattgatct gaaatatttc 60
aatgattcaa caaaaaagaa aattgagaag atacgaccac ttctggtcga tgggactgct 120
tcactgagtc ctggcatgat gatgggaatg ttcaacatgt tgagcactgt actaggtgta 180
tccatattaa acctgggcca gaggaaatac acaaagacca catactggtg ggatggtctg 240
caatcatccg atgattttgc tttgatagtg aatgcgccta atcatgaagg aatacaggct 300
ggagtagaca gattctatag aacttgcaaa ctggtcggga tcaacatgag caaaaagaag 360
tcctacataa atagaaccgg cacattcgaa ttcacaagct tttctaccg gtatggtttt 420 gtcgccaatt tcagcatgga gctacccagt tttggggttt ccgggataaa tgaatctgca 480
gacatgagca ttggaatgac agttatcaaa aacaacatga taaataatga tctcggtccc 540
gccacggcac aaatggcact ccaactcttc attaaggatt atcggtacac ataccggtgt 600
caaagaggcg atacccagat acaaaccaga agatcctttg agttgaagaa actgtgggaa 660
cagactcgat caaagactgg tctactggta tcagatgggg gtccaaacct atacaacatc 720
agaaacctac acatcccgga agtctgtttg aaatgggagc tgatggatga agattataaa 780
gggaggctat gtaatccatt gaatcctttc gttagccaca aagaaattga atcagtgaac 840
agtgcagtag taatgcctgc gcatggccct gccaaaagca tggagtatga tgctgttgca 900
acaacacact cttggatccc caagaggaac cggtccatat tgaacacaag tcaaagggga 960
atactcgaag atgagcagat gtatcagaaa tgctgcaacc tgtttgaaaa attcttcccc 1020
agcagctcat acagaagacc agtcggaatt tctagtatgg ttgaggccat ggtgtccagg 1080
gcccgcattg atgcacgaat tgacttcgaa tctggacgga taaagaagga tgagttcgct 1140
gagatcatga agatctgttc caccattgaa gagctcagac ggcaaaaa 1188

<210> SEQ ID NO 97
<211> LENGTH: 20
<212> TYPE: DNA
<213> ORGANISM: Artificial sequence
<220> FEATURE:
<223> OTHER INFORMATION: Synthetic Primer

<400> SEQUENCE: 97
taaatagaac cggcacattc 20

<210> SEQ ID NO 98
<211> LENGTH: 17

-continued

<212> TYPE: DNA
<213> ORGANISM: Artificial sequence
<220> FEATURE:
<223> OTHER INFORMATION: Synthetic Primer

<400> SEQUENCE: 98
caaagaaatt gaatcag 17

<210> SEQ ID NO 99
<211> LENGTH: 18
<212> TYPE: DNA
<213> ORGANISM: Artificial sequence
<220> FEATURE:
<223> OTHER INFORMATION: Synthetic Primer

<400> SEQUENCE: 99
caagcattac tactgcac 18

<210> SEQ ID NO 100
<211> LENGTH: 19
<212> TYPE: DNA
<213> ORGANISM: Artificial sequence
<220> FEATURE:
<223> OTHER INFORMATION: Synthetic Primer

<400> SEQUENCE: 100
agtctgttcc cacagtttc 19

<210> SEQ ID NO 101
<211> LENGTH: 20
<212> TYPE: DNA
<213> ORGANISM: Artificial sequence
<220> FEATURE:
<223> OTHER INFORMATION: Synthetic Primer

<400> SEQUENCE: 101
gaattcgaat gtgccggttc 20

<210> SEQ ID NO 102
<211> LENGTH: 20
<212> TYPE: DNA
<213> ORGANISM: Artificial sequence
<220> FEATURE:
<223> OTHER INFORMATION: Synthetic Primer

<400> SEQUENCE: 102
aaaacaagga ttttttcacg 20

<210> SEQ ID NO 103
<211> LENGTH: 2341
<212> TYPE: DNA
<213> ORGANISM: Equine influenza virus H3N8
<220> FEATURE:
<221> NAME/KEY: CDS
<222> LOCATION: (25)..(2295)
<223> OTHER INFORMATION:
<220> FEATURE:
<221> NAME/KEY: misc_feature
<222> LOCATION: (1489)..(1489)
<223> OTHER INFORMATION: At nucleotide 1489, w = a or t/u
At amino acid residue 489, Xaa = Thr or Ser

<400> SEQUENCE: 103

```
agcaaaagca ggcaaactat ttga atg gat gtc aat ccg act cta ctc ttc        51
                           Met Asp Val Asn Pro Thr Leu Leu Phe
                           1               5

tta aag gtg cca gcg caa aat gct ata agc aca aca ttc cct tat act       99
```

-continued

```
Leu Lys Val Pro Ala Gln Asn Ala Ile Ser Thr Thr Phe Pro Tyr Thr
10                  15                  20                  25

gga gat cct ccc tac agt cat gga aca ggg aca gga tac acc atg gat      147
Gly Asp Pro Pro Tyr Ser His Gly Thr Gly Thr Gly Tyr Thr Met Asp
                30                  35                  40

act gtc aac aga aca cat caa tac tca gaa aag ggg aaa tgg aca aca      195
Thr Val Asn Arg Thr His Gln Tyr Ser Glu Lys Gly Lys Trp Thr Thr
            45                  50                  55

aac act gag att gga gca cca caa ctt aat cca atc gat gga ccg ctt      243
Asn Thr Glu Ile Gly Ala Pro Gln Leu Asn Pro Ile Asp Gly Pro Leu
        60                  65                  70

cct gaa gac aat gaa cca agt ggg tac gcc caa aca gat tgt gta ttg      291
Pro Glu Asp Asn Glu Pro Ser Gly Tyr Ala Gln Thr Asp Cys Val Leu
    75                  80                  85

gaa gca atg gct ttc ctt gaa gaa tcc cat ccc gga atc ttt gaa aat      339
Glu Ala Met Ala Phe Leu Glu Glu Ser His Pro Gly Ile Phe Glu Asn
90                  95                  100                 105

tcg tgt ctt gaa aca atg gag gtg gtt cag cag aca aga gtg gac aaa      387
Ser Cys Leu Glu Thr Met Glu Val Val Gln Gln Thr Arg Val Asp Lys
                110                 115                 120

cta aca caa ggc cga caa act tac gat tgg acc ttg aat agg aat caa      435
Leu Thr Gln Gly Arg Gln Thr Tyr Asp Trp Thr Leu Asn Arg Asn Gln
            125                 130                 135

cct gcc gca aca gca ctt gct aat aca att gaa gtg ttc aga tca aat      483
Pro Ala Ala Thr Ala Leu Ala Asn Thr Ile Glu Val Phe Arg Ser Asn
        140                 145                 150

gat ctg act tcc agt gag tca ggg aga tta atg gac ttc ctc aaa gat      531
Asp Leu Thr Ser Ser Glu Ser Gly Arg Leu Met Asp Phe Leu Lys Asp
    155                 160                 165

gtc atg gag tcc atg aac aag gaa gaa atg gaa ata aca aca cac ttc      579
Val Met Glu Ser Met Asn Lys Glu Glu Met Glu Ile Thr Thr His Phe
170                 175                 180                 185

caa cgg aag aga aga gta aga gac aac atg aca aag aga atg gtg aca      627
Gln Arg Lys Arg Arg Val Arg Asp Asn Met Thr Lys Arg Met Val Thr
                190                 195                 200

cag aga acc ata ggg aag aaa aaa caa cga tta aac aga aag agc tat      675
Gln Arg Thr Ile Gly Lys Lys Lys Gln Arg Leu Asn Arg Lys Ser Tyr
            205                 210                 215

ctg atc agg gca tta acc tta aac aca atg acc aag gac gct gag aga      723
Leu Ile Arg Ala Leu Thr Leu Asn Thr Met Thr Lys Asp Ala Glu Arg
        220                 225                 230

ggg aaa ttg aaa cga cga gca att gca acc cca gga atg cag ata aga      771
Gly Lys Leu Lys Arg Arg Ala Ile Ala Thr Pro Gly Met Gln Ile Arg
    235                 240                 245

ggg ttt gta tat ttt gtt gaa aca tta gcc cga aga ata tgt gaa aag      819
Gly Phe Val Tyr Phe Val Glu Thr Leu Ala Arg Arg Ile Cys Glu Lys
250                 255                 260                 265

ctt gaa caa tca gga ttg cca gtt ggc ggt aat gag aaa aag gcc aaa      867
Leu Glu Gln Ser Gly Leu Pro Val Gly Gly Asn Glu Lys Lys Ala Lys
                270                 275                 280

ctg gct aat gtc gtc aga aaa atg atg act aat tcc caa gac act gaa      915
Leu Ala Asn Val Val Arg Lys Met Met Thr Asn Ser Gln Asp Thr Glu
            285                 290                 295

ctc tcc ttc acc atc act ggg gac aat acc aaa tgg aat gaa aat cag      963
Leu Ser Phe Thr Ile Thr Gly Asp Asn Thr Lys Trp Asn Glu Asn Gln
        300                 305                 310

aac cca cgc atg ttc ctg gca atg atc aca tac ata act aga aac cag     1011
Asn Pro Arg Met Phe Leu Ala Met Ile Thr Tyr Ile Thr Arg Asn Gln
    315                 320                 325
```

-continued

```
cca gaa tgg ttc aga aat gtt cta agc att gca ccg att atg ttc tca      1059
Pro Glu Trp Phe Arg Asn Val Leu Ser Ile Ala Pro Ile Met Phe Ser
330                 335                 340                 345

aat aaa atg gca aga ctg ggg aaa gga tat atg ttt gaa agc aaa agt      1107
Asn Lys Met Ala Arg Leu Gly Lys Gly Tyr Met Phe Glu Ser Lys Ser
                350                 355                 360

atg aaa ttg aga act caa ata cca gca gaa atg ctc gca agc att gat      1155
Met Lys Leu Arg Thr Gln Ile Pro Ala Glu Met Leu Ala Ser Ile Asp
            365                 370                 375

ctg aaa tat ttc aat gat tca aca aaa aag aaa att gag aag ata cga      1203
Leu Lys Tyr Phe Asn Asp Ser Thr Lys Lys Lys Ile Glu Lys Ile Arg
        380                 385                 390

cca ctt ctg gtc gat ggg act gct tca ctg agt cct ggc atg atg atg      1251
Pro Leu Leu Val Asp Gly Thr Ala Ser Leu Ser Pro Gly Met Met Met
    395                 400                 405

gga atg ttc aac atg ttg agc act gta cta ggt gta tcc ata tta aac      1299
Gly Met Phe Asn Met Leu Ser Thr Val Leu Gly Val Ser Ile Leu Asn
410                 415                 420                 425

ctg ggc cag agg aaa tac aca aag acc aca tac tgg tgg gat ggt ctg      1347
Leu Gly Gln Arg Lys Tyr Thr Lys Thr Thr Tyr Trp Trp Asp Gly Leu
                430                 435                 440

caa tca tcc gat gat ttt gct ttg ata gtg aat gcg cct aat cat gaa      1395
Gln Ser Ser Asp Asp Phe Ala Leu Ile Val Asn Ala Pro Asn His Glu
            445                 450                 455

gga ata cag gct gga gta gac aga ttc tat aga act tgc aaa ctg gtc      1443
Gly Ile Gln Ala Gly Val Asp Arg Phe Tyr Arg Thr Cys Lys Leu Val
        460                 465                 470

ggg atc aac atg agc aaa aag aag tcc tac ata aat aga acc ggc wca      1491
Gly Ile Asn Met Ser Lys Lys Lys Ser Tyr Ile Asn Arg Thr Gly Xaa
    475                 480                 485

ttc gaa ttc aca agc ttt ttc tac cgg tat ggt ttt gtc gcc aat ttc      1539
Phe Glu Phe Thr Ser Phe Phe Tyr Arg Tyr Gly Phe Val Ala Asn Phe
490                 495                 500                 505

agc atg gag cta ccc agt ttt ggg gtt tcc ggg ata aat gaa tct gca      1587
Ser Met Glu Leu Pro Ser Phe Gly Val Ser Gly Ile Asn Glu Ser Ala
                510                 515                 520

gac atg agc att gga atg aca gtt atc aaa aac aac atg ata aat aat      1635
Asp Met Ser Ile Gly Met Thr Val Ile Lys Asn Asn Met Ile Asn Asn
            525                 530                 535

gat ctc ggt ccc gcc acg gca caa atg gca ctc caa ctc ttc att aag      1683
Asp Leu Gly Pro Ala Thr Ala Gln Met Ala Leu Gln Leu Phe Ile Lys
        540                 545                 550

gat tat cgg tac aca tac cgg tgc cat aga ggc gat acc cag ata caa      1731
Asp Tyr Arg Tyr Thr Tyr Arg Cys His Arg Gly Asp Thr Gln Ile Gln
    555                 560                 565

acc aga aga tcc ttt gag ttg aag aaa ctg tgg gaa cag act cga tca      1779
Thr Arg Arg Ser Phe Glu Leu Lys Lys Leu Trp Glu Gln Thr Arg Ser
570                 575                 580                 585

aag act ggt cta ctg gta tca gat ggg ggt cca aac cta tac aac atc      1827
Lys Thr Gly Leu Leu Val Ser Asp Gly Gly Pro Asn Leu Tyr Asn Ile
                590                 595                 600

aga aac cta cac atc ccg gaa gtc tgt ttg aaa tgg gag ctg atg gat      1875
Arg Asn Leu His Ile Pro Glu Val Cys Leu Lys Trp Glu Leu Met Asp
            605                 610                 615

gaa gat tat aaa ggg agg cta tgt aat cca ttg aat cct ttc gtt agc      1923
Glu Asp Tyr Lys Gly Arg Leu Cys Asn Pro Leu Asn Pro Phe Val Ser
        620                 625                 630

cac aaa gaa att gaa tca gtg aac agt gca gta gta atg cct gcg cat      1971
His Lys Glu Ile Glu Ser Val Asn Ser Ala Val Val Met Pro Ala His
    635                 640                 645
```

-continued

```
ggc cct gcc aaa agc atg gag tat gat gct gtt gca aca aca cac tct     2019
Gly Pro Ala Lys Ser Met Glu Tyr Asp Ala Val Ala Thr Thr His Ser
650                 655                 660                 665

tgg atc ccc aag agg aac cgg tcc ata ttg aac aca agt caa agg gga     2067
Trp Ile Pro Lys Arg Asn Arg Ser Ile Leu Asn Thr Ser Gln Arg Gly
                670                 675                 680

ata ctc gaa gat gag cag atg tat cag aaa tgc tgc aac ctg ttt gaa     2115
Ile Leu Glu Asp Glu Gln Met Tyr Gln Lys Cys Cys Asn Leu Phe Glu
            685                 690                 695

aaa ttc ttc ccc agc agc tca tac aga aga cca gtc gga att tct agt     2163
Lys Phe Phe Pro Ser Ser Ser Tyr Arg Arg Pro Val Gly Ile Ser Ser
        700                 705                 710

atg gtt gag gcc atg gtg tcc agg gcc cgc att gat gca cga att gac     2211
Met Val Glu Ala Met Val Ser Arg Ala Arg Ile Asp Ala Arg Ile Asp
    715                 720                 725

ttc gaa tct gga cgg ata aag aag gat gag ttc gct gag atc atg aag     2259
Phe Glu Ser Gly Arg Ile Lys Lys Asp Glu Phe Ala Glu Ile Met Lys
730                 735                 740                 745

atc tgt tcc acc att gaa gag ctc aga cgg caa aaa tagtgaattt          2305
Ile Cys Ser Thr Ile Glu Glu Leu Arg Arg Gln Lys
                750                 755

agcttgatct tcgtgaaaaa atgccttgtt tctact                             2341


<210> SEQ ID NO 104
<211> LENGTH: 757
<212> TYPE: PRT
<213> ORGANISM: Equine influenza virus H3N8
<220> FEATURE:
<221> NAME/KEY: misc_feature
<222> LOCATION: (489)..(489)
<223> OTHER INFORMATION: The 'Xaa' at location 489 stands for Thr or Ser

<400> SEQUENCE: 104

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Asp Leu Thr Ser Ser Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190
```

-continued

```
Asp Asn Met Thr Lys Arg Met Val Thr Gln Arg Thr Ile Gly Lys Lys
        195                 200                 205

Lys Gln Arg Leu Asn Arg Lys Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Lys Ile Arg Pro Leu Leu Val Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Arg Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Xaa Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Met Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Thr Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Lys Gly Arg Leu
```

-continued

```
    610                 615                 620

Cys Asn Pro Leu Asn Pro Phe Val Ser His Lys Glu Ile Glu Ser Val
625                 630                 635                 640

Asn Ser Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Asp Glu Phe Ala Glu Ile Met Lys Ile Cys Ser Thr Ile Glu Glu
            740                 745                 750

Leu Arg Arg Gln Lys
        755
```

<210> SEQ ID NO 105
<211> LENGTH: 2271
<212> TYPE: DNA
<213> ORGANISM: Equine influenza virus H3N8

<400> SEQUENCE: 105

```
atggatgtca atccgactct actcttctta aaggtgccag cgcaaaatgc tataagcaca     60

acattccctt atactggaga tcctccctac agtcatggaa cagggacagg atacaccatg    120

gatactgtca acagaacaca tcaatactca gaaaagggga aatggacaac aaacactgag    180

attggagcac cacaacttaa tccaatcgat ggaccgcttc ctgaagacaa tgaaccaagt    240

gggtacgccc aaacagattg tgtattggaa gcaatggctt tccttgaaga atcccatccc    300

ggaatctttg aaaattcgtg tcttgaaaca atggaggtgg ttcagcagac aagagtggac    360

aaactaacac aaggccgaca aacttacgat tggaccttga ataggaatca acctgccgca    420

acagcacttg ctaatacaat tgaagtgttc agatcaaatg atctgacttc cagtgagtca    480

gggagattaa tggacttcct caaagatgtc atggagtcca tgaacaagga agaaatggaa    540

ataacaacac acttccaacg gaagagaaga gtaagagaca acatgacaaa gagaatggtg    600

acacagagaa ccatagggaa gaaaaaacaa cgattaaaca gaaagagcta tctgatcagg    660

gcattaacct taaacacaat gaccaaggac gctgagagag ggaaattgaa acgacgagca    720

attgcaaccc caggaatgca gataagaggg tttgtatatt ttgttgaaac attagcccga    780

agaatatgtg aaaagcttga acaatcagga ttgccagttg gcggtaatga gaaaaaggcc    840

aaactggcta atgtcgtcag aaaaatgatg actaattccc aagacactga actctccttc    900

accatcactg gggacaatac caaatggaat gaaaatcaga acccacgcat gttcctggca    960

atgatcacat acataactag aaaccagcca gaatggttca gaaatgttct aagcattgca   1020

ccgattatgt tctcaaataa aatggcaaga ctggggaaag gatatatgtt tgaaagcaaa   1080

agtatgaaat tgagaactca aataccagca gaaatgctcg caagcattga tctgaaatat   1140

ttcaatgatt caacaaaaaa gaaaattgag aagatacgac cacttctggt cgatgggact   1200

gcttcactga gtcctggcat gatgatggga atgttcaaca tgttgagcac tgtactaggt   1260
```

-continued

```
gtatccatat taaacctggg ccagaggaaa tacacaaaga ccacatactg gtgggatggt   1320

ctgcaatcat ccgatgattt tgctttgata gtgaatgcgc ctaatcatga aggaatacag   1380

gctggagtag acagattcta tagaacttgc aaactggtcg ggatcaacat gagcaaaaag   1440

aagtcctaca taaatagaac cggcwcattc gaattcacaa gctttttcta ccggtatggt   1500

tttgtcgcca atttcagcat ggagctaccc agttttgggg tttccgggat aaatgaatct   1560

gcagacatga gcattggaat gacagttatc aaaaacaaca tgataaataa tgatctcggt   1620

cccgccacgg cacaaatggc actccaactc ttcattaagg attatcggta cacataccgg   1680

tgccatagag gcgataccca gatacaaacc agaagatcct ttgagttgaa gaaactgtgg   1740

gaacagactc gatcaaagac tggtctactg gtatcagatg ggggtccaaa cctatacaac   1800

atcagaaacc tacacatccc ggaagtctgt ttgaaatggg agctgatgga tgaagattat   1860

aaagggaggc tatgtaatcc attgaatcct ttcgttagcc acaaagaaat tgaatcagtg   1920

aacagtgcag tagtaatgcc tgcgcatggc cctgccaaaa gcatggagta tgatgctgtt   1980

gcaacaacac actcttggat ccccaagagg aaccggtcca tattgaacac aagtcaaagg   2040

ggaatactcg aagatgagca gatgtatcag aaatgctgca acctgtttga aaaattcttc   2100

cccagcagct catacagaag accagtcgga atttctagta tggttgaggc catggtgtcc   2160

agggcccgca ttgatgcacg aattgacttc gaatctggac ggataaagaa ggatgagttc   2220

gctgagatca tgaagatctg ttccaccatt gaagagctca gacggcaaaa a            2271


<210> SEQ ID NO 106
<211> LENGTH: 2341
<212> TYPE: DNA
<213> ORGANISM: Equine influenza virus H3N8
<220> FEATURE:
<221> NAME/KEY: CDS
<222> LOCATION: (25)..(2295)
<223> OTHER INFORMATION:
<220> FEATURE:
<221> NAME/KEY: misc_feature
<222> LOCATION: (2144)..(21434)
<223> OTHER INFORMATION: At nucleotide 2144, r = a or g
      At amino acid residue 707, Xaa = Arg or Lys

<400> SEQUENCE: 106

agcaaaagca ggcaaactat ttga atg gat gtc aat ccg act cta ctc ttc        51
                           Met Asp Val Asn Pro Thr Leu Leu Phe
                           1               5

tta aag gtg cca gcg caa aat gct ata agc aca aca ttc cct tat act       99
Leu Lys Val Pro Ala Gln Asn Ala Ile Ser Thr Thr Phe Pro Tyr Thr
10                  15                  20                  25

gga gat cct ccc tac agt cat gga aca ggg aca gga tac acc atg gat      147
Gly Asp Pro Pro Tyr Ser His Gly Thr Gly Thr Gly Tyr Thr Met Asp
                30                  35                  40

act gtc aac aga aca cat caa tac tca gaa aag ggg aaa tgg aca aca      195
Thr Val Asn Arg Thr His Gln Tyr Ser Glu Lys Gly Lys Trp Thr Thr
            45                  50                  55

aac act gag att gga gca cca caa ctt aat cca atc gat gga ccg ctt      243
Asn Thr Glu Ile Gly Ala Pro Gln Leu Asn Pro Ile Asp Gly Pro Leu
        60                  65                  70

cct gaa gac aat gaa cca agt ggg tac gcc caa aca gat tgt gta ttg      291
Pro Glu Asp Asn Glu Pro Ser Gly Tyr Ala Gln Thr Asp Cys Val Leu
    75                  80                  85

gaa gca atg gct ttc ctt gaa gaa tcc cat ccc gga atc ttt gaa aat      339
Glu Ala Met Ala Phe Leu Glu Glu Ser His Pro Gly Ile Phe Glu Asn
90                  95                  100                 105
```

-continued

```
tcg tgt ctt gaa aca atg gag gtg gtt cag cag aca aga gtg gac aaa      387
Ser Cys Leu Glu Thr Met Glu Val Val Gln Gln Thr Arg Val Asp Lys
            110                 115                 120

cta aca caa ggc cga caa act tac gat tgg acc ttg aat agg aat caa      435
Leu Thr Gln Gly Arg Gln Thr Tyr Asp Trp Thr Leu Asn Arg Asn Gln
            125                 130                 135

cct gcc gca aca gca ctt gct aat aca att gaa gtg ttc aga tca aat      483
Pro Ala Ala Thr Ala Leu Ala Asn Thr Ile Glu Val Phe Arg Ser Asn
        140                 145                 150

gat ctg act tcc agt gag tca ggg aga tta atg gac ttc ctc aaa gat      531
Asp Leu Thr Ser Ser Glu Ser Gly Arg Leu Met Asp Phe Leu Lys Asp
    155                 160                 165

gtc atg gag tcc atg aac aag gaa gaa atg gaa ata aca aca cac ttc      579
Val Met Glu Ser Met Asn Lys Glu Glu Met Glu Ile Thr Thr His Phe
170                 175                 180                 185

caa cgg aag aga aga gta aga gac aac atg aca aag aga atg gtg aca      627
Gln Arg Lys Arg Arg Val Arg Asp Asn Met Thr Lys Arg Met Val Thr
            190                 195                 200

cag aga acc ata ggg aag aaa aaa caa cga tta aac aga aag agc tat      675
Gln Arg Thr Ile Gly Lys Lys Lys Gln Arg Leu Asn Arg Lys Ser Tyr
            205                 210                 215

ctg atc agg gca tta acc tta aac aca atg acc aag gac gct gag aga      723
Leu Ile Arg Ala Leu Thr Leu Asn Thr Met Thr Lys Asp Ala Glu Arg
        220                 225                 230

ggg aaa ttg aaa cga cga gca att gca acc cca gga atg cag ata aga      771
Gly Lys Leu Lys Arg Arg Ala Ile Ala Thr Pro Gly Met Gln Ile Arg
    235                 240                 245

ggg ttt gta tat ttt gtt gaa aca tta gcc cga aga ata tgt gaa aag      819
Gly Phe Val Tyr Phe Val Glu Thr Leu Ala Arg Arg Ile Cys Glu Lys
250                 255                 260                 265

ctt gaa caa tca gga ttg cca gtt ggc ggt aat gag aaa aag gcc aaa      867
Leu Glu Gln Ser Gly Leu Pro Val Gly Gly Asn Glu Lys Lys Ala Lys
            270                 275                 280

ctg gct aat gtc gtc aga aaa atg atg act aat tcc caa gac act gaa      915
Leu Ala Asn Val Val Arg Lys Met Met Thr Asn Ser Gln Asp Thr Glu
            285                 290                 295

ctc tcc ttc acc atc act ggg gac aat acc aaa tgg aat gaa aat cag      963
Leu Ser Phe Thr Ile Thr Gly Asp Asn Thr Lys Trp Asn Glu Asn Gln
        300                 305                 310

aac cca cgc atg ttc ctg gca atg atc aca tac ata act aga aac cag     1011
Asn Pro Arg Met Phe Leu Ala Met Ile Thr Tyr Ile Thr Arg Asn Gln
    315                 320                 325

cca gaa tgg ttc aga aat gtt cta agc att gca ccg att atg ttc tca     1059
Pro Glu Trp Phe Arg Asn Val Leu Ser Ile Ala Pro Ile Met Phe Ser
330                 335                 340                 345

aat aaa atg gca aga ctg ggg aaa gga tat atg ttt gaa agc aaa agt     1107
Asn Lys Met Ala Arg Leu Gly Lys Gly Tyr Met Phe Glu Ser Lys Ser
            350                 355                 360

atg aaa ttg aga act caa ata cca gca gaa atg ctc gca agc att gat     1155
Met Lys Leu Arg Thr Gln Ile Pro Ala Glu Met Leu Ala Ser Ile Asp
            365                 370                 375

ctg aaa tat ttc aat gat tca aca aaa aag aaa att gag aag ata cga     1203
Leu Lys Tyr Phe Asn Asp Ser Thr Lys Lys Lys Ile Glu Lys Ile Arg
        380                 385                 390

cca ctt ctg gtc gat ggg act gct tca ctg agt cct ggc atg atg atg     1251
Pro Leu Leu Val Asp Gly Thr Ala Ser Leu Ser Pro Gly Met Met Met
    395                 400                 405

gga atg ttc aac atg ttg agc act gta cta ggt gta tcc ata tta aac     1299
Gly Met Phe Asn Met Leu Ser Thr Val Leu Gly Val Ser Ile Leu Asn
410                 415                 420                 425
```

-continued

```
ctg ggc cag agg aaa tac aca aag acc aca tac tgg tgg gat ggt ctg     1347
Leu Gly Gln Arg Lys Tyr Thr Lys Thr Thr Tyr Trp Trp Asp Gly Leu
                430                 435                 440

caa tca tcc gat gat ttt gct ttg ata gtg aat gcg cct aat cat gaa     1395
Gln Ser Ser Asp Asp Phe Ala Leu Ile Val Asn Ala Pro Asn His Glu
            445                 450                 455

gga ata cag gct gga gta gac aga ttc tat aga act tgc aaa ctg gtc     1443
Gly Ile Gln Ala Gly Val Asp Arg Phe Tyr Arg Thr Cys Lys Leu Val
        460                 465                 470

ggg atc aac atg agc aaa aag aag tcc tac ata aat aga acc ggc aca     1491
Gly Ile Asn Met Ser Lys Lys Lys Ser Tyr Ile Asn Arg Thr Gly Thr
    475                 480                 485

ttc gaa ttc aca agc ttt ttc tac cgg tat ggt ttt gtc gcc aat ttc     1539
Phe Glu Phe Thr Ser Phe Phe Tyr Arg Tyr Gly Phe Val Ala Asn Phe
490                 495                 500                 505

agc atg gag cta ccc agt ttt ggg gtt tcc ggg ata aat gaa tct gca     1587
Ser Met Glu Leu Pro Ser Phe Gly Val Ser Gly Ile Asn Glu Ser Ala
                510                 515                 520

gac atg agc att gga atg aca gtt atc aaa aac aac atg ata aat aat     1635
Asp Met Ser Ile Gly Met Thr Val Ile Lys Asn Asn Met Ile Asn Asn
            525                 530                 535

gat ctc ggt ccc gcc acg gca caa atg gca ctc caa ctc ttc att aag     1683
Asp Leu Gly Pro Ala Thr Ala Gln Met Ala Leu Gln Leu Phe Ile Lys
        540                 545                 550

gat tat cgg tac aca tac cgg tgt caa aga ggc gat acc cag ata caa     1731
Asp Tyr Arg Tyr Thr Tyr Arg Cys Gln Arg Gly Asp Thr Gln Ile Gln
    555                 560                 565

acc aga aga tcc ttt gag ttg aag aaa ctg tgg gaa cag act cga tca     1779
Thr Arg Arg Ser Phe Glu Leu Lys Lys Leu Trp Glu Gln Thr Arg Ser
570                 575                 580                 585

aag act ggt cta ctg gta tca gat ggg ggt cca aac cta tac aac atc     1827
Lys Thr Gly Leu Leu Val Ser Asp Gly Gly Pro Asn Leu Tyr Asn Ile
                590                 595                 600

aga aac cta cac atc ccg gaa gtc tgt ttg aaa tgg gag ctg atg gat     1875
Arg Asn Leu His Ile Pro Glu Val Cys Leu Lys Trp Glu Leu Met Asp
            605                 610                 615

gaa gat tat aaa ggg agg cta tgt aat cca ttg aat cct ttc gtt agc     1923
Glu Asp Tyr Lys Gly Arg Leu Cys Asn Pro Leu Asn Pro Phe Val Ser
        620                 625                 630

cac aaa gaa att gaa tca gtg aac agt gca gta gta atg cct gcg cat     1971
His Lys Glu Ile Glu Ser Val Asn Ser Ala Val Val Met Pro Ala His
    635                 640                 645

ggc cct gcc aaa agc atg gag tat gat gct gtt gca aca aca cac tct     2019
Gly Pro Ala Lys Ser Met Glu Tyr Asp Ala Val Ala Thr Thr His Ser
650                 655                 660                 665

tgg atc ccc aag agg aac cgg tcc ata ttg aac aca agt caa agg gga     2067
Trp Ile Pro Lys Arg Asn Arg Ser Ile Leu Asn Thr Ser Gln Arg Gly
                670                 675                 680

ata ctc gaa gat gag cag atg tat cag aaa tgc tgc aac ctg ttt gaa     2115
Ile Leu Glu Asp Glu Gln Met Tyr Gln Lys Cys Cys Asn Leu Phe Glu
            685                 690                 695

aaa ttc ttc ccc agc agc tca tac aga ara cca gtc gga att tct agt     2163
Lys Phe Phe Pro Ser Ser Ser Tyr Arg Xaa Pro Val Gly Ile Ser Ser
        700                 705                 710

atg gtt gag gcc atg gtg tcc agg gcc cgc att gat gca cga att gac     2211
Met Val Glu Ala Met Val Ser Arg Ala Arg Ile Asp Ala Arg Ile Asp
    715                 720                 725

ttc gaa tct gga cgg ata aag aag gat gag ttc gct gag atc atg aag     2259
Phe Glu Ser Gly Arg Ile Lys Lys Asp Glu Phe Ala Glu Ile Met Lys
```

-continued

```
730                 735                 740                 745

atc tgt tcc acc att gaa gag ctc aga cgg caa aaa tagtgaattt          2305
Ile Cys Ser Thr Ile Glu Glu Leu Arg Arg Gln Lys
                750                 755

agcttgatct tcgtgaaaaa atgccttgtt tctact                             2341


<210> SEQ ID NO 107
<211> LENGTH: 757
<212> TYPE: PRT
<213> ORGANISM: Equine influenza virus H3N8
<220> FEATURE:
<221> NAME/KEY: misc_feature
<222> LOCATION: (707)..(707)
<223> OTHER INFORMATION: The 'Xaa' at location 707 stands for Arg, or
      Lys.

<400> SEQUENCE: 107

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Asp Leu Thr Ser Ser Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu Asn Arg Lys Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
```

-continued

```
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Lys Ile Arg Pro Leu Leu Val Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Arg Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Met Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys Gln Arg Gly Asp Thr Gln Ile Gln Thr Arg Arg Ser Phe Glu Leu
                565                 570                 575

Lys Lys Leu Trp Glu Gln Thr Arg Ser Lys Thr Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Lys Gly Arg Leu
    610                 615                 620

Cys Asn Pro Leu Asn Pro Phe Val Ser His Lys Glu Ile Glu Ser Val
625                 630                 635                 640

Asn Ser Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Xaa Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735
```

-continued

```
Lys Asp Glu Phe Ala Glu Ile Met Lys Ile Cys Ser Thr Ile Glu Glu
            740                 745                 750

Leu Arg Arg Gln Lys
        755


<210> SEQ ID NO 108
<211> LENGTH: 2271
<212> TYPE: DNA
<213> ORGANISM: Equine influenza virus H3N8

<400> SEQUENCE: 108

atggatgtca atccgactct actcttctta aaggtgccag cgcaaaatgc tataagcaca     60

acattccctt atactggaga tcctccctac agtcatggaa cagggacagg atacaccatg    120

gatactgtca acagaacaca tcaatactca gaaaagggga aatggacaac aaacactgag    180

attggagcac cacaacttaa tccaatcgat ggaccgcttc ctgaagacaa tgaaccaagt    240

gggtacgccc aaacagattg tgtattggaa gcaatggctt tccttgaaga atcccatccc    300

ggaatctttg aaaattcgtg tcttgaaaca atggaggtgg ttcagcagac aagagtggac    360

aaactaacac aaggccgaca aacttacgat tggaccttga ataggaatca acctgccgca    420

acagcacttg ctaatacaat tgaagtgttc agatcaaatg atctgacttc cagtgagtca    480

gggagattaa tggacttcct caaagatgtc atggagtcca tgaacaagga agaaatggaa    540

ataacaacac acttccaacg gaagagaaga gtaagagaca acatgacaaa gagaatggtg    600

acacagagaa ccatagggaa gaaaaaacaa cgattaaaca gaaagagcta tctgatcagg    660

gcattaacct taaacacaat gaccaaggac gctgagagag ggaaattgaa acgacgagca    720

attgcaaccc caggaatgca gataagaggg tttgtatatt ttgttgaaac attagcccga    780

agaatatgtg aaaagcttga acaatcagga ttgccagttg gcggtaatga gaaaaaggcc    840

aaactggcta atgtcgtcag aaaaatgatg actaattccc aagacactga actctccttc    900

accatcactg gggacaatac caaatggaat gaaaatcaga acccacgcat gttcctggca    960

atgatcacat acataactag aaaccagcca gaatggttca gaaatgttct aagcattgca   1020

ccgattatgt tctcaaataa aatggcaaga ctggggaaag gatatatgtt tgaaagcaaa   1080

agtatgaaat tgagaactca aataccagca gaaatgctcg caagcattga tctgaaatat   1140

ttcaatgatt caacaaaaaa gaaaattgag aagatacgac cacttctggt cgatgggact   1200

gcttcactga gtcctggcat gatgatggga atgttcaaca tgttgagcac tgtactaggt   1260

gtatccatat taaacctggg ccagaggaaa tacacaaaga ccacatactg gtgggatggt   1320

ctgcaatcat ccgatgattt tgctttgata gtgaatgcgc ctaatcatga aggaatacag   1380

gctggagtag acagattcta tagaacttgc aaactggtcg ggatcaacat gagcaaaaag   1440

aagtcctaca taaatagaac cggcacattc gaattcacaa gctttttcta ccggtatggt   1500

tttgtcgcca atttcagcat ggagctaccc agttttgggg tttccgggat aaatgaatct   1560

gcagacatga gcattggaat gacagttatc aaaaacaaca tgataaataa tgatctcggt   1620

cccgccacgg cacaaatggc actccaactc ttcattaagg attatcggta cacataccgg   1680

tgtcaaagag gcgataccca gatacaaacc agaagatcct ttgagttgaa gaaactgtgg   1740

gaacagactc gatcaaagac tggtctactg gtatcagatg gggtccaaa cctatacaac   1800

atcagaaacc tacacatccc ggaagtctgt ttgaaatggg agctgatgga tgaagattat   1860

aaagggaggc tatgtaatcc attgaatcct ttcgttagcc acaaagaaat tgaatcagtg   1920
```

-continued

| | |
|---|---|
| aacagtgcag tagtaatgcc tgcgcatggc cctgccaaaa gcatggagta tgatgctgtt | 1980 |
| gcaacaacac actcttggat ccccaagagg aaccggtcca tattgaacac aagtcaaagg | 2040 |
| ggaatactcg aagatgagca gatgtatcag aaatgctgca acctgtttga aaaattcttc | 2100 |
| cccagcagct catacagaar accagtcgga atttctagta tggttgaggc catggtgtcc | 2160 |
| agggcccgca ttgatgcacg aattgacttc gaatctggac ggataaagaa ggatgagttc | 2220 |
| gctgagatca tgaagatctg ttccaccatt gaagagctca gacggcaaaa a | 2271 |

COLD-ADAPTED EQUINE INFLUENZA VIRUSES

CROSS REFERENCE TO RELATED APPLICATIONS

This application is a division of application Ser. No. 09/506,286 filed Feb. 16, 2000, now U.S. Pat. No. 6,482, 414, which is a continuation in part of application Ser. No. 09/133,921 filed Aug. 13, 1998, now U.S. Pat. No. 6,177, 082, and continuation in part of PCT/US99/18583 filed Aug. 12, 1999.

FIELD OF THE INVENTION

The present invention relates to experimentally-generated cold-adapted equine influenza viruses, and particularly to cold-adapted equine influenza viruses having additional phenotypes, such as attenuation, dominant interference, or temperature sensitivity. The invention also includes reassortant influenza A viruses which contain at least one genome segment from such an equine influenza virus, such that the reassortant virus includes certain phenotypes of the donor equine influenza virus. The invention further includes genetically-engineered equine influenza viruses, produced through reverse genetics, which comprise certain identifying phenotypes of a cold-adapted equine influenza virus of the present invention. The present invention also relates to the use of these viruses in therapeutic compositions to protect animals from diseases caused by influenza viruses.

BACKGROUND OF THE INVENTION

Equine influenza virus has been recognized as a major respiratory pathogen in horses since about 1956. Disease symptoms caused by equine influenza virus can be severe, and are often followed by secondary bacterial infections. Two subtypes of equine influenza virus are recognized, namely subtype-1, the prototype being A/Equine/Prague/1/56 (H7N7), and subtype-2, the prototype being A/Equine/Miami/1/63 (H3N8). Presently, the predominant virus subtype is subtype-2, which has further diverged among Eurasian and North American isolates in recent years.

The currently licensed vaccine for equine influenza is an inactivated (killed) virus vaccine. This vaccine provides minimal, if any, protection for horses, and can produce undesirable side effects, for example, inflammatory reactions at the site of injection. See, e.g., Mumford, 1987, *Equine Infectious Disease IV*, 207–217, and Mumford, et al., 1993, *Vaccine* 11, 1172–1174. Furthermore, current modalities cannot be used in young foals, because they cannot overcome maternal immunity, and can induce tolerance in a younger animal. Based on the severity of disease, there remains a need for safe, effective therapeutic compositions to protect horses against equine influenza disease.

Production of therapeutic compositions comprising cold-adapted human influenza viruses is described, for example, in Maassab, et al., 1960, *Nature* 7, 612–614, and Maassab, et al., 1969, *J. Immunol.* 102, 728–732. Furthermore, these researchers noted that cold-adapted human influenza viruses, i.e., viruses that have been adapted to grow at lower than normal temperatures, tend to have a phenotype wherein the virus is temperature sensitive; that is, the virus does not grow well at certain higher, non-permissive temperatures at which the wild-type virus will grow and replicate. Various cold-adapted human influenza A viruses, produced by reassortment with existing cold-adapted human influenza A viruses, have been shown to elicit good immune responses in vaccinated individuals, and certain live attenuated cold-adapted reassortant human influenza A viruses have proven to protect humans against challenge with wild-type virus. See, e.g., Clements, et al., 1986, *J. Clin. Microbiol.* 23, 73–76. In U.S. Pat. No. 5,149,531, by Youngner, et al., issued Sep. 22, 1992, the inventors of the present invention further demonstrated that certain reassortant cold-adapted human influenza A viruses also possess a dominant interference phenotype, i.e., they inhibit the growth of their corresponding parental wild-type strain, as well as heterologous influenza A viruses. U.S. Pat. No. 4,683,137, by Coggins et al., issued Jul. 28, 1987, and U.S. Pat. No. 4,693,893, by Campbell, issued Sep. 15, 1987, disclose attenuated therapeutic compositions produced by reassortment of wild type equine influenza viruses with attenuated, cold-adapted human influenza A viruses. Although these therapeutic compositions appear to be generally safe and effective in horses, they pose a significant danger of introducing into the environment a virus containing both human and equine influenza genes.

SUMMARY OF THE INVENTION

The present invention provides experimentally-generated cold-adapted equine influenza viruses, reassortant influenza A viruses that comprise at least one genome segment of an equine influenza virus generated by cold-adaptation such that the equine influenza virus genome segment confers at least one identifying phenotype of a cold-adapted equine influenza virus on the reassortant virus, and genetically-engineered equine influenza viruses, produced through reverse genetics, which comprise at least one identifying phenotype of a cold-adapted equine influenza virus. Identifying phenotypes include cold-adaptation, temperature sensitivity, dominant interference, and attenuation. The invention further provides a therapeutic composition to protect an animal against disease caused by an influenza A virus, where the therapeutic composition includes a cold-adapted equine influenza virus a reassortant influenza A virus, or a genetically-engineered equine influenza virus of the present invention. Also provided is a method to protect an animal from diseases caused by an influenza A virus which includes the administration of such a therapeutic composition. Also provided are methods to produce a cold-adapted equine influenza virus, and methods to produce a reassortant influenza A virus which comprises at least one genome segment of a cold-adapted equine influenza virus, where the equine influenza genome segment confers on the reassortant virus at least one identifying phenotype of the cold-adapted equine influenza virus.

A cold-adapted equine influenza virus is one that replicates in embryonated chicken eggs at a temperature ranging from about 26° C. to about 30° C. Preferably, a cold-adapted equine influenza virus, reassortant influenza A virus, or genetically-engineered equine influenza virus of the present invention is attenuated, such that it will not cause disease in a healthy animal.

In one embodiment, a cold-adapted equine influenza virus, reassortant influenza A virus, or genetically-engineered equine influenza virus of the present invention is also temperature sensitive, such that the virus replicates in embryonated chicken eggs at a temperature ranging from about 26° C. to about 30° C., forms plaques in tissue culture cells at a permissive temperature of about 34° C., but does not form plaques in tissue culture cells at a non-permissive temperature of about 39° C.

In one embodiment, such a temperature sensitive virus comprises two mutations: a first mutation that inhibits plaque formation at a temperature of about 39° C., that mutation co-segregating with the genome segment that encodes the viral nucleoprotein gene; and a second mutation that inhibits all viral protein synthesis at a temperature of about 39° C.

In another embodiment, a cold-adapted, temperature sensitive equine influenza virus of the present invention replicates in embryonated chicken eggs at a temperature ranging from about 26° C. to about 30° C., forms plaques in tissue culture cells at a permissive temperature of about 34° C., but does not form plaques in tissue culture cells or express late viral proteins at a non-permissive temperature of about 37° C.

Typically, a cold-adapted equine influenza virus of the present invention is produced by passaging a wild-type equine influenza virus one or more times, and then selecting viruses that stably grow and replicate at a reduced temperature. A cold-adapted equine, influenza virus produced thereby includes, in certain embodiments, a dominant interference phenotype, that is, the virus, when co-infected with a parental equine influenza virus or heterologous wild-type influenza A virus, will inhibit the growth of that virus.

Examples of cold-adapted equine influenza viruses of the present invention include EIV-P821, identified by accession No. ATCC VR-2625; EIV-P824, identified by accession No. ATCC: VR-2624; EIV-MSV+5, identified by accession No. ATCC VR-627; and progeny of such viruses.

Therapeutic compositions of the present invention include from about $10^5$ $TCID_{50}$ units to about $10^8$ $TCID_{50}$ units, and preferably about $2\times10^6$ $TCID_{50}$ units, of a cold-adapted equine influenza virus, reassortant influenza A virus, or genetically-engineered equine influenza virus of the present invention.

The present invention also includes a method to protect an animal from disease caused by an influenza A virus, which includes the step of administering to the animal a therapeutic composition including a cold-adapted equine influenza virus, a reassortant influenza A virus, or a genetically-engineered equine influenza virus of the present invention. Preferred animals to protect include equids, with horses and ponies being particularly preferred.

Yet another embodiment of the present invention is a method to generate a cold-adapted equine influenza virus. The method includes the steps of passaging a wild-type equine influenza virus; and selecting viruses that grow at a reduced temperature. In one embodiment, the method includes repeating the passaging and selection steps one or more times, while progressively reducing the temperature. Passaging of equine influenza virus preferably takes place in embryonated chicken eggs.

Another embodiment is an method to produce a reassortant influenza A virus through genetic reassortment of the genome segments of a donor cold-adapted equine influenza virus of the present invention with the genome segments of a recipient influenza A virus. Reassortant influenza A viruses of the present invention are produced by a method that includes the steps of: (a) mixing the genome segments of a donor cold-adapted equine influenza virus with the genome segments of a recipient influenza A virus, and (b) selecting viruses which include at least one identifying phenotype of the donor equine influenza virus. Identifying phenotypes include cold-adaptation, temperature sensitivity, dominant interference, and attenuation. Preferably, such reassortant viruses at least include the attenuation phenotype of the donor virus. A typical reassortant virus will have the antigenicity of the recipient virus, that is, it will retain the hemagglutinin (HA) and neuraminidase (NA) phenotypes of the recipient virus.

The present invention further provides methods to propagate cold-adapted equine influenza viruses or reassortant influenza A viruses of the present invention. These methods include propagation in embryonated chicken eggs or in tissue culture cells.

The present invention also describes nucleic acid molecules encoding wild-type and cold-adapted equine influenza proteins M, HA, NS, PB2, PB2-N, PB2-C, PB1, PB1-N, PB1.-C, and PA-C. One embodiment of the present invention is an isolated equine nucleic acid molecule having a nucleic acid sequence selected from a group consisting of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:19, SEQ ID NO:21, SEQ ID NO:22, SEQ ID NO:23, SEQ ID NO:25 SEQ ID NO:44, SEQ ID NO:46, SEQ ID NO:47, SEQ ID NO:49, SEQ ID NO:50, SEQ ID NO:52, SEQ ID NO:53, SEQ ID NO:54, SEQ ID NO:56, SEQ ID NO:57, SEQ ID NO:59, SEQ ID NO:62, SEQ ID NO:64, SEQ ID NO:65, SEQ ID NO:67, SEQ ID NO:68, SEQ ID NO:70, SEQ ID NO:71, SEQ ID NO:76, SEQ ID NO:78, SEQ ID NO:79, SEQ ID NO:80, SEQ ID NO:82, SEQ ID NO:85, SEQ ID NO:87, SEQ ID NO:88, SEQ ID NO:90, SEQ ID NO:91, SEQ ID NO:93, SEQ ID NO:94, SEQ ID NO:96, SEQ ID NO:103, SEQ ID NO:105, SEQ ID NO:106 and SEQ ID NO:108 and a nucleic acid molecule comprising a nucleic acid sequence which is fully complementary to any of such nucleic acid sequences. Another embodiment of the present invention is an isolated equine nucleic acid molecule that encodes a protein comprising an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:24, SEQ ID NO:45, SEQ ID NO:48, SEQ ID NO:51, SEQ ID NO:55, SEQ ID NO:58, SEQ ID NO:63, SEQ ID NO:66, SEQ ID NO:69, SEQ ID NO:77, SEQ ID NO:81, SEQ ID NO:86, SEQ ID NO:89, SEQ ID NO:92, SEQ ID NO:95, SEQ ID NO:104 and SEQ ID NO:107. Another embodiment is an isolated equine influenza protein that comprises an amino acid sequence selected from a group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:24, SEQ ID NO:45, SEQ ID NO:48, SEQ ID NO:51, SEQ ID NO:55, SEQ ID NO:58, SEQ ID NO:63, SEQ ID NO:66, SEQ ID NO:69, SEQ ID NO:77, SEQ ID NO:81, SEQ ID NO:86, SEQ ID NO:89, SEQ ID NO:92, SEQ ID NO:95, SEQ ID NO:104 and SEQ ID NO:107. Also included in the present invention is a virus that include any of these nucleic acid molecules or proteins. In one embodiment, such a virus is equine influenza virus or a reassortant virus.

DETAILED DESCRIPTION

The present invention provides experimentally-generated cold-adapted equine influenza viruses comprising certain defined phenotypes, which are disclosed herein. It is to be noted that the term a or an entity, refers to one or more of that entity; for example, a cold-adapted equine influenza virus can include one or more cold-adapted equine influenza viruses. As such, the terms a (or an), one or more, and at least one can be used interchangeably herein. It is also to be noted that the terms comprising, including, and having can be used interchangeably. Furthermore, an item selected from the group consisting of refers to one or more of the items in that group, including combinations thereof.

A cold-adapted equine influenza virus of the present invention is a virus that has been generated in the laboratory, and as such, is not a virus as occurs in nature. Since the present invention also includes those viruses having the identifying phenotypes of such a cold-adapted equine influenza virus, an equine influenza virus isolated from a mixture of naturally-occurring viruses, i.e., removed from its natural milieu, but having the claimed phenotypes, is included in the present invention. A cold-adapted equine influenza virus of the present invention does not require any specific level of purity. For example, a cold-adapted equine influenza virus grown in embryonated chicken eggs may be in a mixture with the allantoic fluid (AF), and a cold-adapted equine influenza virus grown in tissue culture cells may be in a mixture with disrupted cells and tissue culture medium.

As used herein, an equine influenza virus is an influenza virus that infects and grows in equids, e.g., horses or ponies. As used herein, growth of a virus denotes the ability of the virus to reproduce or replicate itself in a permissive host cell. As such, the terms, growth of a virus and replication of a virus are used interchangeably herein. Growth or replication of a virus in a particular host cell can be demonstrated and measured by standard methods well-known to those skilled in the art of virology. For example, samples containing infectious virus, e.g., as contained in nasopharyngeal secretions from an infected horse, are tested for their ability to cause cytopathic effect (CPE), e.g., virus plaques, in tissue culture cells. Infectious virus may also be detected by inoculation of a sample into the allantoic cavity of embryonated chicken eggs, and then testing the AF of eggs thus inoculated for its ability to agglutinate red blood cells, i.e., cause hemagglutination, due to the presence of the influenza virus hemagglutinin (HA) protein in the AF.

Naturally-occurring, i.e., wild-type, equine influenza viruses replicate well at a temperature from about 34° C. to about 39° C. For example, wild-type equine influenza virus replicates in embryonated chicken eggs at a temperature of about 34° C., and replicates in tissue culture cells at a temperature from about 34° C. to about 39° C. As used herein, a cold-adapted equine influenza virus is an equine influenza virus that has been adapted to grow at a temperature lower than the optimal growth temperature for equine influenza virus. One example of a cold-adapted equine influenza virus of the present invention is a virus that replicates in embryonated chicken eggs at a temperature of about 30° C. A preferred cold-adapted equine influenza virus of the present invention replicates in embryonated chicken eggs at a temperature of about 28° C. Another preferred cold-adapted equine influenza virus of the present invention replicates in embryonated chicken eggs at a temperature of about 26° C. In general, preferred cold-adapted equine influenza viruses of the present invention replicate in embryonated chicken eggs at a temperature ranging from about 26° C. to about 30° C, i.e., at a range of temperatures at which a wild-type virus will grow poorly or not at all. It should be noted that the ability of such viruses to replicate within that temperature range does not preclude their ability to also replicate at higher or lower temperatures. For example, one embodiment is a cold-adapted equine influenza virus that replicates in embryonated chicken eggs at a temperature of about 26° C., but also replicates in tissue culture cells at a temperature of about 34° C. As with wild-type equine influenza viruses, cold-adapted equine influenza viruses of the present invention generally form plaques in tissue culture cells, for example Madin Darby Canine Kidney Cells (MDCK) at a temperature of about 34° C. Examples of suitable and preferred cold-adapted equine influenza viruses of the present invention are disclosed herein.

One embodiment of the present invention is a cold-adapted equine influenza virus that is produced by a method which includes passaging a wild-type equine influenza virus, and then selecting viruses that grow at a reduced temperature. Cold-adapted equine influenza viruses of the present invention can be produced, for example, by sequentially passaging a wild-type equine influenza virus in embryonated chicken eggs at progressively lower temperatures, thereby selecting for certain members of the virus mixture which stably replicate at the reduced temperature. An example of a passaging procedure is disclosed in detail in the Examples section. During the passaging procedure, one or more mutations appear in certain of the single-stranded RNA segments comprising the influenza virus genome, which alter the genotype, i.e., the primary nucleotide sequence of those RNA segments. As used herein, a mutation is an alteration of the primary nucleotide sequence of any given RNA segment making up an influenza virus genome. Examples of mutations include substitution of one or more nucleotides, deletion of one or more nucleotides, insertion of one or more nucleotides, or inversion of a stretch of two or more nucleotides. By selecting for those members of the virus mixture that stably replicate at a reduced temperature, a virus with a cold-adaptation phenotype is selected. As used herein, a phenotype is an observable or measurable characteristic of a biological entity such as a cell or a virus, where the observed characteristic is attributable to a specific genetic configuration of that biological entity, i.e., a certain genotype. As such, a cold-adaptation phenotype is the result of one or more mutations in the virus genome. As used herein, the terms a mutation, a genome, a genotype, or a phenotyperefer to one or more, or at least one mutation, genome, genotype, or phenotype, respectively.

Additional, observable phenotypes in a cold-adapted equine influenza virus may occur, and will generally be the result of one or more additional mutations in the genome of such a virus. For example, a cold-adapted equine influenza virus of the present invention may, in addition, be attenuated, exhibit dominant interference, and/or be temperature sensitive.

In one embodiment, a cold-adapted equine influenza virus of the present invention has a phenotype characterized by attenuation. A cold-adapted equine influenza virus is attenuated, when administration of the virus to an equine influenza virus-susceptible animal results in reduced or absent clinical signs in that animal, compared to clinical signs observed in animals that are infected with wild-type equine influenza virus. For example, an animal infected with wild-type equine influenza virus will display fever, sneezing, coughing, depression, and nasal discharges. In contrast, an animal administered an attenuated, cold-adapted equine influenza virus of the present invention will display minimal or no, i.e., undetectable, clinical disease signs.

In another embodiment, a cold-adapted equine influenza virus of the present invention comprises a temperature sensitive phenotype. As used herein, a temperature sensitive cold-adapted equine influenza virus replicates at reduced temperatures, but no longer replicates or forms plaques in tissue culture cells at certain higher growth temperatures at which the wild-type virus will replicate and form plaques. While not being bound by theory, it is believed that replication of equine influenza viruses with a temperature sensitive phenotype is largely restricted to the cool passages of the upper respiratory tract, and does not replicate efficiently in the lower respiratory tract, where the virus is more prone to cause disease symptoms. A temperature at which a temperature sensitive virus will grow is referred to herein as a permissive temperature for that temperature sensitive virus, and a higher temperature at which the temperature sensitive virus will not grow, but at which a corresponding wild-type virus will grow, is referred to herein as a non-permissive temperature for that temperature sensitive virus. For example, certain temperature sensitive cold-adapted equine influenza viruses of the present invention replicate in embryonated chicken eggs at a temperature at or below about 30° C., preferably at about 28° C. or about 26° C., and will form plaques in tissue culture cells at a permissive temperature of about 34° C., but will not form plaques in tissue culture cells at a non permissive temperature of about 39° C. Other temperature sensitive cold-adapted equine influenza viruses of the present invention replicate in embryonated chicken eggs at a temperature at or below about 30° C., preferably at about 28° C. or about 26° C., and will form plaques in tissue culture cells at a permissive temperature of about 34° C., but will not form plaques in tissue culture cells at a non-permissive temperature of about 37° C.

Certain cold-adapted equine influenza viruses of the present invention have a dominant interference phenotype; that is, they dominate an infection when co-infected into cells with another influenza A virus, thereby impairing the growth of that other virus. For example, when a cold-adapted equine influenza virus of the present invention, having a dominant interference phenotype, is co-infected into MDCK cells with the wild-type parental equine influenza virus, A/equine/Kentucky/1/91 (H3N8), growth of the parental virus is impaired. Thus, in an animal that has recently been exposed to, or may be soon exposed to, a virulent influenza virus, i.e., an influenza virus that causes disease symptoms, administration of a therapeutic composition comprising a cold-adapted equine influenza virus having a dominant interference phenotype into the upper respiratory tract of that animal will impair the growth of the virulent virus, thereby ameliorating or reducing disease in that animal, even in the absence of an immune response to the virulent virus.

Dominant interference of a cold-adapted equine influenza virus having a temperature sensitive phenotype can be measured by standard virological methods. For example, separate monolayers of MDCK cells can be infected with (a) a virulent wild-type influenza A virus, (b) a temperature sensitive, cold-adapted equine influenza virus, and (c) both viruses in a co-infection, with all infections done at multiplicities of infection (MOI) of about 2 plaque forming units (pfu) per cell. After infection, the virus yields from the various infected cells are measured by duplicate plaque assays performed at the permissive temperature for the cold-adapted equine influenza virus and at the non-permissive temperature of that virus. A cold adapted equine influenza virus having a temperature sensitive phenotype is unable to form plaques at its non-permissive temperature, while the wild-type virus is able to form plaques at both the permissive and non-permissive temperatures. Thus it is possible to measure the growth of the wild-type virus in the presence of the cold adapted virus by comparing the virus yield at the non-permissive temperature of the cells singly infected with wild-type virus to the yield at the non-permissive temperature of the wild-type virus in doubly infected cells.

Cold-adapted equine influenza viruses of the present invention are characterized primarily by one or more of the following identifying phenotypes: cold-adaptation, temperature sensitivity, dominant interference, and/or attenuation. As used herein, the phrase an equine influenza virus comprises the identifying phenotype(s) of cold-adaptation, temperature sensitivity, dominant interference, and/or attenuation refers to a virus having such a phenotype(s). Examples of such viruses include, but are not limited to, EIV-P8211, identified by accession No. ATCC VR-2625, EIV-P824, identified by accession No. ATCC VR-2624, and EIV-MSV+5, identified by accession No. ATCC VR-2627, as well as EIV-MSV0, EIV, MSV+1, EIV-MSV+2, EIV-MSV+3, and EIV-MSV+4. Production of such viruses is described in the examples. For example, cold-adapted equine influenza virus EIV-P821 is characterized by, i.e., has the identifying phenotypes of, (a) cold-adaptation, e.g., its ability to replicate in embryonated chicken eggs at a temperature of about 26° C.; (b) temperature sensitivity, e.g., its inability to form plaques in tissue culture cells and to express late gene products at a non-permissive temperature of about 37° C., and its inability to form plaques in tissue culture cells and to synthesize any viral proteins at a non-permissive temperature of about 39° C.; (c) its attenuation upon administration to an equine influenza virus-susceptible animal; and (d) dominant interference, e.g., its ability, when co-infected into a cell with a wild-type influenza A virus, to interfere with the growth of that wild-type virus. Similarly, cold-adapted equine influenza virus EIV-P824 is characterized by (a) cold adaptation, e.g., its ability to replicate in embryonated chicken eggs at a temperature of about 28° C.; (b) temperature sensitivity, e.g., its inability to form plaques in tissue culture cells at a non-permissive temperature of about 39° C.; and (c) dominant interference, e.g., its ability, when co-infected into a cell with a wild-type influenza A virus, to interfere with the growth of that wild-type virus. In another example, cold-adapted equine influenza virus EIV-MSV+5 is characterized by (a) cold-adaptation, e.g., its ability to replicate in embryonated chicken eggs at a temperature of about 26° C.; (b) temperature sensitivity, e.g., its inability to form plaques in tissue culture cells at a non permissive temperature of about 39° C.; and (c) its attenuation upon administration to an equine influenza virus-susceptible animal.

In certain cases, the RNA segment upon which one or more mutations associated with a certain phenotype occur may be determined through reassortment analysis by standard methods, as disclosed herein. In one embodiment, a cold-adapted equine influenza virus of the present invention comprises a temperature sensitive phenotype that correlates with at least two mutations in the genome of that virus. In this embodiment, one of the two mutations, localized by reassortment analysis as disclosed herein, inhibits, i.e., blocks or prevents, the ability of the virus to form plaques in tissue culture cells at a non-permissive temperature of about 39° C. This mutation co-segregates with the segment of the equine influenza virus genome that encodes the nucleoprotein (NP) gene of the virus, i.e., the mutation is located on the same RNA segment as the NP gene. In this embodiment, the second mutation inhibits all protein synthesis at a non-permissive temperature of about 39° C. As such, at the non-permissive temperature, the virus genome is incapable of expressing any viral proteins. Examples of cold-adapted equine influenza viruses possessing these characteristics are EIV-P821 and EIV MSV+5. EIV-P821 was generated by serial passaging of a wild-type equine influenza virus in embryonated chicken eggs by methods described in Example 1A. EIV-MSV+5 was derived by further serial passaging of EIV-P821, as described in Example 1E.

Furthermore, a cold-adapted, temperature sensitive equine influenza virus comprising the two mutations which inhibit plaque formation and viral protein synthesis at a non-permissive temperature of about 39° C. can comprise one or more additional mutations, which inhibit the virus" ability to synthesize late gene products and to form plaques in tissue culture cells at a non-permissive temperature of about 37° C. An example of la cold-adapted equine influenza virus possessing these characteristics is EIV-P821. This virus isolate replicates in embryonated chicken eggs at a temperature of about 26° C., and does not form plaques or express any viral proteins at a temperature of about 39° C. Furthermore, EIV-P821 does not form plaques on MDCK cells at a non-permissive temperature of about 37° C., and at this temperature, late gene expression is inhibited in such a way that late proteins are not produced, i.e., normal levels of NP protein are synthesized, reduced or undetectable levels of M1 or HA proteins are synthesized, and enhanced levels of the polymerase proteins are synthesized. Since this phenotype is typified by differential viral protein synthesis, it is distinct from the protein synthesis phenotype seen at a non-permissive temperature of about 39° C., which is typified by the inhibition of synthesis of all viral proteins.

Pursuant to 37 CFR §1.802 (a–c), cold-adapted equine influenza viruses, designated herein as EIV-P821, an EIV-P824 were deposited with the American Type Culture Collection (ATCC, 10801 University Boulevard, Manassas, Va. 20110-2209) under the Budapest Treaty as ATCC Accession Nos. ATCC VR-2625, and ATCC VR-2624, respectively, on Jul. 11, 1998. Cold-adapted equine influenza virus EIV-MSV+5 was deposited with the ATCC as ATCC Accession No. ATCC VR-2627on Aug. 3, 1998. Pursuant to 37 CFR §1.806, the deposits are made for a term of at least thirty (30) years and at least five (5) years after the most recent request for the furnishing of a sample of the deposit was received by the depository. Pursuant to 37 CFR §1.808 (a)(2), all restrictions imposed by the depositor on the availability to the public will be irrevocably removed upon the granting of the patent.

Preferred cold-adapted equine influenza viruses of the present invention have the identifying phenotypes of EIV-P821, EIV-P824, and EIV-MSV+5. Particularly preferred cold-adapted equine influenza viruses include EIV-P821, EIV-P824, EIV-MSV+5, and progeny of these viruses. As used herein, progeny are offspring, and as such can slightly altered phenotypes compared to the parent virus, but retain identifying phenotypes of the parent virus, for example, cold-adaptation, temperature sensitivity, dominant interference, or attenuation. For example, cold-adapted equine influenza virus EIV-MSV+5 is a progeny of cold-adapted equine influenza virus EIV-P821. Progeny also include reassortant influenza A viruses that comprise one or more identifying phenotypes of the donor parent virus.

Reassortant influenza A viruses of the present invention are produced by genetic reassortment of the genome segments of a donor cold-adapted equine influenza virus of the present invention with the genome segments of a recipient influenza A virus, and then selecting a reassortant virus that derives at least one of its eight RNA genome segments from the donor virus, such that the reassortant virus acquires at least one identifying phenotype of the donor cold-adapted equine influenza virus. Identifying phenotypes include cold-adaptation, temperature sensitivity, attenuation, and dominant interference. Preferably, reassortant influenza A viruses of the present invention derive at least the attenuation phenotype of the donor virus. Methods to isolate reassortant influenza viruses are well known to those skilled in the art of virology and are disclosed, for example, in Fields, et al., 1996*, Fields Virology*, 3d ed. Lippincott-Raven; and Palese, et al., 1976, J. ., 17, 876–884. Fields, et al., ibid. and Palese, et al., ibid.

A suitable donor equine influenza virus is a cold-adapted equine influenza virus of the present invention, for example, EIV-P821, identified by accession No. ATCC VR-2625, EIV-P824, identified by accession No. ATCC VR-2624, or EIV-MSV+5, identified by accession No. ATCTC VR-2627. A suitable recipient influenza A virus can be another equine influenza virus, for example a Eurasian subtype 2 equine influenza virus such as A/equine/Suffolk/89 (H3N8) or a subtype 1 equine influenza virus such as A/Prague/1/56 (H7N7). A recipient influenza A virus can also be any influenza A virus capable of forming a reassortant virus with a donor cold-adapted equine influenza virus. Examples of such influenza A viruses include, but are not limited to, human influenza viruses such as A/Puerto Rico/8/34 (H1N1), A/Hong Kong/156/97 (H5N1), A/Singapore/1/57 (H2N2), and A/Hong Kong/1/68 (H3N2); swine viruses such as A/Swine/Iowa/15/30 (1N1); and avian viruses such as A/mallard/New York/6750/78 (H2N2) and A/chicken/Hong Kong/258/97 (H5N1). A reassortant virus of the present invention can include any combination of donor and recipient gene segments, as long as the resulting reassortant virus possesses at least one identifying phenotype of the donor virus.

One example of a reassortant virus of the present invention is a 6+2" reassortant virus, in which the six internal gene segments, i.e., those comprising the NP, PB2, PB1, PA, M, and NS genes, are derived from the donor cold-adapted equine influenza virus genome, and the two external gene segments, i.e., those comprising the HA and NA genes, are derived from the recipient influenza A virus. A resultant virus thus produced has the attenuated, cold-adapted, temperature sensitive, and/or dominant interference phenotypes of the donor cold-adapted equine influenza virus, but the antigenicity of the recipient strain.

In yet another embodiment, a cold-adapted equine influenza virus of the present invention can be produced through recombinant means. In this approach, one or more specific mutations, associated with identified cold-adaptation, attenuation, temperature sensitivity, or dominant interference phenotypes, are identified and are introduced back into a wild-type equine influenza virus strain using a reverse genetics approach. Reverse genetics entails using RNA polymerase complexes isolated from influenza virus-infected cells to transcribe artificial influenza virus genome segments containing the mutation(s), incorporating the synthesized RNA segment(s) into virus particles using a helper virus, and then selecting for viruses containing the desired changes. Reverse genetics methods for influenza viruses are described, for example, in Enami, et al., 1990*, Proc. Natl. Acad. Sci.* 87, 3802–3805; and in U.S. Pat. No. 5,578,473, by Palese, et al., issued Nov. 26, 1996. This approach allows one skilled in the art to produce additional cold-adapted equine influenza viruses of the present invention without the need to go through the lengthy cold-adaptation process, and the process of selecting mutants both in vitro and in vivo with the desired virus phenotype.

A cold-adapted equine influenza virus of the present invention may be propagated by standard virological methods well-known to those skilled in the art, examples of which are disclosed herein. For example, a cold-adapted equine influenza virus can be grown in embryonated chicken eggs or in eukaryotic tissue culture cells. Suitable continuous eukaryotic cell lines upon which to grow a cold-adapted equine influenza virus of the present invention include those that support growth of influenza viruses, for example, MDCK cells. Other suitable cells upon which to grow a cold-adapted equine influenza virus of the present invention include, but are not limited to, primary kidney cell cultures of monkey, calf, hamster or chicken.

In one embodiment, the present invention provides a therapeutic composition to protect an animal against disease caused by an influenza A virus, where the therapeutic composition includes either a cold-adapted equine influenza virus or a reassortant influenza A virus comprising at least one genome segment of an equine influenza virus generated by cold-adaptation, wherein the equine influenza virus genome segment confers at least one identifying phenotype of the cold-adapted equine influenza virus. In addition, a therapeutic composition of the present invention can include an equine influenza virus that has been genetically engineered to comprise one or more mutations, where those mutations have been identified to confer a certain identifying phenotype on a cold-adapted equine influenza virus of the present invention. As used herein, the phrase disease caused by an influenza A virus refers to the clinical manifestations observed in an animal which has been infected with a virulent influenza A virus. Examples of such clinical manifestations include, but are not limited to, fever, sneezing, coughing, nasal discharge, rales, anorexia and depression. In addition, the phrase disease caused by an influenza A virus is defined herein to include shedding of virulent virus by the infected animal. Verification that clinical manifestations observed in an animal correlate with infection by virulent equine influenza virus may be made by several methods, including the detection of a specific antibody and/or T-cell responses to equine influenza virus in the animal. Preferably, verification that clinical manifestations observed in an animal correlate with infection by a virulent influenza A virus is made by the isolation of the virus from the afflicted animal, for example, by swabbing the nasopharyngeal cavity of that animal for virus-containing secretions. Verification of virus isolation may be made by the detection of CPE in tissue culture cells inoculated with the isolated secretions, by inoculation of the isolated secretions into embryonated chicken eggs, where virus replication is dejectedly the ability of AF from the inoculated eggs to agglutinate erythrocytes, suggesting the presence of the influenza virus hemagglutinin protein, or by use of a commercially available diagnostic test, for example, the Directigen® FLU A test.

As used herein, the term to protect includes, for example, to prevent or to treat influenza A virus infection in the subject animal. As such, a therapeutic composition of the present invention can be used, for example, as a prophylactic vaccine to protect a subject animal from influenza disease by administering the therapeutic composition to that animal at some time prior to that animal's exposure to the virulent virus.

A therapeutic composition of the present invention, comprising a cold-adapted equine influenza virus having a dominant interference phenotype, can also be used to treat an animal that has been recently infected with virulent influenza A virus or is likely to be subsequently exposed in a few days, such that the therapeutic composition immediately interferes with the growth of the virulent virus, prior to the animal's production of antibodies to the virulent virus. A therapeutic composition comprising a cold-adapted equine influenza virus having a dominant interference phenotype may be effectively administered prior to subsequent exposure for a length of time corresponding to the approximate length of time that a cold-adapted equine influenza virus of the present invention will replicate in the upper respiratory tract of a treated animal, for example, up to about seven days. A therapeutic composition comprising a cold-adapted equine influenza virus having a dominant interference phenotype may be effectively administered following exposure to virulent equine influenza virus for a length of time corresponding to the time required for an infected animal to show disease symptoms, for example, up to about two days.

Therapeutic compositions of the present invention can be administered to any animal susceptible to influenza virus disease, for example, humans, swine, horses and other equids, aquatic birds, domestic and game fowl, seals, mink, and whales. Preferably, a therapeutic composition of the present invention is administered equids. Even more preferably, a therapeutic composition of the present invention is administered to a horse, to protect against equine influenza disease.

Current vaccines available to protect horses against equine influenza virus disease are not effective in protecting young foals, most likely because they cannot overcome the maternal antibody present in these young animals, and often, vaccination at an early age, for example 3 months of age, can lead to tolerance rather than immunity. In one embodiment, and in contrast to existing equine influenza virus vaccines, a therapeutic composition comprising a cold-adapted equine influenza virus of the present invention apparently can produce immunity in young animals. As such, a therapeutic composition of the present invention can be safely and effectively administered to young foals, as young as about 3 months of age, to protect against equine influenza disease without the induction of tolerance.

In one embodiment, a therapeutic composition of the present invention can be multivalent. For example, it can protect an animal from more than one strain of influenza A virus by providing a combination of one or more cold-adapted equine influenza viruses of the present invention, one or more reassortant influenza A viruses, and/or one or more genetically-engineered equine influenza viruses of the present invention. Multivalent therapeutic compositions can include at least two cold-adapted equine influenza viruses, e.g., against North American subtype-2 virus isolates such as A/equine/Kentucky/1/91 (H1N8), and Eurasian subtype-2 virus isolates such as A/equine/Suffolk/89 (H3N8); or one or more subtype-2 virus isolates and a subtype-1 virus isolate such as A/equine/Prague/1/56 (H7N7). Similarly, a multivalent therapeutic composition of the present invention can include a cold-adapted equine influenza virus and a reassortant influenza A virus of the present invention, or two reassortant influenza A viruses of the present invention. A multivalent therapeutic composition of the present invention can also contain one or more formulations to protect against one or more other infectious agents in addition to influenza A virus. Such other infectious agents include, but not limited to: viruses; bacteria; fungi and fungal-related microorganisms; and parasites. Preferable multivalent therapeutic compositions include, but are not limited to, a cold-adapted equine influenza virus, reassortant influenza A virus, or genetically-engineered equine influenza virus of the present invention plus one or more compositions protective against one or more other infectious agents that afflict horses. Suitable infectious agents to protect against include, but are not limited to, equine infectious anemia virus, equine herpes virus, eastern, western, or Venezuelan equine encephalitis virus, tetanus, *Streptococcus equi*, and *Ehrlichia resticii.*

A therapeutic composition of the present invention can be formulated in an excipient that the animal to be treated can tolerate. Examples of such excipients include water, saline, Ringer's solution, dextrose solution, Hank's solution, and other aqueous physiologically balanced salt solutions. Excipients can also contain minor amounts of additives, such as substances that enhance isotonicity and chemical or biological stability. Examples of buffers include phosphate buffer, bicarbonate buffer, and Tris buffer, while examples of stabilizers include A1/A2 stabilizer, available from Diamond Animal Health, Des Moines, Iowa. Standard formulations can either be liquids or solids which can be taken up in a suitable liquid as a suspension or solution for administration to an animal. In one embodiment, a non-liquid formulation may comprise the excipient salts, buffers, stabilizers, etc., to which sterile water or saline can be added prior to administration.

A therapeutic composition of the present invention may also include one or more adjuvants or carriers. Adjuvants are typically substances that enhance the immune response of an animal to a specific antigen, and carriers include those compounds that increase the half-life of a therapeutic composition in the treated animal. One advantage of a therapeutic composition comprising a cold-adapted equine influenza virus or a reassortant influenza A virus of the present invention is that adjuvants and carriers are not required to produce an efficacious vaccine. Furthermore, in many cases known to those skilled in the art, the advantages of a therapeutic composition of the present invention would be hindered by the use of some adjuvants or carriers. However, it should be noted that use of adjuvants or carriers is not precluded by the present invention.

Therapeutic compositions of the present invention include an amount of a cold-adapted equine influenza virus that is sufficient to protect an animal from challenge with virulent equine influenza virus. In one embodiment, a therapeutic composition of the present invention can include an amount of a cold-adapted equine influenza virus ranging from about $10^5$ tissue culture infectious dose-50 ($TCID_{50}$) units of virus to about $10^8$ $TCID_{50}$ units of virus. As used herein, a $TCID_{50}$ unit" is amount of a virus which results in cytopathic effect in 50% of those cell cultures infected. Methods to measure and calculate $TCID_{50}$ are known to those skilled in the art and are available, for example, in Reed and Muench, 1938, *Am. J. of Hyg*. 27, 493–497. A preferred therapeutic composition of the present invention comprises from about $10^6$ $TCID_{50}$ units to about $10^7$ $TCID_{50}$ units of a cold-adapted equine influenza virus or reassortant influenza A virus of the present invention. Even more preferred is a therapeutic composition comprising about $2\times10^6$ $TCID_{50}$ units of a cold-adapted equine influenza virus or reassortant influenza A virus of the present invention.

The present invention also includes methods to protect an animal against disease caused by an influenza A virus comprising administering to the animal a therapeutic composition of the present invention. Preferred are those methods which protect an equid against disease caused by equine influenza virus, where those methods comprise administering to the equid a cold-adapted equine influenza virus. Acceptable protocols to administer therapeutic compositions in an effective manner include individual dose size, number of doses, frequency of dose administration, and mode of administration. Determination of such protocols can be accomplished by those skilled in the art, and examples are disclosed herein.

A preferable method to protect an animal against disease caused by an influenza A virus includes administering to that animal a single dose of a therapeutic composition comprising a cold-adapted equine influenza virus, a reassortant influenza A virus, or genetically-engineered equine influenza virus of the present invention. A suitable single dose is a dose that is capable of protecting an animal from disease when administered one or more times over a suitable time period. The method of the present invention may also include administering subsequent, or booster doses of a therapeutic composition. Booster administrations can be given from about 2 weeks to several years after the original administration. Booster administrations preferably are administered when the immune response of the animal becomes insufficient to protect the animal from disease. Examples of suitable and preferred dosage schedules are disclosed in the Examples section.

A therapeutic composition of the present invention can be administered to an animal by a variety of means, such that the virus will enter and replicate in the mucosal cells in the upper respiratory tract of the treated animal. Such means include, but are not limited to, intranasal administration, oral administration, and intraocular administration. Since influenza viruses naturally infect the mucosa of the upper respiratory tract, a preferred method to administer a therapeutic composition of the present invention is by intranasal administration. Such administration may be accomplished by use of a syringe fitted with cannula, or by use of a nebulizer fitted over the nose and mouth of the animal to be vaccinated.

The efficacy of a therapeutic composition of the present invention to protect an animal against disease caused by influenza A virus can be tested in a variety of ways including, but not limited to, detection of antibodies by, for example, hemagglutination inhibition (HAI) tests, detection of cellular immunity within the treated animal, or challenge of the treated animal with virulent equine influenza virus to determine whether the treated animal is resistant to the development of disease. In addition, efficacy of a therapeutic composition of the present invention comprising a cold-adapted equine influenza virus having a dominant interference phenotype to ameliorate or reduce disease symptoms in an animal previously inoculated or susceptible to inoculation with a virulent, wild-type equine influenza virus can be tested by screening for the reduction or absence of disease symptoms in the treated animal.

The present invention also includes methods to produce a therapeutic composition of the present invention. Suitable and preferred methods for making a therapeutic composition of the present invention are disclosed herein. Pertinent steps involved in producing one type of therapeutic composition of the present invention, i.e., a cold-adapted equine influenza virus, include (a) passaging a wild-type equine influenza virus in vitro, for example, in embryonated chicken eggs; (b) selecting viruses that grow at a reduced temperature; (c) repeating the passaging and selection steps one or more times, at progressively lower temperatures, until virus populations are selected which stably grow at the desired lower temperature; and (d) mixing the resulting virus preparation with suitable excipients.

The pertinent steps involved in producing another type of therapeutic composition of the present invent on, i.e., a reassortant influenza A virus having at least one genome segment of an equine influenza virus generated by adaptation, includes the steps of (a) mixing the genome segments of a donor cold-adapted equine influenza virus, which preferably also has the phenotypes of attenuation, temperature sensitivity, or dominant interference, with the genome segments of a recipient influenza A virus, and (b) selecting reassortant viruses that have at least one identifying phenotype of the donor equine influenza virus. Identifying phenotypes to select for include attenuation, cold-adaptation, temperature sensitivity, and dominant interference. Methods to screen for these phenotypes are well known to those skilled in the art, and are disclosed herein. It is preferable to screen for viruses that at least have the phenotype of attenuation.

Using this method to generate a reassortant influenza A virus having at least one genome segment of a equine influenza virus generated by cold-adaptation, one-type of reassortant virus to select for is a 6+2" reassortant, where the six internal gene segments, i.e., those coding for the NP, PB2, PB1, PA, M, and NS genes, are derived from the donor cold adapted equine influenza virus genome, and the two external gene segments, i.e., those coding for the HA and NA genes, are derived from the recipient influenza A virus. A resultant virus thus produced can have the cold-adapted, attenuated, temperature sensitive, and/or interference phenotypes of the donor cold-adapted equine influenza virus, but the antigenicity of the recipient strain.

The present invention includes nucleic acid molecules isolated from equine influenza virus wild type strain A/equine/Kentucky/1/91 (H3N8), and cold-adapted equine influenza virus EIV-P821.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified.

The present invention includes nucleic acid molecules encoding wild-type and cold-adapted equine influenza virus proteins. Nucleic acid molecules of the present invention can be prepared by methods known to one skilled in the art. Proteins of the present invention can be prepared by methods known to one skilled in the art, i.e., recombinant DNA technology. Preferred nucleic acid molecules have coding strands comprising nucleic acid sequences SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:19, SEQ ID NO:21, SEQ ID NO:22, SEQ ID NO:23, SEQ ID NO:25, SEQ ID NO:44, SEQ ID NO:46, SEQ ID NO:47, SEQ ID NO:49, SEQ ID NO:50, SEQ ID NO:52, SEQ ID NO:53, SEQ ID NO:54, SEQ ID NO:56, SEQ ID NO:57, SEQ ID NO:59, SEQ ID NO:62, SEQ ID NO:64, SEQ ID NO:65, SEQ ID NO:67, SEQ ID NO:68, SEQ ID NO:70, SEQ ID NO:71, SEQ ID NO:76, SEQ ID NO:78, SEQ ID NO:79, SEQ ID NO:80, SEQ ID NO:82, SEQ ID NO:85, SEQ ID NO:87, SEQ ID NO:88, SEQ ID NO:90, SEQ ID NO:91, SEQ ID NO:93, SEQ ID NO:94, SEQ ID NO:96, SEQ ID NO:103, SEQ ID NO:105, SEQ ID NO:106 and SEQ ID NO:108 and/or a complement thereof. Complements are defined as two single strands of nucleic acid in which the nucleotide sequence is such that they will hybridize as a result of base pairing throughout their full length. Given a nucleotide sequence, one of ordinary skill in the art can deduce the complement.

Preferred nucleic acid molecules encoding equine influenza M proteins are nei$_{wt}$M$_{1023}$, nei$_{wt1}$M$_{1023}$, nei$_{wt2}$M$_{1023}$, nei$_{wt}$M$_{756}$, nei$_{wt1}$M$_{756}$, nei$_{wt2}$M$_{756}$, nei$_{ca1}$M$_{1023}$, nei$_{ca2}$M$_{1023}$, nei$_{ca1}$M$_{756}$, and/or nei$_{ca2}$M$_{756}$, the coding strands of which are represented by SEQ ID NO:1, SEQ ID NO:3, SEQ ID NO:4, and/or SEQ ID NO:6.

Preferred nucleic acid molecules encoding equine influenza HA proteins are nei$_{wt}$HA$_{1762}$, nei$_{wt}$HA$_{1695}$, nei$_{ca1}$HA$_{1762}$, nei$_{ca2}$HA$_{1762}$, nei$_{ca1}$HA$_{1695}$, and/or nei$_{ca2}$HA$_{1695}$, the coding strands of which are represented by SEQ ID NO:7, SEQ ID NO:9, SEQ ID NO:10, and/or SEQ ID NO:12.

Preferred nucleic acid molecules encoding equine influenza PB2-N proteins are nei $_{wt}$PB2-N nei$_{1241}$, nei$_{wt}$PB2-N$_{1214}$, nei$_{ca1}$PB2-N$_{1241}$nei$_{ca2}$PB2-N$_{1241}$, nei$_{ca1}$PB2-N$_{1214}$, nei$_{ca2}$, and/or PB2-N$_{1214}$, the coding strands of which are represented by SEQ ID NO:13, SEQ ID NO:15, SEQ ID NO:16, and/or SEQ ID NO:18.

Preferred nucleic acid molecules encoding equine influenza PB2-C proteins are nei$_{wt1}$PB2-C$_{1233}$, nei$_{wt2}$PB2-C$_{1223}$, nei$_{wt}$PB2-C$_{1194}$, nei$_{ca1}$PB2-C$_{1232}$, nei$_{ca2}$PB2-C$_{1231}$, and/or nei$_{ca1}$PB2-C$_{1194}$, the coding strands of which are represented by SEQ ID NO:19, SEQ ID NO:22, SEQ ID NO:21, SEQ ID NO:23, and/or SEQ ID NO:25.

Preferred nucleic, acid molecules encoding equine influenza PB2 proteins are nei$_{wt}$PB2$_{2341}$, nei$_{wt}$PB2$_{2277}$, nei$_{ca1}$PB2$_{2341}$, and/or nei$_{ca1}$PB$_{2277}$, the coding strands of which are represented by SEQ ID NO:44, SEQ ID NO:46, SEQ ID NO:47, and/or SEQ ID NO:49.

Preferred nucleic acid molecules encoding equine influenza NS proteins are nei$_{wt1}$NS$_{891}$, nei$_{wt2}$NS$_{891}$, nei$_{wt1}$NS$_{690}$, nei$_{wt2}$NS$_{690}$, nei$_{wt3}$NS$_{888}$, nei$_{wt3}$NS$_{690}$, nei$_{wt4}$NS$_{468}$, nei$_{wt4}$NS$_{293}$, nei$_{ca1}$NS$_{888}$, nei$_{ca2}$NS$_{888}$, nei$_{ca1}$NS$_{690}$, and/or nei$_{ca2}$NS$_{690}$ the coding strands of which are represented by SEQ ID NO:50, SEQ ID NO:52, SEQ ID NO:53, SEQ ID NO:54, SEQ ID NO:56, SEQ ID NO:57 and/or SEQ ID NO:59.

Preferred nucleic acid molecules encoding equine influenza PB1-N proteins are nei$_{wt1}$PB1-N$_{1229}$, nei$_{wt1}$PB1-N$_{1194}$, nei$_{wt2}$PB1-N$_{673}$, nei$_{wt2}$PB1-N$_{636}$, nei$_{ca1}$PB1-N$_{1225}$, nei$_{ca1}$PB1-N$_{1185}$, nei$_{ca2}$PB1-N$_{1221}$, and/or nei$_{ca2}$PB1-N$_{1185}$ the coding strands of which are represented by SEQ ID NO:62, SEQ ID NO:64, SEQ ID NO:65, SEQ ID NO:67, SEQ ID NO:68, SEQ ID NO:70, and/or SEQ ID NO:71.

Preferred nucleic acid molecules encoding equine influenza PA-C proteins are nei$_{wt1}$PA-C$_{1228}$, nei$_{wt1}$PA-C$_{1164}$, nei$_{wt2}$PA-C$_{1223}$, nei$_{wt2}$PA-C$_{1164}$, nei$_{ca1}$PA-C$_{1233}$, nei$_{ca2}$PA-C$_{1233}$, nei$_{ca1}$PA-C$_{1170}$, and/or nei$_{ca2}$PA-C$_{1170}$ the coding strands of which are represented by SEQ ID NO:76, SEQ ID NO:78, SEQ ID NO:79, SEQ ID NO:80, and/or SEQ ID NO:82.

Preferred nucleic acid molecules encoding equine influenza PB1-C proteins are nei$_{wt1}$PB1-C$_{1234}$, nei$_{wt1}$PB1-C$_{1188}$, nei$_{wt2}$PB1-C$_{1240}$, nei$_{wt2}$PB1-C$_{1188}$, nei$_{ca1}$PB1-C$_{1241}$, nei$_{ca1}$PB1-C$_{1188}$, nei$_{ca2}$PB1-C$_{1241}$ and/or nei$_{ca2}$PB1-C$_{1188}$, the coding strands of which are represented by SEQ ID NO:85, SEQ ID NO:87, SEQ ID NO:88, SEQ ID NO:90, SEQ ID NO:91, SEQ ID NO:93, SEQ ID NO:94 and/or SEQ ID NO:96.

Preferred nucleic acid molecules encoding equine influenza PB1 proteins are nei$_{wt}$PB1$_{2341}$, nei$_{wt}$PB1$_{2271}$, nei$_{ca1}$PB1$_{2341}$, nei$_{ca1}$PB1$_{2271}$, the coding strands of which are represented by SEQ ID NO:103, SEQ ID NO:105, SEQ ID NO:106, and/or SEQ ID NO:108.

The present invention includes proteins comprising SEQ ID NO:2, SEQ ID NO:5, SEQ ID NO:8, SEQ ID NO:11, SEQ ID NO:14, SEQ ID NO:17, SEQ ID NO:20, SEQ ID NO:24, SEQ ID NO:45, SEQ ID NO:48, SEQ ID NO:51, SEQ ID NO:55, SEQ ID NO:58, SEQ ID NO:63, SEQ ID NO:66, SEQ ID NO:69, SEQ ID NO:77, SEQ ID NO:81, SEQ ID NO:86, SEQ ID NO:89, SEQ ID NO:92, SEQ ID NO:95, SEQ ID NO:104 and SEQ ID NO:107 as well as nucleic acid molecules encoding such proteins.

Preferred equine influenza M proteins of the present invention include proteins encoded by a nucleic acid molecule comprising nei$_{wt}$M$_{1023}$, nei$_{wt1}$M$_{1023}$, nei$_{wt2}$M$_{1023}$, nei$_{wt}$M$_{756}$, nei$_{wt1}$M$_{756}$, nei$_{wt2}$M$_{756}$, nei$_{ca1}$M$_{1023}$, nei$_{ca2}$M$_{1023}$, nei$_{ca1}$M$_{756}$, and/or nei$_{ca2}$M$_{756}$. Preferred equine influenza M proteins are $Pei_{wt}M_{252}$, $Pei_{ca1}M_{252}$, and/or $Pei_{ca2}M_{252}$. In one embodiment, a preferred equine influenza M protein of the present invention is encoded by SEQ ID NO:1, SEQ ID NO:3, SEQ ID NO:4, and/or SEQ ID NO:6, and, as such, has an amino acid sequence that includes SEQ ID NO:2 and/or SEQ ID NO:5.

Preferred equine influenza HA proteins of the present invention include proteins encoded by a nucleic acid molecule comprising $nei_{wt}HA_{1762}$, $nei_{wt}HA_{1695}$, $nei_{ca1}HA_{1762}$, $nei_{ca2}HA_{1762}$, $nei_{ca1}HA_{1695}$, and/or $nei_{ca2}HA_{1695}$. Preferred equine influenza HA proteins are P $Pei_{wt}HA_{565}$, $Pei_{ca1}HA_{565}$, and/or $Pei_{ca2}HA_{565}$. In one embodiment, a preferred equine influenza HA protein of the present invention is encoded by SEQ ID NO:7, SEQ ID NO:9, SEQ ID NO:10, and/or SEQ ID NO:12, and, as such, has an amino acid sequence that includes SEQ ID NO:8 and/or SEQ ID NO:11.

Preferred equine influenza PB2-N proteins of the present invention include proteins encoded by a nucleic acid molecule comprising $nei_{wt}PB2\text{-}N_{1241}$, $nei_{wt}PB2\text{-}N_{1214}$, $nei_{ca1}PB2\text{-}N_{1241}nei_{ca2}PB2\text{-}N_{1241}$, $nei_{ca1}PB2\text{-}N_{1214}nei_{ca2}$, and/or $PB2\text{-}N_{1214}$. Preferred equine influenza PB2-N proteins are $P_{wt}PB2\text{-}N_{404}$, $P_{ca1}PB2\text{-}N_{404}$, and/or $P_{ca2}PB2\text{-}N_{404}$. In one embodiment, a preferred equine influenza PB2-N protein of the present invention is encoded by SEQ ID NO:13, SEQ ID NO:15, SEQ ID NO:16, and/or SEQ ID NO:18, and, as such, has an amino acid sequence that includes SEQ ID NO:14 and/or SEQ ID NO:17.

Preferred equine influenza PB2-C proteins of the present invention include proteins encoded by a nucleic acid molecule comprising $nei_{wt1}PB2\text{-}C_{1233}$, $nei_{wt2}PB2\text{-}C_{1232}$, $nei_{wt}PB2\text{-}C_{1194}$, $nei_{ca1}PB2\text{-}C_{1232}$, $nei_{ca2}PB2\text{-}C_{1231}$, and/or $nei_{ca1}PB2\text{-}C_{1194}$. Preferred equine influenza PB2-N proteins are $P_{wt}PB2\text{-}C_{398}$, $P_{ca1}PB2\text{-}C_{398}$, and/or $P_{ca2}PB2\text{-}C_{398}$. In one embodiment, a preferred equine influenza PB2-C protein of the present invention is encoded by SEQ ID NO:19, SEQ ID NO:22, SEQ ID NO:21, SEQ ID NO:23, and/or SEQ ID NO:25, and, as such, has an amino acid sequence that includes SEQ ID NO:20 and/or SEQ ID NO:24.

Preferred equine influenza PB2 proteins of the present invention include proteins encoded by a nucleic acid molecule comprising $nei_{wt}PB2_{2341}$, $nei_{wt}PB2_{2277}$, $nei_{ca1}PB2_{2341}$, and or $nei_{ca1}PB2_{2277}$. Preferred equine influenza PB2 proteins are $Pei_{wt}PB2_{759}$, and/or $Pei_{ca1}PB2_{759}$. In one embodiment, a preferred equine influenza PB2 protein of the present invention is encoded by SEQ ID NO:44, SEQ ID NO:46, SEQ ID NO:47, and/or SEQ ID NO:49, and, as such, has an amino acid sequence that includes SEQ ID NO:45 and/or SEQ ID NO:48.

Preferred equine;influenza NS proteins of the present invention include proteins encoded by a nucleic acid molecule comprising $nei_{wt1}NS_{891}$, $nei_{wt2}NS_{891}$, $nei_{wt1}NS_{690}$, $nei_{wt3}NS_{888}$, $nei_{wt4}NS_{468}$, $nei_{wt4}NS_{293}$, $nei_{ca1}NS_{888}$, $nei_{ca2}NS_{888}$, and/or $nei_{ca1}NS_{690}$. Preferred equine influenza NS proteins are $Pei_{wt}NS_{230}$, $Pei_{wt4}NS_{97}$, and/or $Pei_{ca1}NS_{230}$. In one embodiment, a preferred equine influenza NS protein of the present invention is encoded by SEQ ID NO:50, SEQ ID NO:52, SEQ ID NO:53, SEQ ID NO:54, SEQ ID NO:56, SEQ ID NO:57 and/or SEQ ID NO:59, and, as such, has an amino acid sequence that includes SEQ ID NO:51, SEQ ID NO:55 and/or SEQ ID NO:58.

Preferred equine influenza PB1-N proteins of the present invention include proteins encoded by a nucleic acid molecule comprising $nei_{wt1}PB1\text{-}N_{1229}$, $nei_{wt1}PB1N_{1194}$, $nei_{wt2}PB1\text{-}N_{673}$, $nei_{wt2}PB1\text{-}N_{636}$, $nei_{ca1}PB21\text{-}N_{1225}$, $nei_{ca1}PB1\text{-}N_{1185}$, and/or $nei_{ca2}PB1\text{-}N_{1221}$. Preferred equine influenza PB1-N proteins are $Pei_{wt1}PB1\text{-}N_{398}$, $P_{wt2}PB1\text{-}N_{212}$, and/or $P_{ca1}PB1\text{-}N_{395}$. In one embodiment, a prefer red equine influenza PB1-N protein of the present invention is encoded by SEQ ID NO:62, SEQ ID NO:64, SEQ ID NO:65, SEQ ID NO:67, SEQ ID NO:68, SEQ ID NO:70, and/or SEQ ID NO:71, and, as such, has an amino acid sequence that includes SEQ ID NO:63, SEQ ID NO:66 and/or SEQ ID NO:69.

Preferred equine influenza PB1-C proteins of the present invention include proteins encoded by a nucleic acid molecule comprising $nei_{wt1}PB1\text{-}C_{1234}$, $nei_{wt1}PB1\text{-}C_{1188}$, $nei_{wt2}PB1\text{-}C_{1240}$, $nei_{wt2}PB1\text{-}C_{1188}$, $nei_{ca1}PB1\text{-}C_{1241}$, $nei_{ca1}PB1\text{-}C_{1188}$, $nei_{ca2}PB1\text{-}C_{1241}$ and/or $nei_{ca2}PB1\text{-}C_{1188}$. Preferred equine influenza PB1-C proteins are $Pei_{wt1}PB1\text{-}C_{396}$, $Pei_{wt2}PB1\text{-}C_{396}Pei_{ca1}PB1\text{-}C_{396}$, and/or $Pei_{ca2}PB1\text{-}C_{396}$. In one embodiment, a preferred equine influenza PB1-C protein of the present invention is encoded by SEQ ID NO:85, SEQ ID NO:87, SEQ ID NO:88, SEQ ID NO:90, SEQ ID NO:91, SEQ ID NO:93, SEQ ID NO:94, and/or SEQ ID NO:96, and, as such, has an amino acid sequence that includes SEQ ID NO:86, SEQ ID NO:89, SEQ ID NO 92, and/or SEQ ID NO:95.

Preferred equine influenza PB1 proteins of the present invention include proteins encoded by a nucleic, acid molecule comprising $nei_{wt}PB_{2341}$, $nei_{wt}PB1_{2271}$, $nei_{ca1}PB1_{2341}$, $nei_{ca1}PB1_{2271}$. Preferred equine influenza PB1 proteins are $Pei_{wt}PB1_{757}$, and/or $Pei_{ca1}PB1_{757}$. In one embodiment, a preferred equine influenza PB1 protein of the present invention is encoded by SEQ ID NO:103, SEQ ID NO:105, SEQ ID NO:106, and/or SEQ ID NO:108, and, as such, has an amino acid sequence that includes SEQ ID NO:104 and/or SEQ ID NO:107.

Preferred equine, influenza PA-C proteins of the present invention include proteins encoded by a nucleic acid molecule comprising $nei_{wt1}PA\text{-}C_{1228}$, $nei_{wt1}PA\text{-}C_{1164}$, $nei_{wt2}PA\text{-}C_{1223}$, $nei_{ca1}PA\text{-}C_{1233}$, $nei_{ca2}PA\text{-}C_{1233}$, and/or $nei_{ca1}PA\text{-}C_{1170}$. Preferred equine influenza PA-C proteins are $Pei_{wt1}PA\text{-}C_{388}$, and/or $Pei_{ca1}PA\text{-}C_{390}$. In one embodiment, a preferred equine influenza PA-C protein of the present invention is encoded by SEQ ID NO:76, SEQ ID NO:78, SEQ ID NO:79, SEQ ID NO:80, and/or SEQ ID NO:82, and, as such, has an amino acid sequence that includes SEQ ID NO:77 and/or SEQ ID NO:81.

Nucleic acid sequence SEQ ID NO:1 represents the consensus sequence deduced from the coding strand of PCR amplified nucleic acid molecules denoted herein as $nei_{wt1}M_{1023}$ and $nei_{wt2}M_{1023}$, the production of which is disclosed in the Examples. Nucleic acid sequence SEQ ID NO:4 represents the deduced sequence of the coding strand of PCR amplified nucleic acid molecules denoted herein as $nei_{ca1}M_{1023}$ and $nei_{ca2}M_{1023}$, the production of which is disclosed in the Examples. Nucleic acid sequence SEQ ID NO:7 represents the deduced sequence of the coding strand of a PCR amplified nucleic acid molecule denoted herein as $nei_{wt}HA_{1762}$, the production of which is disclosed in the Examples. Nucleic acid sequence SEQ ID NO:10 represents the deduced sequence of the coding strand of PCR amplified nucleic acid molecules denoted herein as $nei_{ca1}HA_{1762}$ and $nei_{ca2}HA_{1762}$, the production of which is disclosed in the Examples. Nucleic acid sequence SEQ ID NO:13 represents the deduced sequence of the coding strand of a PCR amplified nucleic acid molecule denoted herein as $nei_{wt}PB2\text{-}N_{1241}$, the production of which is disclosed in the Examples. Nucleic acid sequence SEQ ID NO:16 represents the deduced sequence of the coding strand of PCR amplified nucleic acid molecules denoted herein as $nei_{ca1}PB2\text{-}N_{1241}$ and $nei_{ca2}PB2\text{-}N_{1241}$, the production of which is disclosed in the Examples. Nucleic acid sequence SEQ ID NO:19 represents the deduced sequence of the coding strand of a PCR amplified nucleic acid molecule denoted herein as $nei_{wt1}PB2\text{-}C_{1233}$, the production of which is disclosed in the examples. Nucleic acid sequence SEQ ID NO:22 represents the deduced sequence of the coding strand of a PCR amplified nucleic acid molecule denoted herein as $nei_{wt2}PB2\text{-}C_{1232}$, the production of which is disclosed in the examples. Nucleic acid sequence SEQ ID NO:23 represents the deduced sequence of the coding strand of a PCR amplified nucleic acid molecule denoted herein as $nei_{ca1}PB2\text{-}C_{1232}$, the production of which is disclosed in the examples. Nucleic acid sequence SEQ ID NO:44 represents the deduced sequence of the coding strand of a PCR amplified nucleic acid molecule denoted herein as $nei_{wt}PB2_{2341}$ the production of which is disclosed in the Examples. Nucleic acid sequence SEQ ID NO:47 represents the deduced sequence of the coding strand of PCR amplified nucleic acid molecules denoted herein as $nei_{ca1}PB2_{2341}$ the production of which is disclosed in the Examples. Nucleic acid sequence SEQ ID NO:50 represents the deduced sequence of the coding strand of a PCR amplified nucleic acid molecule denoted herein as $nei_{wt1}NS_{891}$ and $nei_{wt2}NS_{891}$the production of which is disclosed in the examples. Nucleic acid sequence SEQ ID NO:53 represents the deduced sequence of the coding strand of a PCR amplified nucleic acid molecule denoted herein as $nei_{wt3}NS_{888}$, the production of which is disclosed in the examples. Nucleic acid sequence SEQ ID NO:54 represents the deduced sequence of the coding strand of a PCR amplified nucleic acid molecule denoted herein as $nei_{wt4}NS_{468}$, the production of which is disclosed in the examples. Nucleic acid sequence SEQ ID NO:57 represents the deduced sequence of the coding strand of a PCR amplified nucleic acid molecule denoted herein as $nei_{ca1}NS_{888}$ and $nei_{ca1}NS_{887}$, the production of which is disclosed in the Examples. Nucleic acid sequence SEQ ID NO:62 represents the deduced sequence of the coding strand of PCR amplified nucleic acid molecules denoted herein as $nei_{wt1}PB1\text{-}N_{1229}$, the production of which is disclosed in the Examples. Nucleic acid sequence SEQ ID NO:65 represents the deduced sequence of the coding strand of a PCR amplified nucleic acid molecule denoted herein as $nei_{wt2}PB2\text{-}N_{673}$, the production of which is disclosed in the examples. Nucleic acid sequence SEQ ID NO:68 represents the deduced sequence of the coding strand of a PCR amplified nucleic acid molecule denoted herein as $nei_{ca1}PB1\text{-}N_{1225}$, the production of which is disclosed in the examples. Nucleic acid sequence SEQ ID NO:71 represents the deduced sequence of the coding strand of a PCR amplified nucleic acid molecule denoted herein as $nei_{ca2}PB1\text{-}N_{1221}$, the production of which is disclosed in the examples. Nucleic acid sequence SEQ ID NO:76 represents the deduced sequence of the coding strand of a PCR amplified nucleic acid molecule denoted herein as $nei_{wt1}PA\text{-}C_{1228}$, the production of which is disclosed in the examples. Nucleic acid sequence SEQ ID NO:79 represents the deduced sequence of the coding strand of a PCR amplified nucleic acid molecule denoted herein as $nei_{wt2}PA\text{-}C_{1223}$, the production of which is disclosed in the examples. Nucleic acid sequence SEQ ID NO:80 represents the deduced sequence of the coding strand of a PCR amplified nucleic acid molecule denoted herein as $nei_{ca1}PA\text{-}C_{1233}$ and $nei_{ca2}PA\text{-}C_{1233}$ the production of which is disclosed in the examples. Nucleic acid sequence SEQ ID NO:85 represents the deduced sequence of the coding strand of a PCR amplified nucleic acid molecule denoted herein as $nei_{ca1}PB1\text{-}C_{1234}$ the production of which is disclosed in the examples. Nucleic acid sequence SEQ ID NO:88 represents the deduced sequence of the coding strand of a PCR amplified nucleic acid molecule denoted herein as $nei_{wt2}PB1\text{-}C_{1240}$ the production of which is disclosed in the examples. Nucleic acid sequence SEQ ID NO:91 represents the deduced sequence of the coding strand of a PCR amplified nucleic acid molecule denoted herein as $nei_{ca1}PB1\text{-}C_{1241}$ the production of which is disclosed in the examples. Nucleic acid sequence SEQ ID NO:94 represents the deduced sequence of the coding strand of a PCR amplified nucleic acid molecule denoted herein as $nei_{ca2}PB1\text{-}C_{1241}$ the production of which is disclosed in the examples. Nucleic acid sequence SEQ ID NO:103 represents the deduced sequence of the coding strand of a PCR amplified nucleic acid molecule denoted herein as $nei_{wt}PB1_{2341}$ the production of which is disclosed in the examples. Nucleic acid sequence SEQ ID NO:105 represents the deduced sequence of the coding strand of a PCR amplified nucleic acid molecule denoted herein as $nei_{wt}PB1_{2271}$ the production of which is disclosed in the examples. Nucleic acid sequence SEQ ID NO:106 represents the deduced sequence of the coding strand of a PCR amplified nucleic acid molecule denoted herein as $nei_{ca}PB1_{2341}$ the production of which is disclosed in the examples. Nucleic acid sequence SEQ ID NO:108 represents the deduced sequence of the coding strand of a PCR amplified nucleic acid molecule denoted herein as $nei_{ca}PB1_{2271}$ the production of which is disclosed in the examples. Additional nucleic acid molecules, nucleic acid sequences, proteins and amino acid sequences are described in the Examples.

The present invention includes nucleic acid molecule comprising a cold-adapted equine influenza virus encoding an M protein having an amino acid sequence comprising SEQ ID NO:5. Another embodiment of the present invention includes a nucleic acid molecule comprising a cold-adapted equine influenza virus encoding an HA protein having an amino acid sequence comprising SEQ ID NO:11. Another embodiment of the present invention includes a nucleic acid molecule comprising a cold-adapted equine influenza virus encoding a PB2-N protein having an amino acid sequence comprising SEQ ID NO:17. Another embodiment of the present invention includes a nucleic acid molecule comprising a cold-adapted equine influenza virus encoding a PB2-C protein having an amino acid sequence comprising SEQ ID NO:24. Another embodiment of the present invention includes a nucleic acid molecule comprising a cold-adapted equine influenza virus encoding a PB protein having an amino acid sequence comprising SEQ ID NO:48. Another embodiment of the present invention includes a nucleic acid molecule comprising a cold-adapted equine influenza virus encoding a NS protein having an amino acid sequence comprising SEQ ID NO:58. Another embodiment of the present invention includes a nucleic acid molecule comprising a cold-adapted equine influenza virus encoding a PB1-N protein having an amino acid sequence comprising SEQ ID NO:69. Another embodiment of the present invention includes a nucleic acid molecule comprising a cold-adapted equine influenza virus encoding a PA-C protein having an amino acid sequence comprising SEQ ID NO:81. Another embodiment of the present invention includes a nucleic acid molecule comprising a cold-adapted equine influenza virus encoding a PB1-C protein having an amino acid sequence comprising SEQ ID NO:92. Another embodiment of the present invention includes a nucleic acid molecule comprising a cold-adapted equine influenza virus encoding a PB1 protein having an amino acid sequence comprising SEQ ID NO:107.

It should be noted that since nucleic acid sequencing technology is not entirely error-free, the nucleic acid sequences and amino acid sequences presented herein represent, respectively, apparent nucleic acid sequences of nucleic acid molecules of the present invention and apparent amino acid sequences of M, HA, PB2-N, PB2-C, PB2, NS, PB1-N, PA-C, PB1-C and PB1 proteins of the present invention.

Another embodiment of the present invention is an antibody that selectively binds to an wild-type virus M, HA, PB2-N, PB2-C, PB2, NS, PB1-N, PA-C, PB1-C and PB1 protein of the present invention. Another embodiment of the present invention is an antibody that selectively binds to a cold-adapted virus M, HA, PB2-N, PB2-C, PB2, NS, PB1-N, PA-C, PB1-C and PB1 protein of the present invention. Preferred antibodies selectively bind to SEQ ID NO:2, SEQ ID NO:5, SEQ ID NO:8, SEQ ID NO:11, SEQ ID NO:14, SEQ ID NO:17, SEQ ID NO:20, SEQ ID NO:24, SEQ ID NO:45, SEQ ID NO:48, SEQ ID NO:51, SEQ ID NO:55, SEQ ID NO:58, SEQ ID NO:63, SEQ ID NO:66, SEQ ID NO:69, SEQ ID NO:77, SEQ ID NO:81, SEQ ID NO:86, SEQ ID NO:89, SEQ ID NO:92, SEQ ID NO:95, SEQ ID NO:104 and SEQ ID NO:107.

The following examples are provided for the purposes of illustration and are not intended to limit the scope of the present invention.

EXAMPLE 1

This example discloses the production and phenotypic characterization of several cold-adapted equine influenza viruses of the present invention.

A. Parental equine influenza virus, A/equine/Kentucky/1/91 (H3N8) (obtained from Tom Chambers, the University of Kentucky, Lexington, Ky.) was subjected to cold-adaptation in a,foreign host species, i.e., embryonated chicken eggs, in the following manner. Embryonated, 10 or 11-day old chicken eggs, available, for example, from Truslow Farms, Chestertown, Md. or from HyVac, Adel, Iowa, were inoculated with the parental equine influenza virus by injecting about 0.1 milliliter (ml) undiluted AF containing approximately $10^6$ plaque forming units (pfu) of virus into the allantoic cavity through a small hole punched in the shell of the egg. The holes in the eggs were sealed with nail polish and the eggs were incubated in a humidified incubator set at the appropriate temperature for three days. Following incubation, the eggs were candied and any non-viable eggs were discarded. AF was harvested from viable embryos by aseptically removing a portion of the egg shell, pulling aside the chorioallantoic membrane (CAM) with sterile forceps and removing the AF with a sterile pipette. The harvested AF was frozen between passages. The AF was then used, either undiluted or diluted 1:1000 in phosphate-buffered saline (PBS) as noted in Table 1, to inoculateda new set of eggs for a second passage, and so on. A total of 69 passages were competed. Earlier passages were done at either about 34° C. (passages 1–2) or about 30° C. and on subsequent passages, the incubation temperature was shifted down either to about 28° C., or to about 26° C. In order to increase the possibility of the selection of the desired phenotype of a stable, attenuated virus, the initial serial passage was expanded to included five different limbs of the serial passage tree, A through E, as shown in Table 1.

TABLE 1

Passage history of the limbs A through E.
[t1]

| | Passage # | | | | |
|---|---|---|---|---|---|
| Temperature | Limb A | Limb B | Limb C | Limb D | Limb E |
| 341 C. | 1–2 | 1–2 | 1–2 | 1–2 | 1–2 |
| 301 C. | 3–8 | 3–29 | 3–29 | 3–29 | 3–29 |
| 281 C. | | 30–33* | 30–68* | 30–33 | 30–69 |
| 261 C. | 9–65 | 34–69* | | 34–65 | |

*= the infectious allantoic fluid was diluted 1:1000 in these passages.

B. Virus isolates carried through the cold-adaptation procedure described in section A were tested: for temperature sensitivity, i.e., a phenotype in which the cold-adapted virus grows at the lower, or permissive temperature (e.g., about 34° C.), but no longer forms plaques at a higher, or non-permissive temperature (e.g., about 37° C. or about 39° C.), as follows. At each cold-adaptation passage, the AF was titered by plaque assay at about 34° C. Periodically, individual plaques from the assay were clonally isolated by excision of the plaque area and placement of the excised agar plug in a 96-well tray containing a monolayer of MDCK cells. The 96-well trays were incubated overnight and the yield assayed for temperature sensitivity by CPE assay in duplicate 96-well trays incubated at about 34° C. and at about 39° C. The percent of the clones that scored as temperature sensitive mutants by this assay, i.e., the number of viral plaques that grew at 34° C. but did not grow at 39° C., divided by the total number of plaques, was calculated, and is shown in Table 2. Temperature sensitive isolates were then evaluated for protein synthesis at the non-permissive temperature by visualization of radiolabeled virus-synthesized proteins by SDS polyacrylamide gel electrophoresis (SDS-PAGE).

TABLE 2

Percent of isolated Clones that were temperature sensitive.
[t21]

| | Percent Temperature Sensitive | | | | |
|---|---|---|---|---|---|
| Passage # | Limb A | Limb B | Limb C | Limb D | Limb E |
| p36 | 56% | 66% | 0% | 66% | 54% |
| p46 | | 80% | 60% | | 75% |
| p47 | | | 80% | | |
| p48 | | | 100% | | |
| p49 | | 100% | | 100% | 50% |
| p50 | | | 90% | | |
| p51 | | 100% | | | |
| p52 | | | | | 57% |
| p62 | 100% | | | 100% | |
| p65 | | | 100% | | |
| p66 | | 100% | | | 88% |

From the clonal isolates tested for temperature sensitivity, two were selected for further study. Clone EIV-P821 was selected from the 49th passage of limb B and clone EIV-P824 was selected, from the 48th passage of limb C, as defined in Table 1. Both of these virus isolates were temperature sensitive, with plaque formation of both isolates inhibited at a temperature of about 39° C. At this temperature, protein synthesis was completely inhibited by EIV-P821, but EIV-P824 exhibited normal levels of protein synthesis. In addition, plaque formation by EIV-P821 was inhibited at a temperature of about 37° C., and at this temperature, late gene expression was inhibited, i.e., normal levels of NP protein were synthesized, reduced or no M1 or HA proteins were synthesized, and enhanced levels of the polymerase proteins were synthesized. The phenotype observed at 37° C., being typified by differential viral protein synthesis, was distinct from the protein synthesis phenotype seen at about 39° C., which was typified by the inhibition of synthesis of all viral proteins. Virus EIV-P821 has been deposited with the American Type Culture Collection (ATCC) under Accession No. ATCC VR-2625, and virus EIV-P824 has been deposited with the ATCC under Accession No. ATCC VR-2624.

C. Further characterization of the mutations in isolate EIV-P821 were carried out by reassortment analysis, as follows. Reassortment analysis in influenza viruses allows one skilled in the art, under certain circumstances, to correlate phenotypes of a given virus with putative mutations occurring on certain of the eight RNA segments that comprise an influenza A virus genome. This technique is described, for example, in Palese, et al., ibid. A mixed infection of EIV-P821 and an avian influenza virus, A/mallard/New York/6750/78 was performed as follows. MDCK cells were co-infected with EIV-P821 at a multiplicity of infection (MOI) of 2 pfu/cell and A/mallard/New York/6750/78 at an MOI of either 2, 5, or 10 pfu/cell. The infected cells were incubated at a temperature of about 34° C. The yields of the various co-infections were titered and individual plaques were isolated at about 34° C., and the resultant clonal isolates were characterized as to whether they were able to grow at about 39° C. and about 37° C., and express their genes, i.e., synthesize viral proteins, at about 39° C., about 37° C., and about 34° C. Protein synthesis was evaluated by SDS-PAGE analysis of radiolabeled infected-cell lysates. The HA, NP and NS-1 proteins of the two parent viruses, each of which is encoded by a separate genome segment, were distinguishable by SDS-PAGE analysis, since these particular viral proteins, as derived from either the equine or the avian influenza virus, migrate at different apparent molecular weights. In this way it was possible, at least for the HA, NP, and NS-1 genes, to evaluate whether certain phenotypes of the parent virus, e.g., the temperature sensitive and the protein synthesis phenotypes, co-segregate with the genome segments carrying these genes. The results of the reassortment analyses investigating co-segregation of a) the mutation inhibiting plaque formation, i.e., the induction of CPE, at a non-permissive temperature of about 39° C. or b) the mutation inhibiting protein synthesis at a non-permissive temperature of about 39° C. with each of the EIV-P821 HA, NP and NS-1 proteins are shown in Tables 3 and 4, respectively.

TABLE 3

Reassortment analysis of the EIV-P821 39° C. plaque formation phenotype with avian influenza virus, A/mallard/New York/6750/78.

[t17]

| Gene | Virus | ts+[1] | ts−[2] |
|---|---|---|---|
| HA | avian | 26 | 13 |
| equine | 11 | 44 | |
| NP | avian | 37 | 8 |
| equine | 0 | 49 | |
| NS-1 | avian | 9 | 8 |
| equine | 12 | 20 | |

[1]number of clonal isolates able to induce CPE in tissue culture cells at a temperature of about 39° C.
[2]number of clonal isolates inhibited in the ability to induce CPE in tissue culture cells at a temperature of about 39° C.

TABLE 4

Reassortment analysis of the EIV-P821 39° C. protein synthesis phenotype with avian influenza virus, A/mallard/New York/6750/78.

[t3]

| Gene | Virus | ts+[1] | ts−[2] |
|---|---|---|---|
| HA | avian | 18 | 1 |
| equine | 11 | 7 | |
| NP | avian | 34 | 5 |
| equine | 7 | 8 | |
| NS-1 | avian | 10 | 4 |
| equine | 14 | 5 | |

[1]number of clonal isolates which synthesize all viral proteins at a temperature of about 39° C.
[2]number of clonal isolates inhibited in the ability to synthesize all viral proteins at a temperature of about 39° C.

The results demonstrated an association of the equine NP gene with a mutation causing the inability of EIV-P821 to form plaques at a non-permissive temperature of about 39° C., but the results did not suggest an association of any of the HA, NP, or NS-1 genes with a mutation causing the inability of EIV-P821 to express viral proteins at a non-permissive temperature of about 39° C. Thus, these data also demonstrated that the plaque formation phenotype and the protein synthesis phenotype observed in virus EIV-P821 were the result of separate mutations.

D. Studies were also conducted to determine if cold-adapted equine influenza viruses of the present invention have a dominant interference phenotype, that is, whether they dominate in mixed infection with the wild type parental virus A/Kentucky/1/91 (H:3N8). The dominant interference phenotype of viruses EIV-P821 and EIV-P824 were evaluated in the following manner. Separate monolayers of MDCK cells were singly infected with the parental virus A/Kentucky/1/91 (H3N8) at an MOI of 2, singly infected with either cold-adapted virus EIV-P821 or EIV-P824 at an MOI of 2, or simultaneously doubly infected with both the parental virus and one of the cold adapted viruses at an MOI of 2+2, all at a temperature of about 34° C. At 24 hours after infection, the media from the cultures were harvested and the virus yields from the various infected cells were measured by duplicate plaque assays performed at temperatures of about 34° C. and about 39° C. This assay took advantage of the fact that cold adapted equine influenza viruses EIV-P821 or EIV-P824 are temperature sensitive and are thus unable to form plaques at a non-permissive temperature of about 39° C., while the parental virus is able to form plaques at both temperatures, thus making it possible to measure the growth of the parental virus in the presence of the cold adapted virus. Specifically, the dominant interference effect of the cold adapted virus on the growth of the parental virus was quantitated by comparing the virus yield at about 39° C. of the cells singly infected with parental virus to the yield of the parental virus in doubly infected cells. EIV-P821, in mixed infection, was able to reduce the yield of the parental virus by approximately 200 fold, while EIV-P824, in mixed infection, reduced the yield of the parental virus by approximately 3200 fold. This assay therefore showed that cold-adapted equine influenza viruses EIV-P821 and EIV-P824 both exhibit the dominant interference phenotype.

E. Virus isolate EIV-MSV+5 was derived from EIV-P821, as follows. EIV-P821 was passaged once in eggs, as described above, to produce a Master Seed Virus isolate, denoted herein as EIV-MSV0. EIV-MSV0 was then subjected to passage three additional times in eggs, the virus isolates at the end of each passage being designated EIV-MSV+1, EIV-MSV+2, and EIV-MSV+3, respectively. EIV- MSV+3 was then subjected to two additional passages in MDCK cells, as follows. MDCK cells were grown in 150 $cm^2$ tissue culture flasks in MEM tissue culture medium with Hanks Salts, containing 10% calf serum. The cells were then washed with sterile PBS and the growth medium was replaced with about 8 ml per flask of infection medium (tissue culture medium comprising MEM with Hanks Salts, 1 μg/ml TPCK trypsin solution, 0.125% bovine serum albumin (BSA), and 10 mM HEPES buffer). MDCK cells were inoculated with AF containing virus EIV-MSV+3 (for the first passage in MDCK cells) or virus stock harvested from EIV-MSV+4 (for the second passage in MDCK cells), and the viruses were allowed to adsorb for 1 hour at about 34° C. The inoculum was removed from the cell monolayers, the cells were washed again with PBS, and about 100 ml of infection medium was added per flask. The infected cells were incubated at about 34° C. for 24 hours. The virus-infected MDCK cells were harvested by shaking the flasks vigorously to disrupt the cell monolayer, resulting in virus isolates EIV-MSV+4 (the first passage in MDCK cells), and EIV-MSV+5 (the second passage in MDCK cells). Viruses EIV-MSV0 and EIV-MSV+5 were subjected to phenotypic analysis, as described in section B above, to determine their ability to form plaques and synthesize viral proteins at temperatures of about 34° C., about 37° C., and about 39° C. Both EIV-MSV0 and EIV-MSV+5 formed plaques in tissue culture cells at a temperature of about 34° C., and neither virus isolate formed plaques or exhibited detectable viral protein synthesis at a temperature of about 39° C. Virus EIV-MSV0 had a similar temperature sensitive phenotype as EIV-P821 at a temperature of about 37° C., i.e., it was inhibited in plaque formation, and late gene expression was inhibited. However, EIV-MSV+5, unlike its parent virus, EIV-P821, did form plaques in tissue culture at a temperature of about 37° C., and at this temperature, the virus synthesized normal amounts of all proteins. Virus EIV-MSV+5 has been deposited with the ATCC under Accession No. ATCC VR-2627.

EXAMPLE 2

Therapeutic compositions of the present invention were produced as follows.

A. A large stock of EIV-P821 was propagated in eggs as follows. About 60 specific pathogen-free embryonated chicken eggs were candled and non-viable eggs were discarded. Stock virus was diluted to about $1.0\times10^5$ pfu/ml in sterile PBS. Virus was inoculated into the allantoic cavity of the eggs as described in Example 1A. After a 3-day incubation in a humidified chamber at a temperature of about 34° C., AF was harvested from the eggs according to the method described in Example 1A. The harvested AF was mixed with a stabilizer solution, for example A1/A2 stabilizer, available from Diamond Animal Health, Des Moines, Iowa, at 25% V/V (stabilizer/AF). The harvested AF was batched in a centrifuge tube and was clarified by centrifugation for 10 minutes at 1000 rpm in an IEC Centra-7R refrigerated table top centrifuge fitted with a swinging bucket rotor. The clarified fluid was distributed into 1-ml cryovials and was frozen at about −70° C. Virus stocks were titrated on MDCK cells by CPE and plaque assay at about 34° C.

B. A large stock of EIV-P821 was propagated in MDCK cells as follows. MDCK cells were grown in 150 $cm^2$ tissue culture flasks in MEM tissue culture medium with Hanks Salts, containing 10% calf serum. The cells were then washed with sterile PBS and the growth medium was replaced with about 8 ml per flask of infection medium. The MDCK cells were inoculated with virus stock at an MOI ranging from about 0.5 pfu per cell to about 0.005 pfu per cell, and the viruses were allowed to adsorb for 1 hour at about 34° C. The inoculum was removed from the cell monolayers, the cells were washed again with PBS, and about 100 ml of infection medium was added per flask. The infected cells were incubated at about 34° C. for 24 hours. The virus-infected MDCK cells were harvested by shaking the flasks vigorously to disrupt the cell monolayer and stabilizer solution was added to the flasks at 25% V/V (stabilizer/virus solution). The supernatants were distributed aseptically into cryovials and frozen at −70° C.

C. Therapeutic compositions comprising certain cold-adapted temperature sensitive equine influenza viruses of the present invention were formulated as follows. Just prior to vaccination procedures, such as those described in Examples 3–7 below, stock vials of EIV-P821 or EIV-MSV+5 were thawed and were diluted in an excipient comprising either water, PBS, or in MEM tissue culture medium with Hanks Salts, containing 0.125% bovine serum albumin (BSA-MEM solution) to the desired dilution for administration to animals. The vaccine compositions were held on ice prior to vaccinations. All therapeutic compositions were titered on MDCK cells by standard methods just prior to vaccinations and wherever possible, an amount of the composition, treated identically to those administered to the animals, was titered after the vaccinations to ensure that the virus remained viable during the procedures.

EXAMPLE 3

A therapeutic composition comprising cold-adapted equine influenza virus EIV-P821 was tested for safety and its ability to replicate in three horses showing detectable prior immunity to equine influenza virus as follows. EIV-P821, produced as described in Example 1A, was grown in eggs as described in Example 2A and was formulated into a therapeutic composition comprising $10^7$ pfu EIV-P821/2ml BSA-MEM solution as described in Example 2C.

Three ponies having prior detectable hemagglutination inhibition (HAI) titers to equine influenza virus were inoculated with a therapeutic composition comprising EIV-P821 by the following method. Each pony was given a 2-ml dose of EIV-P821, administered intranasally using a syringe fitted with a blunt cannula long enough to reach past the false nostril, 1 ml per nostril.

The ponies were observed for approximately 30 minutes immediately following and at approximately four hours after vaccination for immediate type allergic reactions such as sneezing, salivation, labored or irregular breathing, shaking, anaphylaxis, or fever. The animals were further monitored on days 1–11 post-vaccination for delayed type allergic reactions, such as lethargy or anorexia. None of the three ponies in this study exhibited any allergic reactions from the vaccination.

The ponies were observed daily, at approximately the same time each day, starting two days before vaccination and continuing through day 11 following vaccination for clinical signs consistent with equine influenza. The ponies were observed for nasal discharge, ocular discharge, anorexia, disposition, heart rate, capillary refill time, respiratory rate, dyspnea, coughing, lung sounds, presence of toxic line on upper gum, and body temperature. In addition submandibular and parietal lymph nodes were palpated and any abnormalities were described. None of the three ponies in this study exhibited any abnormal reactions or overt clinical signs during the observation period.

To test for viral shedding in the animals, on days 0 through 11 following vaccination, nasopharyngeal swabs were collected from the ponies as described in Chambers, et al., 1995, *Equine Practice*, 17, 19–23. Chambers, et al., ibid. Briefly, two sterile Dacron polyester tipped applicators (available, e.g., from Hardwood Products Co., Guilford, Me.) were inserted, together, into each nostril of the ponies. The swabs (four total, two for each nostril) were broken off into a 15-ml conical centrifuge tube containing 2.5 ml of chilled transport medium comprising 5% glycerol, penicillin, streptomycin, neomycin, and gentamycin in PBS at physiological pH. Keeping the samples on wet ice, the swabs were aseptically wrung out into the medium and the nasopharyngeal samples were divided into two aliquots. One aliquot was used to attempt isolation of EIV by inoculation of embryonated eggs, using the method described in Example 1. The AF of the inoculated eggs was then tested for its ability to cause hemagglutination, by standard methods, indicating the presence of equine influenza virus in the AF. On days 2 and 3 post-vaccination, the other aliquots were tested for virus by the Directigen® Flu A test, available from Becton-Dickinson (Cockeysville, Md.).

Attempts to isolate, EIV from the nasopharyngeal secretions of the three animals by egg inoculation were unsuccessful. However on days 2 and 3, all animals tested positive for the presence of virus shedding using the Directigen Flu A test, consistent with the hypothesis that EIV-P821 was replicating in the seropositive ponies.

To test the antibody titers to EIV in the inoculated animals described in this example, as well as in the animals described in Examples 4–7, blood was collected from the animals prior to vaccination and on designated days post-vaccination. Serum was isolated and was treated either with trypsin/periodate or kaolin to block the nonspecific inhibitors of hemagglutination present in normal sera. Serum samples were tested for hemagglutination inhibition (HAI) titers against a recent EIV isolate by standard methods, described, for example in the Supplemental assay method for conducting the hemagglutination inhibition assay for equine influenza virus antibody (SAM 124), provided by the U.S.D.A. National Veterinary Services Laboratory under 9 CFR 113.2.

The HAI titers of the three ponies are shown in Table 5. As can be seen, regardless of the initial titer, the, serum HAI titers increased at least four-fold in all three animals after vaccination with, EIV-P821.

These data demonstrate that cold-adapted equine influenza virus EIV-P821 is safe, and non-reactogenic in seropositive ponies, and that these animals exhibited an increase in antibody titer to equine influenza virus, even though they had prior demonstrable titers.

TABLE 5

HAI titers of vaccinated animals*
[t20]

| ID | Animal HAI Titer (days after vaccination) 0 | 7 | 14 | 21 |
|---|---|---|---|---|
| 18 | 40 | 80 | 160 | 160 |
| 19 | 10 | 20 | 40 | 80 |
| 25 | 20 | 40 | 320 | 80 |

*HAI titers are expressed as the reciprocal of the highest dilution of serum which inhibited hemagglutination of erythrocytes by a recent isolate of equine influenza virus.

EXAMPLE 4

This Example discloses an animal study to evaluate the safety and efficacy of a therapeutic composition comprising cold-adapted equine influenza virus EIV-P821.

A therapeutic composition comprising cold-adapted equine influenza virus EIV-P821 was tested for attenuation, as well as its ability to protect horses from challenge with virulent equine influenza virus, as follows. EIV-P821, produced as described in Example 1, was grown in eggs as described in Example 2A and was formulated into a therapeutic composition comprising $10^7$ pfu of virus/2 ml water, as described in Example 2C. Eight EIV-seronegative ponies were used in this study. Three of the eight ponies were vaccinated with a 2-ml dose comprising $10^7$ pfu of the EIV-P821 therapeutic composition, administered intranasally, using methods similar to those described in Example 3. One pony was given $10^7$ pfu of the EIV-P821 therapeutic composition, administered orally, by injecting 6 ml of virus into the pharynx, using a 10-ml syringe which was adapted to create a fine spray by the following method. The protruding seat for the attachment of needles was sealed off using modeling clay and its cap was left in place. About 10 holes were punched through the bottom of the syringe, i.e., surrounding the seat, using a 25-gauge needle. The syringe was placed into the interdental space and the virus was forcefully injected into the back of the mouth. The remaining four ponies were held as non-vaccinated controls.

The vaccinated ponies were observed for approximately 30 minutes immediately following and at approximately four hours after vaccination for immediate type allergic reactions, and the animals were further monitored on days 1–11 post-vaccination for delayed type allergic reactions, both as described in Example 3. None of the four vaccinated ponies in this study exhibited any abnormal reactions from the vaccination.

The ponies were observed daily, at approximately the same time each day, starting two days before virus vaccination and continuing through day 11 following vaccination for clinical signs, such as those described in Example 3. None of the four vaccinated ponies in this study exhibited any clinical signs during the observation period. This result demonstrated that cold-adapted equine influenza virus EIV-P821 exhibits the phenotype of attenuation.

To test for viral shedding in the vaccinated animals, on days 0 through 11 following vaccination, nasopharyngeal swabs were collected from the ponies as described in Example 3. The nasopharyngeal samples were tested for virus in embryonated chicken eggs according to the method described in Example 3.

As shown in Table 6, virus was isolated from only one vaccinated animal using the egg method. However, as noted in Example 3, the lack of isolation by this method does not preclude the fact that virus replication is taking place, since replication may be detected by more sensitive methods, e.g., the Directigen Flu A test.

TABLE 6

Virus isolation in eggs after vaccination.
[t22]

| ID # | Route | Virus Isolation (days after vaccination) 0 | 1 | 2 | 3 | 4 | 5 | 6 | 7 | 8 | 9 | 10 | 11 |
|---|---|---|---|---|---|---|---|---|---|---|---|---|---|
| 91 | IN | – | – | + | + | + | + | + | + | + | + | + | – |
| 666 | IN | – | – | – | – | – | – | – | – | – | – | – | – |
| 673 | IN | – | – | – | – | – | – | – | – | – | – | – | – |
| 674 | Oral | – | – | – | – | – | – | – | – | – | – | – | – |

To test the antibody titers to equine influenza virus in the vaccinated animals, blood was collected from the animals prior to vaccination and on days 7, 14, 21, and 28 post-vaccination. Serum samples were isolated and were tested for hemagglutination inhibition (HAI) titers against a recent EIV isolate according to the methods described in Example 3.

The HAI titers of the four vaccinated ponies are shown in Table 7.

TABLE 7

HAI titers after vaccination.
[t11]

| | | HAI Titer (days after vaccination) | | | | |
|---|---|---|---|---|---|---|
| ID # | Route | 0 | 7 | 14 | 21 | 28 |
| 91 | IN | <10 | <10 | <10 | <10 | <10 |
| 666 | IN | 10 | 10 | 10 | 20 | 20 |
| 673 | IN | 10 | 10 | 10 | 20 | 20 |
| 674 | Oral | 20 | 40 | 40 | 40 | 40 |

Unlike the increase in HAI titer observed with the three animals described in the study in Example 3, the animals in this study did not exhibit a significant increase, i.e., greater than four-fold, in HAI titer following vaccination with EIV-P821.

Approximately four and one-half months after vaccine virus administration, all 8 ponies, i.e., the four that were vaccinated and the four non-vaccinated controls, were challenged by the following method. For each animal, $10^7$ pfu of the virulent equine influenza virus strain;A/equine/Kentucky/1/91 (H3N8) was suspended in 5 ml of water. A mask was connected to a nebulizer, and the mask was placed over the animal's muzzle, including the nostrils. Five (5) ml was nebulized for each animal, using settings such that it took 5–10 minutes to deliver the full 5 ml. Clinical observations, as described in Example 3, were performed on all animals three days before challenge and daily for 11 days after challenge.

Despite the fact that the vaccinated animals did not exhibit marked increases in their HAI titers to equine influenza virus, all four vaccinated animals were protected against equine influenza virus challenge. None of the vaccinated animals showed overt clinical signs or fever, although one of the animals had a minor wheeze for two days. On the other hand, all four non-vaccinated ponies shed virus and developed clinical signs and fever typical of equine influenza virus infection. Thus, this example demonstrates that a therapeutic composition of the present invention can protect horses from equine influenza disease.

EXAMPLE 5

This Example discloses an additional animal study to evaluate attenuation of a therapeutic composition comprising cold-adapted equine influenza virus EIV-P821, and its ability to protect vaccinated horses from subsequent challenge with virulent equine influenza virus. Furthermore, this study evaluated the effect of exercise stress on the safety and efficacy of the therapeutic composition.

A therapeutic composition comprising cold-adapted equine influenza virus EIV-P821 was tested for safety and efficacy in horses, as follows. EIV-P821, produced as described in Example; 1, was grown in eggs as described in Example 2A and was formulated into a therapeutic composition comprising $10^7$ pfu virus/5 ml water, as described in Example 2C. Fifteen ponies were used in this study. The ponies were randomly assigned to three groups of five animals each, as shown in Table 8, there being two vaccinated groups and one unvaccinated control group. The ponies in group 2 were exercise stressed before vaccination, while the ponies in vaccinate group 1 were held in,a stall.

TABLE 8

Vaccination/challenge protocol.
[t12]

| Group | No. Ponies | Exercise | Vaccine | Challenge |
|---|---|---|---|---|
| 1 | 5 | — | Day 0 | Day 90 |
| 2 | 5 | Days −4 to 0 | Day 0 | Day 90 |
| 3 | 5 | — | — | Day 90 |

The ponies in group 2 were subjected to exercise stress on a treadmill prior to vaccination, as follows. The ponies were acclimated to the use of the treadmill by 6 hours of treadmill use at a walk only. The actual exercise stress involved a daily exercise regimen starting 4 days before and ending on the day of vaccination (immediately prior to vaccination). The treadmill exercise regimen is shown in Table 9.

TABLE 9

Exercise regimen for the ponies in Group 2.
[t13]

| Speed (m/sec) | Time (min.) | Incline (°) |
|---|---|---|
| 1.5 | 2 | 0 |
| 3.5 | 2 | 0 |
| 3.5 | 2 | 7 |
| 4.5† | 2 | 7 |
| 5.5† | 2 | 7 |
| 6.5† | 2 | 7 |
| 7.5† | 2 | 7 |
| 8.5† | 2 | 7 |
| 3.5 | 2 | 7 |
| 1.5 | 10 | 0† |

†Speed, in meters per second (m/sec) was increased for each animal every 2 minutes until the heart rate reached and maintained ≧200 per minute Groups 1 and 2 were given a therapeutic composition comprising $10^7$ pfu of EIV-P821, by the nebulization method described for the challenge described in Example 4. None of the vaccinated ponies in this study exhibited any immediate or delayed allergic reactions from the vaccination.

The ponies were observed daily, at approximately the same time each day, starting two days before vaccination and continuing through day 11 following vaccination for clinical signs, such as those described in Example 3. None of the vaccinated ponies in this study exhibited any overt clinical signs during the observation period.

To test for viral shedding in the vaccinated animals, before vaccination and on days 1 through 11 following vaccination, nasopharyngeal swabs were collected from the ponies as described in Example 3. The nasopharyngeal samples were tested for virus in embryonated chicken eggs according to the method described in Example 3. Virus was isolated from the vaccinated animals, i.e., Groups 1 and 2, as shown in Table 10.

TABLE 10

| Virus isolation after vaccination. [t7] Virus Isolation (days after isolation) | | | | | | | | | | | | | | |
|---|---|---|---|---|---|---|---|---|---|---|---|---|---|---|
| Group | ID # | Exercise | 0 | 1 | 2 | 3 | 4 | 5 | 6 | 7 | 8 | 9 | 10 | 11 |
| 1 | 12 | No | − | − | + | + | + | + | + | − | + | + | − | − |
| 1 | 16 | No | − | − | + | + | + | + | + | − | − | − | − | − |
| 1 | 17 | No | − | − | + | + | + | + | + | + | + | − | + | − |
| 1 | 165 | No | − | − | − | − | − | − | − | − | − | − | − | − |
| 1 | 688 | No | − | − | − | − | − | + | − | + | − | − | − | − |
| 2 | 7 | Yes | − | − | − | + | + | + | + | − | − | − | − | − |
| 2 | 44 | Yes | − | − | − | − | − | − | − | − | − | − | − | − |
| 2 | 435 | Yes | − | − | + | + | + | + | − | − | − | − | − | − |
| 2 | 907 | Yes | − | − | − | + | − | + | + | − | − | − | − | − |
| 2 | 968 | Yes | − | − | − | − | − | + | − | + | − | − | − | — |

To test the antibody titers to equine influenza virus in the vaccinated animals, blood was collected prior to vaccination and on days 7, 14, 21, and 28 post-vaccination. Serum samples were isolated and were tested for HAI titers against a recent EIV isolate according to the methods described in Example 3. These titers are shown in Table 11.

TABLE 11

| HAI titers after vaccination and after challenge on day 90. | | | | | | | | | | | |
|---|---|---|---|---|---|---|---|---|---|---|---|
| | Animal | Day Post-vaccination | | | | | | | | | |
| Group | ID | −1 | 7 | 14 | 21 | 28 | 91 | 105 | 112 | 119 | 126 |
| 1 | 12 | <10 | <10 | <10 | <10 | <10 | <10 | 80 | 320 | 320 | 640 |
| 1 | 16 | <10 | <10 | 20 | 20 | <10 | <10 | 20 | 160 | 320 | 320 |
| 1 | 17 | <10 | <10 | 10 | 10 | 10 | 10 | 80 | 160 | 160 | 160 |
| 1 | 165 | <10 | <10 | 10 | 10 | 10 | 10 | 80 | 80 | 80 | 80 |
| 1 | 688 | <10 | <10 | 20 | 20 | 20 | 20 | 20 | 20 | 20 | 40 |
| 2 | 7 | <10 | <10 | 10 | 10 | <10 | <10 | 20 | 80 | 80 | 40 |
| 2 | 44 | <10 | <10 | 20 | 20 | 20 | 10 | 80 | 320 | 320 | 320 |
| 2 | 435 | <10 | <10 | 20 | 20 | 10 | <10 | 20 | 80 | 80 | 80 |
| 2 | 907 | <10 | <10 | 10 | 10 | 20 | 10 | 10 | 40 | 80 | 80 |
| 2 | 968 | <10 | <10 | <10 | <10 | <10 | <10 | 40 | 160 | 160 | 160 |
| 3 | 2 | | | | | | <10 | 80 | 640 | 640 | 320 |
| 3 | 56 | | | | | | <10 | 80 | 320 | 320 | 320 |
| 3 | 196 | | | | | | <10 | 20 | 160 | 80 | 80 |
| 3 | 198 | | | | | | 10 | 40 | 160 | 320 | 320 |
| 3 | 200 | | | | | | <10 | 20 | 80 | 80 | 40 |
| Group | Description | | | | | | | | | | |

On day 90 post vaccination, all 15 ponies were challenged with $10^7$ pfu of equine influenza virus strain A/equine/Kentucky/1/91 (H3N8) by the nebulizer method as described in Example 4. Clinical observations, as described in Example 3, were performed on all animals three days before challenge and daily for 11 days after challenge. There were no overt clinical signs observed in any of the vaccinated ponies. For of the five non-vaccinated ponies developed fever and clinical signs typical of equine influenza virus infection.

Thus, this, this example demonstrates that a therapeutic composition of the present invention protects horses against equine influenza disease, even if the animals are stressed prior to vaccination.

EXAMPLE 6

This Example compared the infectivities of therapeutic compositions of the present invention grown in eggs and grown in tissue culture cells. From a production standpoint, there is an advantage to growing therapeutic compositions of the present invention in tissue culture rather than in embryonated chicken eggs. Equine influenza virus, however, does not grow to as high a titer in cells as in eggs. In addition, the hemagglutinin of the virus requires an extracellular proteolytic cleavage by trypsin-like proteases for infectivity. Since serum contains trypsin inhibitors, virus grown in cell culture must be propagated in serum-free medium that contains trypsin in order to be infectious. It is well known by those skilled in the art that such conditions are less than optimal for the viability of tissue culture cells. In addition, these growth conditions may select for virus with altered binding affinity for equine cells, which may affect viral infectivity since the virus needs to bind efficiently to the animal's nasal mucosa to replicate and to stimulate immunity. Thus, the objective of the study disclosed in this example was to evaluate whether the infectivity of therapeutic compositions of the present invention was adversely affected by growth for multiple passages in in vitro tissue culture.

EIV-P821, produced as described in Example 1, was grown in eggs as described in Example 2A or in MDCK cells as described in Example 2B. In each instance, the virus was passaged five times. EIV-P821 was tested for its cold-adaptation and temperature sensitive phenotypes after each passage. The egg and cell-passaged virus preparations were formulated into therapeutic compositions comprising $10^7$ pfu virus/2 ml BSA-MEM solution, as described in Example 2C, resulting in an egg-grown EIV-P821 therapeutic composition and an MDCK cell-grown EIV-P821 therapeutic composition, respectively.

Eight ponies were used in this study. Serum from each of the animals was tested for HAI titers to equine influenza virus prior to the study. The animals were randomly assigned into one of two groups of four ponies each. Group A received the egg-grown EIV-P821 therapeutic composition, and Group B received the MDCK-grown EIV-P821 therapeutic composition, prepared as described in Example 2B. The therapeutic compositions were administered intranasally by the method described in Example 3.

The ponies were observed daily, at approximately the same time each day, starting two days before vaccination and continuing through day 11 following vaccination for allergic reactions or clinical signs as described in Example 3. No allergic reactions or overt clinical signs were observed in any of the animals.

Nasopharyngeal swabs were collected before vaccination and daily for 11 after vaccination. The presence of virus material in the nasal swabs was determined by the detection of CPE on MDCK cells infected as described in Example 1, or by inoculation into eggs and examination of the ability of the infected AF to cause hemagglutination, as described in Example 3. The material was tested for the presence of virus only, and not for titer of virus in the sample. Virus isolation results are listed in Table 12. Blood was collected and serum samples from days 0, 7, 14, 21 and 28 after vaccination were tested for agglutination inhibition antibody titer against a recent isolate. HAI titers are so in Table 12.

TABLE 12

HAI titers and virus isolation after vaccination.

| | | HAI Titer (DPV[3]) | | | | | Virus Isolation[1] (DPV[3]) | | | | | | | | | | | |
|---|---|---|---|---|---|---|---|---|---|---|---|---|---|---|---|---|---|---|
| Group[2] | ID | 0 | 7 | 14 | 21 | 28 | 0 | 1 | 2 | 3 | 4 | 5 | 6 | 7 | 8 | 9 | 10 | 11 |
| 1 | 31 | <10 | 20 | 160 | 160 | 160 | - | EC | — | C | EC | EC | C | C | EC | — | — | — |
| | 37 | <10 | 40 | 160 | 160 | 160 | — | EC | C | C | EC | C | C | C | — | — | — | — |
| | 40 | <10 | 20 | 80 | 160 | 80 | — | EC | EC | C | — | C | EC | C | — | EC | EC | — |
| | 41 | <10 | 40 | 160 | 160 | 80 | — | EC | EC | C | EC | C | EC | EC | — | — | — | — |
| 2 | 32 | <10 | <10 | 80 | 80 | 40 | — | EC | — | C | — | C | — | C | — | EC | — | — |
| | 34 | <10 | 20 | 160 | 160 | 160 | — | EC | — | C | EC | C | EC | C | — | — | — | — |
| | 35 | <10 | <10 | 80 | 80 | 40 | — | EC | — | C | — | C | — | C | — | EC | — | — |
| | 42 | <10 | <10 | 80 | 80 | 40 | — | — | — | C | — | C | EC | EC | — | — | — | — |

[1]E = Egg isolation positive; C = CPE isolation positive; — = virus not detected by either of the methods
[2]Group 1: Virus passaged 5X in MDCK cells; Group 2: Virus passaged 5X in Eggs
[3]Days Post-vaccination The results in Table 12 show that there were no significant differences in infectivity or immunogenicity between the egg-grown and MDCK-grown EIV-P821 therapeutic compositions.

EXAMPLE 7

The example evaluated the minimum dose of a therapeutic composition comprising a cold-adapted equine influenza virus required to protect a horse from equine influenza virus infection.

The animal studies disclosed in Examples 3–6 indicated that a therapeutic composition of the present invention was efficacious and safe. In those studies, a dose of $10^7$ pfu, which correlates to approximately $10^8$ $TCID_{50}$ units, was used. However, from the standpoints of cost and safety, it is advantageous to use the minimum virus titer that will protect a horse from disease caused by equine influenza virus. In this study, ponies were vaccinated with four different doses of a therapeutic composition comprising a cold-adapted equine influenza virus to determine the minimum dose which protects a horse against virulent equine influenza virus challenge.

EIV-P821, produced as described in Example 1A, was passaged and grown in MDCK cells as described in Example 2B and was formulated into a therapeutic composition comprising either $2\times10^4$, $2\times10^5$, $2\times10^6$, or $2\times10^7$ $TCID_{50}$ units/1 ml BSA-MEM solution as described in Example 2C. Nineteen horses of various ages and breeds were used for this study. The horses were assigned to four vaccine groups, one group of three horses and three groups of four horses, and one control group of four horses (see Table 13). Each of the ponies in the vaccine groups were given a 1-ml dose of the indicated therapeutic composition, administered intranasally by methods similar to those described in Example 3.

TABLE 13

Vaccination protocol.
[t19]

| Group No. | No. Animals | Vaccine Dose, $TCID_{50}$ Units |
|---|---|---|
| 1 | 3 | $2 \times 10^7$ |
| 2 | 4 | $2 \times 10^6$ |
| 3 | 4 | $2 \times 10^5$ |
| 4 | 4 | $2 \times 10^4$ |
| 5 | 4 | control |

The ponies were observed for approximately 30 minutes immediatelyfollowing and at approximately four hours after vaccination for immediate type reactions, and the animals were further monitored on days 1–11 post-vaccination for delayed type reactions, both as described in Example 3. None of the vaccinated ponies in this study exhibited any abnormal reactions or overt clinical signs from the vaccination.

Blood for serum analysis was collected 3 days before vaccination, on days 7, 14, 21, and 28 after vaccination, and after challenge on Days 35 and 42. Serum samples were tested for HAI titers against a recent EIV isolate according to the methods described in Example 3. These titers are shown in Table 14. Prior to challenge on day 29, 2 of the 3 animals in group 1, 4 of the 4 animals in group 2, 3 of the 4 animals in group 3, and 2 of the 4 animals in group 4 showed at least 4-fold increases in HAI titers after vaccination In addition, 2 of the 4 control horses also exhibited increases in HAI titers. One interpretation for this result is that the control horses were exposed to vaccine virus transmitted from the vaccinated horses, since all the horses in this study were housed in the same barn.

TABLE 14: HAI titers post-vaccination and post-challenge, and challenge results.

TABLE 14

HAI titers post-vaccination and post-challenge, and challenge results.

| No. | Dose in $TCID_{50}$ units | Animal ID | Vaccination on Day 0, Challenge on Day 29: −1 | 7 | 14 | 21 | 28 | 35 | 42 | Chall. Sick +/− |
|---|---|---|---|---|---|---|---|---|---|---|
| 1 | $2 \times 10^7$ | 41 | <10 | <10 | 10 | 40 | 10 | 20 | 80 | − |
| | | 42 | 40 | 40 | 40 | 40 | 40 | <10 | 80 | − |
| | | 200 | <10 | <10 | 80 | 40 | 160 | 40 | 40 | − |
| 2 | $2 \times 10^6$ | 679 | <10 | 10 | 40 | 40 | 40 | 20 | 20 | − |
| | | 682 | <10 | <10 | 40 | 40 | 40 | 40 | 40 | − |
| | | 795 | 20 | 80 | 160 | 160 | 320 | 320 | 640 | − |
| | | R | <10 | 10 | 40 | 20 | 160 | 40 | 40 | − |
| 3 | $2 \times 10^5$ | 73 | <10 | <10 | 160 | 40 | 80 | 160 | 160 | − |
| | | 712 | <10 | <10 | 20 | 20 | 40 | 40 | 20 | − |
| | | 720 | <10 | 20 | 80 | 40 | 80 | 80 | 160 | − |
| | | 796 | <10 | <10 | <10 | <10 | <10 | 10 | 80 | + |
| 4 | $2 \times 10^4$ | 75 | <10 | <10 | <10 | <10 | <10 | <10 | 160 | + |
| | | 724 | <10 | >10 | <10 | <10 | <10 | 20 | 320 | + |
| | | 789 | <10 | 10 | 320 | 160 | 320 | 320 | 320 | − |
| | | 790 | <10 | <10 | 80 | 40 | 160 | 80 | 40 | |
| 5 | Control | 12 | <10 | <10 | <10 | 20 | 20 | 40 | 40 | − |
| | | 22 | 10 | 20 | 40 | 10 | 160 | 40 | 640 | − |
| | | 71 | <10 | <10 | <10 | <10 | 10 | 20 | 160 | + |
| | | 74 | <10 | <10 | <10 | <10 | <10 | <10 | 20 | + |

On day 29 post vaccination, all 19 ponies were challenged with equine influenza virus strain A/equine/Kentucky/1/91 (H3N8) by the nebulizer method as described in Example 4. The challenge dose was prospectively calculated to contain about $10^8$ $TCID_{50}$ units of challenge virus in a volume of 5 ml for each animal. Clinical observations, as described in Example 3, were monitored beginning two days before challenge, the day of challenge, and for 11 days following challenge. As shown in Table 14, no animals in groups 1 or 2 exhibited clinical signs indicative of equine influenza disease, and only one out of four animals in group 3 became sick. Two out of four animals in group 4 became sick, and only two of the four control animals became sick. The results in Table 14 suggest a correlation between seroconversion and protection from disease, since, for example, the two control animals showing increased HAI titers during the vaccination period did not show clinical signs of equine influenza disease following challenge. Another interpretation, however, was that the actual titer of the challenge virus may have been less than the calculated amount of $10^8$ $TCID_{50}$ units, since, based on prior results, this level of challenge should have caused disease in all the control animals.

Nonetheless, the levels of seroconversion and the lack of clinical signs in the groups that received a therapeutic composition comprising at least $2\times10^6$ $TCID_{50}$ units of a cold-adapted equine influenza virus suggests that this amount was sufficient to protect a horse against equine influenza disease. Furthermore, a dose of $2\times10^5$ $TCID_{50}$ unit induced seroconversion and gave clinical protection from challenge in 3 out of 4 horses, and thus even this amount may be sufficient to confer significant protection in horses against equine influenza disease.

EXAMPLE 8

This example discloses an animal study to evaluate the duration of immunity of a therapeutic composition comprising cold-adapted equine influenza virus EIV-P821.

A therapeutic composition comprising cold-adapted equine influenza virus EIV-P821, produced as described in Example 1, was grown in eggs similarly to the procedure described in Example 2A, was expanded by passage in MDCK cells similarly to the procedure described in Example 2B, and was formulated into a therapeutic composition as described in Example 2C. Thirty horses approximately 11 to 12 months of age were used for this study. Nineteen of the horses were each vaccinated intranasally into one nostril using a syringe with a delivery device tip attached to the end, with a 1.0 ml dose comprising 6 logs of $TCID_{50}$ units of the EIV-P821 therapeutic composition. Vaccinations were performed on Day 0.

The horses were observed on Day 0 (before vaccination and up to 4 hours post-vaccination) and on Study Days 1, 2, 3, 7, 15, and 169 post-vaccination. On these days, a distant examination for a period of at least 15 minutes was performed. This distant examination included observation for demeanor, behavior, coughing, sneezing, and nasal discharge. The examination on Day 169 also served to confirm that the horses were a condition of health suitable for transport to the challenge site which was located approximately 360 miles from the vaccination site.

The animals were acclimated to the challenge site and were observed approximately daily by a veterinarian or animal technician for evidence of disease. A general physical examination was performed on Day 171 post-vaccination to monitor the following: demeanor, behavior, coughing, sneezing, and nasal discharge. From Days 172 to 177, similar observations as well as rectal temperature were recorded, according to the judgment of the attending veterinarian for any individual horse with abnormal clinical presentation.

No vaccinated horses showed any adverse reactions post-vaccination. One vaccinate was found dead about two months after vaccination. This horse showed no evidence of adverse reaction when observed for at least one month after vaccination. Although no cause oft death could be firmly established, the death was not instantaneous and was considered to be consistent with possible contributing factors such as colic, bone fracture, or severe worm burden. Since there was no other evidence for any adverse reactions post-vaccination in any other vaccinates, it is highly unlikely that the vaccine contributed to any adverse reaction in this case.

Challenges were performed on Day 181 post-vaccination. The following wild-type isolate of equine influenza virus previously shown to cause disease in horses was used as the challenge virus: A/equine/2/Kentucky/91. Prior to infection of each challenge group, the challenge; material was rapidly thawed at approximately 37° C. The virus was diluted with phosphate-buffered saline to a total volume of approximately 21 ml. The diluted material was stored chilled on ice until immediately before inoculation. Before inoculation and at the end of nebulization for each challenge group, a sample of diluted challenge virus was collected for pre- and post-inoculation virus titer confirmation. Vaccinates and controls were randomly assigned to 4 challenge groups of 6 horses each and, one challenge group of 5 horses so that each challenge group contained a mixture of 4 vaccinates and 2 controls or 3 vaccinates and 2 controls.

Challenge virus in aerosol form was delivered through a tube inserted through a small opening centrality in the plastic ceiling with an ultrasonic nebulizer (e.g., DeVilbiss Model 099HD, DeVilbiss Healthcare Inc., Somerset, Pa.) for a period of approximately 10 minutes. The horses remained in the chamber for a further period of appiroximately 30 minutes after the nebulization had been completed (total exposure time, approximately 40 minutes). At that time, the plastic was removed to vent the chamber, and the horses were released and returned to their pen. The challenge procedure was repeated for each group.

All statistical methods in this study were performed using SAS (SAS Institute, Cary, N.C. and P<0.05 was considered to be statistically significant. Beginning on Day 178 post-vaccination (three days prior to challenge) through Day 191 (day 10 postthe horses were observed daily by both distant and individual examinations. Rectal temperatures were measured at these times. Data from day 0 (challenge day) to day 10 were included in the analysis; see Table 15.

TABLE 15

Effect of challenge on daily temperatures (E C) in vaccinated and controlhorses (least squares means). [t9]

| Day post challenge | Vaccinated (n = 19) | non-vaccinated (n = 10) | P-value |
|---|---|---|---|
| 0 | 100.7 | 100.8 | 0.8434 |
| 1 | 100.5 | 100.4 | 0.7934 |
| 2 | 103.4 | 104.9 | 0.0024 |
| 3 | 101.8 | 103.9 | 0.0001 |
| 4 | 101.5 | 103.2 | 0.0002 |
| 5 | 101.7 | 103.8 | 0.0001 |
| 6 | 101.3 | 103.6 | 0.0001 |
| 7 | 100.7 | 102.3 | 0.0007 |
| 8 | 100.5 | 101.4 | 0.0379 |
| 9 | 100.1 | 100.3 | 0.7416 |
| 10 | 100.3 | 100.5 | 0.7416 |
| pooled SEM* | 0.27 | 0.38 | |

*Standard error of the mean.

Table 15 shows that on days 2 through 8, vaccinated horses had lower temperatures (P<0.05 than the non-vaccinated control horses.

The distant examination consisted of a period of 20 minutes where the following observations were made: coughing, nasal discharge, respiration, and depression. Scoring criteria are shown in Table 16.

TABLE 16

Clinical signs and scoring index.

| Clinical Sign | Description | Score |
|---|---|---|
| Coughing | normal during observation period of 15 min | 0 |
| | coughing once during observation | 1 |
| | coughing twice or more during observation | 2 |
| Nasal discharge | normal | 0 |
| | abnormal, serous | 1 |
| | abnormal, mucopurulent | 2 |
| | abnormal, profuse | 3 |
| Respiration | normal | 0 |
| | abnormal (dyspnea, tachypnea) | 1 |
| Depression | normal | 0 |
| | depression present† | 1 |

†Depression was assessed by subjective evaluation of individual animal behavior that included the following: failure to approach food rapidly, general lethargy, inappetence, and anorexia.

Each horse was scored for each of these categories. Additionally, submandibular lymph nodes were palpated to monitor for possible bacterial infection. In any case where there was a different value recorded for a subjective clinical sign score from an observation on the same day at the distant versus the individual examination, the greater score was used in the compilation and analysis of results. For purposes of assessing the health of the horses prior to final disposition, distant examinations were performed at 14, 18, and 21 days post-challenge. Data from days 1 through 10 post-challenge were included in the analysis. These scores were summed on each day for each horse, and the vaccinates and controls were compared using the Wilcoxon rank sums test. In addition, these scores were summed across all days for each horse, and compared in the same manner. The mean ranks and mean clinical scores are shown in Tables 17 and 18, respectively. Five days post-challenge, the mean rank of scores in the vaccinated horses was lower (P<0.05) than in the non-vaccinated control horses; and this effect continued on days 6, 7, 8, 9, and 10 (P<0.05). The cumulative rank over the entire test period was also lower (P<0.05) in the vaccinated horses than the noncontrols.

TABLE 17

Effect of challenge on clinical sign scores in vaccinated and control horses (mean rank). [t4]

| Day post challenge | Vaccinated (n = 19), mean rank* | Non-vaccinated (n = 10), mean rank | P-value |
|---|---|---|---|
| 0 | 13.6 | 17.6 | 0.1853 |
| 1 | 16.4 | 12.4 | 0.2015 |
| 2 | 15.1 | 14.9 | 0.9812 |
| 3 | 13.3 | 18.3 | 0.1331 |
| 4 | 13.5 | 17.9 | 0.1721 |
| 5 | 12.4 | 19.9 | 0.0237 |
| 6 | 12.7 | 19.4 | 0.0425 |
| 7 | 12.1 | 20.6 | 0.0074 |
| 8 | 12.6 | 19.6 | 0.0312 |
| 9 | 13.1 | 18.7 | 0.0729 |
| 10 | 12.3 | 20.1 | 0.0135 |
| total over 11 days | 11.8 | 21.2 | 0.0051 |

*By Wilcoxon rank sum test.

horses (mean scores).

| Day post challenge | Vaccinated (n = 19) | Non-vaccinated (n = 10) |
|---|---|---|
| 0 | 1.2 | 1.6 |
| 1 | 1.5 | 0.9 |
| 2 | 2.4 | 2.5 |
| 3 | 3.2 | 4.1 |
| 4 | 3.4 | 4.3 |
| 5 | 3.2 | 4.7 |
| 6 | 3.4 | 4.8 |
| 7 | 3.3 | 4.7 |
| 8 | 3.2 | 4.5 |
| 9 | 3.2 | 3.9 |
| 10 | 2.4 | 3.4 |

Nasopharyngeal swabs were obtained on the day prior to challenge and on days 1 to 8 post-challenge, as described in Example 3, and tested for shed virus by cell culture assay. The percent of horses shedding challenge virus in each group is shown in Table 19. The percent of horses shedding the challenge virus in the vaccinated group was lower (P<0.05) on days 5 and 6 post-challenge than in the non-vaccinated controls. The mean number of days the challenge virus was shed was also lower (P<0.05) in the vaccinated group as compared to the non-vaccinated controls.

TABLE 19

Percent of horses shedding virus per day post-challenge and mean number of days of shedding per group.
[t18]

| Day post challenge | Vaccinated (n = 19) | Non-vaccinated (n = 10) |
|---|---|---|
| −1 | 0 | 0 |
| 1 | 63.2 | 90 |
| 2 | 100 | 100 |
| 3 | 84.2 | 100 |
| 4 | 100 | 100 |
| 5 | 47.4 | 88.9* |
| 6 | 10.5 | 77.8* |
| 7 | 5.3 | 20 |
| 8 | 0 | 0 |
| average number of days shedding | 4.1 | 5.6* |

*Within a time point, vaccinates different from non-vaccinates (P0.05) by either Fisher"s exact test (percent data) or Wilcoxon rank sums test (days shedding).

The scores from clinical signs relevant to influenza and the objective temperature measurements both demonstrated a statistically significant reduction in the group of vaccinates when compared to those from the control group; this is consistent with an interpretation that the vaccine conferred significant protection from disease.

The ability of horses to shed influenza virus post-challenge was also significantly reduced in vaccinates as compared to controls in both the incidence of horses positive for shedding on certain days post-challenge and the mean number of days of shedding per horse. This decreased shedding by vaccinates is important in that it should serve to reduce the potential for exposure of susceptible animals to the wild-type virus in an outbreak of influenza.

The results of this study are consistent with the interpretation that the vaccine safely conferred protection for 6 months from clinical disease caused by equine influenza and reduced the potential for the spread of naturally occurring virulent equine influenza virus. While the degree of protection from disease was not complete (13 out of 19 vaccinates were protected, while 10/10 controls were sick), there was a clear reduction in the severity and duration of clinical illness and a noticeable effect on the potential for viral shedding after exposure to a virulent strain of equine influenza. The finding that both vaccinates and controls were seronegative immediately prior to challenge at 6 months post-immunization suggests that immunity mediated by something other than serum antibody may be of primary importance in the ability of this vaccine to confer measurable and durable protection.

EXAMPLE 9

This Example discloses an animal study to evaluate the ability of a therapeutic composition comprising cold-adapted equine influenza virus EIV-P821 to aid in the prevention of disease following exposure to a heterologous strain of equine influenza virus.

The heterologous strain tested was A/equine/2/Saskatoon/90, described genetically as a Eurasian strain (obtained from Hugh Townsend, University of Saskatchewan). Twenty female Percheron horses approximately 15 months of age (at the time of vaccination) were used for the efficacy study. The horses were assigned to two groups, one group of 10 to be vaccinated and another group of 10 to serve as non-vaccinated controls. On day 0, the vaccinate group was vaccinated in the manner described in Example 8.

The challenge material, i.e. equine flu strain A/equine/2/Saskatoon/90 [H3N8] was prepared similarly to the preparation in Example 8. Vaccinates and controls were randomly assigned to 4 challenge groups of 5 horses each such that each challenge group contained a mixture of 2 vaccinates and three controls or vice versa. The challenge procedure was similar to that described in Example 8. Challenges were performed on Day 28 post-vaccination.

Clinical observations were performed for the vaccinates and controls on Day -4 and on Study Days 0 (before vaccination and up to 4 hours post-vaccination), 1 to 7, 12, 15 to 17, 19 to 23, 25 to 38, and 42. For days on which clinical observations were performed during Days -4 to 42, clinical observations including rectal temperature were recorded according to the judgment of the attending veterinarian for any individual horse with abnormal clinical presentation. Horses were scored using the same criteria as in Example 8 (Table 15). Distant examinations were performed on these days as described in Example 8. On Day 20 and from Days 25 to 38, the horses were also observed by both distant and individual examinations (also performed as described in Example 8).

Rectal temperatures were measured daily beginning 3 days prior to challenge, and continuing until 10 days post-challenge. Day 0 is the day relative to challenge. Data from days 0 through 10 were included in the analysis. Statistical methods and criteria were identical to those used in Example 8. On days 2, 5 and 7, vaccinated horses had statistically significant lower body temperatures than the non-vaccinated control horses (Table 20).

TABLE 20

| Effect of challenge on daily temperatures (E C) in vaccinated and control horses (least squares means). [t5] | | | |
|---|---|---|---|
| Day post challenge | Vaccinated (n = 10) | Non-vaccinated (n = 10) | P-value |
| 0 | 99.9 | 99.8 | 0.9098 |
| 1 | 100.5 | 100.3 | 0.4282 |
| 2 | 101.0 | 102.8 | 0.0001 |
| 3 | 100.7 | 100.6 | 0.7554 |
| 4 | 101.0 | 101.3 | 0.4119 |
| 5 | 100.8 | 102.1 | 0.0004 |
| 6 | 100.4 | 100.4 | 0.9774 |
| 7 | 100.3 | 101.1 | 0.0325 |
| 8 | 100.6 | 100.7 | 0.8651 |
| 9 | 100.5 | 100.6 | 0.8874 |
| 10 | 100.5 | 100.1 | 0.2465 |

Standard error of the mean = 0.249.

Data from days 1 through 10 post-challenge were included in the analysis. These scores were summed on each day for each horse, and the vaccinates and controls were compared using the Wilcoxon rank sums test. All statistical methods were performed as described in Example 9. In addition, these scores were summed across all days for each horse, and compared in the same manner. Mean ranks are shown in Table 21.

TABLE 21

| Effect of challenge on clinical sign scores in vaccinated and control horses (mean rank). [t6] | | | |
|---|---|---|---|
| Day post challenge | Vaccinated (n = 10) | Non-vaccinated (n = 10) | P-value* |
| 1 | 8.85 | 12.15 | 0.1741 |
| 2 | 8.80 | 12.20 | 0.1932 |
| 3 | 8.90 | 12.10 | 0.2027 |
| 4 | 7.60 | 13.40 | 0.0225 |
| 5 | 6.90 | 14.10 | 0.0053 |
| 6 | 7.00 | 14.00 | 0.0059 |
| 7 | 6.90 | 14.10 | 0.0053 |
| 8 | 7.60 | 13.40 | 0.0251 |
| 9 | 6.90 | 14.10 | 0.0048 |
| 10 | 6.10 | 14.90 | 0.0006 |
| total over 10 days | 5.70 | 15.30 | 0.0003 |

*By Wilcoxon 2 sample test.

On day 4 post-challenge, the mean rank of scores in the vaccinated horses was lower (P<0.05) than the non-vaccinated control horses, and this effect continued throughout the remainder of the study (P<0.05). The cumulative rank over the entire test period was also lower in the vaccinated horses than the noncontrols (P<0.05).

Nasopharyngeal:swabs were collected on days 1 and 8 post-challenge, as described in Example 3. The nasal samples were analyzed for the presence of virus by cell inoculation with virus detection by cytopathogenic effect (CPE) or by egg inoculation with virus detection by hemagglutination (HA). The cell-culture assay was performed as generally described by Youngner et al, 1994, *J. Clin. Microbiol.* 32, 750–754. Serially diluted nasal samples were added to wells containing monolayers of Madin Darby Canine Kidney (MDCK) cells. After incubation, wells were examined for the presence and degree of cytopathogenic effect. The quantity of virus in $TCID_{50}$ units was calculated by the Reed-Muench technique. The egg infectivity assay was performed as described in Example 1. The percent of horses shedding challenge virus for each assay in each group is shown in Tables 22 and 23. The percent of horses shedding the challenge virus in the vaccinated group was lower (P<0.05) on days 2 through 7 post-challenge by either method. No differences were seen on days 1 or 8 post-challenge. The number of days the challenge virus was shed was also lower (P<0.05) in the vaccinated group as compared to the non-vaccinated controls; see Tables 22 and 23.

TABLE 22

| Percent of horses shedding virus following challenge-cell culture assay. [t15] | | |
|---|---|---|
| Day post challenge | Vaccinated (n = 10) | Non-vaccinated (n = 10) |
| 1 | 0 | 0 |
| 2 | 0 | 70* |
| 3 | 0 | 70* |
| 4 | 20 | 100* |
| 5 | 10 | 100* |
| 6 | 20 | 100* |
| 7 | 0 | 80* |
| 8 | 0 | 30 |
| average number of days shedding | 0.5 | 5.5* |

*Within a time point, vaccinates different from non-vaccinates, P < 0.05 by either Fisher's exact test (percent data) or Wilcoxon 2 sample test (days shedding)

TABLE 23

| Percent of horses shedding virus following challenge-egg infectivity assay. [t16] | | |
|---|---|---|
| Day post challenge | Vaccinated (n = 10) | Non-vaccinated (n = 10) |
| 1 | 0 | 0 |
| 2 | 0 | 70* |
| 3 | 10 | 70* |
| 4 | 0 | 90* |
| 5 | 10 | 70* |
| 6 | 20 | 90* |
| 7 | 0 | 50* |
| 8 | 0 | 0 |
| average number of days shedding | 0.4 | 4.4* |

*Within a time point, vaccinates different from non-vaccinates, P < 0.05 by either Fisher"s exact test (percent data) or Wilcoxon 2 sample test (days shedding).

The extent (severity and duration) of clinical signs of influenza among vaccinates was substantially reduced relative to the controls. The scores from clinical signs relevant to influenza and the objective temperature measurements both demonstrated a statistically significant reduction in the group of vaccinates when compared to those from the control group; indicating that the vaccine conferred significant protection from disease by the heterologous strain.

The ability of horses to shed influenza virus post-challenge was also significantly reduced in vaccinates as opposed to controls in both the incidence of horses positive for shedding on certain days post-challenge and the mean number of days of shedding per horse. This decreased shedding by vaccinates is important in that it should serve to reduce the potential for exposure of susceptible animals to the wild-type virus in an outbreak of influenza.

Overall, the results of this study show that the vaccine conferred protection against a heterologous challenge by a member of the Eurasian lineage of equine influenza virus strains.

EXAMPLE 10

This Example discloses an animal study to evaluate the ability of a therapeutic composition comprising cold-adapted equine influenza virus EIV-P821 to aid in the prevention of disease following exposure to a heterologous strain of equine influenza virus.

The heterologous strain tested was A/equine/2/Kentucky/98 [H3N8](obtained from Tom Chambers, University of Kentucky). Eight ponies aged 5 to 7 months were used for this efficacy study. The horses were assigned to two groups, one group of 4 to be vaccinated and another group of 4 to serve as non-vaccinated controls. Ponies were vaccinated as described in Example 8, on Day 0.

Clinical observations were performed for the vaccinates on Study Day 0 (before vaccination and at 4 hours post-vaccination), as well as on Days 1 to 8, 23, 30 to 50, and 57 post-vaccination. Controls were observed clinically on Days 29 to 50 and 57. The observations were performed and scored as described in Example 8.

The challenge material i.e. equine flu strain from Kentucky/98, was prepared by passing the isolated virus two times in eggs. The inoculum for each horse was prepared by thawing 0.5 ml of the virus, then diluting in 4.5 ml of sterile phosphate-buffered saline. The inoculum was administered by nebulization using a mask for each individual horse on Day 36 post-vaccination.

The clinical observation scores were summed on each day for each horse, and horses were ranked according to the cumulative total score from days 1 to 9 post-challenge. Theses results are shown in Table 24.

TABLE 24

Clinical sign observations: total scores, ranked by total score.
[t2]

| Group | Halter Identity | Total Score# Days 1 to 9 post-challenge |
|---|---|---|
| 1-Vaccinate | 50 | 0 |
| 1-Vaccinate | 52 | 0 |
| 1-Vaccinate | 55 | 1 |
| 1-Vaccinate | 15 | 2 |
| 2-Control | 61 | 21 |
| 2-Control | 20 | 25 |
| 2-Control | 7 | 26 |
| 2-Control | 13 | 26 |

#Total scores represent the sum of daily scores (where daily scores equal the sum of scores for coughing, nasal discharge, respiration, and depression) and are ranked from the lowest (least severe) to highest (most severe) scores.

The results of Table 24 show that the scores for vaccinates were between 0 and 2, which was significantly lower than the score for controls, which were between 21 and 26.

Rectal temperatures were measured daily beginning 6 days prior to challenge, and continuing until 9 days post-challenge. Day 0 is the day relative to challenge. Data from days 0 through 9 were included in the analysis. These results are shown in Table 25.

TABLE 25

Effect of challenge on daily mean temperatures (E C) in vaccinated and control horses.
[t14]

| Day post challenge | control | vaccinate | difference |
|---|---|---|---|
| 0 | 99.7 | 99.5 | 0.2 |
| 1 | 100.0 | 99.6 | 0.4 |
| 2 | 103.9 | 100.2 | 3.7 |
| 3 | 99.8 | 99.2 | 0.6 |
| 4 | 99.6 | 99.1 | 0.5 |
| 5 | 99.8 | 99.3 | 0.5 |
| 6 | 99.6 | 99.3 | 0.3 |
| 7 | 99.3 | 99.0 | 0.3 |
| 8 | 99.7 | 99.6 | 0.1 |
| 9 | 99.5 | 99.1 | 0.4 |

The temperatures of the control horses were higher than the temperatures of the vaccinated horses on all days. The temperature in control horses was significantly higher on day 2.

Nasopharyngeal swabs were collected on days 1 and 8, post-challenge, as described in Example 3. These samples were tested for shed virus by an egg infectivity assay as described in Example 1. The results of the assay are shown in Table 26.

TABLE 26

Virus shedding post-challenge detected by egg infectivity.

| Study day | | 35 | 37 | 38 | 39 | 40 | 41 | 42 | 43 | 44 | |
|---|---|---|---|---|---|---|---|---|---|---|---|
| Days post-challenge | | −1 | 1 | 2 | 3 | 4 | 5 | 6 | 7 | 8 | |
| Group | Identity No. | Detection of virus* | | | | | | | | | No. days positive per horse |
| Vacci-nates | 15 | 0 | 2 | 0 | 3 | 3 | 0 | 2 | 1 | 0 | 5 |
| | 50 | 0 | 0 | 0 | 0 | 0 | 1 | 0 | 0 | 0 | 1 |
| | 52 | 0 | 0 | 3 | 3 | 2 | 2 | 0 | 0 | 0 | 4 |
| | 55 | 0 | 2 | 3 | 1 | 3 | 0 | 0 | 0 | 0 | 4 |
| No. horses positive per day | | 0 | 2 | 2 | 3 | 3 | 2 | 1 | 1 | 0 | |
| Con-trols | 07 | 0 | 3 | 3 | 3 | 3 | 3 | 3 | 1 | 0 | 7 |
| | 13 | 0 | 3 | 3 | 3 | 3 | 3 | 3 | 1 | 0 | 7 |
| | 20 | 0 | 2 | 3 | 3 | 3 | 3 | 3 | 1 | 0 | 7 |
| | 61 | 0 | 3 | 3 | 3 | 3 | 3 | 3 | 2 | 0 | 7 |
| No. horses positive per day | | 0 | 4 | 4 | 4 | 4 | 4 | 4 | 4 | 0 | |

*Values refer to the number of eggs testing positive of 3 eggs tested per sample. For statistical analysis, a sample was considered positive for virus if at least 1 egg was positive per sample.

The results of Table 26 show that the number of horses positive per day was higher for the controls than for the vaccinates. Additionally, control horses were positive for more days than vaccinates.

The scores from clinical signs relevant to influenza and the objective temperature measurements both:demonstrated significant differences in the group of vaccinates when compared to the control group; this shows that the vaccine conferred significant protection from disease caused by the heterologous strain Kentucky/98.

The ability of horses to shed influenza virus post-challenge was also significantly reduced in vaccinates as opposed to controls in the mean number of days of shedding per horse. This decreased shedding by vaccinates is important in that it should serve to reduce the potential for exposure of susceptible animals to the wild-type virus in an outbreak of influenza.

Overall, the results of this study show that the vaccine safely conferred protection to a heterologous challenge by a recent and clinically relevant isolate. When the results of this study are viewed in the light of the protection previously demonstrated against heterologous challenge with a Eurasian strain (Example 9), there is clear evidence to support the assertion that this modified live vaccine can confer protection against heterologous as well as homologous equine influenza infection.

EXAMPLE 11

This example describes the cloning and sequencing of equine influenza M (matrix) protein nucleic acid molecules for wild type and cold-adapted equine influenza viruses.

A. Nucleic acid molecules encoding wild type or cold-adapted equine influenza virus M protein, were produced as follows. A PCR product containing an equine M gene was produced by PCR amplification from equine influenza virus DNA, and primers w584 and w585, designated SEQ ID NO:26, and SEQ ID NO:27, respectively. A nucleic acid molecule of 1023 nucleotides, denoted nei$_{wt}$M$_{1023}$, with a coding strand having a nucleic acid sequence designated SEQ ID NO:1 was produced by further PCR amplification using the above described PCR product as a template, and cloned into pCR 2.1® TA cloning vector, available from Invitrogen, Carlsbad, Calif., using standard procedures recommended by the manufacturer. The primers used were the T7 primer,designated by SEQ ID NO:29 and the REV primer, designated by SEQ ID NO:28. Plasmid DNA was purified using a mini-prep method available from Qiagen, Valencia, Calif., PCR products were prepared for sequencing using a Prism™ Dye Terminator Cyle Sequencing Ready Reaction kit, a Prism™ dRhodamine Terminator Cycle Sequencing Ready Reaction kit, or a Prism™ BigDye™ Terminator Cycle Sequencing Ready Reaction kit, all available from PE Applied Biosystems, Foster City, Calif., following the manufacturer's protocol. Specific PCR conditions used with the kit were a rapid ramp to 95 E C, hold for 10 seconds followed by a rapid ramp to 50 E C with a 5 second hold then a rapid ramp to 60 E C with a 4 minute hold, repeating for 25 cycles. Different sets of primers were used in different reactions: T7 and REV were used in one reaction; w584 and w585 were used in a second reaction; and efM-a1, designated SEQ ID NO:31 and efM-s1, designated SEQ ID NO:30 were used in a third reaction. PCR products were purified by ethanol/magnesium chloride precipitation. Automaied sequencing of DNA samples was performed using an ABI Prism™ Model 377 with XL upgrade DNA Sequencer, available from PE Applied Biosystems.

Translation of SEQ ID NO:1 indicates that nucleic acid molecule nei$_{wt}$M$_{1023}$ encodes a full-length equine influenza M protein of about 252 amino acids, referred to herein as Pei$_{wt}$M$_{252}$, having amino acid sequence SEQ ID NO:2, assuming an open reading frame in which the initiation codon spans from nucleotide 25 through nucleotide 28 of SEQ ID NO:1 and the termination codon spans from nucleotide 781 through nucleotide 783 of SEQ ID NO:1. The region encoding Pei$_{wt}$M$_{252}$, designated nei$_{wt}$M756, and having a coding strand comprising nucleotides 25 to 780 of SEQ ID NO:1, is represented by SEQ ID NO:3.

SEQ ID NO:1 and SEQ ID NO:3 represent the consensus sequence obtained from two wild type nucleic acid molecules, which differ in one nucleotide. Nucleotide 663 of nei$_{wt1}$M$_{1023}$, i.e., nucleotide 649 of nei$_{wt2}$M$_{756}$, was adenine, while nucleotide 663 of nei$_{wt2}$M$_{1023}$, i.e., nucleotide 649 of nei$_{wt2}$M$_{756}$, was guanine. Translation of these sequences does not result in an amino acid change at the corresponding amino acid; both translate to valine at residue 221 in Pei$_{wt}$M$_{252}$.

B. A nucleic acid molecule of 1023 nucleotides encoding a cold-adapted equine influenza virus M, denoted nei$_{ca1}$M$_{1023}$, with a coding strand having a sequence designated SEQ ID NO:4 was produced by further PCR amplification and cloned into the pCR®-Blunt cloning vector available from Invitrogen, using conditions recommended by the manufacturer, and primers T7 and REV. Plasmid DNA purification and cycle sequencing were performed as described in Example 11, part A. Translation of SEQ ID NO:4 indicates that nucleic acid molecule nei$_{ca1}$M$_{1023}$ encodes a full-length equine influenza M protein of about 252 amino acids, referred to herein as Pei$_{ca1}$M$_{252}$, having amino acid sequence SEQ ID NO:5, assuming an open reading frame in which the initiation codon spans from nucleotide 25 through nucleotide 28 of SEQ ID NO:4 and the termination codon spans from nucleotide 781 through nucleotide 783 of SEQ ID NO:4. The region encoding Pei$_{ca1}$M$_{252}$, designated nei$_{ca1}$M$_{756}$ and having a coding strand comprising nucleotides 25 to 780 of SEQ ID NO:4, is represented by SEQ ID NO:6. PCR amplification of a second nucleic acid molecule encoding a cold-adapted equine influenza M protein in the same manner resulted in molecules nei$_{ca2}$M$_{1023}$, identical to nei$_{ca1}$M$_{1023}$, and nei$_{ca2}$M$_{756}$, identical to nei$_{ca1}$M$_{756}$.

C. Comparison of the nucleic acid sequences of the coding strands of nei$_{wt}$M$_{1023}$ (SEQ ID NO:1) and nei$_{ca1}$M$_{1023}$ (SEQ ID NO:4) by DNA alignment reveals the following differences: a G to T shift at base 67, a C to T shift at base 527, and a G to C shift at base 886. Comparison of the amino acid sequences of proteins Pei$_{wt}$M$_{252}$ (SEQ ID NO:2) and Pei$_{ca1}$M$_{252}$ (SEQ ID NO:5) reveals the following differences: a V to L shift at amino acid 23 relating to the G to T shift at base 67 in the DNA sequences; and a T to I shift at amino acid 187 relating to the C to T shift at base 527 in the DNA sequences.

EXAMPLE 12

This example describes the cloning and sequencing of equine influenza HA (hemagglutinin) protein nucleic acid molecules for wild type or cold-adapted equine influenza viruses.

A. Nucleic acid molecules encoding wild type or cold-adapted equine influenza virus HA proteins were produced as follows. A PCR product containing an equine HA gene was produced by PCR amplification from equine influenza virus DNA and primers w578 and w579, designated SEQ ID NO:32 and SEQ ID NO:33, respectively. A nucleic acid molecule of 1762 nucleotides encoding a wild-type HA protein, denoted nei$_{wt}$HA$_{1762}$ with a coding strand having a nucleic acid sequence designated SEQ ID NO:7 was produced by further PCR amplification using the above-described PCR product as a template and cloned into pCR 2.1® TA cloning vector as described in Example 11A. Plasmid DNA was purified and sequenced as in Example 11A, except that primers used in the sequencing kits were either T7 and REV in one case, or HA-1, designated SEQ ID NO:34, and HA-2, designated SEQ ID NO:35, in a second case.

Translation of SEQ ID NO:7 indicates that nucleic acid molecule nei$_{wt}$HA$_{1762}$encodes a full-length equine influenza HA protein of about 565 amino acids, referred to herein as Pei$_{wt}$HA$_{565}$, having amino acid sequence SEQ ID NO:8, assuming an open reading frame in which the initiation codon spans from nucleotide 30 through nucleotide 33 of SEQ ID NO:7 and the termination codon spans from nucleotide 1725 through nucleotide 1727 of SEQ ID NO:7. The region encoding $Pei_{wt}HA_{565}$, designated $nei_{wt}HA_{1695}$, and having a coding strand comprising nucleotides 30 to 1724 of SEQ ID NO:7 is represented by SEQ ID NO:9.

B. A nucleic acid molecule of 1762 nucleotides encoding a cold-adapted equine influenza virus HA protein, denoted $nei_{ca1}HA_{1762}$, with a coding strand having a sequence designated, SEQ ID NO:10 was produced as described in Example 11B. Plasmid DNA purification and cycle sequencing were performed as described in Example 12, part A.

Translation of SEQ ID NO:10 indicates that nucleic acid molecule $nei_{ca1}HA_{1762}$ encodes a full-length equine influenza HA protein of about 565 amino acids, referred to herein as $Pei_{ca1}HA_{565}$, having amino acid sequence SEQ ID NO:11, assuming an open reading frame in which the initiation codon spans from nucleotide 30 through nucleotide 33 of SEQ ID NO:10 and the termination codon spans from nucleotide 1725 through nucleotide 1727 of SEQ ID NO:10. The region encoding $Pei_{ca1}$HA565, designated $nei_{ca1}HA_{1695}$, and having a coding strand comprising nucleotides 30 to 1724 of SEQ ID NO:10, is represented by SEQ ID NO:12.

PCR amplification of a second nucleic acid molecule encoding a cold-adapted equine influenza HA protein in the same manner resulted in molecules $nei_{ca2}HA_{1762}$, identical to $nei_{ca1}HA_{1762}$, and $nei_{ca2}HA_{1695}$, identical to $nei_{ca1}HA_{1695}$.

C. Comparison of the nucleic acid sequences of the coding strands of $nei_{wt}HA_{1762}$ (SEQ ID NO:7) and $nei_{ca1}HA_{1762}$ (SEQ ID NO:10) by DNA alignment reveals the following differences: a C to T shift at base 55, a G to A shift at base 499, a G to A shift at base 671, a C to T shift at base 738, a T to C shift at base 805, a G to A shift at base 1289, and an A to G shift at base 1368. Comparison of the amino, acid sequences of proteins $Pei_{wt}HA_{565}$ (SEQ ID NO:8) and $Pei_{ca1}HA_{565}$ (SEQ ID NO:11) reveals the following differences: a P to L shift at amino acid 18 relating to the C to T shift at base 55 in the DNA sequences; a G to E shift at amino acid 166 relating to the G to A shift at base 499 in the DNA sequences; an R to W shift at amino acid 246 relating to the C to T shift at base 738 in the DNA sequences; an M to T shift at amino acid 268 relating to the T to C shift at base 805 in the DNA sequences; a K to E shift at amino acid 456 relating to the A to G shift at base 1368 in the DNA sequences. There is no change of the serine (S) at residue 223 relating to the G to A shift at base 671 in the DNA sequences, nor is there a change of the arginine (R) at residue 429 relating to the G to A shift at base 1289 in the DNA sequences.

EXAMPLE 13

This example describes the cloning and sequencing of equine influenza PB2 protein (RNARNA polymerase) nucleic acid molecules corresponding to the N-terminal portion of the protein, for wild type or cold-adapted equine influenza viruses.

A. Nucleic acid molecules encoding wild type or cold-adapted equine influenza virus PB2-N proteins were produced as follows. A PCR product containing an N-terminal portion of the equine PB2 gene was produced by PCR amplification from equine influenza virus DNA, and primers w570 and w571, designated SEQ ID NO:36 and SEQ ID NO:37, respectively. A nucleic acid molecule of 1241 nucleotides encoding a wild type PB2-N protein, denoted $nei_{wt}PB2\text{-}N_{1241}$, with a coding strand having a nucleic acid sequence designated SEQ ID NO:13 was produced by further PCR amplification using the above described PCR product as a template and cloned as described in Example 11B. Plasmid DNA was purified and sequenced as in Example 11B, except that only T7 and REV primers were used in the sequencing kits.

Translation of SEQ ID NO:13 indicates that nucleic acid molecule $nei_{wt}PB2\text{-}N_{1241}$ encodes an N-terminal portion of influenza PB2 protein of about 404 amino acids, referred to herein as $P_{wt}PB2\text{-}N_{404}$, having amino acid sequence SEQ ID NO:14, assuming an, open reading frame in which the initiation codon spans from nucleotide 28 through nucleotide 30 of SEQ ID NO:13, and the last codon spans from nucleotide 1237 through nucleotide 1239. The region encoding $P_{wt}PB2\text{-}N_{404}$, designated $nei_{wt}PB2\text{-}N_{1214}$, and having a coding strand comprising nucleotides 28 to 1239 of SEQ ID NO:13 is represented by SEQ ID NO:15.

B. A nucleic acid molecule of 1239 nucleotides encoding an N-terminal portion of influenza PB2 cold-adapted equine influenza virus PB2-N protein, denoted $nei_{ca1}PB2\text{-}N_{1241}$, with a coding strand having a sequence designated SEQ ID NO:16 was produced, and sequenced as described in as in Example 12, part A.

Translation of SEQ ID NO:16 indicates that nucleic acid molecule $nei_{ca1}PB2\text{-}N_{1241}$ encodes an N-terminal portion of equine influenza PB-2 protein of about 404 amino acids, referred to herein as $P_{ca1}PB2\text{-}N_{404}$, having amino acid sequence SEQ ID NO:17, assuming an open reading frame in which the initiation codon spans from nucleotide 28 through nucleotide 30 of SEQ ID NO:16, and the last codon spans from nucleotide 1237 through nucleotide 1239. The region encoding $P_{ca1}PB2\text{-}N_{404}$, designated $nei_{ca1}PB2\text{-}N_{1214}$, and having a coding strand comprising nucleotides 28 to 1239 of SEQ ID NO:16, is represented by SEQ ID NO:18.

PCR amplification of a second nucleic acid molecule encoding a cold-adapted equine influenza PB2-N protein in the same manner resulted in molecules $nei_{ca2}PB2\text{-}N_{1241}$, identical to $nei_{ca1}PB2\text{-}N_{1241}$, and $nei_{ca2}PB2\text{-}N_{1214}$, identical to $nei_{ca1}PB2\text{-}N_{1214}$. C. Comparison of the nucleic acid sequences of the coding strands of $nei_{wt}PB2\text{-}N_{1241}$ (SEQ ID NO:13) and $nei_{ca1}PB2\text{-}N_{1241}$ (SEQ ID NO:16) by DNA alignment reveals the following difference: a T to C base shift at base 370. Comparison of the amino acid sequences of proteins $P_{wt}PB2\text{-}N_{404}$ (SEQ ID NO:14) and $P_{ca1}PB2\text{-}N_{404}$ (SEQ ID NO:17) reveals the following difference: a Y to H shift at amino acid 124 relating to the a T to C shift at base 370 in the DNA sequence.

EXAMPLE 14

This example describes the cloning and sequencing of equine influenza PB2 protein (RNARNA polymerase) nucleic acid molecules corresponding to the C-terminal portion of the protein, for wild type or cold-adapted equine influenza viruses.

A. Nucleic acid molecules encoding wild type or cold-adapted equine influenza virus PB2-C proteins were produced as follows. A PCR product containing the C-terminal portion of the equine PB2 gene was produced by PCR amplification using from equine influenza virus DNA and primers w572 and w573, designated SEQ ID NO:38 and SEQ ID NO:39, respectively. A nucleic acid molecule of 1233 nucleotides encoding a wild type PB2-C protein, denoted $nei_{wt}PB2\text{-}C_{1233}$, with a coding strand having a nucleic acidic sequence designated SEQ ID NO:19 was produced by further PCR amplification using the above-described PCR product as a template and cloned as described in Example 11B. Plasmid DNA was purified and sequenced as in Example 11A, except that different primers were used in the sequencing kits. T7 and REV were used in one instance, efPB2-a1, designated SEQ ID NO:40 and efPB2-s1, designated SEQ ID NO:41 were used in another instance, and efPB2-a2, designated SEQ ID NO:42 and efPB2-s2, designated SEQ ID NO:43 were used in another instance.

Translation of SEQ ID NO:19 indicates that nucleic acid molecule nei$_{wt1}$PB2-C$_{1233}$ encodes a C-terminal portion of influenza PB2 protein of about 398 amino acids, referred to herein as P$_{wt}$PB2-C$_{398}$, having amino acid sequence SEQ ID NO:20, assuming an open reading frame having a first codon spans from nucleotide 3 through nucleotide 5 and a termination codon which spans from nucleotide 1197 through nucleotide 1199 of SEQ ID NO:19. Because SEQ ID NO:19 is only a partial gene sequence, it does not contain an initiation codon. The region encoding P$_{wt}$PB2-C$_{398}$, designated nei$_{wt}$PB2-C$_{1194}$, and having a coding strand comprising nucleotides 3 to 1196 of SEQ ID NO:19 is represented by SEQ ID NO:21.

PCR amplification of a second nucleic acid molecule encoding a wild type equine influenza PB2-N protein in the same manner resulted in a nucleic acid molecule of 1232 nucleotides denoted nei$_{wt2}$PB2-N$_{1232}$, with a coding strand with a sequence designated SEQ ID NO:22. nei$_{wt2}$PB2-N$_{1232}$ is identical to nei$_{wt1}$PB2-C$_{1233}$, expect that nei$_{wt2}$PB2-N$_{1232}$ lacks one nucleotide on the 5'-end. Translation of SEQ ID NO:22 indicates that nucleic acid molecule nei$_{wt1}$PB2-C$_{1233}$ also encodes P$_{wt}$PB2-C$_{398}$ (SEQ ID NO:20), assuming an open reading frame having a first codon which spans from nucleotide 2 through nucleotide 4 and a termination codon spans from nucleotide 1196 through nucleotide 1198 of SEQ ID NO:22. Because SEQ ID NO:22 is only a partial gene sequence, it does not contain an initiation codon. The nucleic acid molecule having a coding strand comprising nucleotides 2 to 1195 of SEQ ID NO:22, denoted nei$_{wt2}$PB2-C$_{1194}$, is identical to SEQ ID NO:21.

B. A nucleic acid molecule of 1232 nucleotides encoding a C-terminal portion of influenza PB2 cold-adapted equine influenza virus protein, denoted nei$_{ca1}$PB2-C$_{1232}$, and having a coding strand having a sequence designated SEQ ID NO:23 was produced as described in as in Example 14, part A, except that the pCR®-Blunt cloning vector was used.

Translation of SEQ ID NO:23 indicates that nucleic acid molecule nei$_{ca1}$PB2-C$_{1232}$ encodes a C-terminal portion of equine influenza PB-2 protein of about 398 amino acids, referred to herein as P$_{ca1}$PB2-C$_{398}$, having amino acid sequence SEQ ID NO:24, assuming an open reading frame having a first codon which spans from nucleotide 2 through nucleotide 4 and a termination codon spans from nucleotide 1196 through nucleotide 1198 of SEQ ID NO:23. Because SEQ ID NO:23 is only a partial gene sequence, it does not contain an initiation codon. The region encoding P$_{ca1}$PB2-C$_{398}$, designated nei$_{ca1}$PB2-C1194, and having a coding strand comprising nucleotides 2 to 1195 of SEQ ID NO:23, is represented by SEQ ID NO:25. PCR amplification of a second nucleic acid molecule encoding a cold-adapted equine influenza PB2-C protein in the same manner resulted in molecules nei$_{ca2}$PB2-C$_{1231}$, containing one less nucleotide at the 3'end than nei$_{ca1}$PB2-N$_{1241}$; and nei$_{ca2}$PB2-N$_{1214}$, identical to nei$_{ca1}$PB2-N$_{1214}$.

C. Comparison of the nucleic acid sequences of the coding strands of nei$_{wt1}$PB2-C$_{1233}$ (SEQ ID NO:19) and nei$_{ca1}$PB2-C$_{1232}$ (SEQ ID NO:23) by DNA alignment reveals the following differences: an A to C base shift at base 153 of SEQ ID NO:19, and a G to A base shift at base 929 of SEQ ID NO:19. Comparison of the amino acid sequences of proteins P$_{wt}$PB2-C$_{398}$ (SEQ ID NO:20) and P$_{ca1}$PB2-$_{398}$ (SEQ ID NO:24) reveals thee following difference: a K to Q shift at amino acid 51 when relating to the an A to C base shift at base 153 in the DNA sequences. There is no amino acid shift resulting from the G to A base shift at base 929.

EXAMPLE 15

This example describes the cloning and sequencing of equine influenza PB2 protein (RNA-directed RNA polymerase) nucleic acid molecules for wild type or cold-adapted equine influenza viruses.

A. Nucleic acid molecules encoding wild type or cold-adapted equine influenza virus PB2 proteins were produced as follows. The wild type or cold-adapted equine influenza genes were cloned in two fragments, the N-terminal portion was produced as in Example 13 and the C-terminal portion of the gene was produced as in Example 14.

The DNA sequence for the wild type equine influenza PB2 gene was generated by combining the consensus sequences for the wild type PB2-N protein, denoted nei$_{wt}$PB2-N$_{1241}$ (SEQ ID NO:13) with the gene fragments for the wild type PB2-C protein, denoted nei$_{wt1}$PB2-C$_{1233}$ (SEQ ID NO:19) and nei$_{wt2}$PB2-C$_{1232}$ (SEQ ID NO:22). The result of combining the consensus sequences from the N-terminal and C-terminal portions of the PB2 wild type influenza virus yielded a complete DNA sequence denoted nei$_{wt}$PB2$_{2341}$ (SEQ ID NO:44). Translation of SEQ ID NO:44 indicates that the nucleic acid molecule nei$_{wt}$PB2$_{2341}$ encodes a full length equine influenza PB2 protein of about 759 amino acids referred to herein as Pei$_{wt}$PB2$_{759}$, having amino acid sequence SEQ ID NO:45, assuming an open reading frame in which the initiation codon spans from nucleotide 28 through nucleotide 30 of SEQ ID NO:44 and the termination codon spans from nucleotide 2305 through nucleotide 2307 of SEQ ID NO:44. The region encoding Pei$_{wt}$PB2$_{759}$, designated nei$_{wt}$PB2$_{2277}$, and having a coding strand comprising nucleotides 28 to 2304 of SEQ ID NO:44, is SEQ ID NO:46.

B. A DNA sequence of 2341 nucleotides encoding a cold-adapted equine influenza virus PB2, denoted nei$_{ca1}$PB2$_{2341}$, with a sequence denoted SEQ ID NO:47 was produced by combining the sequences for the N-terminal and C-terminal portions of the PB2 cold-adapted equine influenza gene. The clones for the N-terminal sequences are denoted nei$_{ca1}$PB2-N$_{1241}$ and nei$_{ca2}$PB2-N$_{1241}$ which are identical and are represented by SEQ ID NO:16. The clones for the C-terminal sequences are denoted nei$_{ca1}$PB2-C$_{1232}$ and nei$_{ca2}$PB2-C$_{1231}$, represented by SEQ ID NO:23.

Translation of SEQ ID NO:47 indicates that nucleic acid molecule nei$_{ca1}$PB2$_{2341}$ encodes a full-length equine influenza PB2 protein of about 759 amino acids, referred to herein as Pei$_{ca1}$PB2$_{759}$, having amino acid sequence SEQ ID NO:48, assuming an open reading frame in which the initiation codon spans from nucleotide 28 through nucleotide 30 of SEQ ID NO:47 and the termination codon spans from nucleotide 2305 through nucleotide 2307 of SEQ ID NO:47. The region encoding Pei$_{ca1}$PB2$_{759}$ designated nei$_{ca1}$PB2$_{2277}$ and having a coding strand comprising nucleotides 28 to 2304 of SEQ ID NO 49.

C. Comparison of the nucleic acid sequences of the coding strands of nei$_{wt}$PB$_{2341}$ (SEQ ID NO:44) and nei$_{ca1}$PB2$_{2341}$ (SEQ ID NO:47) by DNA alignment reveals the following differences: a T to C base shift at base 370, an A to C base shift at base 1261, and a G to A base shift at base 2037. Comparison of the amino acid sequences of proteins Pei$_{wt}$PB2$_{759}$ (SEQ ID NO:45) and Pei$_{ca1}$PB2$_{759}$ (SEQ ID NO:48) reveals the following differences: a Y to H shift at amino acid 124 relating to the a T to C shift at base 370 in the DNA sequence, a K to Q shift at amino acid 421 relating to the A to C shift at base 1261 in the DNA sequence. The third nucleotide shift at base 2037 does not result in an amino acid shift at amino.

EXAMPLE 16

This example describes the cloning and sequencing of equine influenza NS (nonstructural) protein nucleic acid molecules for wild type or cold-adapted equine influenza viruses.

A. Nucleic acid molecules encoding wild type or cold-adapted equine influenza virus NS proteins were produced as follows. A PCR product containing an equine NS gene was produced by PCR amplification from equine influenza virus DNA and primers w586 and w587, designated SEQ ID NO:59 and SEQ ID NO:$60_7$, respectively. A nucleic acid molecule of 891 nucleotides encoding a wild-type NS protein, denoted nei$_{wt}$NS$_{891}$, with a coding strand having a nucleic acid sequence designated SEQ ID NO:50 was produced by further PCR amplification using the above-described PCR product as a template and cloned into pCR 2.1® TA cloning vector as described in Example 11A. Plasmid DNA was purified and sequenced as in Example 11A, except that primers used in the sequencing kits were only T7 and REV were used in the sequencing kits.

Translation of SEQ ID NO:50 indicates that nucleic acid molecule nei$_{wt1}$NS$_{891}$ encodes a full-length equine influenza NS protein of about 230 amino acids, referred to herein as Pei$_{wt1}$NS$_{230}$, having amino acid sequence SEQ ID NO:51, assuming an open reading frame in which the initiation codon spans from nucleotide 27 through nucleotide 29 of SEQ ID NO:50 and the termination codon spans from nucleotide 717 through nucleotide 719 of SEQ ID NO:50. The region encoding Pei$_{wt1}$NS$_{230}$, designated nei$_{wt1}$NS$_{690}$, and having a coding strand comprising nucleotides 27 to 716 of SEQ ID NO:50 is represented by SEQ ID NO:52.

PCR amplification of a second nucleic acid molecule encoding a wild type equine influenza NS protein in the same manner resulted in molecules nei$_{wt2}$NS$_{891}$, identical to nei$_{wt1}$NS$_{891}$ in the coding region i.e. nei$_{wt2}$NS$_{690}$, is identical to nei$_{wt1}$NS$_{690}$. nei$_{wt2}$NS$_{891}$ differs from nei$_{wt1}$NS$_{891}$ in one nucleotide at base 827 (G to A) which is 111 bases downstream from the stop codon. PCR amplification of a third nucleic acid encoding a wild type equine influenza NS protein in the same manner resulted in a nucleic acid molecule of 888 nucleotides denoted nei$_{wt3}$NS$_{888}$, with a coding strand with a nucleic acid sequence designated SEQ ID NO:53. nei$_{wt3}$NS$_{888}$ is identical to nei$_{wt1}$NS$_{891}$, except that nei$_{wt3}$NS$_{888}$, lacks two nucleotides on the 5' end and one nucleotide on the 3' end. Translation of SEQ ID NO:53 indicates that nucleic acid molecule nei$_{wt3}$NS$_{888}$ also encodes Pei$_{wt1}$NS$_{230}$ (SEQ ID NO:51), assuming an open reading frame having an initiation codon which spans from nucleotide 25 through nucleotide 27 of SEQ ID NO:53 and a termination codon which spans from nucleotide 715 through nucleotide 717 of SEQ ID NO:53. The nucleic acid molecule having a coding strand comprising nucleotides 25 to 714 of SEQ ID 53, denoted nei$_{wt3}$NS$_{690}$, is identical to SEQ ID NO:52.

PCR amplification of a fourth nucleic acid of 468 nucleotides encoding a C-terminal portion of the wild type equine influenza NS protein, denoted nei$_{wt4}$NS$_{468}$ and having a coding sequence designated SEQ ID NO:54 was produced. Translation of SEQ ID NO:54 indicates that nucleic acid molecule nei$_{wt4}$NS$_{468}$ encodes a C-terminal portion of equine influenza NS protein of about 97 amino acids, referred to herein as Pei$_{wt4}$NS$_{97}$, having amino acid sequence SEQ ID NO:55, assuming an open reading frame having a first codon which spans from nucleotide 3 to 5 of SEQ ID NO:54, and a termination codon spans from nucleotide 294 through 296 of SEQ ID NO:54. Because SEQ ID NO:54 is only a partial gene sequence, it does not contain an initiation codon. The region encoding Pei$_{wt4}$NS$_{97}$, designated nei$_{wt4}$NS$_{293}$, and having a coding strand comprising nucleotides 1 to 293 of SEQ ID NO:54, is represented by SEQ ID NO:56.

B. A nucleic acid molecule of 888 nucleotides encoding a cold-adapted equine influenza virus NS protein, denoted nei$_{ca1}$NS$_{888}$, with a coding strand having a sequence designated SEQ ID NO:57 was produced and sequenced as described in Example 16, part A.

Translation of SEQ ID NO:57 indicates that nucleic acid molecule nei$_{ca1}$NS$_{888}$ encodes a full-length equine influenza NS protein of about 230 amino acids, referred to herein as Pei$_{ca1}$NS$_{230}$, having amino acid sequence SEQ ID NO:58, assuming an open reading frame in which the initiation codon spans from nucleotide 27 through nucleotide 29 of SEQ ID NO:57 and the termination codon spans from nucleotide 717 through nucleotide 719 of SEQ ID NO:57. The region encoding Pei$_{ca1}$NS$_{230}$, designated nei$_{ca1}$NS$_{690}$, and having a coding strand comprising nucleotides 27 to 716 of SEQ ID NO:57, is represented by SEQ ID NO:59.

PCR amplification of a second nucleic acid molecule encoding a cold-adapted equine influenza NS protein in the same manner resulted in molecules nei$_{ca2}$NS$_{887}$, containing one less nucleotide at the 3' end than nei$_{ca1}$NS$_{888}$; the coding region nei$_{ca2}$NS$_{690}$ is identical to nei$_{ca1}$NS$_{690}$.

C. Comparison of the nucleic acid sequences of the coding strands of nei$_{wt}$NS$_{891}$ (SEQ ID NO:50) and nei$_{ca1}$NS$_{888}$ (SEQ ID NO:57) by DNA alignment reveals the following difference: an A to G shift at base 827 which is 111 bases downstream from the stop codon. The 3' fragment encoding nei$_{wt4}$NS$_{468}$ (SEQ ID NO:54) has one shift T to C found at base 633 relative to the full-length consensus sequence. Comparison of the amino acid sequences of proteins Pei$_{wt}$NS$_{230}$ (SEQ ID NO:51) and Pei$_{ca1}$NS$_{230}$ ('SEQ ID NO:58) reveals that there are no differences between amino acid sequences of the wild type and cold-adapted proteins.

EXAMPLE 17

This example describes the cloning and sequencing of equine influenza PB1 protein (RNA-directed RNA polymerase 1) nucleic acid molecules corresponding to the N-terminal portion of the protein, for wild type or cold-adapted equine influenza viruses.

A. Nucleic acid molecules encoding wild type or cold-adapted equine influenza virus PB1-N proteins were produced as follows. A PCR product containing an N-terminal portion of the equine PB1 gene was produced by PCR amplification from equine influenza virus DNA, and primers T7 and REV. A nucleic acid molecule of 1229 nucleotides encoding,a wild type PB1-N protein, denoted nei$_{wt1}$PB1-N$_{1229}$, with a coding strand having a nucleic acid sequence designated SEQ ID NO:62 was produced by further PCR amplification using the above described PCR product as a template and cloned as described in Example 11B . Plasmid DNA was purified and sequenced as in Example 11B, except that only T7 and REV primers were used in the sequencing kits.

Translation of SEQ ID NO:62 indicates that nucleic acid molecule nei$_{wt1}$PB1-N$_{1229}$ encodes an N-terminal portion of influenza PB1 protein of about 398 amino acids, referred to herein as Pei$_{wt1}$PB1-N$_{398}$, having amino acid sequence SEQ ID NO:63, assuming an open reading frame in which the initiation codon spans from nucleotide 36 through nucleotide 38 of SEQ ID NO:62, and the last codon spans from nucleotide 1227 through nucleotide 1229 of SEQ ID NO:62. The region encoding Pei$_{wt1}$PB1-N$_{398}$, designated nei$_{wt1}$PB1-N$_{1194}$, and having a coding strand comprising nucleotides 36 to 1229 of SEQ ID NO:62 is represented by SEQ ID NO:64.

PCR amplification of a second nucleic acid molecule encoding a wild type equine influenza PB1-N protein in the same manner resulted in a nucleic acid molecule of 673 nucleotides denoted nei$_{wt1}$PB1-N$_{673}$, with a coding strand with a sequence designated SEQ ID NO:65. Translation of SEQ ID NO:65 indicates that nucleic acid molecule nei$_{wt2}$PB1-N$_{673}$ encodes Pei$_{wt2}$PB1-N$_{212}$ (SEQ ID NO:66), assuming an open reading frame having an initiation codon which spans from nucleotide 36 through nucleotide 38 of SEQ ID NO:65 and a last codon which spans from nucleotide 671 through nucleotide 673 of SEQ ID NO:65. Because SEQ ID NO:65 is only a partial gene sequence, it does not contain a stop codon. The nucleic acid molecule having a coding strand comprising nucleotides 36 to 671 of SEQ ID NO:65, denoted nei$_{wt2}$PB1-N$_{636}$, is designated SEQ ID NO:67.

B. A nucleic acid molecule of 1225 nucleotides encoding an N-terminal portion of influenza PB1 cold-adapted equine influenza virus PB1-N protein, denoted nei$_{ca1}$PB1-N$_{1225}$, with a coding strand having a sequence designated SEQ ID NO:68 was produced, and sequenced as described in as in Example 17, part A.

Translation of SEQ ID NO:68 indicates that nucleic acid molecule nei$_{ca1}$PB1-N$_{1225}$ encodes an N-terminal portion of equine influenza PB-1 protein of about 395 amino acids, referred to herein as Pei$_{ca1}$PB1-N$_{395}$, having amino acid sequence SEQ ID NO:69, assuming an open reading frame in which the initiation codon spans from nucleotide 34 through nucleotide 36 of SEQ ID NO:68, and a last codon which spans from nucleotide 1216 through nucleotide 1218 of SEQ ID NO:68. The region encoding Pei$_{ca1}$PB1-N$_{395}$, designated nei$_{ca1}$PB1-N$_{1185}$, and having a coding strand comprising nucleotides 34 to 1218 of SEQ ID NO:68, is represented by SEQ ID NO:70.

PCR amplification of a second nucleic acid molecule encoding a cold-adapted equine influenza PB1-N protein in the same manner resulted in molecules nei$_{ca2}$PB1-N$_{1221}$, designated SEQ ID NO:71, containing four less nucleotides at the 5' end than nei$_{ca1}$PB1-N$_{1225}$; the coding region nei$_{ca2}$PB1-N$_{1185}$, is identical to nei$_{ca1}$PNB1-N$_{1185}$.

C. Comparison of the nucleic acid sequences of the coding strands of nei$_{wt}$PB1-N$_{1229}$ (SEQ ID NO:62) and nei$_{ca1}$PB1-N$_{1225}$ (SEQ ID NO:68) by DNA alignment reveals no differences in the coding regions. Comparison of the amino acid sequences of proteins Pei$_{wt}$PB1-N$_{395}$ (SEQ ID NO:63) and Pei$_{ca1}$PB1-N$_{395}$ (SEQ ID NO:69) also reveals no differences.

EXAMPLE 18

This example describes the cloning and sequencing of equine influenza PB1 protein (RNA-directed RNA polymerasel) nucleic acid molecules corresponding to the C-terminal portion of the protein, for wild type or cold-adapted equine influenza viruses.

A. Nucleic acid molecules encoding wild type or cold-adapted equine influenza virus PB1-C proteins were produced as follows. A PCR product containing an C-terminal portion of the equine PB1 gene was produced by PCR amplification from equine influenza virus DNA, and primer w569 designated SEQ ID NO:102. A nucleic acid molecule of 1234 nucleotides encoding a wild type PB1-C protein, denoted nei$_{wt1}$PB1-C$_{1234}$, with a coding strand having a nucleic acid sequence designated SEQ ID NO:85 was produced by further PCR amplification using the above described PCR product as a template and cloned as described in Example 11B. Plasmid DNA was purified and sequenced as in Example 11A, except that different primers were used in the sequencing kits. T7, REV, w569, efPB1-a1, designated SEQ ID NO:97, efPB1-a2, designated SEQ ID NO:98, efPB1-s1, designated SEQ ID NO:99, efPB1-s2, designated SEQ ID NO:100, and efPB1-s3, designated SEQ ID NO:101 were used in one instance, T7, REV, efPB1-a1, efPB1-a2, efPB1-s1, efPB1-s2, and efPB1-s3 were used in another instance and T7 and REV were used in another instance.

Translation of SEQ ID NO:85 indicates that nucleic acid molecule nei$_{wt1}$PB1-C$_{1234}$ encodes an C-terminal portion of influenza PB1 protein of about 396 amino acids, referred to herein as Pei$_{wt1}$PB1-C$_{396}$, having amino acid sequence SEQ ID NO:86, assuming an open reading frame in which the first codon spans from nucleotide 1 through, nucleotide 3 of SEQ ID NO:85 and a termination codon which spans from nucleotide 1189 through nucleotide 1191 of SEQ ID NO:85. Because SEQ ID NO:85 is only a partial gene sequence, it does not contain an initiation codon. The region encoding Pei$_{wt1}$PB1-C$_{396}$, designated nei$_{wt1}$PB1-C$_{1188}$, and having a coding strand comprising nucleotides 1 to 1188 of SEQ ID NO:85 is represented by SEQ ID NO:87.

PCR amplification of a second nucleic acid molecule encoding a wild type equine influenza PB1-C protein in the same manner resulted in a nucleic acid molecule of 1240 nucleotides denoted nei$_{wt2}$PB1-C$_{1240}$ with a coding strand with a sequence designated SEQ ID NO:88. Translation of SEQ ID NO:88 indicates that nucleic acid molecule nei$_{wt2}$PB1-N$_{1240}$ encodes a molecule designated Pei$_{wt2}$PB1-C$_{396}$ (SEQ ID NO:89) which differs from Pei$_{wt1}$PB1-C$_{396}$ (SEQ ID NO:85) in one nucleotide. Nucleotide 382 of nei$_{wt1}$PB1-C$_{1234}$, i.e. nucleotide 382 of nei$_{wt1}$PB1-C$_{1188}$ was A, while nucleotide 389 of nei$_{wt2}$ PB1-C$_{1240}$, i.e. nucleotide 382 of nei$_{wt}$2PB1-C$_{1188}$ was T. Translation of nei$_{wt2}$PB1-C$_{1240}$ results in an amino acid change of T to S.

B. A nucleic acid molecule of 1241 nucleotides encoding an C-terminal portion of influenza PB1 cold-adapted equine influenza virus PB1-C protein, denoted nei$_{ca1}$PB1-C$_{1241}$, with a coding strand having a sequence designated SEQ ID NO:91 was produced, and sequenced as described in as in Example 18, part A.

Translation of SEQ ID NO:91 indicates that nucleic acid molecule nei$_{ca1}$PB1-C$_{1241}$ encodes an C-terminal portion of equine influenza PB-1 protein of about 396 amino acids, referred to herein as Pei$_{ca1}$PB1-C$_{396}$, having amino acid sequence SEQ ID NO:92, assuming an open reading frame in which the first codon spans from nucleotide 8 through nucleotide 10 of SEQ ID NO:91 and a termination codon that spans from nucleotide 1196 through nucleotide 1198 of SEQ ID NO:91. Because SEQ ID NO:91 is only a partial gene sequence, it does not contain an initiation codon. The region encoding Pei$_{ca}$1PB1-C$_{396}$, designated nei$_{ca1}$PB1-C$_{1188}$, and having a coding strand comprising nucleotides 8 to 1195 of SEQ ID NO:91, is represented by SEQ ID NO:93.

PCR amplification of a second nucleic acid molecule encoding a cold-adapted equine influenza PB1-C protein in the same manner resulted in a nucleic acid molecule of 1241 nucleotides denoted nei$_{ca2}$PB1-C$_{1241}$, with a coding strand with a sequence designated SEQ ID NO:94. Translation of SEQ ID NO:94 indicates that nucleic acid molecule nei$_{ca2}$PB1-C$_{1241}$ encodes a molecule designated Pei$_{ca2}$PB1-C$_{396}$ (SEQ ID NO:95) which differs from Pei$_{ca1}$PB1-C$_{396}$ (SEQ ID NO:92) in one nucleotide. Nucleotide 1044 of nei$_{ca1}$PB1-C$_{1241}$, i.e. nucleotide 1037 of nei$_{ca1}$PB1-N$_{1188}$ was A, while nucleotide 1044 of nei$_{ca2}$PB1-C$_{1241}$, i.e. nucleotide 1037 of nei$_{ca2}$PB1-C$_{1188}$ was G. Translation of nei$_{ca2}$PB1-C$_{1241}$ results in an amino acid change of R to K.

C. Comparison of the nucleic acid sequences of the coding strands of nei$_{wt1}$PB1-C$_{1234}$ (SEQ ID NO:85) and nei$_{ca1}$PB1-C$_{1241}$ (SEQ ID NO:91) by DNA alignment reveals the following differences: a C to T shift at base 600 of SEQ ID NO:85, and a T to A shift at base 603 of SEQ ID NO:85. Comparison of the amino acid sequences of proteins Pei$_{wt1}$PB1-C$_{396}$ (SEQ ID NO:86) and Pei$_{ca1}$PB1-N$_{396}$ (SEQ ID NO:92) reveals the following difference: a H to Q amino acid shift 203 when relating to the T to A, base shift at base 603 in the DNA sequences. There is no amino acid shift resulting from the C to T base shift at base 600.

EXAMPLE 19

This example describes the cloning and sequencing of equine influenza PB1 protein (RNA-directed RNA polymerase) nucleic acid molecules for wild type or cold-adapted equine influenza viruses.

A. Nucleic acid molecules encoding wild type or cold-adapted equine influenza virus PB1 proteins were produced as follows. The wild type or cold-adapted equine influenza genes were cloned in two fragments, the N-terminal portion was produced as in Example 17 and the C-terminal portion of the gene was produced as in Example 18.

The DNA sequence for the wild type equine influenza PB1 gene was generated by combining the sequences for the wild type PB1-N protein, nei$_{wt1}$PB1-N$_{1229}$ (SEQ ID NO:62) and nei$_{wt2}$PB1-N$_{673}$ (SEQ ID NO:65) with the gene fragments for the wild type PB1-C protein, denoted nei$_{wt1}$PB1-C$_{1234}$ (SEQ ID NO:85) and nei$_{wt2}$PB1-C$_{1240}$ (SEQ ID NO:88). The result of combining the N-terminal and C-terminal portions of the PB1 wild type influenza virus yielded a complete DNA sequence of 2341 nucleotides denoted nei$_{wt}$PB1$_{2341}$ (SEQ ID NO:103). Translation of SEQ ID NO:103 indicates that the nucleic acid molecule nei$_{wt}$PB2$_{2341}$ encodes a full length equine influenza PB1 protein of about 757 amino acids referred to herein as Pei$_{wt}$PB1$_{757}$, having amino acid sequence SEQ ID NO:104, assuming an open reading frame in which the initiation codon spans from nucleotide 25 through nucleotide 27 of SEQ ID NO:103 and tie termination codon spans from nucleotide 2293 through nucleotide 2295 of SEQ ID NO:103. The region encoding Pei$_{wt}$PB1$_{757}$ designated nei$_{wt}$PB1$_{2271}$, and having a coding strand comprising nucleotides 25 to 2292 of SEQ ID NO:103, is SEQ ID NO:105.

B. A DNA sequence of 2341 nucleotides encoding a cold-adapted equine influenza virus PB1, denoted nei$_{ca1}$PB1$_{2341}$, with a sequence denoted SEQ ID NO:106 was produced by combining the sequences for the N-terminal and C-terminal portions of the PB1 cold-adapted equine influenza gene. The clones for the N-terminal sequences are denoted nei$_{ca1}$PB1-N$_{1225}$(SEQ ID NO:68) and nei$_{ca2}$PB1-N$_{1221}$ (SEQ ID NO: 71). The clones for the C-terminal sequences are denoted nei$_{ca1}$PB1-C$_{1241}$ (SEQ ID NO:91) and nei$_{ca1}$PB1-C$_{1241}$, (SEQ ID NO:94).

Translation of SEQ ID NO:106 indicates that nucleic acid molecule nei$_{ca1}$PB1$_{2341}$ encodes a full-length equine influenza PB1 protein of about 757 amino acids, referred to herein as Pei$_{ca1}$PB1$_{757}$, having amino acid sequence SEQ ID NO:107, assuming an open reading frame in which the initiation codon spans from nucleotide 25 through nucleotide 27 SEQ ID NO:106 and the termination codon spans from nucleotide 2296 through nucleotide 2298 of SEQ ID NO:106. The region encoding Pei$_{ca1}$PB1$_{757}$ designated nei$_{ca1}$PB1$_{2271}$ and having a coding strand comprising nucleotides 25 to 2295 of SEQ ID NO:108.

C. Comparison of the nucleic acid sequences of the coding strands of nei$_{wt}$PB1$_{2341}$ (SEQ ID NO:103) and nei$_{ca1}$PB1$_{2341}$ (SEQ ID NO:106) by DNA alignment reveals the following differences: a C to T base shift at base 1683, and a T to A base shift at base 1686. Comparison of the amino acid sequences of proteins Pei$_{wt}$PB1$_{757}$ (SEQ ID NO:104) and Pei$_{ca1}$PB1$_{757}$ (SEQ ID NO:107) reveals the following differences: no shift in base C at amino acid 561 relating to the C to T shift at base 1683, and a H to Q shift at amino acid 562 relating to the a T to A shift at base 1683 in the DNA sequence.

EXAMPLE 20

This example describes the cloning and sequencing of equine influenza PA protein (RNA polymerase A) nucleic acid molecules corresponding to the C-terminal portion of the protein, for wild type or cold-adapted equine influenza viruses.

A. Nucleic acid molecules encoding wild type or cold-adapted equine influenza virus PA-C proteins were produced as follows. A PCR product containing the C-terminal portion of the equine PA gene was produced by PCR amplification using from equine influenza virus DNA and primers C+PA and C−PA, designated SEQ ID NO:83 and SEQ ID NO:84 respectively. A nucleic acid molecule of 1228 nucleotides encoding a wild type PA-C protein, denoted nei$_{wt1}$PA-C$_{1228}$, with a coding strand having a nucleic acid sequence designated SEQ ID NO:76 was produced by further PCR amplification using the above-described PCR product as a template and cloned as described in Example 11B . Plasmid DNA was purified and sequenced as in Example 11A, except that different primers were used in the sequencing kits. T7 and REV were used in one instance; PAC-1, designated SEQ ID NO:72, PAC-2, designated SEQ ID NO:73, PAC-3, designated SEQ ID NO:74, PAC-4, designated SEQ ID NO:75, T7 and REV were used in another instance; and PAC-1, PAC-2, T7 and REV were used in another instance.

Translation of SEQ ID NO:76 indicates that nucleic acid molecule nei$_{wt1}$PA-C$_{1228}$ encodes a C-terminal portion of influenza PA protein of about 388 amino acids, referred to herein as Pei$_{wt1}$PA-C$_{388}$, having amino acid sequence SEQ ID NO:77, assuming an open reading frame having a first codon spans from nucleotide 3 through nucleotide 5 of SEQ ID NO:76 and a termination codon which spans from nucleotide 1167 through nucleotide 1169 of SEQ ID NO:76. Because SEQ ID NO:76 is only a partial gene sequence, it does not contain an initiation codon. The region encoding Pei$_{wt1}$PA-C$_{388}$, designated nei$_{wt1}$PA-C$_{1164}$, and having a coding strand comprising nucleotides 3 to 1166 of SEQ ID NO:76 is represented by SEQ ID NO:78.

PCR amplification of a second nucleic acid molecule encoding a wild type equine influenza PA-C protein in the same manner resulted in a nucleic acid molecule of 1223 nucleotides denoted nei$_{wt2}$PA-C$_{1223}$, with a coding strand with a sequence designated SEQ ID NO:79. nei$_{wt2}$PA-C$_{1223}$ is identical to nei$_{wt1}$PA-C$_{1228}$, with the exception of a T to C base shift at base 753 and that nei$_{wt2}$PA-C$_{1223}$ lacks five nucleotides on the 3'-end. Translation of SEQ ID NO:79 indicates that nucleic acid molecule nei$_{wt2}$PA-C$_{1223}$ also encodes Pei$_{wt1}$PA-C$_{388}$ (SEQ ID NO:77), assuming an open reading frame having a first codon which spans from nucleotide 3 through nucleotide 5 of SEQ ID NO:79 and a termination codon which spans from nucleotide 1167 through nucleotide 1169 of SEQ ID NO:79. Because SEQ ID NO:79 is only a partial gene sequence, it does not contain an initiation codon. The nucleic acid molecule having a coding strand comprising nucleotides 3 to 1166 of SEQ ID NO:79, denoted nei$_{wt2}$PA-C$_{1223}$, is identical to SEQ ID NO 78.

B. A nucleic acid molecule of 1233 nucleotides encoding a C-terminal portion of influenza PA-C cold-adapted equine influenza virus protein, denoted nei$_{ca1}$PA-C$_{1233}$, and having al coding strand having a sequence designated SEQ ID NO:80 was produced as described in as in Example 20, part A, except that the pCR®-Blunt cloning vector was used.

Translation of SEQ ID NO:80 indicates that nucleic acid molecule nei$_{ca1}$PA-C$_{1233}$ encodes a C-terminal portion of equine influenza PA protein of about 390 amino acids, referred to herein as Pei$_{ca1}$PA-C$_{390}$, having amino acid sequence SEQ ID NO:81, assuming an open reading frame having a first codon which spans from nucleotide 3 through nucleotide 5 of SEQ ID NO:80 and a termination codon which spans from nucleotide 1173 through nucleotide 1175 of SEQ ID NO:80. Because SEQ ID NO:80 is only a partial gene sequence, it does not contain an initiation codon. The region encoding Pei$_{ca1}$PA-C$_{390}$, designated nei$_{ca1}$PA-C$_{1170}$, and having a coding strand comprising nucleotides 3 to 1172 of SEQ ID NO:80, is represented by SEQ ID NO:82.

PCR amplification of a second nucleic acid molecule encoding a cold-adapted equine influenza PA-C protein in the same manner resulted in molecule nei$_{ca2}$PA-C$_{1233}$, containing one A to C base shift at base 953 as compared to nei$_{ca1}$PA-C$_{1233}$; this base shift at does not result in an amino acid change so Pei$_{ca2}$PA-C$_{390}$, is identical to Pei$_{ca1}$PA-C$_{390}$ (SEQ ID NO:81.) C. Comparison of the nucleic acid sequences of the coding strands of nei$_{wt1}$PA-C$_{1228}$ (SEQ ID NO:76) and nei$_{ca1}$PA-C$_{1233}$ (SEQ ID NO:80) by DNA alignment reveals the following difference: an C to T base shift at base 753 of SEQ ID NO:80. Comparison of the amino acid sequences of proteins Pei$_{wt1}$PA-C$_{388}$ (SEQ ID NO:77) and Pei$_{ca1}$PA-$_{390}$ (SEQ ID NO:81) reveals the following difference: a W to R shift at amino acid 251 when relating to the C to T base shift at base 753 in the DNA sequences.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated equine influenza nucleic acid molecule selected from the group consisting of:

a. an insolated nucleic acid molecule that encodes a protein comprising an amino acid sequence selected from the group consisting of SEQ ID NO:69, SEQ ID NO:92, and SEQ ID NO:107; and b. an isolated nucleic acid molecule fully complementary to a nucleic acid molecule of (a);

wherein said nucleic acid molecule of (a) or (b) is not an entire equine influenza virus genome.

2. The nucleic acid molecule of claim 1, wherein said nucleic acid molecule comprises a nucleic acid sequence selected from the group consisting of SEQ ID NO:68, SEQ ID NO:70, SEQ ID NO:91, SEQ ID NO:93, SEQ ID NO:106 and SEQ ID NO:108 and a nucleic acid molecule comprising a nucleic acid sequence which is fully complementary to any of said nucleic acid sequences.

3. A nucleic acid molecule of claim 1, wherein said nucleic acid molecule encodes a protein.

4. A nucleic acid molecule of claim 1, wherein said nucleic acid molecule encodes a protein selected from the group consisting of $Pei_{ca1}PB1\text{-}C_{396}$, and $Pei_{ca1}PB1_{757}$.

* * * * *

UNITED STATES PATENT AND TRADEMARK OFFICE

CERTIFICATE OF CORRECTION

PATENT NO. : 6,685,946 B2 
DATED : February 3, 2004
INVENTOR(S) : Patricia W. Dowling; Julius S. Youngner It is certified that error appears in the above-identified patent and that said Letters Patent is hereby corrected as shown below:

Column 234,
Line 25, before "$Pei_{ca1}$" insert -- $Pei_{ca1}PB1\text{-}N_{395}$, --.

Signed and Sealed this

First Day of June, 2004

JON W. DUDAS
*Acting Director of the United States Patent and Trademark Office*